US010160760B2

(12) United States Patent
Charrier et al.

(10) Patent No.: US 10,160,760 B2
(45) Date of Patent: Dec. 25, 2018

(54) COMPOUNDS USEFUL AS INHIBITORS OF ATR KINASE

(71) Applicant: Vertex Pharmaceuticals Incorporated, Boston, MA (US)

(72) Inventors: Jean-Damien Charrier, Wantage (GB); Christopher John Davis, Salisbury (GB); Damien Fraysse, Abingdon (GB); Gorka Etxebarria I Jardi, Abingdon (GB); Simon Pegg, Oxford (GB); Francoise Pierard, Abingdon (GB); Joanne Pinder, Didcot (GB); John Studley, Witney (GB); Carl Zwicker, Brighton, MA (US); Tapan Sanghvi, Watertown, MA (US); Michael Waldo, Grafton, MA (US); Ales Medek, Winchester, MA (US); David Matthew Shaw, Oxford (GB); Maninder Panesar, Didcot (GB); Yuegang Zhang, Wayland, MA (US); Naziha Alem, Reading (GB)

(73) Assignee: VERTEX PHARMACEUTICALS INCORPORATED, Boston, MA (US)

(*) Notice: Subject to any disclaimer, the term of this patent is extended or adjusted under 35 U.S.C. 154(b) by 0 days.

(21) Appl. No.: 14/561,368

(22) Filed: Dec. 5, 2014

(65) Prior Publication Data
US 2015/0158872 A1 Jun. 11, 2015

Related U.S. Application Data

(60) Provisional application No. 61/912,636, filed on Dec. 6, 2013, provisional application No. 62/008,220, filed on Jun. 5, 2014, provisional application No. 62/058,819, filed on Oct. 2, 2014.

(51) Int. Cl.
*C07D 487/04* (2006.01)
*A61K 31/519* (2006.01)
*C07C 45/00* (2006.01)
*C07C 45/63* (2006.01)
*C07B 59/00* (2006.01)
*A61P 35/00* (2006.01)

(52) U.S. Cl.
CPC .......... *C07D 487/04* (2013.01); *C07B 59/002* (2013.01); *C07C 45/00* (2013.01); *C07C 45/63* (2013.01); *C07B 2200/05* (2013.01); *C07B 2200/13* (2013.01)

(58) Field of Classification Search
CPC ................... C07D 487/04; A61K 31/519
USPC ...................... 544/281; 514/259.3
See application file for complete search history.

(56) References Cited

U.S. PATENT DOCUMENTS

| 4,309,430 A | 1/1982 | Bock et al. |
| 5,143,824 A | 9/1992 | Yamakawa et al. |
| 5,902,773 A | 5/1999 | Benoit et al. |
| 6,060,478 A | 5/2000 | Gilligan et al. |

(Continued)

FOREIGN PATENT DOCUMENTS

| CN | 101537007 A | 9/2009 |
| CN | 101671336 A | 3/2010 |

(Continued)

OTHER PUBLICATIONS

Bhattacharya et al. (Brittain, ed. Polymorphism in Pharmaceutical Solids, 2009, p. 334.*

(Continued)

*Primary Examiner* — Susanna Moore
(74) *Attorney, Agent, or Firm* — Andrea L. C. Reid; Dechert LLP

(57) ABSTRACT

The present invention relates to compounds useful as inhibitors of ATR protein kinase. The invention relates to pharmaceutically acceptable compositions comprising the compounds of this invention; methods of treating of various diseases, disorders, and conditions using the compounds of this invention; processes for preparing the compounds of this invention; intermediates for the preparation of the compounds of this invention; and solid forms of the compounds of this invention.
The compounds of this invention have formula I-A or I-B:

I-A

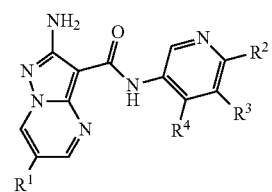

I-B
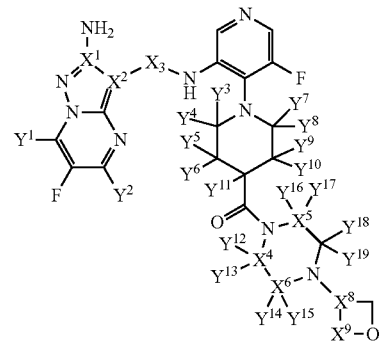

wherein the variables are as defined herein.

63 Claims, 34 Drawing Sheets

(56) References Cited

U.S. PATENT DOCUMENTS

| | | |
|---|---|---|
| 6,191,131 B1 | 2/2001 | He et al. |
| 6,235,741 B1 | 5/2001 | Bilodeau et al. |
| 6,420,367 B1 | 7/2002 | Ueda et al. |
| 6,660,753 B2 | 12/2003 | Van Wagenen et al. |
| 6,858,600 B2 | 2/2005 | Hamilton et al. |
| 6,992,087 B2 | 1/2006 | Verhoest et al. |
| 7,041,672 B2 | 5/2006 | Verhoest et al. |
| 7,199,123 B2 | 4/2007 | Munchhof |
| 7,452,993 B2 | 11/2008 | Arnold et al. |
| 7,528,138 B2 | 5/2009 | Knegtel et al. |
| 7,550,470 B2 | 6/2009 | Fraley |
| 7,622,583 B2 | 11/2009 | Ungashe et al. |
| 7,626,021 B2 | 12/2009 | Arnold et al. |
| 7,700,601 B2 | 4/2010 | Chan et al. |
| 7,704,995 B2 | 4/2010 | Buhr et al. |
| 7,829,558 B2 | 11/2010 | Arnold et al. |
| 7,872,031 B2 | 1/2011 | Lauffer et al. |
| 7,902,197 B2 | 3/2011 | Elworthy et al. |
| 7,932,254 B2 | 4/2011 | DuBois et al. |
| 7,939,531 B2 | 5/2011 | Bamberg et al. |
| 7,981,893 B2 | 7/2011 | Mortensen et al. |
| 8,063,032 B2 | 11/2011 | Chytil et al. |
| 8,106,197 B2 | 1/2012 | Cui et al. |
| 8,410,112 B2 | 4/2013 | Charrier et al. |
| 8,492,582 B2 | 7/2013 | Yokotani et al. |
| 8,623,869 B2 | 1/2014 | Charrier et al. |
| 8,822,469 B2 | 9/2014 | MacCormick et al. |
| 8,957,078 B2 | 2/2015 | Brenchley et al. |
| 8,962,631 B2 | 2/2015 | Charrier et al. |
| 8,969,360 B2 | 3/2015 | Charrier et al. |
| 8,999,632 B2 | 4/2015 | Falcon et al. |
| 9,096,602 B2 | 8/2015 | Everitt et al. |
| 9,309,250 B2 | 3/2016 | Storck et al. |
| 9,340,546 B2* | 5/2016 | Ahmad ............... C07D 487/04 |
| 9,365,557 B2 | 6/2016 | Charrier et al. |
| 9,701,674 B2 | 7/2017 | Charrier et al. |
| 9,718,827 B2 | 8/2017 | Ahmad et al. |
| 9,791,456 B2 | 10/2017 | Falcon et al. |
| 9,862,709 B2 | 1/2018 | Charrier et al. |
| 2002/0041880 A1 | 4/2002 | DeFeo-Jones et al. |
| 2003/0008882 A1 | 1/2003 | Hamilton et al. |
| 2003/0055085 A1 | 3/2003 | Wagenen et al. |
| 2004/0034037 A1 | 2/2004 | Harbeson et al. |
| 2004/0043998 A1 | 3/2004 | Kato et al. |
| 2004/0180905 A1 | 9/2004 | Munchhof |
| 2005/0261339 A1 | 11/2005 | Ohi et al. |
| 2006/0156482 A1 | 7/2006 | Lim |
| 2006/0211709 A1 | 9/2006 | Buhr et al. |
| 2007/0037794 A1 | 2/2007 | Ungashe et al. |
| 2007/0112006 A1 | 5/2007 | Schiemann et al. |
| 2007/0197389 A1 | 8/2007 | Schwogler et al. |
| 2007/0254868 A1 | 11/2007 | Lauffer et al. |
| 2007/0270420 A1 | 11/2007 | Harbeson et al. |
| 2007/0287711 A1 | 12/2007 | Arnold et al. |
| 2008/0176892 A1 | 7/2008 | Heinrich et al. |
| 2008/0287463 A1 | 11/2008 | Herrmann et al. |
| 2009/0005381 A1 | 1/2009 | Brown et al. |
| 2009/0156512 A1 | 6/2009 | Umemura et al. |
| 2009/0215724 A1 | 8/2009 | DuBois et al. |
| 2009/0215750 A1 | 8/2009 | Bamberg et al. |
| 2009/0215785 A1 | 8/2009 | DuBois et al. |
| 2009/0215788 A1 | 8/2009 | Elworthy et al. |
| 2009/0306087 A1 | 12/2009 | Ibrahim et al. |
| 2009/0318436 A1 | 12/2009 | Albrecht et al. |
| 2010/0036118 A1 | 2/2010 | Arnold et al. |
| 2010/0167931 A1 | 7/2010 | Mueller et al. |
| 2010/0168138 A1 | 7/2010 | DeGoey et al. |
| 2010/0204214 A1 | 8/2010 | Chytil et al. |
| 2010/0222318 A1 | 9/2010 | Charrier et al. |
| 2010/0233091 A1 | 9/2010 | Neumann et al. |
| 2011/0015231 A1 | 1/2011 | Al-Abed et al. |
| 2011/0275797 A1 | 11/2011 | Yokotani et al. |
| 2011/0288067 A1 | 11/2011 | Hendricks et al. |
| 2011/0288097 A1 | 11/2011 | Hendricks et al. |
| 2012/0027874 A1 | 2/2012 | Charrier et al. |
| 2012/0035407 A1 | 2/2012 | Charrier et al. |
| 2012/0035408 A1 | 2/2012 | Charrier et al. |
| 2012/0040020 A1 | 2/2012 | Charrier et al. |
| 2012/0046295 A1 | 2/2012 | Charrier et al. |
| 2012/0065247 A1 | 3/2012 | Thompson et al. |
| 2012/0115874 A1 | 5/2012 | Wang et al. |
| 2012/0122884 A1 | 5/2012 | Charrier et al. |
| 2012/0177748 A1 | 7/2012 | Charrier et al. |
| 2012/0178756 A1 | 7/2012 | Charrier et al. |
| 2012/0178915 A1 | 7/2012 | Xu |
| 2013/0017273 A1 | 1/2013 | Everitt et al. |
| 2013/0018035 A1 | 1/2013 | MacCormick et al. |
| 2013/0034616 A1 | 2/2013 | Storck et al. |
| 2013/0089624 A1 | 4/2013 | Charrier et al. |
| 2013/0089625 A1 | 4/2013 | Charrier et al. |
| 2013/0089626 A1 | 4/2013 | Pollard et al. |
| 2013/0095193 A1 | 4/2013 | Charrier et al. |
| 2013/0096139 A1 | 4/2013 | Charrier et al. |
| 2013/0115310 A1 | 5/2013 | Charrier et al. |
| 2013/0115311 A1 | 5/2013 | Charrier et al. |
| 2013/0115312 A1 | 5/2013 | Charrier et al. |
| 2013/0115313 A1 | 5/2013 | Charrier et al. |
| 2013/0115314 A1 | 5/2013 | Charrier et al. |
| 2013/0172273 A1 | 7/2013 | Aizpurua Iparraguirre et al. |
| 2013/0184292 A1 | 7/2013 | Charrier et al. |
| 2014/0044802 A1 | 2/2014 | Pollard et al. |
| 2014/0100229 A1 | 4/2014 | Follmann et al. |
| 2014/0113005 A1 | 4/2014 | Charrier et al. |
| 2014/0163000 A1* | 6/2014 | Ahmad ............... C07D 487/04 |
| | | 514/210.18 |
| 2014/0249157 A1 | 9/2014 | Ahmad et al. |
| 2014/0275009 A1 | 9/2014 | Brenchley et al. |
| 2014/0275021 A1 | 9/2014 | Charrier et al. |
| 2014/0275130 A1 | 9/2014 | Charrier et al. |
| 2014/0288347 A1 | 9/2014 | Charrier et al. |
| 2014/0356456 A1 | 12/2014 | Pollard et al. |
| 2015/0158868 A1 | 6/2015 | Boyall et al. |
| 2015/0158872 A1 | 6/2015 | Charrier et al. |
| 2015/0216175 A1 | 8/2015 | Heil et al. |
| 2015/0247866 A1 | 9/2015 | Falcon et al. |
| 2015/0274710 A1 | 10/2015 | Charrier et al. |
| 2015/0291601 A1 | 10/2015 | Brenchley et al. |
| 2015/0299205 A1 | 10/2015 | Charrier et al. |
| 2015/0353560 A1 | 12/2015 | Ahmad et al. |
| 2015/0359797 A1 | 12/2015 | Helleday et al. |
| 2015/0376187 A1 | 12/2015 | Everitt et al. |
| 2016/0009723 A1 | 1/2016 | Charrier et al. |
| 2016/0030424 A1 | 2/2016 | Pollard et al. |
| 2016/0311809 A1 | 10/2016 | Charrier et al. |
| 2016/0326180 A1 | 11/2016 | Boyall et al. |
| 2017/0349596 A1 | 5/2017 | Ahmad et al. |
| 2018/0072735 A1 | 3/2018 | Ahmad et al. |

FOREIGN PATENT DOCUMENTS

| | | |
|---|---|---|
| CN | 103373996 A | 10/2013 |
| EP | 0 313 724 A2 | 5/1989 |
| EP | 1 217 000 A1 | 6/2002 |
| EP | 2 157 090 A1 | 2/2010 |
| JP | 2001-302666 A | 10/2001 |
| WO | WO 96/35690 A1 | 11/1996 |
| WO | WO 97/43267 A1 | 11/1997 |
| WO | WO 98/03510 A1 | 1/1998 |
| WO | WO 98/33799 A1 | 8/1998 |
| WO | WO 98/42701 A1 | 10/1998 |
| WO | WO 98/54093 A1 | 12/1998 |
| WO | WO 00/04014 A1 | 1/2000 |
| WO | WO 00/53605 A1 | 9/2000 |
| WO | WO 01/40231 A1 | 6/2001 |
| WO | WO 01/44206 A1 | 6/2001 |
| WO | WO 01/92257 A1 | 12/2001 |
| WO | WO 02/09648 A2 | 2/2002 |
| WO | WO 02/40485 A1 | 5/2002 |
| WO | WO 02/66481 A1 | 8/2002 |
| WO | WO 03/00187 A2 | 1/2003 |
| WO | WO 03/04472 A1 | 1/2003 |
| WO | WO 03/04475 A1 | 1/2003 |
| WO | WO 03/37900 A2 | 5/2003 |
| WO | WO 03/45924 A1 | 6/2003 |

(56) References Cited

FOREIGN PATENT DOCUMENTS

| | | |
|---|---|---|
| WO | WO 03/76422 A1 | 9/2003 |
| WO | WO 03/80610 A1 | 10/2003 |
| WO | WO 03/87057 A1 | 10/2003 |
| WO | WO 03/92686 A1 | 11/2003 |
| WO | WO 03/93297 A2 | 11/2003 |
| WO | WO 03/101968 A1 | 12/2003 |
| WO | WO 03/101993 A1 | 12/2003 |
| WO | WO 2004/000318 A2 | 12/2003 |
| WO | WO 2004/022559 A1 | 3/2004 |
| WO | WO 2004/022560 A1 | 3/2004 |
| WO | WO 2004/022561 A1 | 3/2004 |
| WO | WO 2004/026229 A2 | 4/2004 |
| WO | WO 2004/033431 A2 | 4/2004 |
| WO | WO 2004/052315 A2 | 6/2004 |
| WO | WO 2004/055005 A1 | 7/2004 |
| WO | WO 2004/055006 A1 | 7/2004 |
| WO | WO 2004/076458 A1 | 9/2004 |
| WO | WO 2004/080982 A1 | 9/2004 |
| WO | WO 2004/084813 A2 | 10/2004 |
| WO | WO 2004/084824 A2 | 10/2004 |
| WO | WO 2004/085409 A2 | 10/2004 |
| WO | WO 2004/103279 A2 | 12/2004 |
| WO | WO 2005/028434 A2 | 3/2005 |
| WO | WO 2005/028475 A2 | 3/2005 |
| WO | WO 2005/051906 A2 | 6/2005 |
| WO | WO 2005/054246 A2 | 6/2005 |
| WO | WO 2005/077954 A2 | 8/2005 |
| WO | WO 2005/079802 A1 | 9/2005 |
| WO | WO 2005/080396 A2 | 9/2005 |
| WO | WO 2005/117909 A2 | 12/2005 |
| WO | WO 2005/123672 A2 | 12/2005 |
| WO | WO 2006/015124 A2 | 2/2006 |
| WO | WO 2006/052913 A1 | 5/2006 |
| WO | WO 2006/053342 A2 | 5/2006 |
| WO | WO 2006/058074 A1 | 6/2006 |
| WO | WO 2006/067462 A1 | 6/2006 |
| WO | WO 2006/071548 A2 | 7/2006 |
| WO | WO 2006/071752 A1 | 7/2006 |
| WO | WO 2006/075152 A1 | 7/2006 |
| WO | WO 2006/087120 A2 | 8/2006 |
| WO | WO 2006/088837 A2 | 8/2006 |
| WO | WO 2006/114180 A1 | 11/2006 |
| WO | WO 2006/120573 A2 | 11/2006 |
| WO | WO 2006/128184 A2 | 11/2006 |
| WO | WO 2007/015632 A1 | 2/2007 |
| WO | WO 2007/041712 A1 | 4/2007 |
| WO | WO 2007/044401 A2 | 4/2007 |
| WO | WO 2007/044407 A2 | 4/2007 |
| WO | WO 2007/044410 A1 | 4/2007 |
| WO | WO 2007/044420 A1 | 4/2007 |
| WO | WO 2007/044426 A2 | 4/2007 |
| WO | WO 2007/044441 A2 | 4/2007 |
| WO | WO 2007/044449 A2 | 4/2007 |
| WO | WO 2007/046548 A1 | 4/2007 |
| WO | WO 2007/048066 A2 | 4/2007 |
| WO | WO 2007/058850 A2 | 5/2007 |
| WO | WO 2007/063012 A1 | 6/2007 |
| WO | WO 2007/066805 A1 | 6/2007 |
| WO | WO 2007/076360 A1 | 7/2007 |
| WO | WO 2007/096151 A2 | 8/2007 |
| WO | WO 2007/096764 A2 | 8/2007 |
| WO | WO 2007/096765 A1 | 8/2007 |
| WO | WO 2007/102770 A1 | 9/2007 |
| WO | WO 2007/111904 A2 | 10/2007 |
| WO | WO 2007/126841 A2 | 11/2007 |
| WO | WO 2007/126964 A2 | 11/2007 |
| WO | WO 2007/139732 A1 | 12/2007 |
| WO | WO 2007/139856 A2 | 12/2007 |
| WO | WO 2007/139860 A2 | 12/2007 |
| WO | WO 2007/147874 A1 | 12/2007 |
| WO | WO 2008/004698 A2 | 1/2008 |
| WO | WO 2008/008539 A2 | 1/2008 |
| WO | WO 2008/037477 A1 | 4/2008 |
| WO | WO 2008/038010 A1 | 4/2008 |
| WO | WO 2008/040651 A1 | 4/2008 |
| WO | WO 2008/045266 A2 | 4/2008 |
| WO | WO 2008/045268 A2 | 4/2008 |
| WO | WO 2008/060907 A2 | 5/2008 |
| WO | WO 2008/063671 A2 | 5/2008 |
| WO | WO 2008/071456 A2 | 6/2008 |
| WO | WO 2008/074997 A1 | 6/2008 |
| WO | WO 2008/079291 A2 | 7/2008 |
| WO | WO 2008/079903 A1 | 7/2008 |
| WO | WO 2008/079906 A1 | 7/2008 |
| WO | WO 2008/103277 A2 | 8/2008 |
| WO | WO 2008/106692 A1 | 9/2008 |
| WO | WO 2008/122375 A2 | 10/2008 |
| WO | WO 2008/124850 A1 | 10/2008 |
| WO | WO 2008/130569 A1 | 10/2008 |
| WO | WO 2008/130570 A1 | 10/2008 |
| WO | WO 2008/141065 A1 | 11/2008 |
| WO | WO 2008/144463 A1 | 11/2008 |
| WO | WO 2008/144464 A1 | 11/2008 |
| WO | WO 2008/151735 A2 | 12/2008 |
| WO | WO 2008/157191 A2 | 12/2008 |
| WO | WO 2009/006580 A1 | 1/2009 |
| WO | WO 2009/007390 A2 | 1/2009 |
| WO | WO 2009/012482 A2 | 1/2009 |
| WO | WO 2009/014637 A2 | 1/2009 |
| WO | WO 2009/016460 A2 | 2/2009 |
| WO | WO 2009/017954 A1 | 2/2009 |
| WO | WO 2009/024825 A1 | 2/2009 |
| WO | WO 2009/037247 A1 | 3/2009 |
| WO | WO 2009/053737 A2 | 4/2009 |
| WO | WO 2009/070567 A1 | 6/2009 |
| WO | WO 2009/075790 A1 | 6/2009 |
| WO | WO 2009/088986 A1 | 7/2009 |
| WO | WO 2009/091374 A2 | 7/2009 |
| WO | WO 2009/095254 A1 | 8/2009 |
| WO | WO 2009/106885 A1 | 9/2009 |
| WO | WO 2009/117157 A1 | 9/2009 |
| WO | WO 2010/002483 A1 | 1/2010 |
| WO | WO 2010/006086 A2 | 1/2010 |
| WO | WO 2010/015803 A1 | 2/2010 |
| WO | WO 2010/017047 A1 | 2/2010 |
| WO | WO 2010/034738 A2 | 4/2010 |
| WO | WO 2010/048131 A1 | 4/2010 |
| WO | WO 2010/051549 A1 | 5/2010 |
| WO | WO 2010/054398 A1 | 5/2010 |
| WO | WO 2010/059836 A1 | 5/2010 |
| WO | WO 2010/063634 A1 | 6/2010 |
| WO | WO 2010/068483 A2 | 6/2010 |
| WO | WO 2010/071837 A1 | 6/2010 |
| WO | WO 2010/086040 A1 | 8/2010 |
| WO | WO 2010/091409 A1 | 8/2010 |
| WO | WO 2011/003065 A2 | 1/2011 |
| WO | WO 2011/008830 A1 | 1/2011 |
| WO | WO 2011/022439 A1 | 2/2011 |
| WO | WO 2011/025706 A2 | 3/2011 |
| WO | WO 2011/068667 A1 | 6/2011 |
| WO | WO 2011/113606 A1 | 9/2011 |
| WO | WO 2011/117145 A2 | 9/2011 |
| WO | WO 2011/121096 A1 | 10/2011 |
| WO | WO 2011/124998 A1 | 10/2011 |
| WO | WO 2011/130689 A1 | 10/2011 |
| WO | WO 2011/143399 A1 | 11/2011 |
| WO | WO 2011/143419 A1 | 11/2011 |
| WO | WO 2011/143422 A1 | 11/2011 |
| WO | WO 2011/143423 A2 | 11/2011 |
| WO | WO 2011/143425 A2 | 11/2011 |
| WO | WO 2011/143426 A1 | 11/2011 |
| WO | WO 2011/144584 A1 | 11/2011 |
| WO | WO 2011/144585 A1 | 11/2011 |
| WO | WO 2011/163518 A1 | 12/2011 |
| WO | WO 2012/007375 A1 | 1/2012 |
| WO | WO 2012/022045 A1 | 2/2012 |
| WO | WO 2012/027236 A2 | 3/2012 |
| WO | WO 2012/067822 A1 | 5/2012 |
| WO | WO 2012/074754 A1 | 6/2012 |
| WO | WO 2012/078855 A1 | 6/2012 |
| WO | WO 2012/100342 A1 | 8/2012 |
| WO | WO 2012/138938 A1 | 10/2012 |
| WO | WO 2012/143510 A1 | 10/2012 |
| WO | WO 2012/143796 A2 | 10/2012 |

(56) References Cited

FOREIGN PATENT DOCUMENTS

| | | |
|---|---|---|
| WO | WO 2012/158785 A1 | 11/2012 |
| WO | WO 2012/177997 A1 | 12/2012 |
| WO | WO 2012/178124 A1 | 12/2012 |
| WO | WO 2013/010136 A2 | 1/2013 |
| WO | WO 2013/049720 A1 | 4/2013 |
| WO | WO 2013/049726 A2 | 4/2013 |
| WO | WO 2013/052263 A2 | 4/2013 |
| WO | WO 2013/059587 A1 | 4/2013 |
| WO | WO 2013/138436 A1 | 9/2013 |
| WO | WO 2013/151930 A1 | 10/2013 |
| WO | WO 2013/151938 A1 | 10/2013 |
| WO | WO 2013/154878 A1 | 10/2013 |
| WO | WO 2013/171470 A1 | 11/2013 |
| WO | WO 2013/174930 A2 | 11/2013 |
| WO | WO 2013/174931 A1 | 11/2013 |
| WO | WO 2014/011911 A2 | 1/2014 |
| WO | WO 2014/015521 A1 | 1/2014 |
| WO | WO 2014/023691 A1 | 2/2014 |
| WO | WO 2014/025850 A1 | 2/2014 |
| WO | WO 2014/025852 A1 | 2/2014 |
| WO | WO 2014/025854 A1 | 2/2014 |
| WO | WO 2014/026984 A1 | 2/2014 |
| WO | WO 2014/029723 A1 | 2/2014 |
| WO | WO 2014/035140 A2 | 3/2014 |
| WO | WO 2014/039831 A1 | 3/2014 |
| WO | WO 2014/042433 A2 | 3/2014 |
| WO | WO 2014/044691 A1 | 3/2014 |
| WO | WO 2014/047648 A1 | 3/2014 |
| WO | WO 2014/066435 A1 | 5/2014 |
| WO | WO 2014/066552 A1 | 5/2014 |
| WO | WO 2014/089379 A1 | 6/2014 |

OTHER PUBLICATIONS

International Search Report and Written Opinion dated Sep. 24, 2015 in connection with Application No. PCT/US2015/036137.
International Search Report and Written Opinion dated Feb. 6, 2014 in connection with Application No. PCT/US2013/073482.
International Search Report and Written Opinion in connection with Application No. PCT/US2012/043897 dated Jul. 20, 2012.
International Search Report and Written Opinion in connection with Application No. PCT/US2012/043896 dated Oct. 9, 2012.
International Search Report and Written Opinion in connection with Application No. PCT/US2012/043895 dated Aug. 28, 2012.
International Search Report and Written Opinion dated Oct. 1, 2015 in connection with Application No. PCT/US2015/032879.
International Search Report and Written Opinion dated Jan. 29, 2014 in connection with Application No. PCT/US2013/073457.
International Search Report and Written Opinion dated Jan. 30, 2014 in connection with Application No. PCT/US2013/073477.
Office Communication dated Jun. 27, 2014 for U.S. Appl. No. 14/098,640.
International Search Report and Written Opinion dated Feb. 17, 2014 in connection with Application No. PCT/US2013/073471.
International Search Report and Written Opinion dated Jan. 29, 2015 in connection with Application No. PCT/US2014/068713.
International Search Report and Written Opinion dated Apr. 1, 2014 in connection with Application No. PCT/US2013/073468.
International Search Report and Written Opinion in connection with Application No. PCT/US2011/041705 dated Aug. 23, 2011.
International Search Report and Written Opinion for PCT/US2005/040344 dated Mar. 20, 2006.
Abdel-Magid, Inhibitors of ATR Kinase for Treatment of Cancer. ACS Med Chem Lett. Jun. 13, 2013;4(8):688-9. doi: 10.1021/ml4002198. eCollection 2013.
Ahmed et al., Synthesis and anti-tumor activities of some new pyridines and pyrazolo[1,5-a]pyrimidines. Eur J Med Chem. Sep. 2009;44(9):3519-23. doi: 10.1016/j.ejmech.2009.03.042. Epub Apr. 8, 2009.
Ahmed et al., Synthesis of some Pyrazolopyrimidines as Purine Analogues. J Heterocyclic Chem. 2007;44(4):803-10.

Ammar et al., 3-Ethoxycarbonylmethylenequinoxalin-2-one in heterocyclic synthesis. Part 1: Synthesis of new substituted and condensed quinoxalines. Afinidad. 2005;62(516):151-60.
Boylan et al., Parenteral Products. Chapter 12. In: Modern Pharmaceuticals. Fourth Edition. 1997:34 pages.
Charrier et al., Discovery of potent and selective inhibitors of ataxia telangiectasia mutated and Rad3 related (ATR) protein kinase as potential anticancer agents. J Med Chem. Apr. 14, 2011;54(7):2320-30. doi: 10.1021/jm101488z. Epub Mar. 17, 2011. E-pub version.
Charrier et al., Discovery of Potent and Selective Inhibitors of ATR (Ataxia Telangiectasia Mutated and Rad3 Related) as Potential AntiCancer Agents. Supplementary Information, Apr. 14, 2011: 47 pages.
Charrier, Discovery of potent and selective inhibitors of Ataxia Telangiectasia mutated and Rad3 related (ATR) protein kinase as potential anticancer agents. Presentation, ACS Denver 2011. Aug. 28, 2011. 21 pages.
Chawla et al., Challenges in Polymorphism of Pharmaceuticals. CRIPS. 2004;5(1):9-12.
Clark et al., Mass spectrometry of pyrrolo [2, 3-b] pyrazines and pyrazino [2, 3-b]indole. Organic Mass Spectrometry. 1977;12(7):421-3.
Curtin, Inhibiting the DNA damage response as a therapeutic manoeuvre in cancer. Br J Pharmacol. Aug. 2013;169(8):1745-65. doi: 10.1111/bph.12244.
El-Emary, Synthesis and Biological Activity of Some New Pyrazolo[3,4-b]pyrazines. J Chinese Chem Soc (Taipei, Taiwan). 2006;53(2):391-401.
Elnagdi et al., Synthesis of Substituted Azaindenes: Synthesis of New Pyrazolo[1,5-a]pyrimidine Derivatives . Bull Chem Soc Jpn. 1990;63(6):1854-56.
Fernandes et al., Synthesis and Biological Activity of Heterocyclic Derivatives derived from Ethyl-2-hydroxy-quinoxaline-3-carboxylate. J Indian Chem Soc. 1986;63(4):427-9.
Finlay et al., Modulation of DNA repair by pharmacological inhibitors of the PIKK protein kinase family. Bioorg Med Chem Lett. Sep. 1, 2012;22(17):5352-9. doi: 10.1016/j.bmcl.2012.06.053. Epub Jul. 1, 2012.
Fokas et al., Targeting ATR in DNA damage response and cancer therapeutics. Cancer Treat Rev (2013), http://dx.doi.org/10.1016/j.ctrv.2013.03.002.
Fokas et al., Targeting ATR in vivo using the novel inhibitor VE-822 results in selective sensitization of pancreatic tumors to radiation. Cell Death Dis. Dec. 6, 2012;3:e441. doi: 10.1038/cddis.2012.181.
Gentili et al., Alpha2-adrenoreceptors profile modulation. 4. From antagonist to agonist behavior. J Med Chem. Jul. 24, 2008;51(14):4289-99. doi: 10.1021/jm800250z. Epub Jun. 25, 2008.
Hall-Jackson et al., ATR is a caffeine-sensitive, DNA-activated protein kinase with a substrate specificity distinct from DNA-PK. Oncogene. Nov. 18, 1999;18(48):6707-13.
Hickson et al., Identification and characterization of a novel and specific inhibitor of the ataxia-telangiectasia mutated kinase ATM. Cancer Res. Dec. 15, 2004;64(24):9152-9.
Hilton et al., Identification and characterisation of 2-aminopyridine inhibitors of checkpoint kinase 2. Bioorg Med Chem. Jan. 15, 2010;18(2):707-18. doi: 10.1016/j.bmc.2009.11.058. Epub Dec. 6, 2009.
Ho, Studies on the Synthesis of New 3-(3,5-Diamino-1-substituted-pyrazol-4-yl)azo-thieno[2,3-b]pyridines and 3-(2-Amino-5,7-disubstituted-pyrazolo[1,5-a]pyrimidine-3-yl)azo-thieno[2,3-b]pyridines. Journal of the Chinese Chemical Society. 1999; 46:955-62.
Hubackova et al., Regulation of the PML tumor suppressor in drug-induced senescence of human normal and cancer cells by JAK/STAT-mediated signaling. Cell Cycle. Aug. 1, 2010;9(15):3085-99. doi: 10.4161/cc.9.15.12521. Epub Aug. 26, 2010.
Huntoon et al., ATR inhibition broadly sensitizes ovarian cancer cells to chemotherapy independent of BRCA status. Cancer Res. Jun. 15, 2013;73(12):3683-91. doi: 10.1158/0008-5472.CAN-13-0110. Epub Apr. 2, 2013.
Hussein, Novel Synthesis of Some New Pyrimido[1,6-a]pyrimidine and Pyrazolo[1,5-a]pyrimidine Derivatives. J Heterocyclic Chem. 2012;49(2):446-51.

(56) References Cited

OTHER PUBLICATIONS

Jiang et al., Synthesis and cytotoxicity evaluation of novel indolylpyrimidines and indolylpyrazines as potential antitumor agents. Bioorg Med Chem. May 2001;9(5):1149-54.
Katritzky et al., Efficient synthesis of 3,5-functionalized isoxazoles and isoxazolines via 1,3-dipolar cycloaddition reactions of 1-propargyl- and 1-allylbenzotriazoles. J Heterocyclic Chem. 2000;37(6):1505-10.
Kim et al., Substrate specificities and identification of putative substrates of ATM kinase family members. J Biol Chem. Dec. 31, 1999;274(53):37538-43.
Klicnar et al., Studien in der chinoxalinreihe III. Synthese, reaktionen und ir-spektren einiger 3-hydroxy-2-carboxymethylchinoxalin-derivate. Collection of Czechoslovak Chemical Communications. 1965;30(9):3092-101.
Kumpaty et al., Synthesis of N-methyl secondary amines. Synth Commun. 2003;33(8):1411-6.
Kurasawa et al., Revised Structure for the Product from the Reaction of 3-Hydrazinocarbonylmethylene-2-oxo-1,2,3,4-tetrahydroquinoxaline with Nitrous Acid. Chem. Pharm. Bull. 1984;32(10):4140-3.
Luo et al., Molecular dynamics-based self-organizing molecular field analysis on 3-amino-6-arylpyrazines as the ataxia telangiectasia mutated and Rad3 related (ATR) protein kinase inhibitors. Med Chem Res. Published online: Jun. 19, 2013. 12 pages.
McKenna et al., Evaluation of a potent and highly selective inhibitor of ATR kinase: an approach to selectively sensitize cancer cells to genotoxic drugs. Abstract. Mar. 31, 2012. 1page.
McKenna et al., Evaluation of the first potent and highly selective inhibitor of ATR inhibitor, VE-821: an approach to selectively sensitize cancer cells to ionizing radiation and hypoxia. Poster. Mar. 31, 2012. 1 page.
Middleton et al., ATR as a Therapeutic Target. In: Advances in DNA Repair in Cancer Therapy. Cancer Drug Discovery and Development. 2013;72:211-28.
Nakamura et al., Bimodal Chemiluminescence of 8-Chlorostyryl-6-phenylethynylimidazopyrazinone: Large Bathochromic Shift Caused by a Styryl Group at 8-Position. Tetrahedron Letters. 1998;39:301-4.
Otero et al., Synthesis of Acyclo-C-nucleoside Analogs from 2,3:4,5-Di-O-isopropylidene-D-xylose. J Carbohydrate Chem. 2005;24:809-29.
Otero et al., Synthesis of Iso-C-nucleoside Analogues from I-(Methyl 2-0-benzyl-4,6-O-benzylidene-3-deoxy-et-D-altropyranosid-3-yl)but-3-yn-2-ones. Z. Naturforsch. 2005; 60b:1175-85.
Pires et al., Targeting radiation-resistant hypoxic tumour cells through ATR inhibition. Br J Cancer. Jul. 10, 2012;107(2):291-9. doi: 10.1038/bjc.2012.265. Epub Jun. 19, 2012.
Pollard, Inhibition of the DNA Damage Response Kinase, ATR, as a Promising Anti-Cancer Approach. Presentation, Mar. 8, 2012. 28 pages.
Qi et al., Chemi- and Bio-Iuminescence of Coelenterazine Analogues with Phenyl Homologues at the C-2 Position. J Chem Soc. Perkin Trans 1. 1992:1607-11.
Ram et al., Synthesis of bioisosteric pyrazolo[1,5-a]pyrimidines as leishmanicides. Indian J Chemistry. 1995;34b:514-20.
Reaper et al., Evaluation of a potent and highly selective inhibitor of ATR kinase: an approach to selectively sensitize cancer cells to genotoxic drugs. 102nd AACR Annual Meeting. Orlando, Apr. 2011. Abstract.
Reaper et al., Evaluation of a Potent and Highly Selective Inhibitor of ATR Kinase: An Approach to Selectively Sensitize Cancer Cells to Genotoxic Drugs. 102nd AACR Annual Meeting. Orlando, Apr. 2011. Poster.
Reaper et al., Selective Killing of ATM- or p53-deficient cancer cells through inhibition of ATR. Presentation. Nov. 2011. 31 pages.
Reaper et al., Selective Killing of ATM- or p53-deficient cancer cells through inhibition of ATR. Presentation. Nov. 2011. 25 pages.
Reaper et al., Selective Killing of ATM- or p53-deficient cancer cells through inhibition of ATR. Nat Chem Biol. Apr. 13, 2011;7(7):428-30. doi: 10.1038/nchembio.573. Advance online publication.
Reaper et al., Selective killing of ATM- or p53-deficient cancer cells through inhibition of ATR. Supplementary Information. Nature Chemical Biology. Apr. 13, 2011. doi:10.1038/nchembio.573. 26 pages.
Ried et al., Synthese neuer Heterocyclen ausgehend von Aminopyrazolen. Chemiker•Zeilung. 1989;181-3.
Saito et al., Synthesis and in vitro evaluation of botryllazine B analogues as a new class of inhibitor against human aldose reductase. Tetrahedron. 2009;65(15):3019-26.
Sarkaria et al., Inhibition of ATM and ATR kinase activities by the radiosensitizing agent, caffeine. Cancer Res. Sep. 1, 1999;59(17):4375-82.
Sevilla et al., Microwave-assisted synthesis of 1,3-dihydro-[1,2,5]thiadiazolo[3,4-b]pyrazine-2,2-dioxides. Tetrahedron Letters. 2006;47(48):8603-6.
Smith et al., Addition to Carbon-Hetero Multiple Bonds. Chapter 16. In: March's Advanced Organic Chemistry: Reactions, Mechanisms, and Structure, Sixth Edition. John Wiley & Sons, Inc. 2007. 26 pages.
Sugimoto et al., Imidazopteridines. I. Synthesis of Imidazo[1,2-c]pteridine and Its Alkyl Derivatives. Bull Chem Soc Japan. 1977;50(10):2744-7.
Vippagunta et al., Crystalline solids. Adv Drug Deliv Rev. May 16, 2001;48(1):3-26.
Ward et al., Histone H2AX is phosphorylated in an ATR-dependent manner in response to replicational stress. J Biol Chem. Dec. 21, 2001;276(51):47759-62. Epub Oct. 22, 2001.
Wolff, Burger's Medicinal Chemistry and Drug Discovery. Fifth Edition. vol. I: Principles and Practice. 1995;975-7.
Wuts et al., Protection for the Amino Group. Chapter 7. In: Greene's Protective Groups in Organic Synthesis, 4th Edition. John Wiley & Sons, Inc. 2007. 235 pages.
Wuts et al., Protection for the Carbonyl Group. Chapter 4. In: Greene's Protective Groups in Organic Synthesis, 4th Edition. John Wiley & Sons, Inc. 2007. 106 pages.
Hanawalt, J.D. et al., "Chemical Analysis by X-Ray Diffraction: Classification and Use of X-Ray Diffraction Patterns," Powder Diffractions, Jun. 1986, vol. 1, No. 2, pp. 2-14.
Faber, J. et al., "A Plug-In Program to Perform Hanawalt or Fink Search-Indexing Using Organics Entries in the ICDD PDF-4/Organics 2003 Database," International Center for Diffraction Data, Advances in X-Ray Analysis, 2004, vol. 47, pp. 166-173.
Thangadurai, S. et al., "X-Ray Powder Diffraction Patterns for Certain β-Lactam, Tetracycline and Macrolide Antibiotic Drugs," Analytical Sciences, Jul. 2005, vol. 21, pp. 833-838.
U.S. Appl. No. 15/608,630 of Charrier et al., filed May 30, 2017.
U.S. Appl. No. 15/633,477 of Ahmad et al., filed Jun. 26, 2017.
U.S. Appl. No. 15/693,521 of Falcon et al., filed Sep. 1, 2017.
U.S. Appl. No. 15/849,241 of Charrier et al., filed Dec. 20, 2017.
U.S. Appl. No. 15/763,366 of Pollard et al., filed Mar. 26, 2018.

* cited by examiner

FIGURE 1a: XRPD Compound I-1 (ethanol solvate)
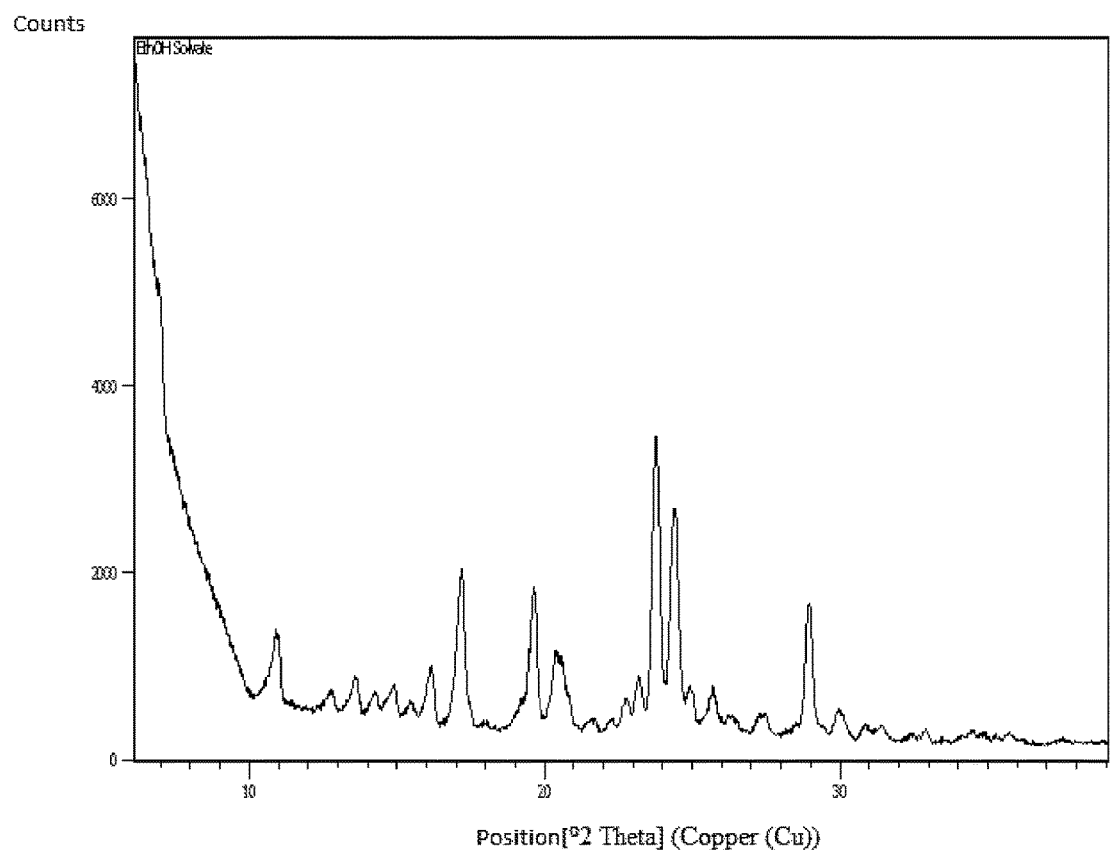

FIGURE 5a: Solid State ¹⁹F NMR Spectrum of Compound I-1 (ethanol solvate)
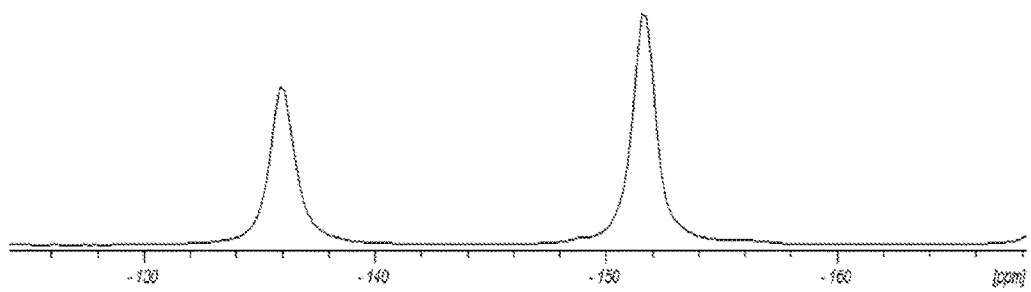
FIGURE 1b: XRPD Compound I-1 (hydrate I)
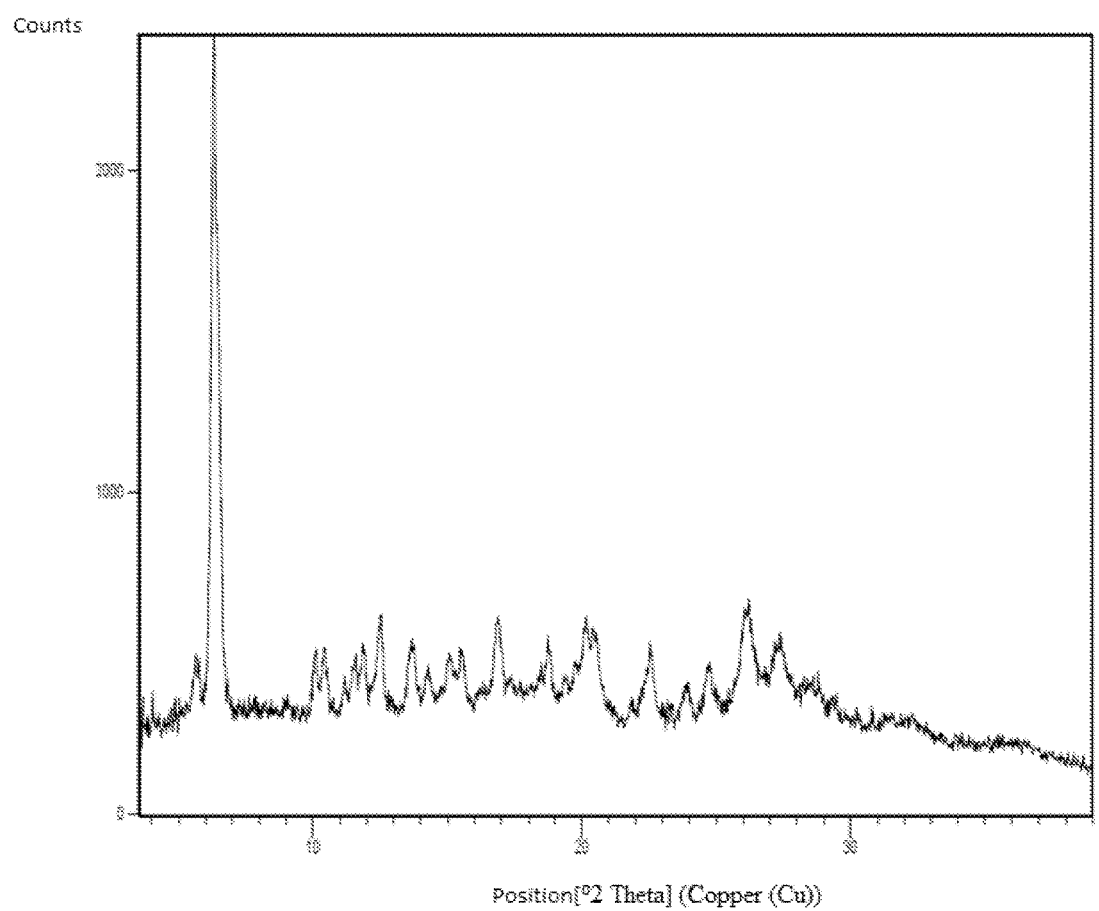

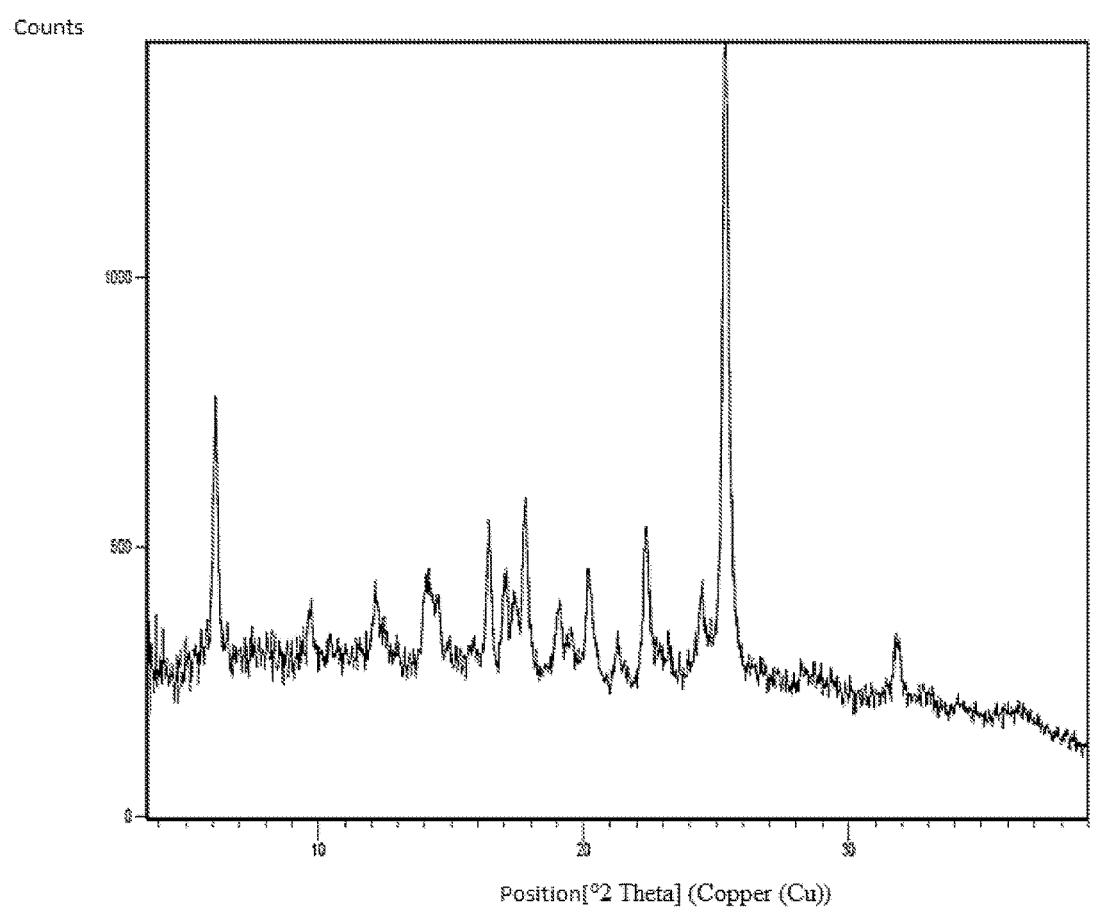
FIGURE 1c: XRPD Compound I-1 (anhydrous form A)

FIGURE 7c: Solid State ¹⁹F NMR Spectrum of Compound I-1 (anhydrous form A)
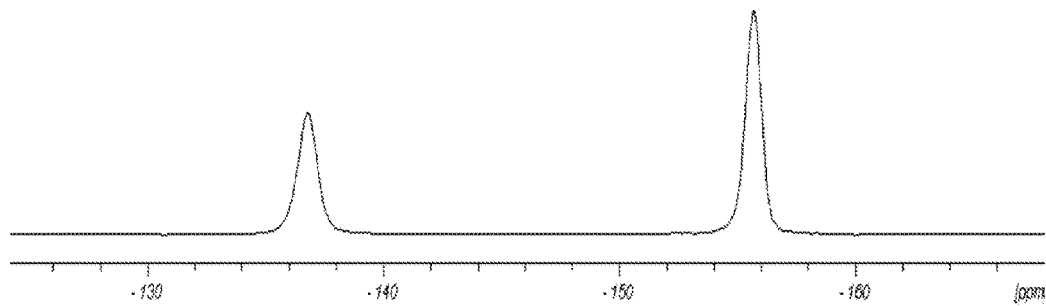
FIGURE 1d: XRPD Compound I-1 (anhydrous form B)
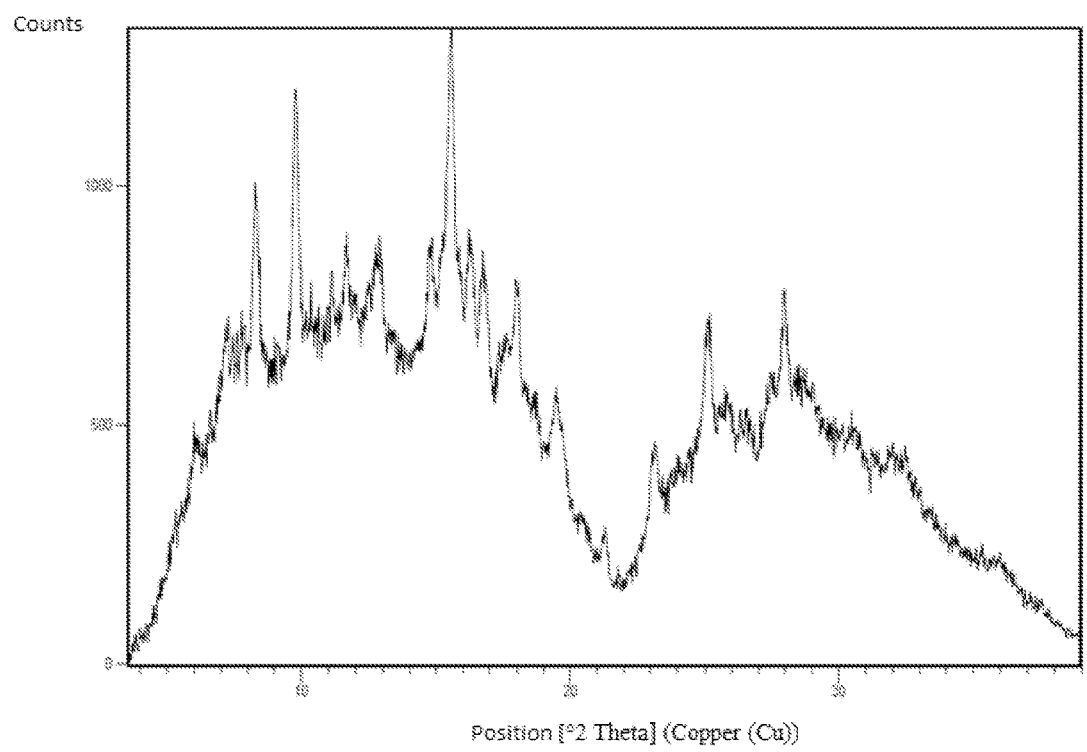

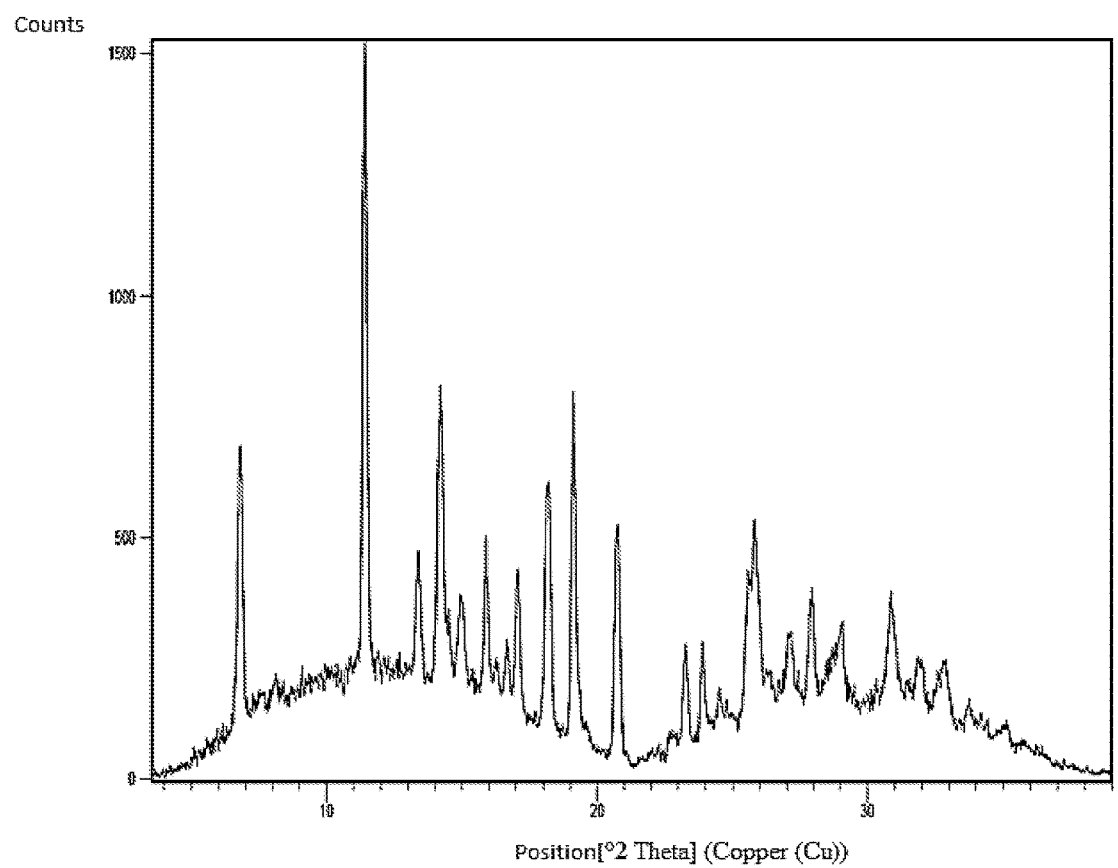
FIGURE 1e: XRPD Compound I-1 (anhydrous form C)

FIGURE 5e: Solid State $^{13}$C NMR Spectrum of Compound I-1 (anhydrous form C)
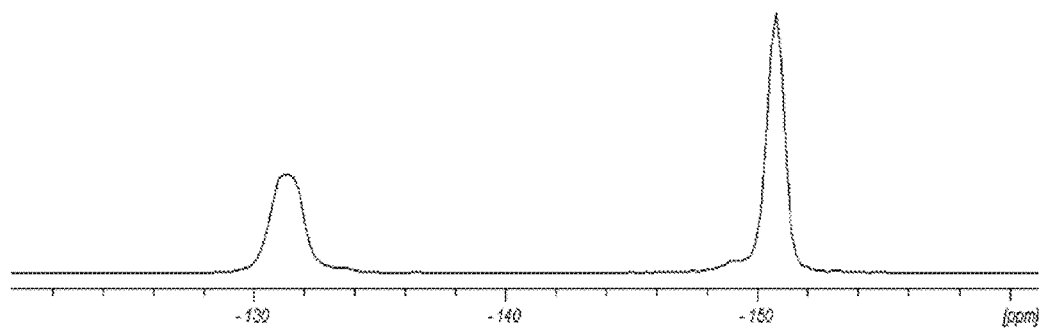
FIGURE 1f: XRPD Compound I-1 (amorphous form)
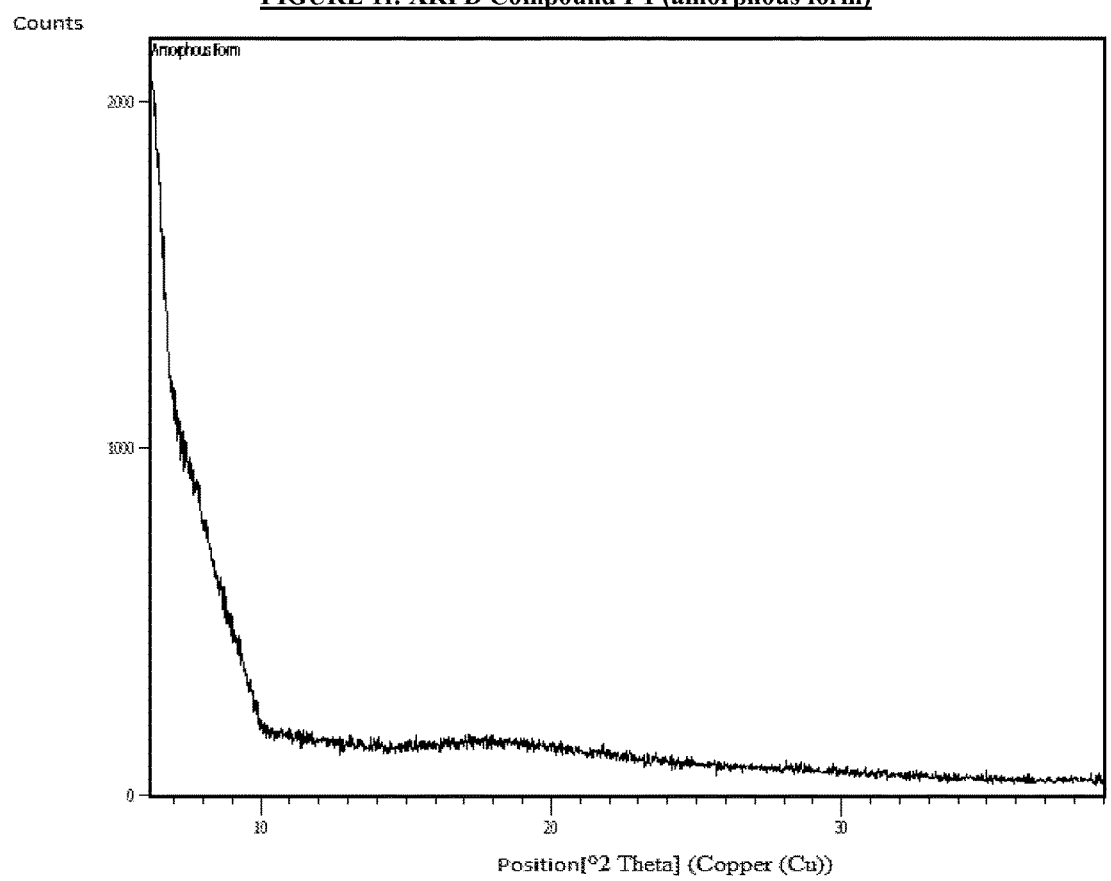

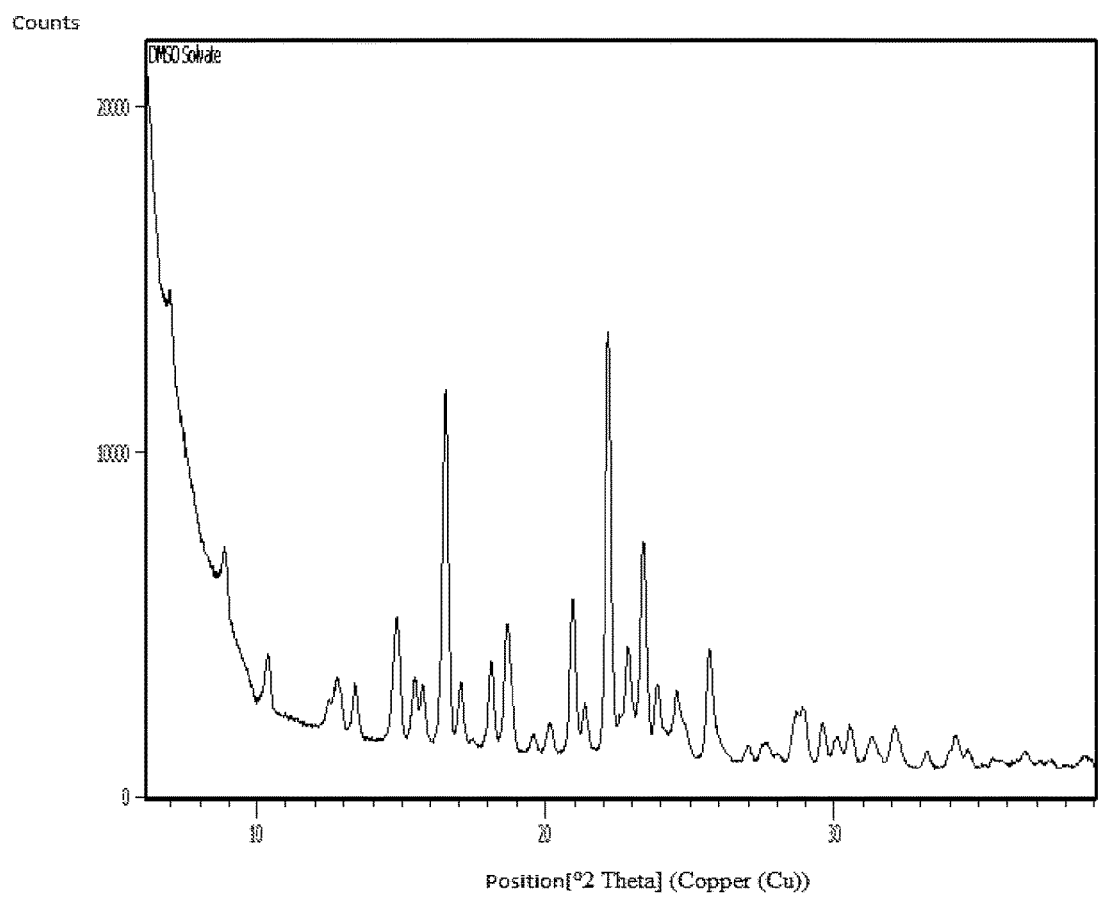
FIGURE 1g: XRPD Compound I-1 (DMSO solvate)

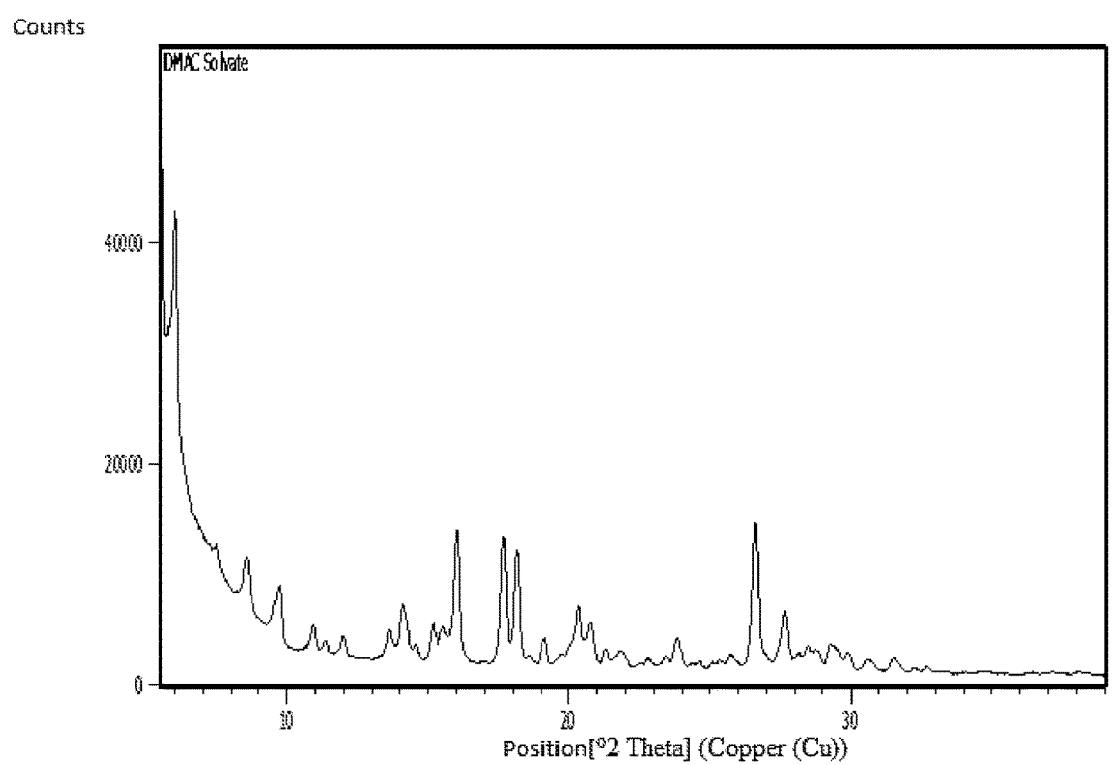
FIGURE 1h: XRPD Compound I-1 (DMAC solvate)

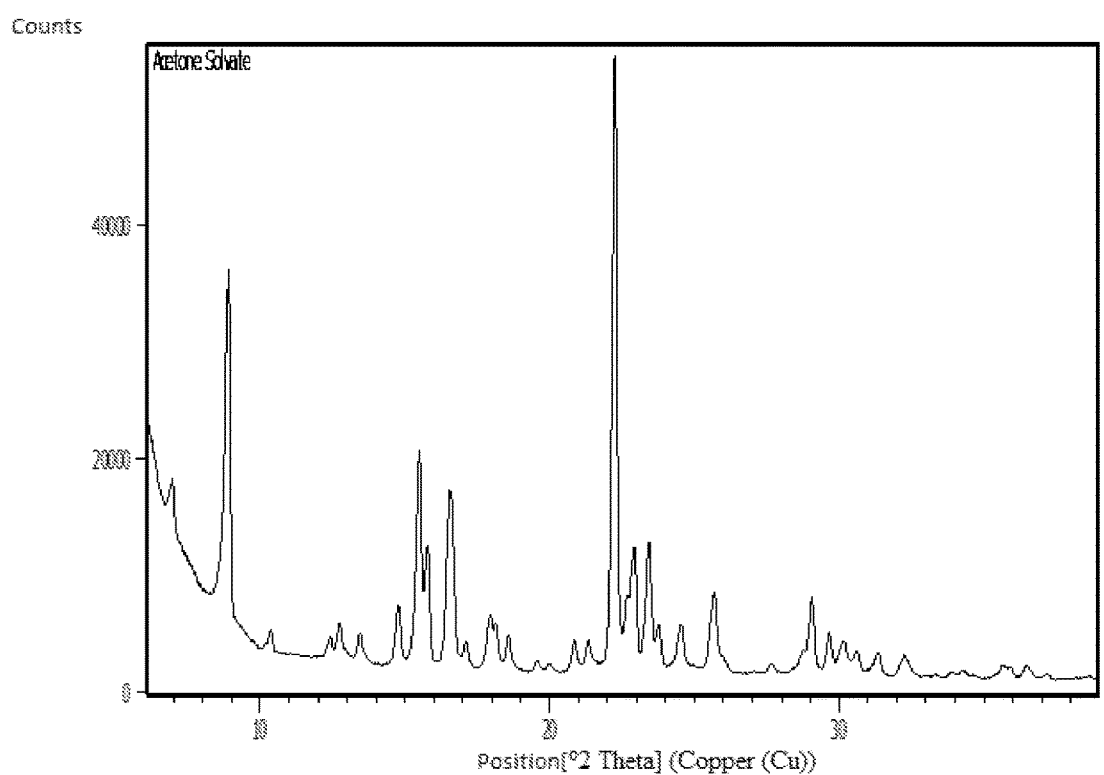
FIGURE 1i: XRPD Compound I-1 (acetone solvate)

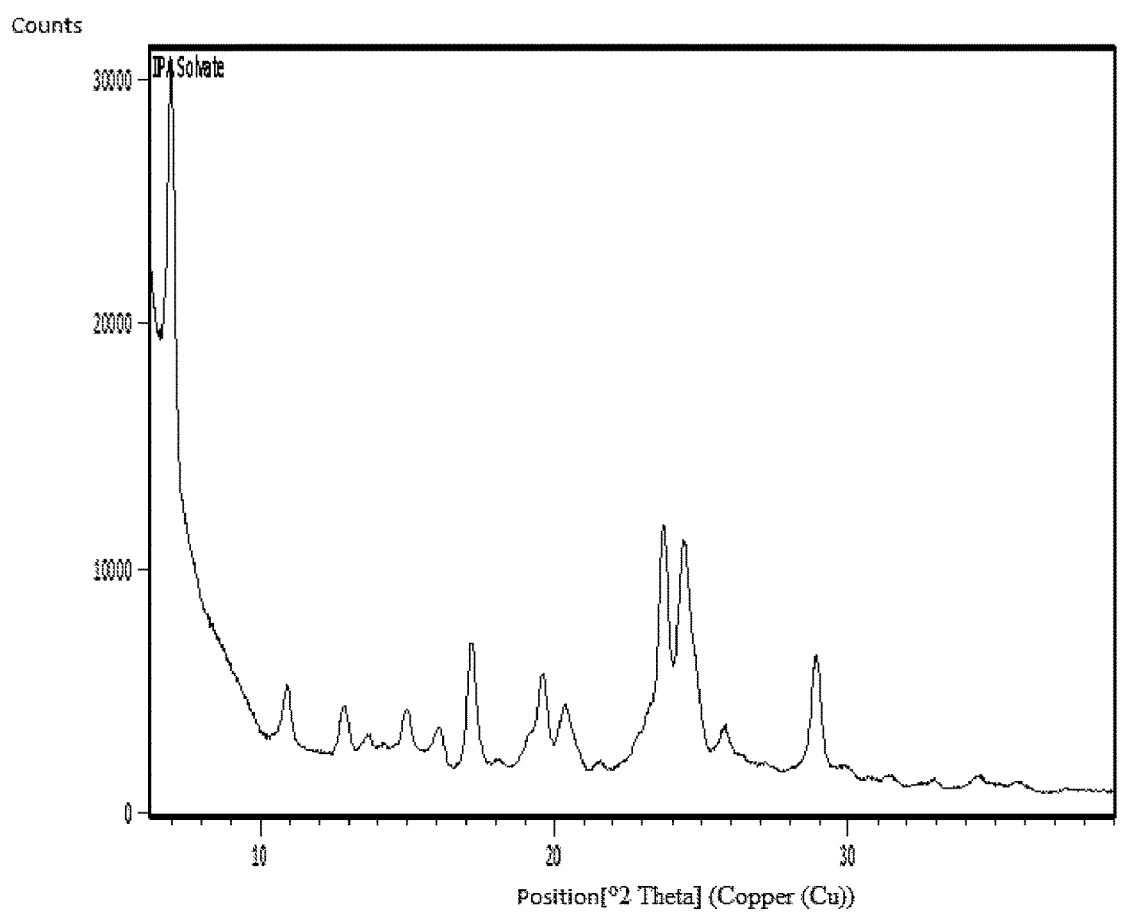
FIGURE 1j: XRPD Compound I-1 (isopropanol solvate)

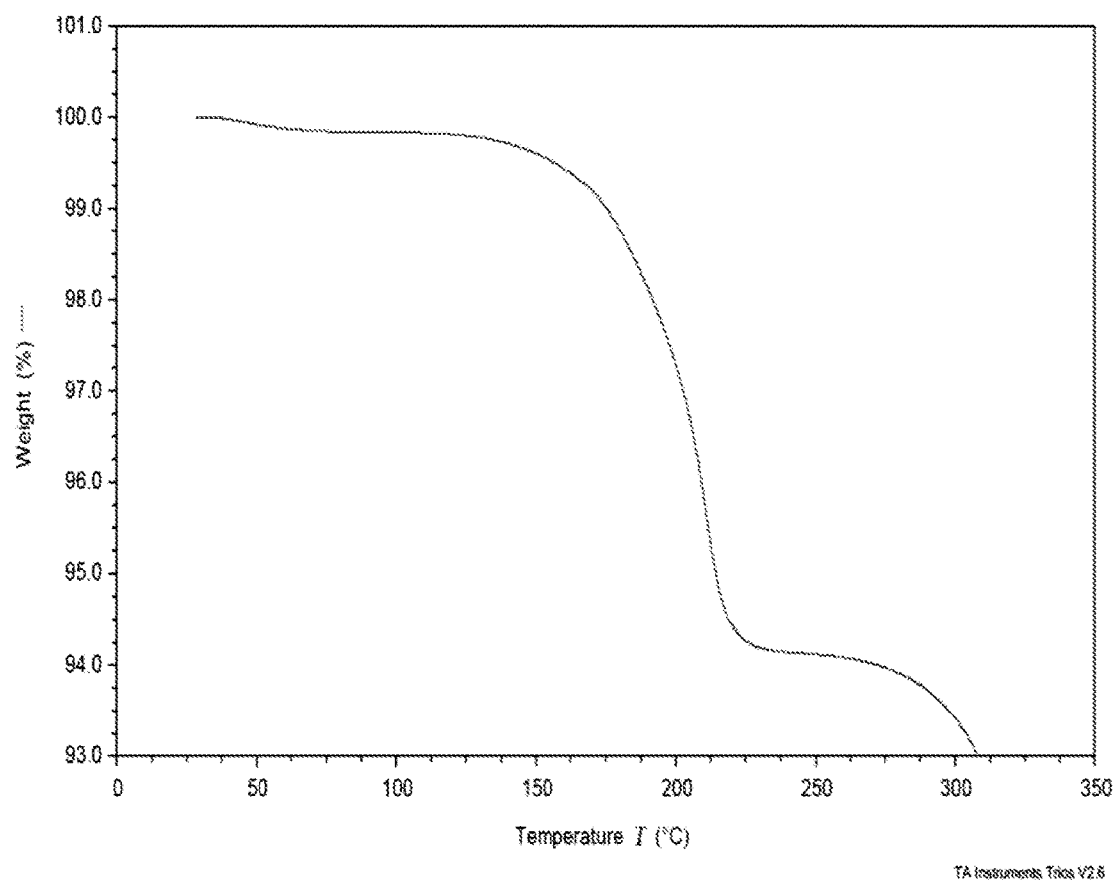
FIGURE 2a: TGA Compound I-1 (ethanol solvate)

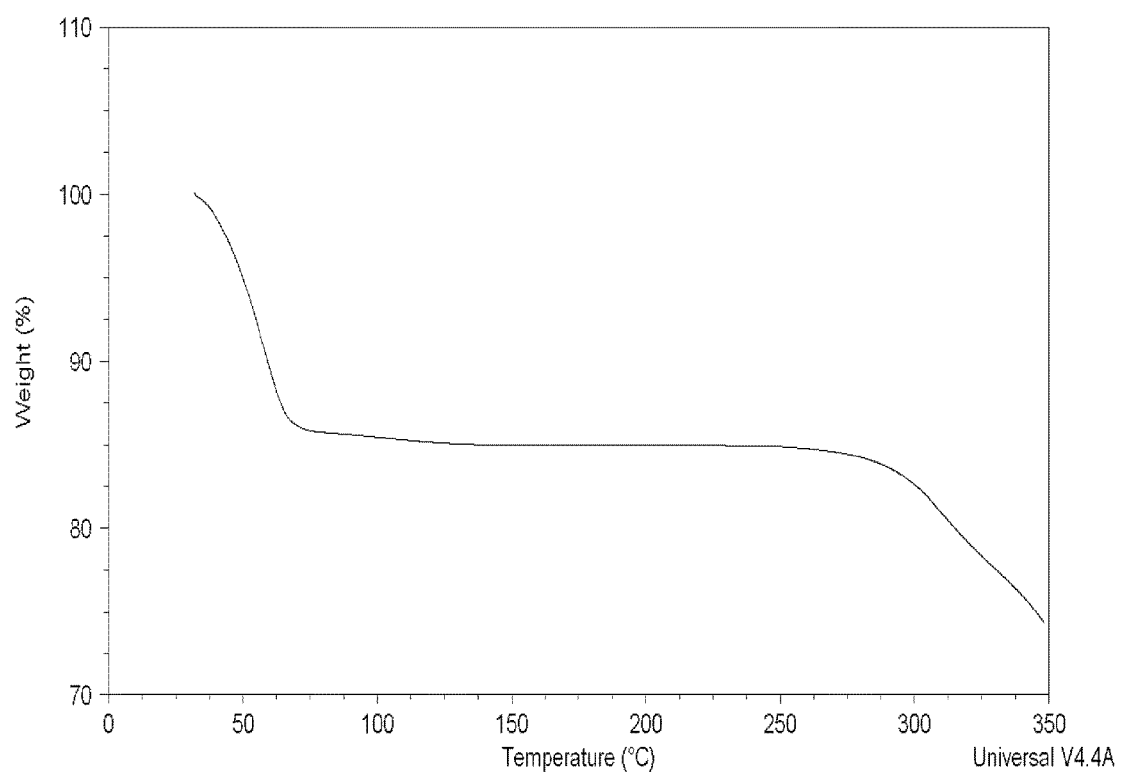
FIGURE 2b: TGA Compound I-1 (hydrate I)

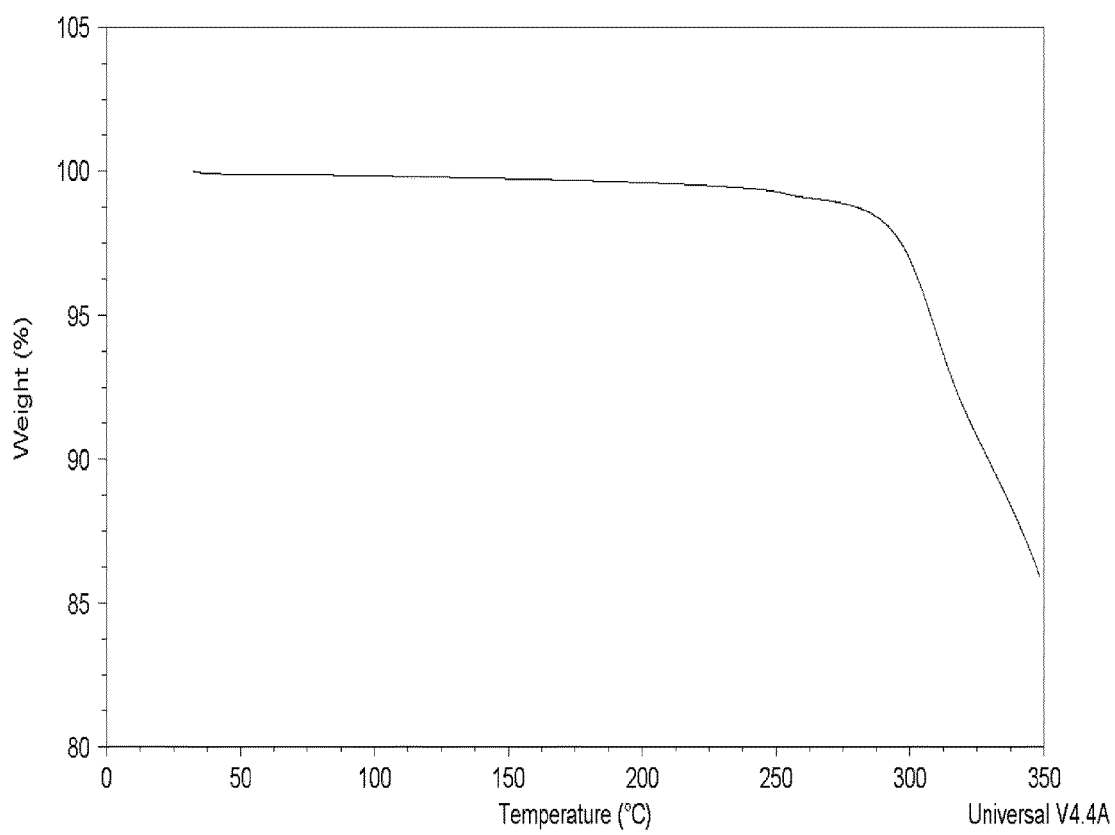
FIGURE 2c: TGA Compound I-1 (anhydrous form A)

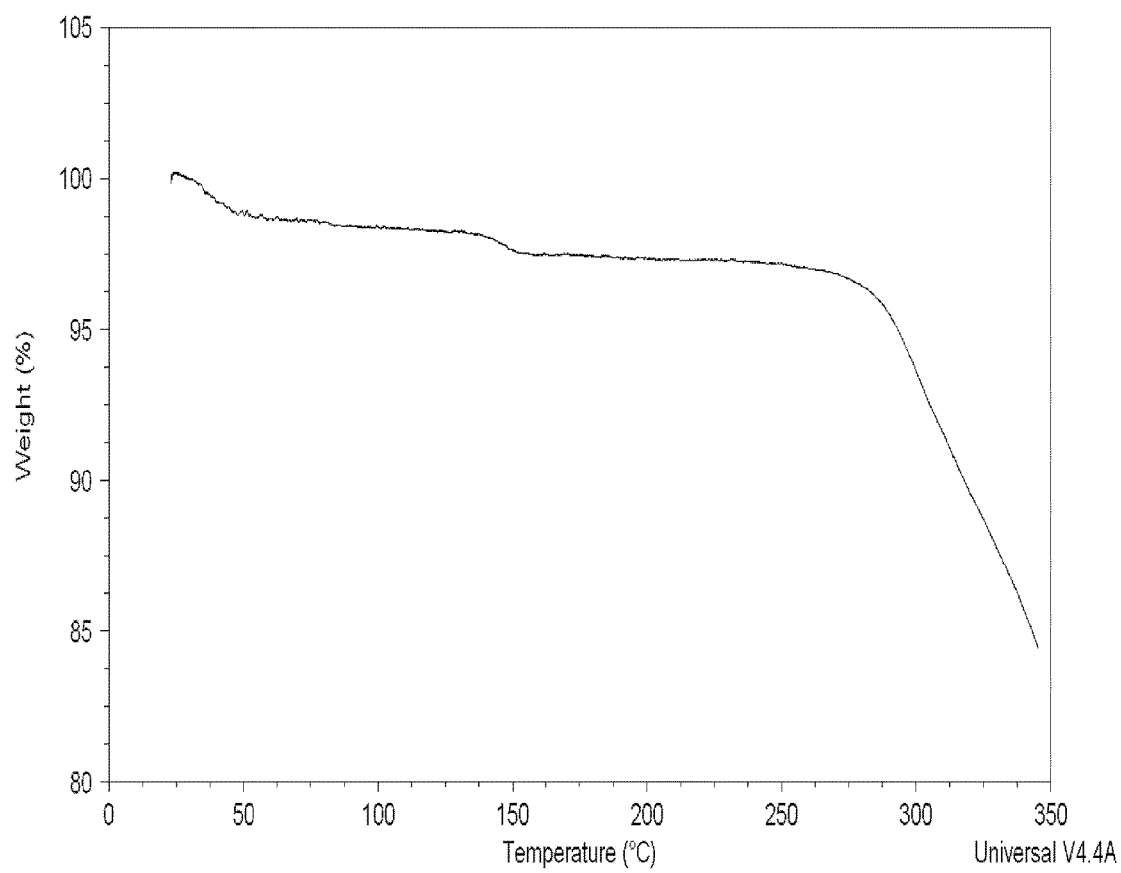
FIGURE 2d: TGA Compound I-1 (anhydrous form B)

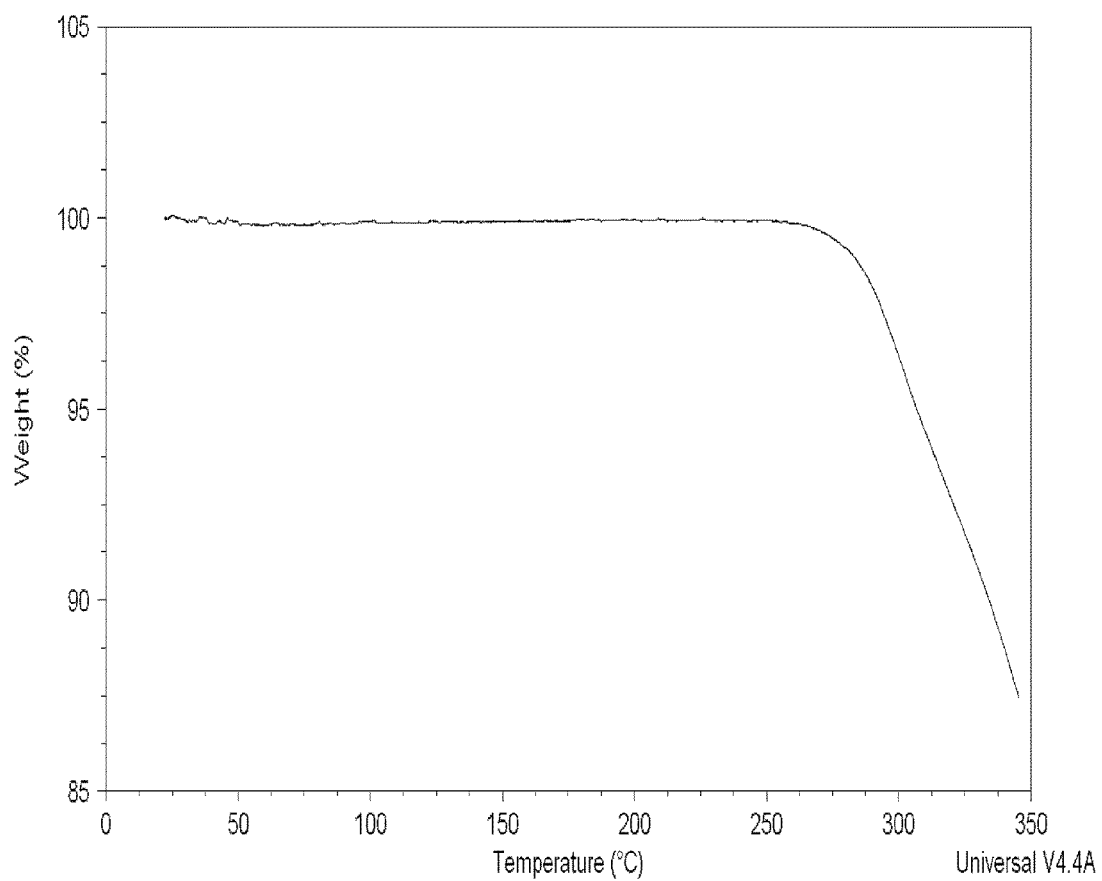
FIGURE 2e: TGA Compound I-1 (anhydrous form C)

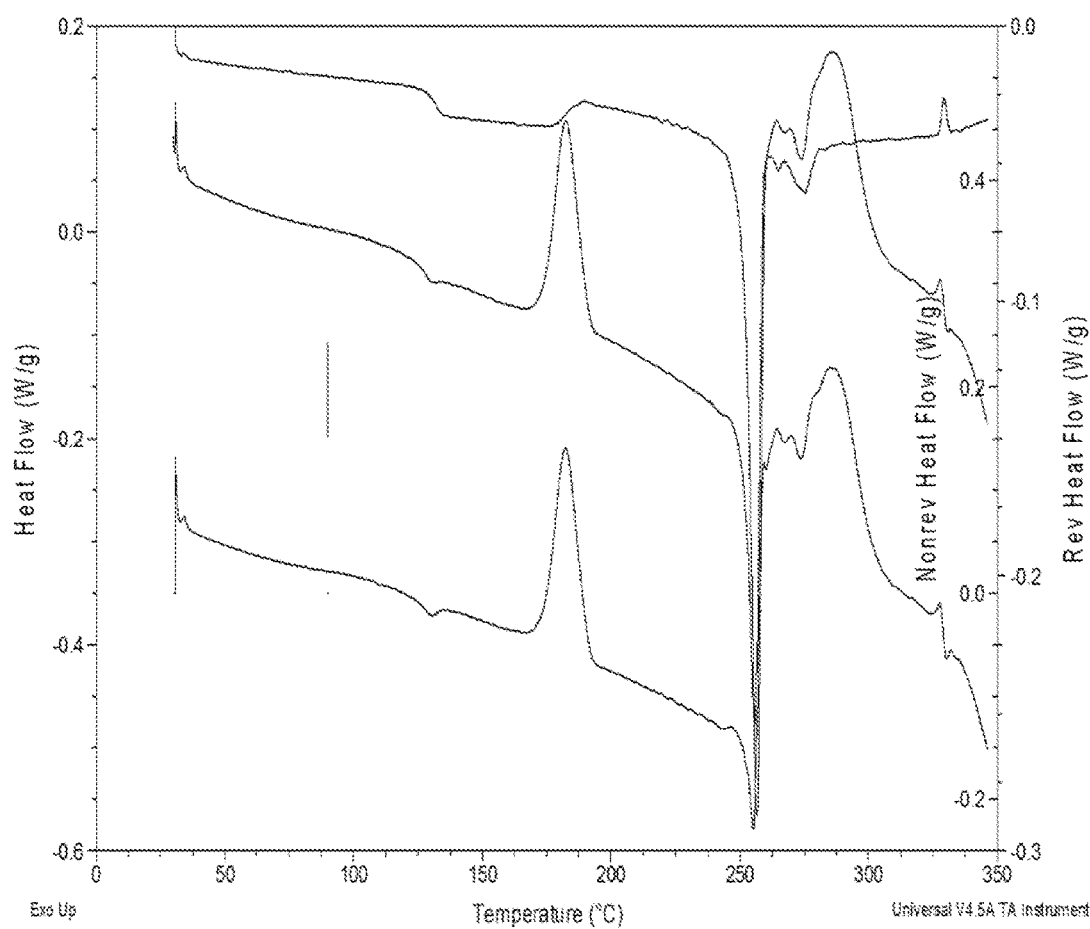
FIGURE 2f: DSC Compound I-1 (amorphous form)

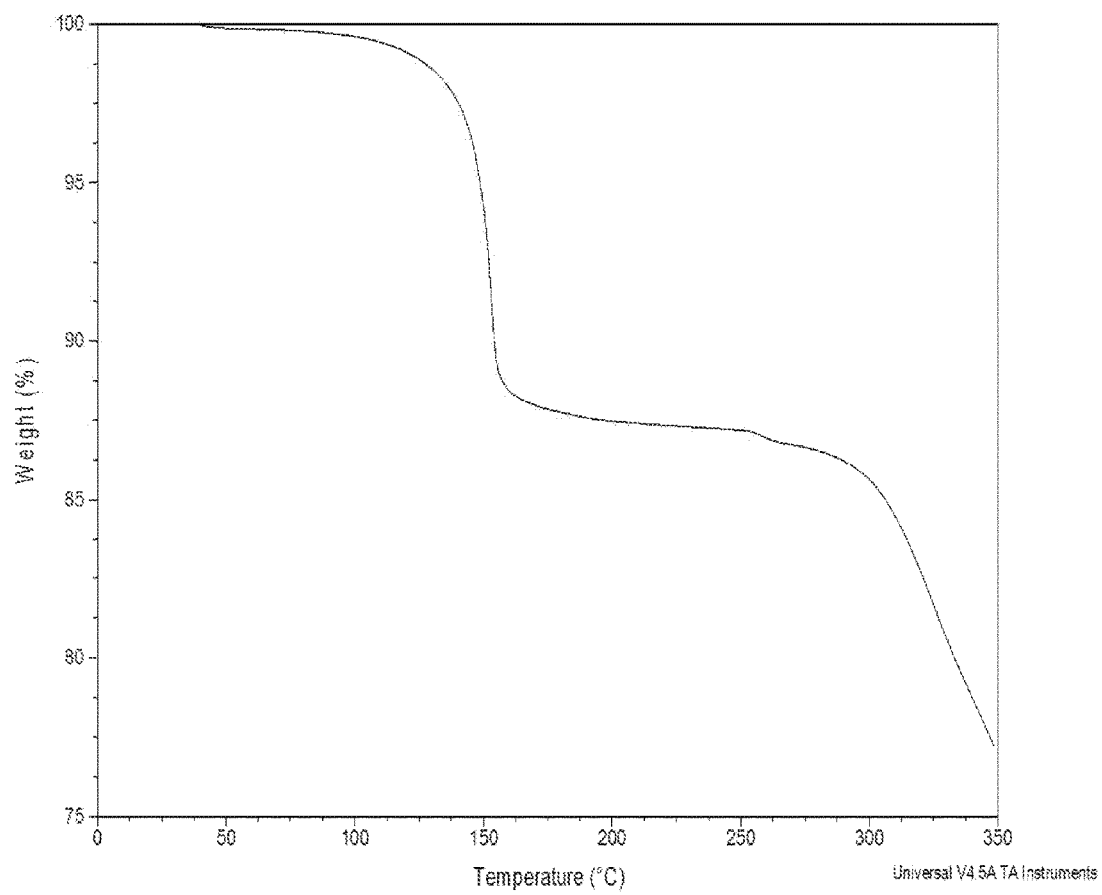
FIGURE 2g: TGA Compound I-1 (DMSO solvate)

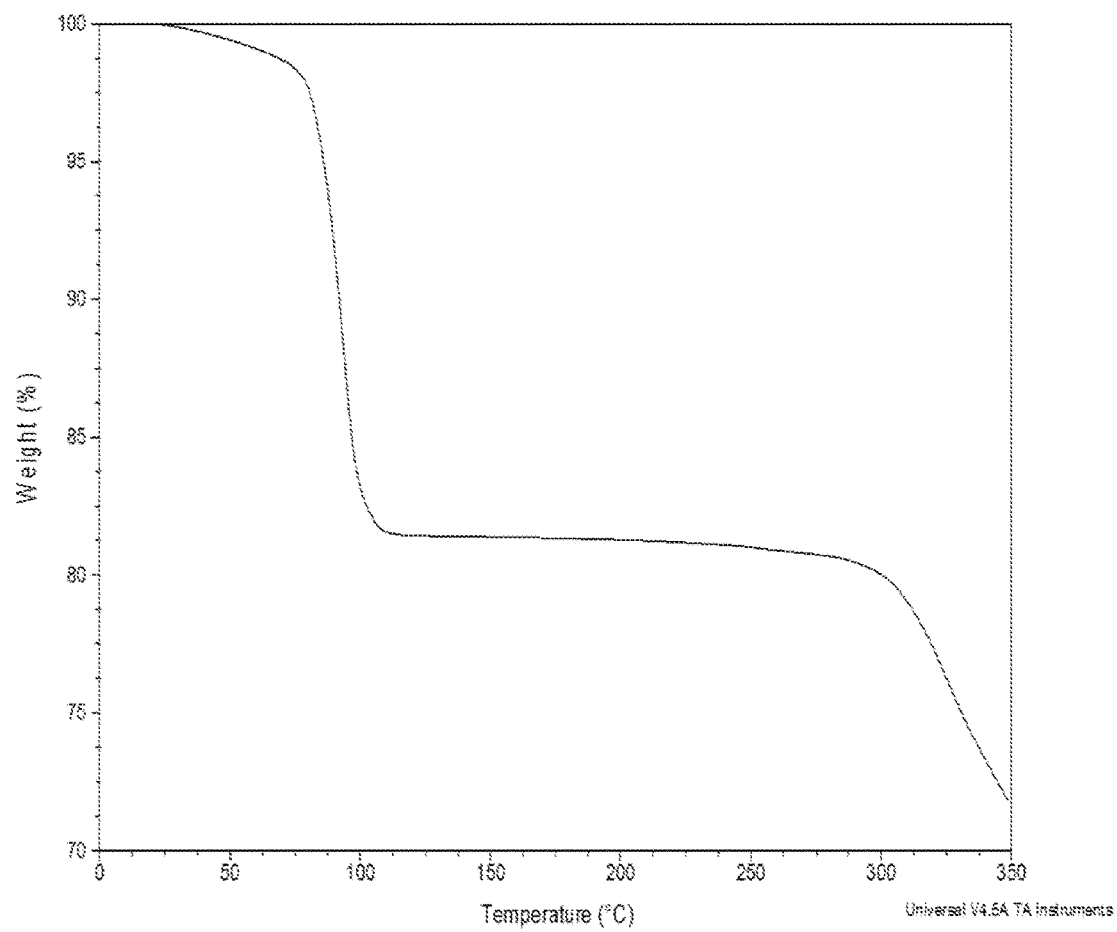
FIGURE 2h: TGA Compound I-1 (DMAC solvate)

FIGURE 2i: TGA Compound I-1 (acetone solvate)
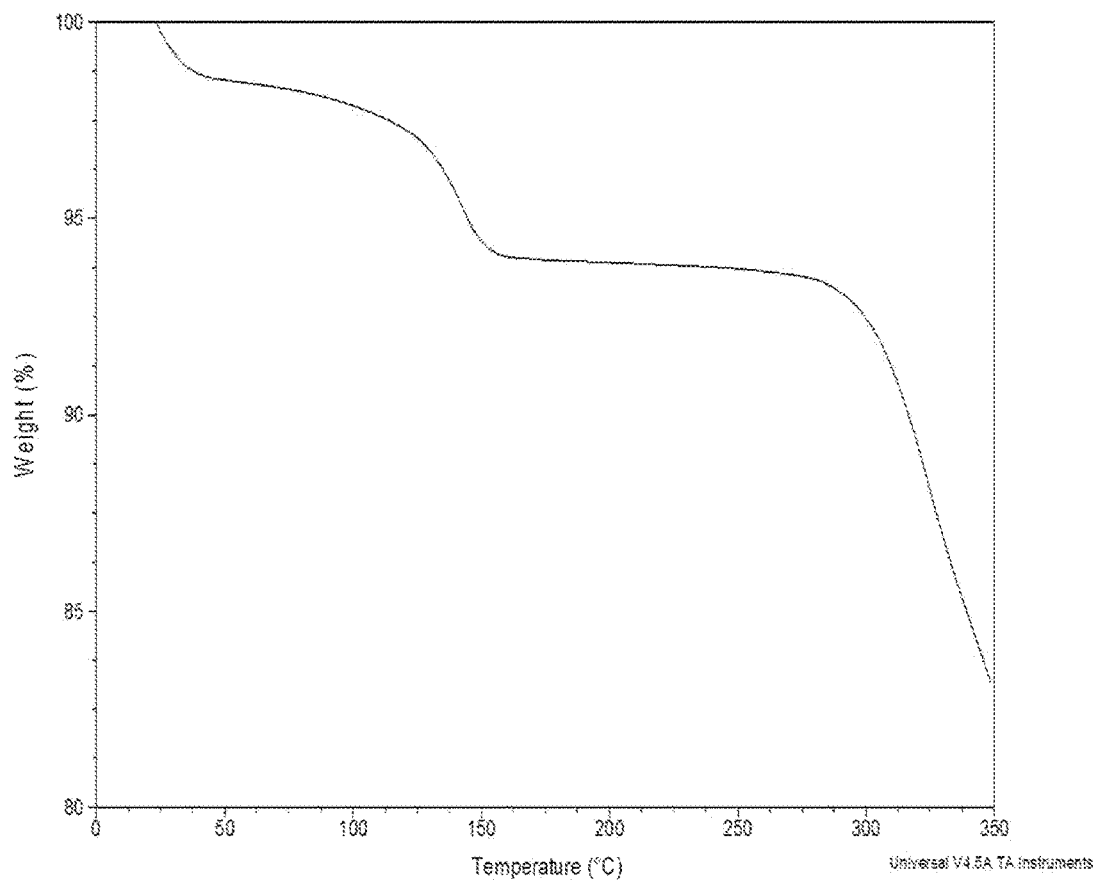

FIGURE 2j: TGA Compound I-1 (isopropanol solvate)
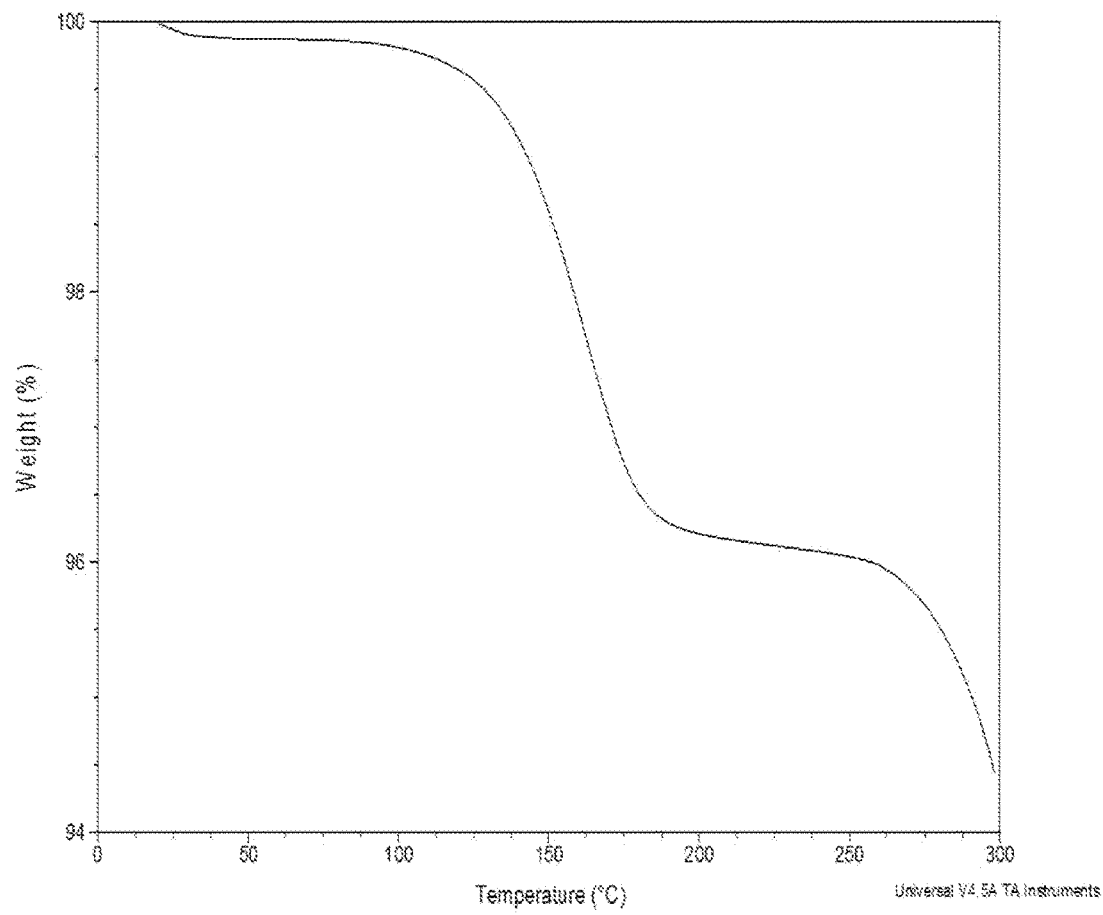

FIGURE 3a: DSC Compound I-1 (ethanol solvate)
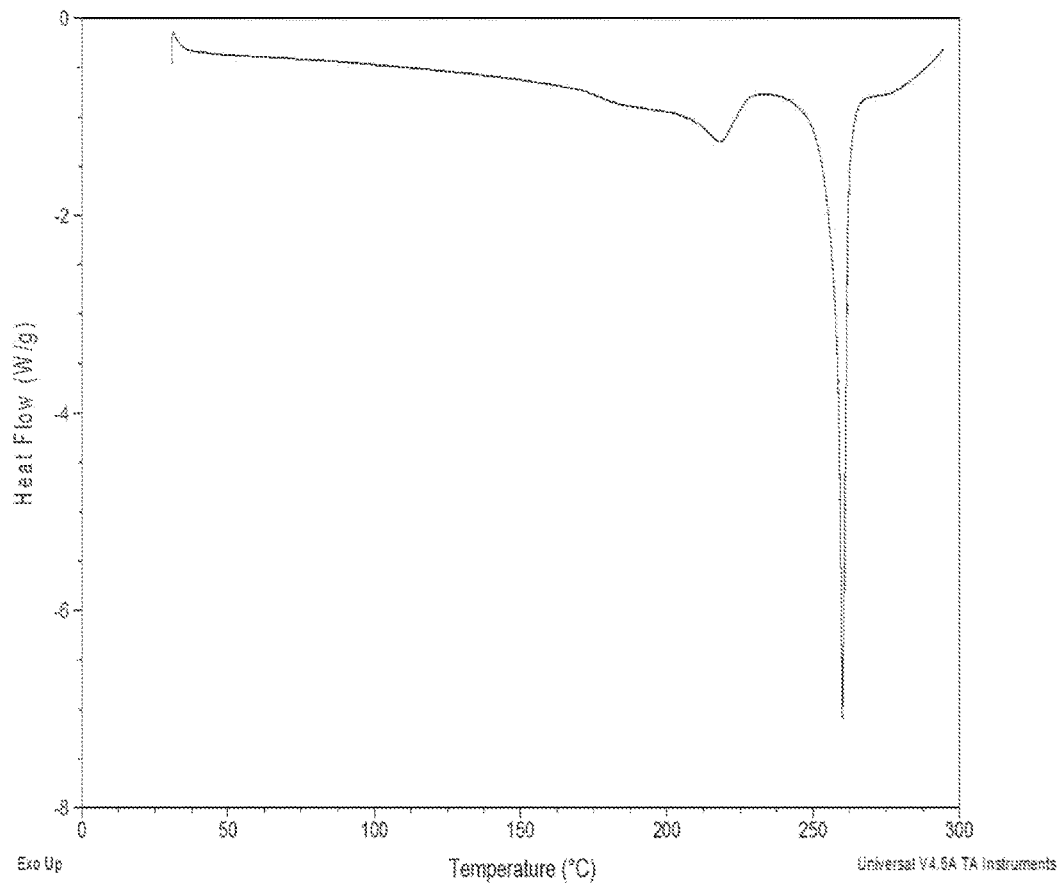
FIGURE 4a: Solid State $^{13}$C NMR Spectrum of Compound I-1 (ethanol solvate)
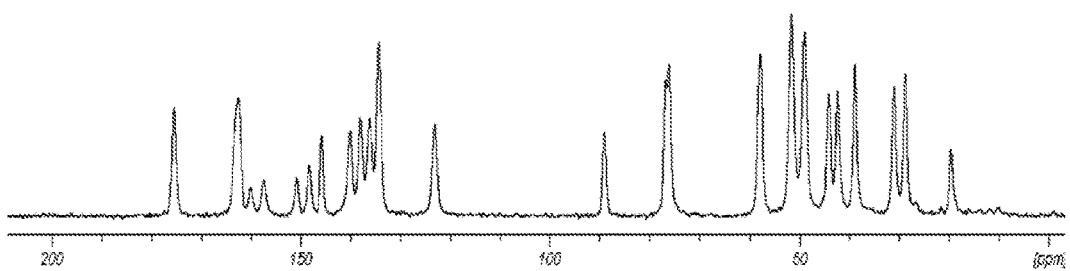

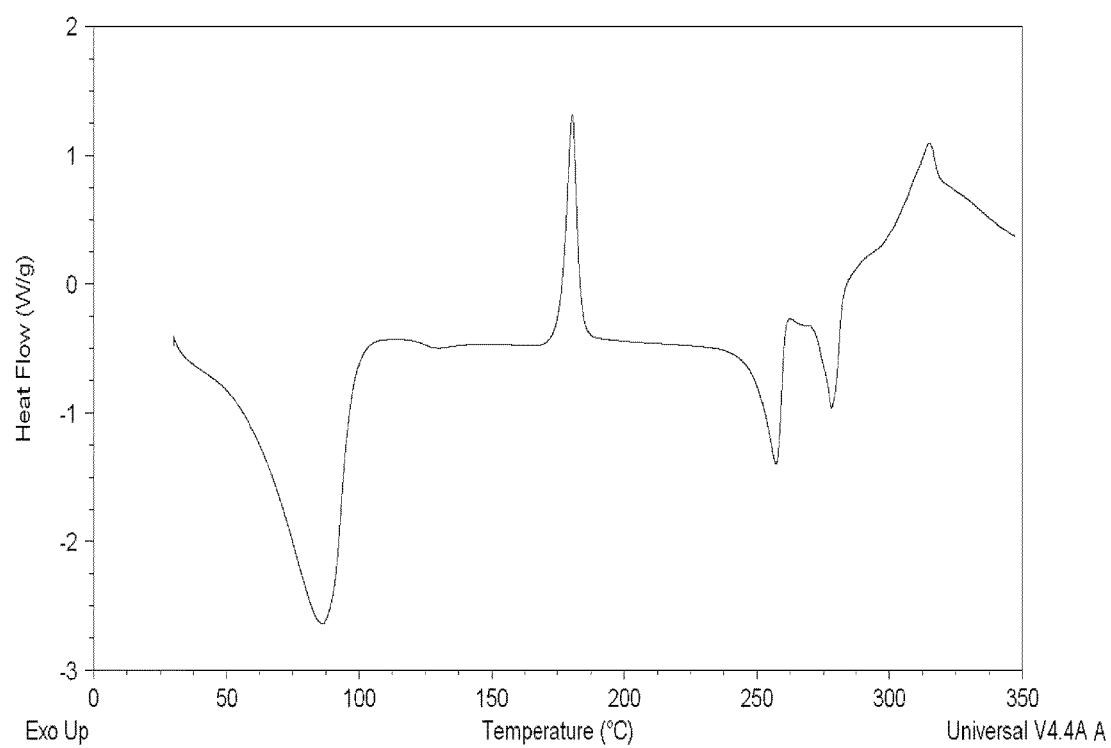
FIGURE 3b: DSC Compound I-1 (hydrate I)

FIGURE 3c: DSC Compound I-1 (anhydrous form A)
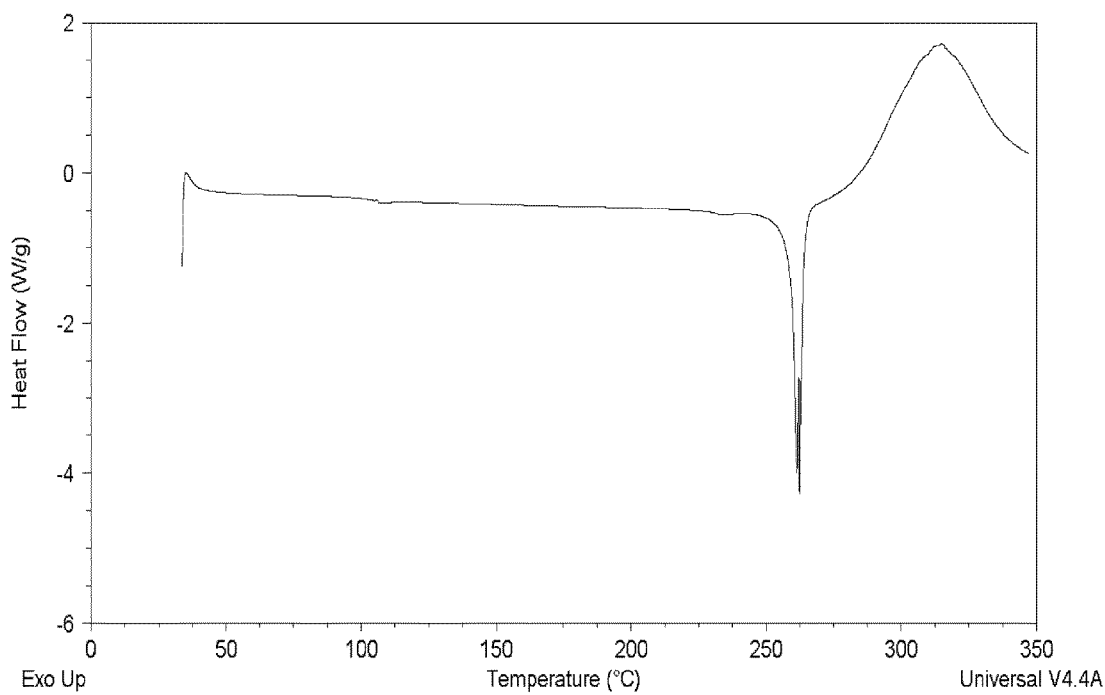
FIGURE 4c: Conformational Plot of Asymmetric Unit of Compound I-1 (anhydrous form A)
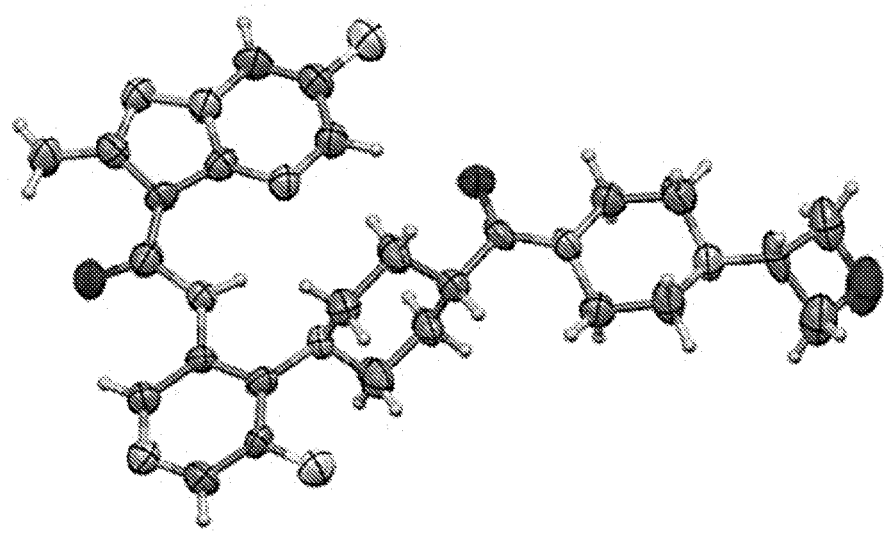

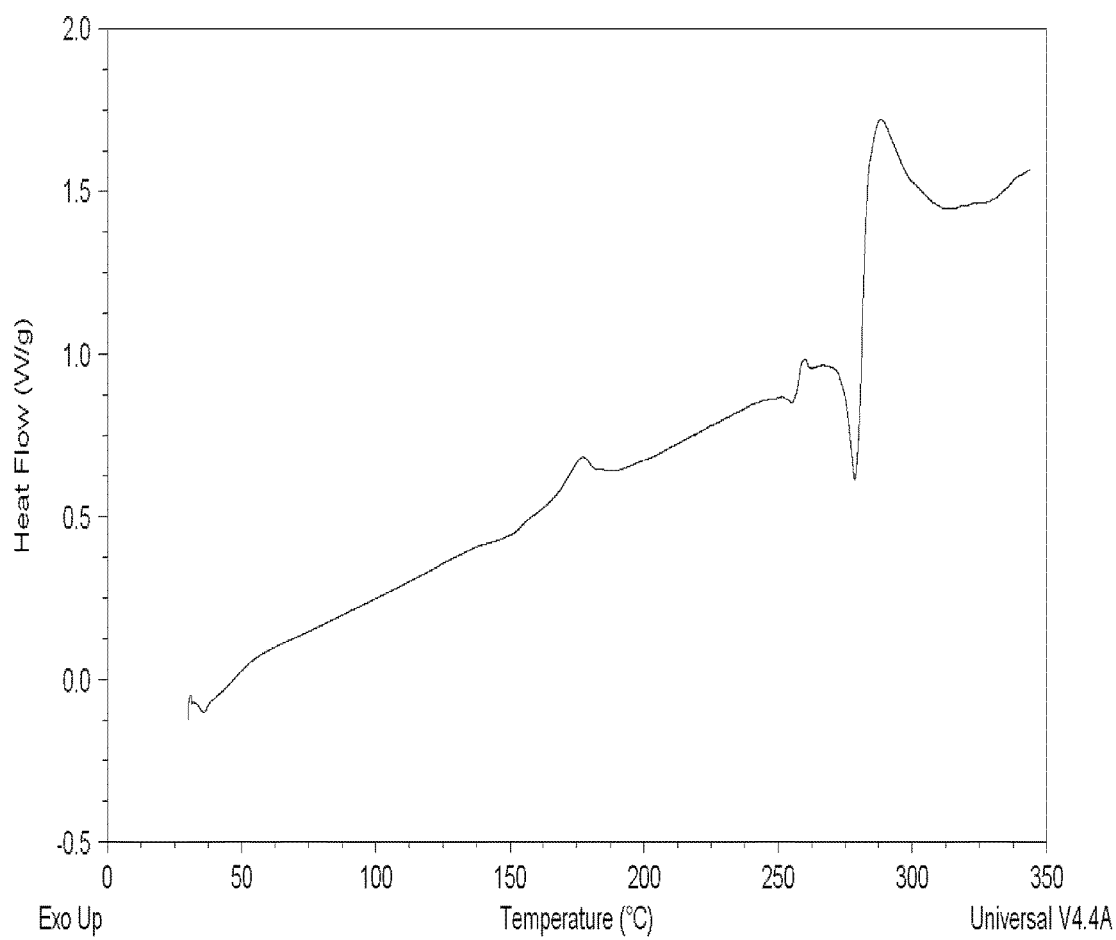
FIGURE 3d: DSC Compound I-1 (anhydrous form B)

FIGURE 3e: DSC Compound I-1 (anhydrous form C)
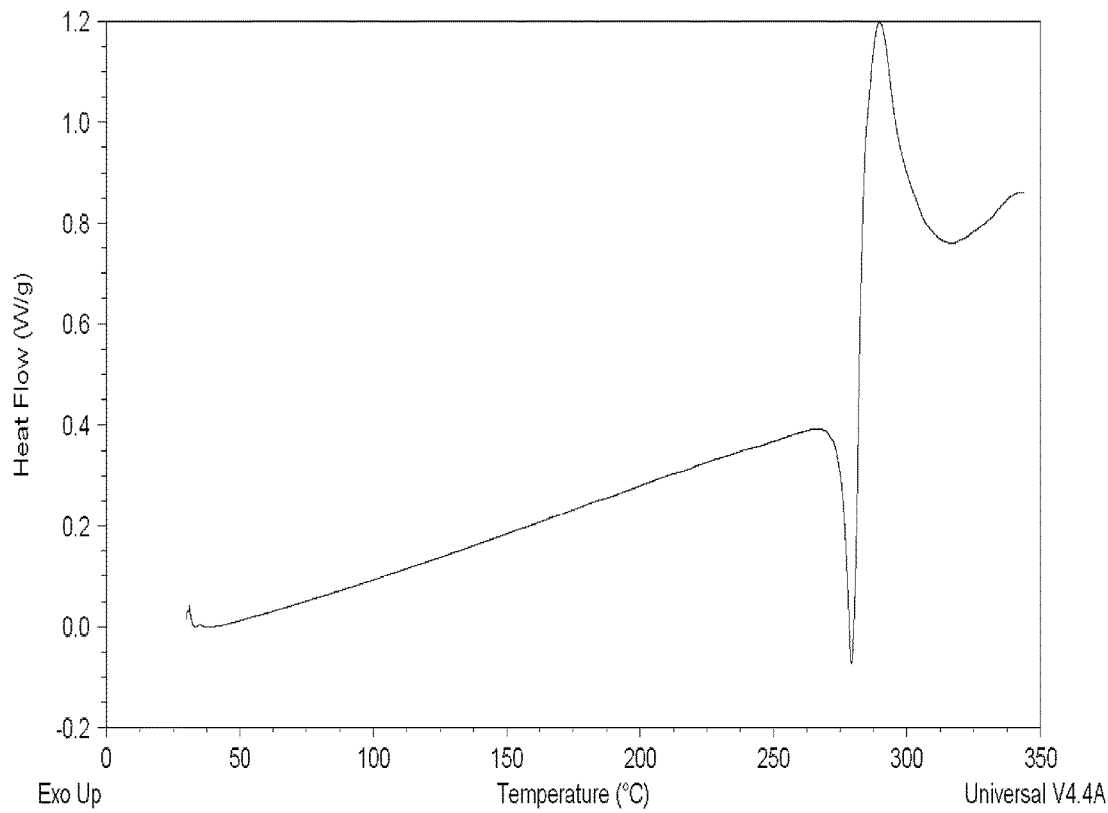
FIGURE 4e: Solid State $^{13}$C NMR Spectrum of Compound I-1 (anhydrous form C)
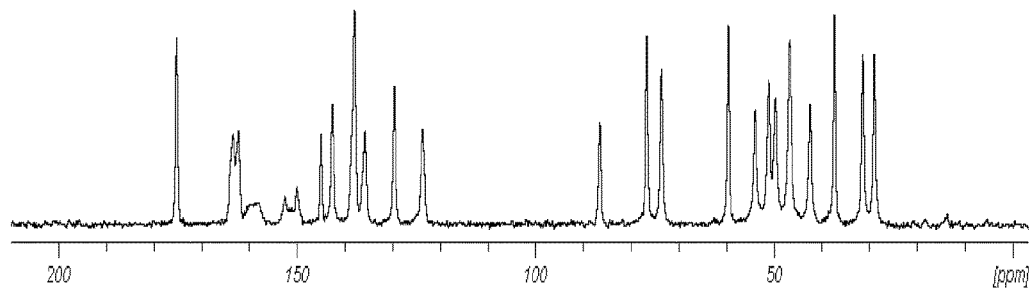

FIGURE 3f: Solid State $^{13}$C NMR Spectrum of Compound I-1 (amorphous)
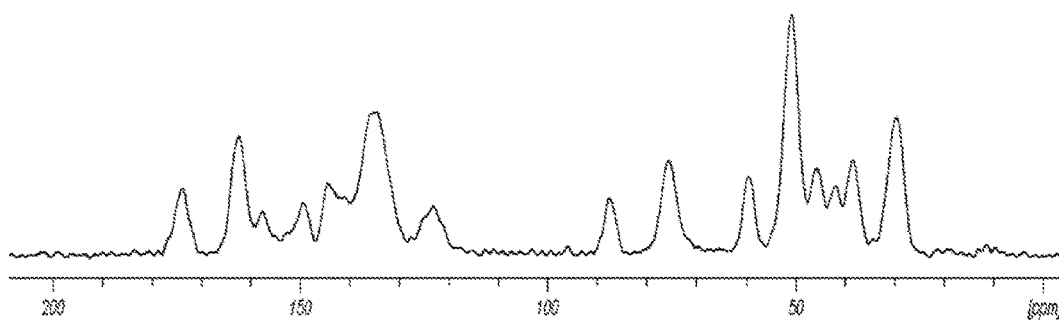
FIGURE 4f: Solid State $^{19}$F NMR Spectrum of Compound I-1 (amorphous)
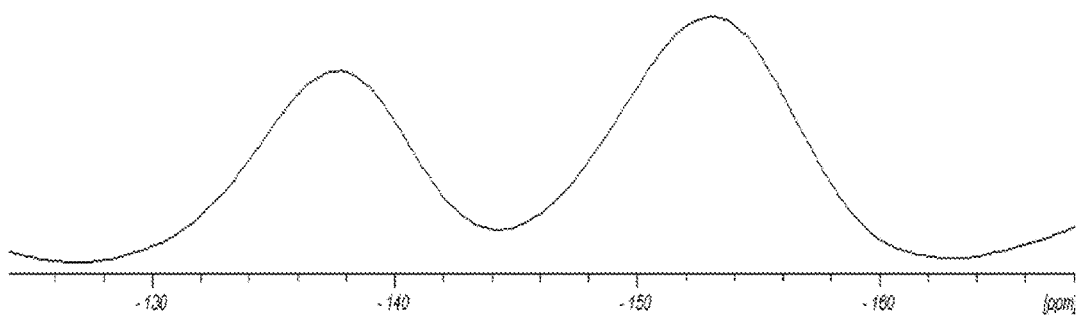

FIGURE 3g: DSC Compound I-1 (DMSO solvate)
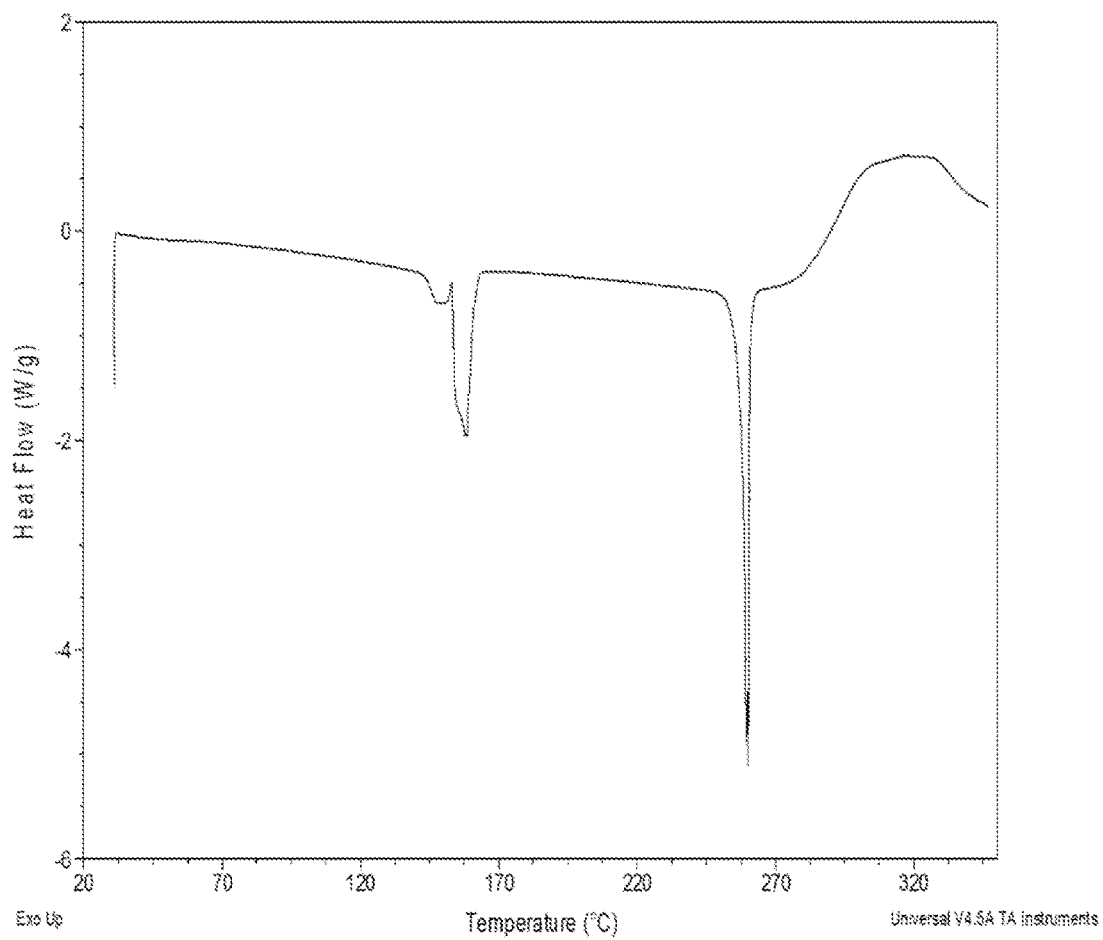

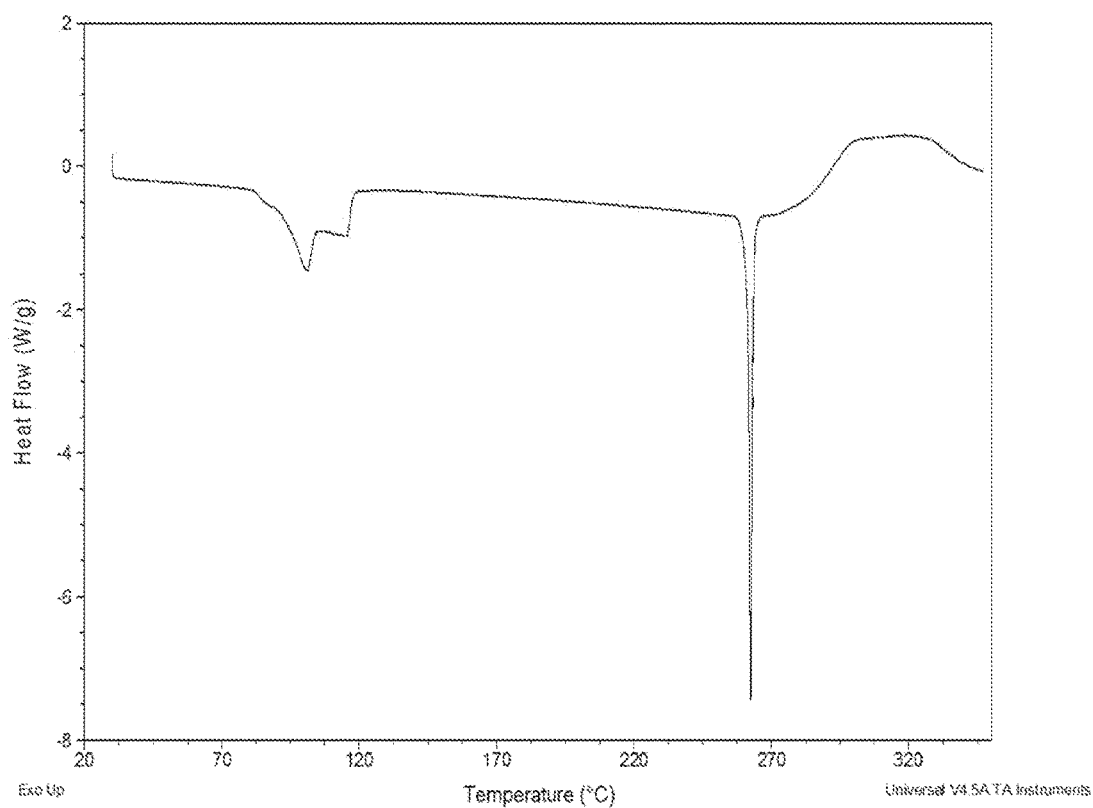
FIGURE 3h: DSC Compound I-1 (DMAC solvate)

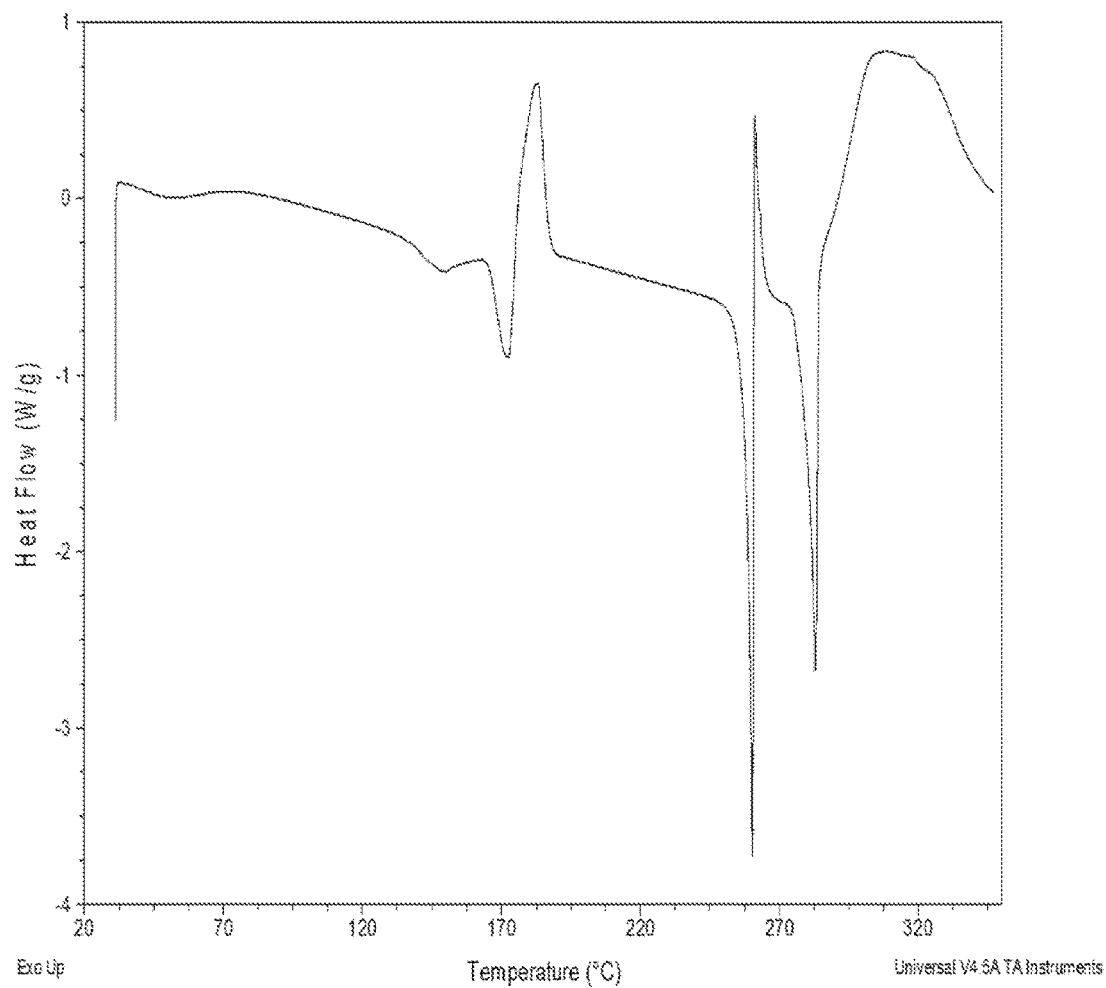
FIGURE 3i: DSC Compound I-1 (acetone solvate)

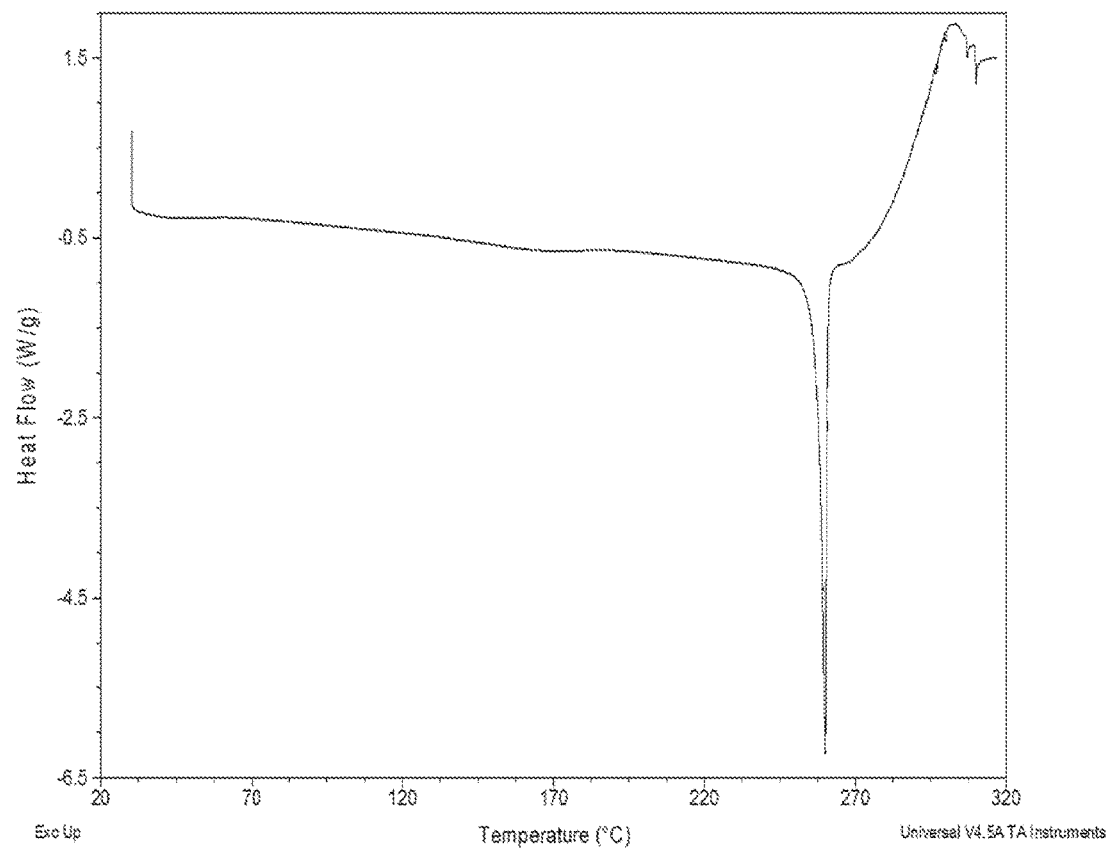
FIGURE 3j: DSC Compound I-1 (isopropanol solvate)

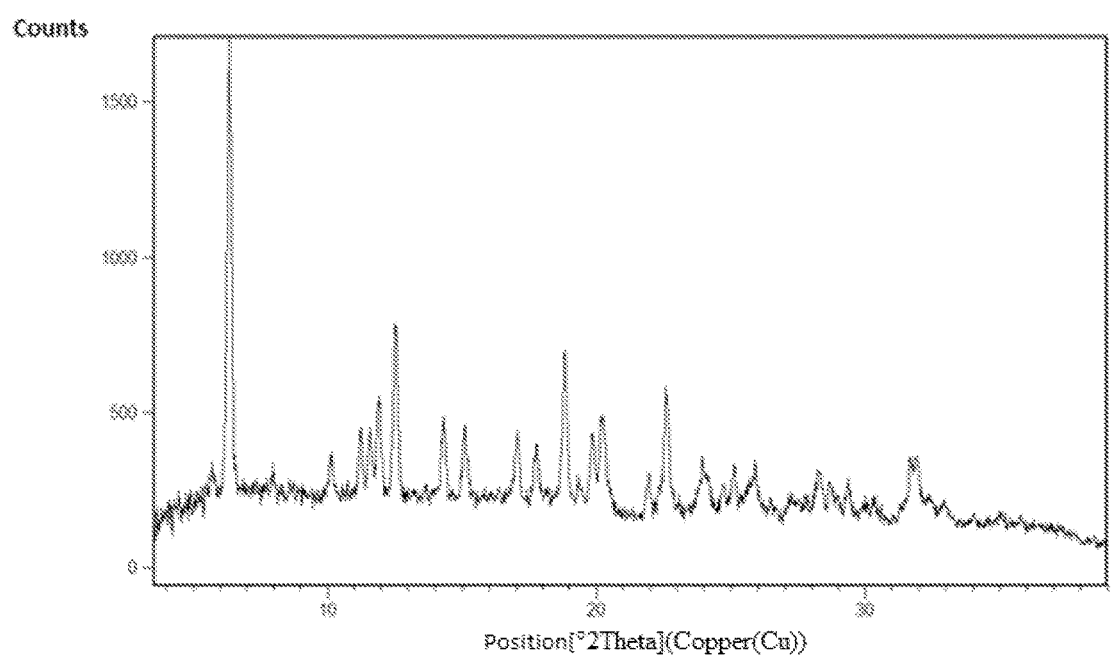
FIGURE 4b: XRPD Compound I-1 (hydrate II)

FIGURE 4d: Solid State $^{13}$C NMR Spectrum of Compound I-1 (anhydrous form B)
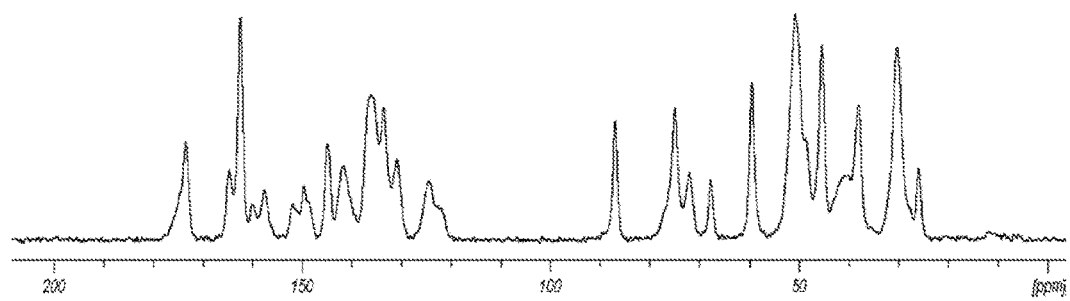
FIGURE 5d: Solid State $^{19}$F NMR Spectrum of Compound I-1 (anhydrous form B)
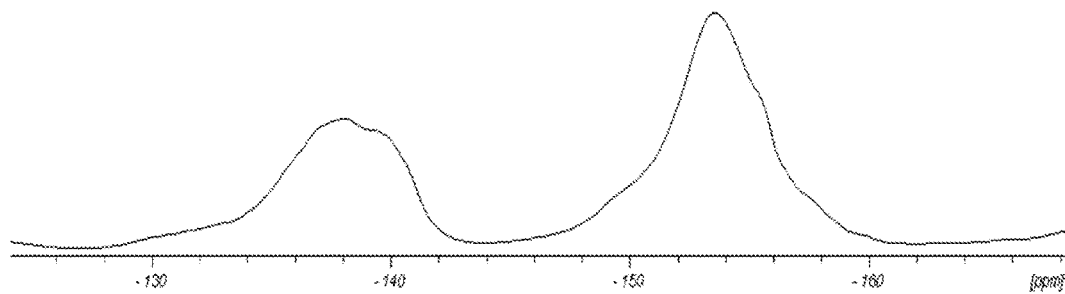

FIGURE 5b: Solid State $^{13}$C NMR Spectrum of Compound I-1 (hydrate II)
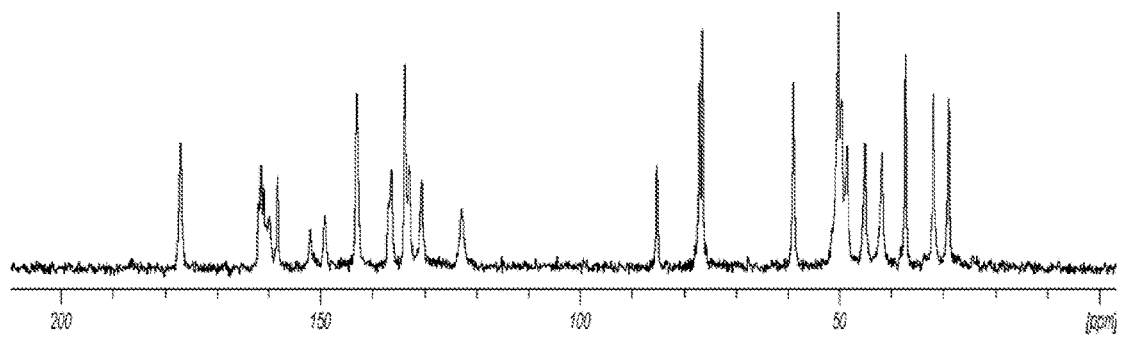
FIGURE 6b: Solid State $^{19}$F NMR Spectrum of Compound I-1 (hydrate II)
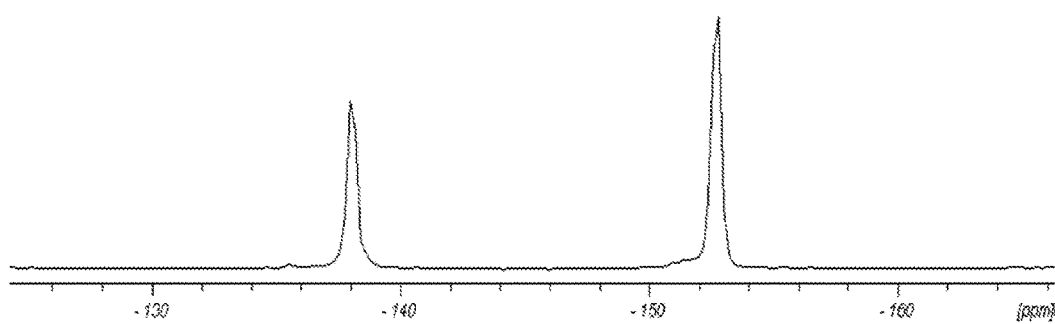

FIGURE 5c: Conformational Plot of Stacking Order of Compound I-1 (anhydrous form A)
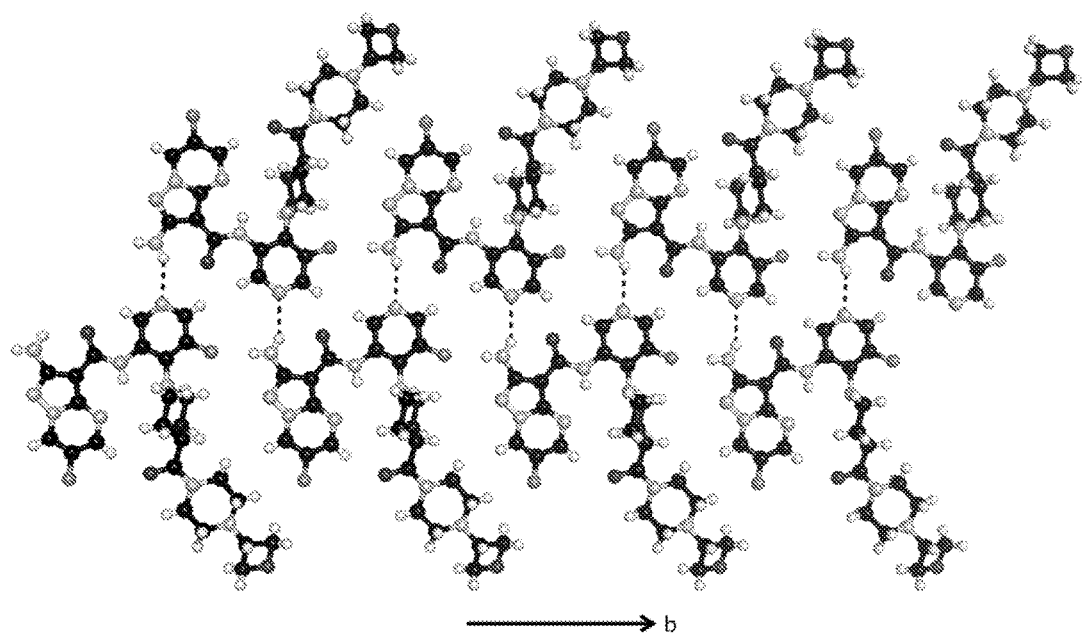
FIGURE 6c: Solid State $^{13}$C NMR Spectrum of Compound I-1 (anhydrous form A)
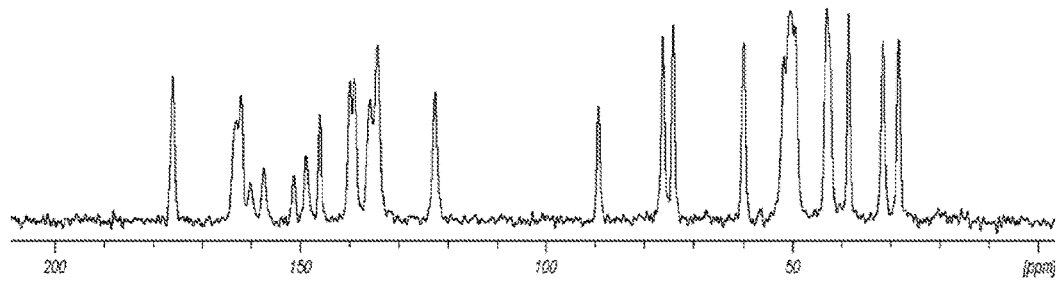

COMPOUNDS USEFUL AS INHIBITORS OF ATR KINASE

CROSS-REFERENCE TO RELATED APPLICATIONS

The present application claims the benefit under 35 U.S.C. § 119 of U.S. Provisional Application No. 61/912,636, filed Dec. 6, 2013; U.S. Provisional Application No. 62/008,220, filed Jun. 5, 2014; and U.S. Provisional Application No. 62/058,819, filed Oct. 2, 2014.

BACKGROUND OF THE INVENTION

ATR ("ATM and Rad3 related") kinase is a protein kinase involved in cellular responses to DNA damage. ATR kinase acts with ATM ("ataxia telangiectasia mutated") kinase and many other proteins to regulate a cell's response to DNA damage, commonly referred to as the DNA Damage Response ("DDR"). The DDR stimulates DNA repair, promotes survival and stalls cell cycle progression by activating cell cycle checkpoints, which provide time for repair. Without the DDR, cells are much more sensitive to DNA damage and readily die from DNA lesions induced by endogenous cellular processes such as DNA replication or exogenous DNA damaging agents commonly used in cancer therapy.

Healthy cells can rely on a host of different proteins for DNA repair including the DDR kinase ATR. In some cases these proteins can compensate for one another by activating functionally redundant DNA repair processes. On the contrary, many cancer cells harbour defects in some of their DNA repair processes, such as ATM signaling, and therefore display a greater reliance on their remaining intact DNA repair proteins which include ATR.

In addition, many cancer cells express activated oncogenes or lack key tumour suppressors, and this can make these cancer cells prone to dysregulated phases of DNA replication which in turn cause DNA damage. ATR has been implicated as a critical component of the DDR in response to disrupted DNA replication. As a result, these cancer cells are more dependent on ATR activity for survival than healthy cells. Accordingly, ATR inhibitors may be useful for cancer treatment, either used alone or in combination with DNA damaging agents, because they shut down a DNA repair mechanism that is more important for cellular survival in many cancer cells than in healthy normal cells.

In fact, disruption of ATR function (e.g. by gene deletion) has been shown to promote cancer cell death both in the absence and presence of DNA damaging agents. This suggests that ATR inhibitors may be effective both as single agents and as potent sensitizers to radiotherapy or genotoxic chemotherapy.

For all of these reasons, there is a need for the development of potent and selective ATR inhibitors for the treatment of cancer, either as single agents or as combination therapies with radiotherapy or genotoxic chemotherapy. Furthermore, it would be desirable to have a synthetic route to ATR inhibitors that is amenable to large-scale synthesis and improves upon currently known methods.

ATR peptide can be expressed and isolated using a variety of methods known in the literature (see e.g., Ünsal-Kaçmaz et al, *PNAS* 99: 10, pp 6673-6678, May 14, 2002; see also Kumagai et al. *Cell* 124, pp 943-955, Mar. 10, 2006; Unsal-Kacmaz et al. *Molecular and Cellular Biology*, February 2004, p 1292-1300; and Hall-Jackson et al. *Oncogene* 1999, 18, 6707-6713).

BRIEF DESCRIPTION OF THE FIGURES

FIG. 1a: XRPD Compound I-1 ethanol solvate
FIG. 2a: TGA Compound I-1•ethanol solvate
FIG. 3a: DSC Compound I-1•ethanol solvate
FIG. 4a: solid state $^{13}$C NMR spectrum (12.5 kHz spinning) of Compound I-1•ethanol solvate
FIG. 5a: solid state $^{19}$F NMR spectrum (12.5 kHz spinning) of Compound I-1•ethanol solvate
FIG. 1b: XRPD Compound I-1•hydrate I
FIG. 2b: TGA Compound I-1•hydrate I
FIG. 3b: DSC Compound I-1•hydrate I
FIG. 4b: XRPD Compound I-1•hydrate II
FIG. 5b: solid state $^{13}$C NMR spectrum (11 kHz spinning) of Compound I-1•hydrate II
FIG. 6b: solid state $^{19}$F NMR spectrum (11 kHz spinning) of Compound I-1•hydrate II
FIG. 1c: XRPD Compound I-1 anhydrous form A
FIG. 2c: TGA Compound I-1 anhydrous form A
FIG. 3c: DSC Compound I-1 anhydrous form A
FIG. 4c: is a conformational plot of Compound I-1•anhydrous form A based on single crystal X-ray analysis.
FIG. 5c: is a conformational plot showing the stacking order of Compound I-1•anhydrous form A.
FIG. 6c: solid state $^{13}$C NMR spectrum (12.5 kHz spinning) of Compound I-1•anhydrous form A
FIG. 7c: solid state $^{19}$F NMR spectrum (12.5 kHz spinning) of Compound I-1•anhydrous form A
FIG. 1d: XRPD Compound I-1•anhydrous form B
FIG. 2d: TGA Compound I-1•anhydrous form B
FIG. 3d: DSC Compound I-1•anhydrous form B
FIG. 4d: solid state $^{13}$C NMR spectrum (12.5 kHz spinning) of Compound I-1•anhydrous form B
FIG. 5d: solid state $^{19}$F NMR spectrum (12.5 kHz spinning) of Compound I-1•anhydrous form B
FIG. 1e: XRPD Compound I-1•anhydrous form C
FIG. 2e: TGA Compound I-1•anhydrous form C
FIG. 3e: DSC Compound I-1•anhydrous form C
FIG. 4e: solid state $^{13}$C NMR spectrum (12.5 kHz spinning) of Compound I-1•anhydrous form C
FIG. 5e: solid state $^{19}$F NMR spectrum (12.5 kHz spinning) of Compound I-1•anhydrous form C
FIG. 1f: XRPD Compound I-1•amorphous form
FIG. 2f: DSC Compound I-1•amorphous form
FIG. 3f: solid state $^{13}$C NMR spectrum (12.5 kHz spinning) of Compound I-1•amorphous
FIG. 4f: solid state $^{19}$F NMR spectrum (12.5 kHz spinning) of Compound I-1•amorphous
FIG. 1g: XRPD Compound I-1•DMSO solvate
FIG. 2g: TGA Compound I-1•DMSO solvate
FIG. 3g: DSC Compound I-1•DMSO solvate
FIG. 1h: XRPD Compound I-1•DMAC solvate
FIG. 2h: TGA Compound I-1•DMAC solvate
FIG. 3h: DSC Compound I-1•DMAC solvate
FIG. 1i: XRPD Compound I-1•acetone solvate
FIG. 2i: TGA Compound I-1•acetone solvate
FIG. 3i: DSC Compound I-1•acetone solvate
FIG. 1j: XRPD Compound I-1•isopropanol solvate
FIG. 2j: TGA Compound I-1•isopropanol solvate
FIG. 3j: DSC Compound I-1•isopropanol solvate

SUMMARY OF THE INVENTION

The present invention relates to solid forms of ATR inhibitors, compositions including ATR inhibitors, as well as deuterated ATR inhibitors. The present invention also relates to processes and intermediates for preparing compounds useful as inhibitors of ATR kinase, such as amino-pyrazolopyrimidine derivatives and related molecules. Amino-pyrazolopyrimidine derivatives are useful as ATR inhibitors and are also useful for preparing ATR inhibitors.

One aspect of the invention provides a process for preparing a compound of formula I-A:

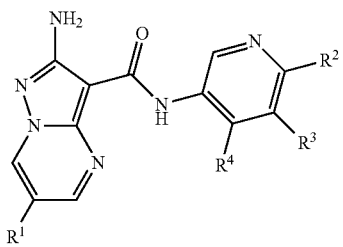

I-A

Another aspect comprises a process for preparing a compound of formula I-1:

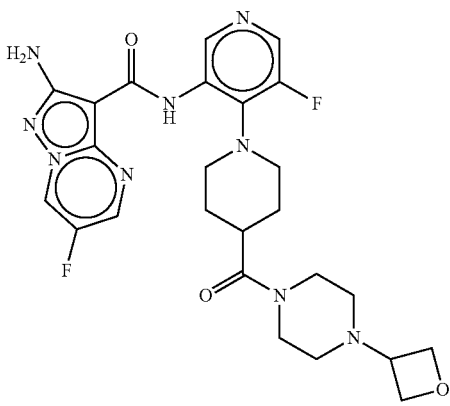

I-1

Another aspect of the present invention comprises a compound of formula I-B:

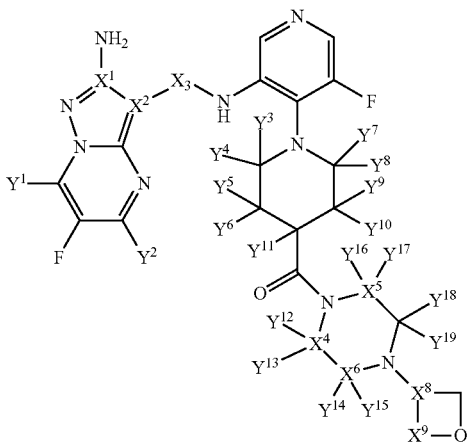

I-B or a pharmaceutically acceptable salt or derivative thereof, wherein:
each $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, and $Y^{19}$ is independently hydrogen or deuterium; provided at least one of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, and $Y^{19}$ is deuterium each $X^1$, $X^2$, $X^4$, $X^5$, $X^6$, $X^7$, $X^8$, and $X^9$ is independently selected from $^{12}C$ or $^{13}C$; and
$X^3$ is independently selected from $-^{12}C(O)-$ or $-^{13}C(O)-$.

Yet another aspect of the invention provides solid forms of a compound of formula I-1:

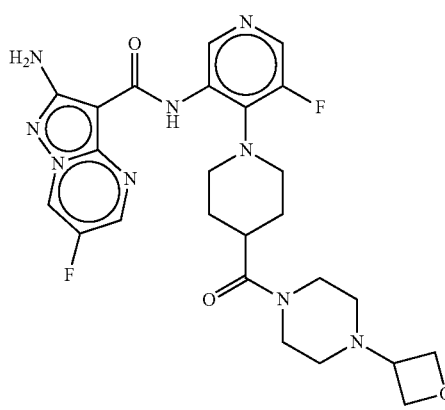

I-1

Some embodiments disclosed herein generally relate to a composition that can include an effective amount of Compound I-1 or polymorphic anhydrous form A of Compound I-1. (hereinafter "Form A"), or a pharmaceutically acceptable salt of the aforementioned compounds.

Other embodiments disclosed herein generally relate to a method of preparing such compositions described herein (for example, a composition that can include an effective amount of Compound I-1 or Form A, or a pharmaceutically acceptable salt of the aforementioned compounds). Still other embodiments disclosed herein generally relate to a method of treating cancer using a composition described herein.

Some embodiments disclosed herein generally relate to the use of a composition described herein (for example, a composition that includes an effective amount of Compound I-1 or Form A, or a pharmaceutically acceptable salt of the aforementioned compounds) in the manufacture of a medicament for treating cancer.

Other aspects of the invention are set forth herein.

DETAILED DESCRIPTION OF THE INVENTION

For purposes of this application, it will be understood that the terms embodiment, example, and aspect are used interchangeably.

Processes

Another aspect of the present invention comprises a process for preparing a compound of formula I-A:

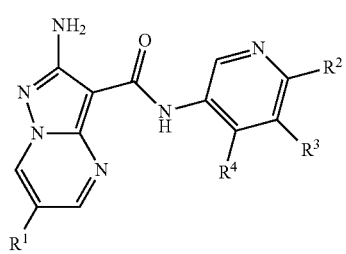

I-A comprising reacting a compound of formula 6:

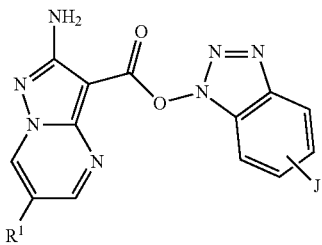

under suitable conditions to form an amide bond, wherein:

$R^1$ is independently selected from fluoro, chloro, or —C($J^1$)$_2$CN;

$J^1$ is independently selected from H or $C_{1-2}$alkyl; or two occurrences of $J^1$, together with the carbon atom to which they are attached, form a 3-4 membered optionally substituted carbocyclic ring;

$R^2$ is independently selected from H; halo; —CN; NH$_2$; a $C_{1-2}$alkyl optionally substituted with 0-3 occurrences of fluoro; or a $C_{1-3}$aliphatic chain wherein up to two methylene units of the aliphatic chain are optionally replaced with —O—, —NR—, —C(O)—, or —S(O)—;

$R^3$ is independently selected from H; halo; $C_{1-4}$alkyl optionally substituted with 1-3 occurrences of halo; $C_{3-4}$cycloalkyl; —CN; or a $C_{1-3}$aliphatic chain wherein up to two methylene units of the aliphatic chain are optionally replaced with —O—, —NR—, —C(O)—, or —S(O)—;

$R^4$ is independently selected from $Q^1$ or a $C_{1-10}$aliphatic chain wherein up to four methylene units of the aliphatic chain are optionally replaced with —O—, —NR—, —C(O)—, or —S(O)$_n$—; each $R^4$ is optionally substituted with 0-5 occurrences of $J^Q$; or $R^3$ and $R^4$, taken together with the atoms to which they are bound, form a 5-6 membered aromatic or non-aromatic ring having 0-2 heteroatoms selected from oxygen, nitrogen or sulfur; the ring formed by $R^3$ and $R^4$ is optionally substituted with 0-3 occurrences of $J^Z$;

$Q^1$ is independently selected from a 3-7 membered fully saturated, partially unsaturated, or aromatic monocyclic ring, the 3-7 membered ring having 0-3 heteroatoms selected from oxygen, nitrogen or sulfur; or an 7-12 membered fully saturated, partially unsaturated, or aromatic bicyclic ring having 0-5 heteroatoms selected from oxygen, nitrogen, or sulfur;

$J^Z$ is independently selected from $C_{1-6}$aliphatic, =O, halo, or →O;

$J^Q$ is independently selected from —CN; halo; =O; $Q^2$; or a $C_{1-8}$aliphatic chain wherein up to three methylene units of the aliphatic chain are optionally replaced with —O—, —NR—, —C(O)—, or —S(O)$_n$—; each occurrence of $J^Q$ is optionally substituted by 0-3 occurrences of $J^R$; or two occurrences of $J^Q$ on the same atom, taken together with the atom to which they are joined, form a 3-6 membered ring having 0-2 heteroatoms selected from oxygen, nitrogen, or sulfur; wherein the ring formed by two occurrences of $J^Q$ is optionally substituted with 0-3 occurrences of $J^X$; or two occurrences of $J^Q$, together with $Q^1$, form a 6-10 membered saturated or partially unsaturated bridged ring system;

$Q^2$ is independently selected from a 3-7 membered fully saturated, partially unsaturated, or aromatic monocyclic ring having 0-3 heteroatoms selected from oxygen, nitrogen, or sulfur; or an 7-12 membered fully saturated, partially unsaturated, or aromatic bicyclic ring having 0-5 heteroatoms selected from oxygen, nitrogen, or sulfur;

$J^R$ is independently selected from —CN; halo; =O; →O; $Q^3$; or a $C_{1-6}$aliphatic chain wherein up to three methylene units of the aliphatic chain are optionally replaced with —O—, —NR—, —C(O)—, or —S(O)$_n$—; each $J^R$ is optionally substituted with 0-3 occurrences of $J^T$; or two occurrences of $J^R$ on the same atom, together with the atom to which they are joined, form a 3-6 membered ring having 0-2 heteroatoms selected from oxygen, nitrogen, or sulfur; wherein the ring formed by two occurrences of $J^R$ is optionally substituted with 0-3 occurrences of $J^X$; or two occurrences of $J^R$, together with $Q^2$, form a 6-10 membered saturated or partially unsaturated bridged ring system;

$Q^3$ is a 3-7 membered fully saturated, partially unsaturated, or aromatic monocyclic ring having 0-3 heteroatoms selected from oxygen, nitrogen, or sulfur; or an 7-12 membered fully saturated, partially unsaturated, or aromatic bicyclic ring having 0-5 heteroatoms selected from oxygen, nitrogen, or sulfur;

$J^X$ is independently selected from —CN; =O; halo; or a $C_{1-4}$aliphatic chain wherein up to two methylene units of the aliphatic chain are optionally replaced with —O—, —NR—, —C(O)—, or —S(O)$_n$—;

$J^T$ is independently selected from halo, —CN; →O; =O; —OH; a $C_{1-6}$aliphatic chain wherein up to two methylene units of the aliphatic chain are optionally replaced with —O—, —NR—, —C(O)—, or —S(O)$_n$—; or a 3-6 membered non-aromatic ring having 0-2 heteroatoms selected from oxygen, nitrogen, or sulfur; each occurrence of $J^T$ is optionally substituted with 0-3 occurrences of $J^M$; or two occurrences of $J^T$ on the same atom, together with the atom to which they are joined, form a 3-6 membered ring having 0-2 heteroatoms selected from oxygen, nitrogen, or sulfur; or two occurrences of $J^T$, together with $Q^3$, form a 6-10 membered saturated or partially unsaturated bridged ring system;

$J^M$ is independently selected from halo or $C_{1-6}$aliphatic;

J is H or Cl;

n is 0, 1 or 2; and

R is independently selected from H or $C_{1-4}$aliphatic.

For purposes of this application, it will be understood that when two occurrences of $J^Q$, together with $Q^1$, form a bridged ring system, the two occurrences of $J^Q$ are attached to separate atoms of $Q^1$. Additionally, when two occurrences of $J^R$, together with $Q^2$, form a bridged ring system, the two occurrences of $J^R$ are attached to separate atoms of $Q^2$. Moreover, when two occurrences of $J^T$, together with $Q^3$, form a bridged ring system, the two occurrence of $J^T$ are attached to separate atoms of $Q^3$.

It will be understood by those skilled in the art that the arrow in →O represents a dative bond.

Reaction Conditions

In some examples, the suitable conditions for forming the amide bond comprises reacting the compound of formula 6 with a substituted 3-amino pyridine in an aprotic solvent under heat. In other examples, the aprotic solvent is selected from NMP, optionally substituted pyridine, or DMF. In another embodiment, the aprotic solvent is optionally substituted pyridine. In still other embodiments, the reaction temperature is at least 80° C. In another embodiment, the reaction temperature is at least 100° C.

In another embodiment, the process, described above, further comprises preparing a compound of formula 6:

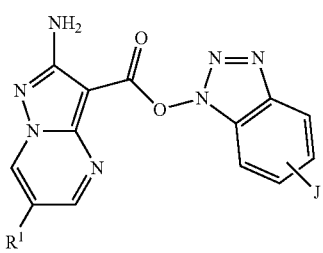

6 by reacting a compound of formula 5:

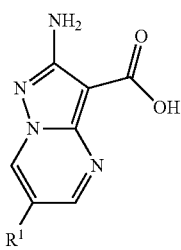

5 under suitable conditions to form an activated ester, wherein $R^1$ and J are as defined herein.

In some embodiments, suitable conditions for forming the activated ester comprises reacting the compound of formula 5 with an amide coupling agent in the presence of an organic base. In other embodiments, the organic base is an aliphatic amine. In still other embodiments, the organic base is independently selected from triethylamine or DIPEA. In one or more embodiments, the amide coupling agent is independently selected from TBTU, TCTU, HATU, T3P, or COMU. In yet another embodiment, the amide coupling agent is independently selected from TBTU or TCTU. In another embodiment, the amide coupling agent is TCTU.

Another aspect of the invention comprises a process for preparing a compound of formula I-A:

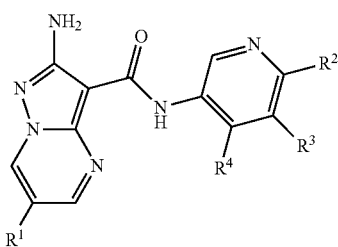

I-A comprising reacting a compound of formula 5:

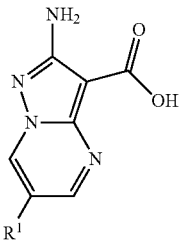

5 under suitable conditions to form an amide bond, wherein $R^1$, $R^2$, $R^3$, and $R^4$ are as defined herein.

Yet another aspect of the present invention comprises a process for preparing a compound of formula 5:

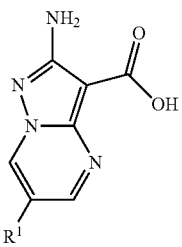

5 by reacting a compound of formula 4:

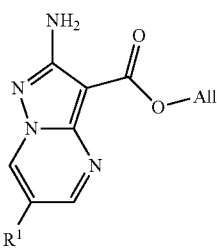

4 under suitable hydrolytic conditions, wherein $R^1$ is as defined herein.

In some embodiments, suitable hydrolytic conditions comprise reacting the compound of formula 4 with a silane in the presence of a metal catalyst. In other embodiments, the silane is a phenylsilane. In another embodiment, the metal catalyst is a palladium catalyst. In yet another embodiment, the palladium catalyst is $Pd(PPh_3)_4$. In another embodiment suitable hydrolytic conditions comprise reacting the compound of formula 4 with 4-methylbenzenesulfinate in the presence of a metal catalyst.

In still other embodiments, suitable hydrolytic conditions comprise reacting the compound of formula 4 with an aqueous alkali. In some embodiments, the aqueous alkali is selected from LiOH, NaOH or KOH.

Another aspect of the present invention comprises a process for preparing a compound of formula 4:

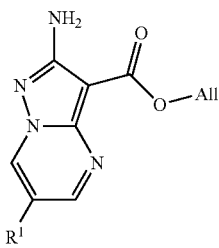

4 by reacting a compound of formula 3:

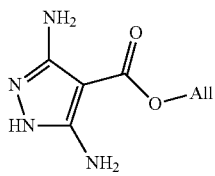

3 under suitable condensation conditions to form a pyrimidine ring.

In some embodiments, suitable condensation conditions to form a pyrimidine ring comprise reacting the compound of formula 3 with a 1,3-dielectrophilic species in the presence of a solvent. In another embodiment, the 1,3-dielectrophilic species is selected from 1,3-dialdehyde or 3-(dialkylamino)-prop-2-enal. In still other embodiments, the solvent is selected from DMF or DMSO. In other embodiments, the 1,3-dielectrophilic species is generated in situ from a protected 1,3-dielectrophilic species. In another embodiment, the 1,3-dielectrophilic species is generated from a ketal in the presence of a sulfonic acid. In yet another embodiment, the sulfonic acid is PTSA.

Another aspect of the present invention comprises a process for preparing the compound of formula 3:

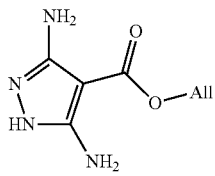

3 by reacting a compound of formula 2:

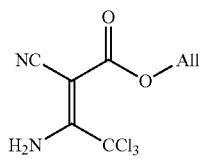

2 under suitable condensation conditions to form a pyrazole ring.

In some embodiments, suitable condensation conditions to form a pyrazole ring comprise reacting the compound of formula 2 with a hydrazine or hydrazine hydrate in the presence of an aprotic solvent under basic conditions. In another embodiment, the aprotic solvent is DMF. In yet another embodiment, the basic conditions comprise reacting the compound of formula 2 in the presence of potassium acetate or sodium acetate.

Yet another aspect of the present invention comprises a process for preparing a compound of formula 2:

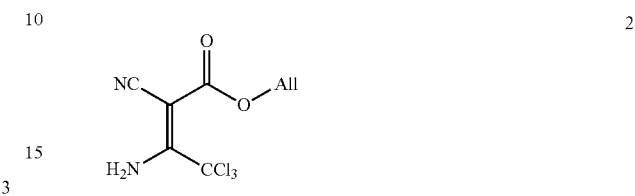

2 by reacting a compound of formula 1:

1 under suitable anion condensation conditions.

In some embodiments, suitable anion condensation conditions comprise 1) reacting the compound of formula 1 with a base, in the presence of a solvent, to generate the anion of the compound of formula 1; and 2) reacting the anion of the compound of formula 1 with trichloroacetonitrile. In still other embodiments, the base is potassium acetate. In yet another embodiment, the solvent is an alcohol. In other embodiments, the solvent is isopropylalcohol.

One embodiment of the present invention comprises a process for preparing a compound of formula I-A:

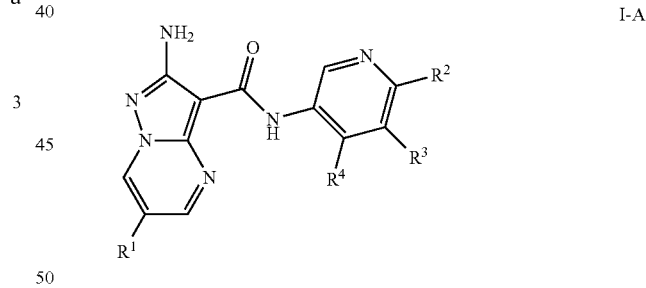

I-A comprising reacting a compound of formula 9:

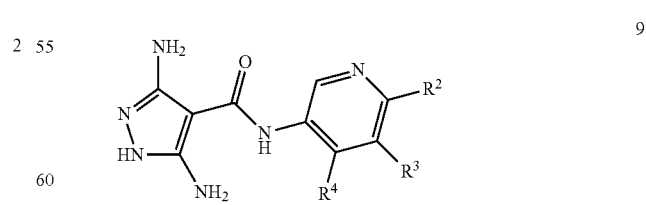

9 under suitable condensation conditions to form a pyrimidine ring, wherein $R^1$, $R^2$, $R^3$ and $R^4$ are as defined herein.

In some embodiments, suitable condensation conditions to form a pyrimidine ring comprise reacting the compound of formula 9 with a 1,3-dielectrophilic species in the presence of a solvent. In another embodiment, the 1,3-dielectrophilic species is selected from 1,3-dialdehyde or 3-(dialkylamino)-prop-2-enal. In still other embodiments, the solvent is selected from DMF or DMSO in water. In other embodiments, the 1,3-dielectrophilic species is generated in situ from a protected 1,3-dielectrophilic species. In another embodiment, the 1,3-dielectrophilic species is generated from a ketal in the presence of a sulfonic acid. In yet another embodiment, the sulfonic acid is PTSA.

Another embodiment of the present invention comprises a process for preparing a compound of formula 9:

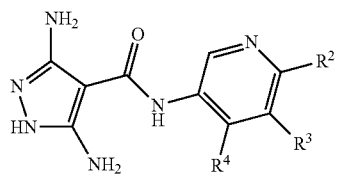

9 by reacting a compound of formula 8:

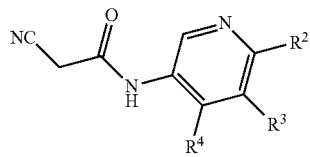

8 under suitable condensation conditions to form a pyrazole ring.

In some embodiments, suitable condensation conditions to form a pyrazole ring comprise 1) reacting the compound of formula 8 with a base, in the presence of a solvent, to generate the anion of the compound of formula 8; 2) reacting the anion with trichloroacetonitrile; and 3) reacting the product from 2) with a hydrazine or hydrazine hydrate in the presence of an aprotic solvent. In another embodiment, the aprotic solvent is NMP or DMF. In some embodiments, the base is selected from sodium acetate or potassium acetate.

Yet another embodiment comprises a process for preparing a compound of formula 8:

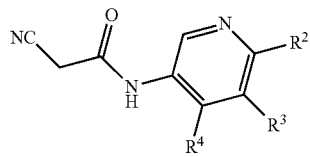

8 by reacting a compound of formula 7:

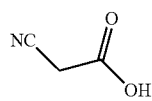

7 under suitable conditions to form an amide bond.

In some examples, the suitable conditions for forming the amide bond comprises reacting the compound of formula 7 with a substituted 3-amino pyridine with an amide coupling agent in the presence of an aprotic solvent and an organic base. In other examples, the aprotic solvent is selected from NMP or DMF. In another embodiment, the organic base is an aliphatic amine. In still other embodiments, the organic base is independently selected from triethylamine or DIPEA. In yet another embodiment, the amide coupling agent is independently selected from TBTU or TCTU.

Synthesis of Compound I-1

Another aspect of the present invention provides a process of preparing a compound of formula I-1:

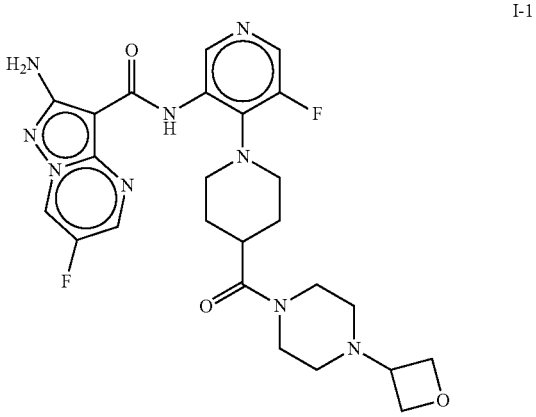

I-1 comprising the step of reacting the compound of formula 30:

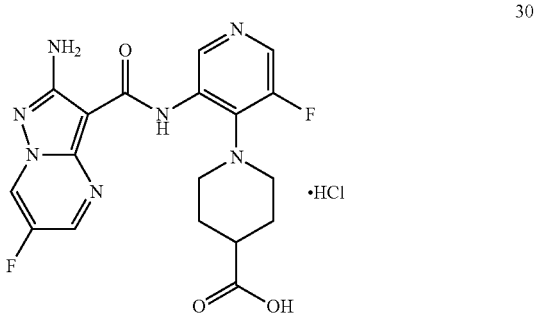 [SMILES: Nc1nn2cc(F)cnc2c1C(=O)Nc1cncc(F)c1N1CCC(C(=O)O)CC1 ; Cl]

30 with a compound of formula 25:

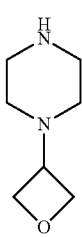

25 under suitable conditions to form an amide bond.

Still other embodiments of the present invention comprise provides a process for preparing the compound of formula 30:

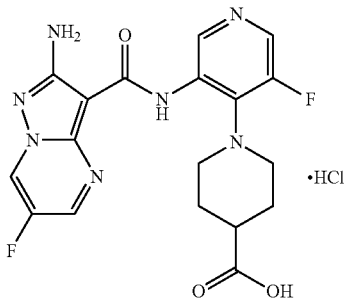

by reacting the compound of formula 28:

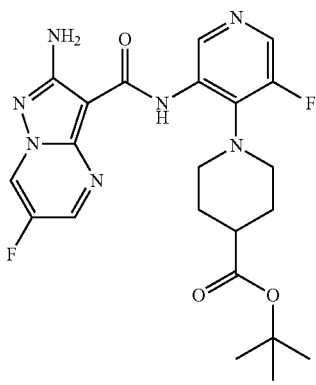

under suitable deprotection conditions to form the carboxylic acid.

Another embodiment provides a process for preparing a compound of formula 28:

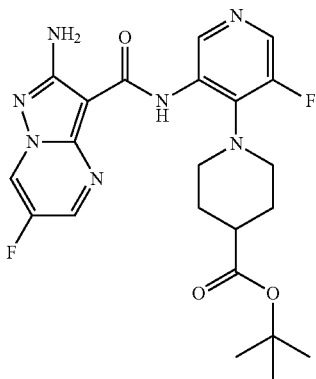

by reacting the compound of formula 6a*:

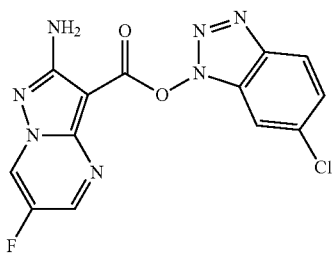

with a compound of formula 27:

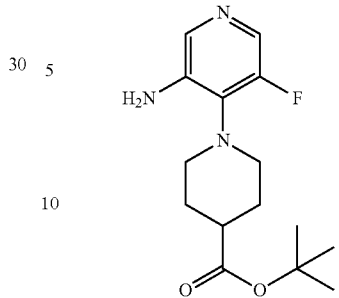

under suitable conditions to form an amide bond.

In some embodiments, suitable conditions for forming the amide bond comprise reacting the compound of formula 30 with the compound of formula 25 in the presence of an amide coupling partner, an aprotic solvent, and a base. In other embodiments, the aprotic solvent is independently selected from NMP, DMF, or tetrahydrofuran. In still other embodiments, the aprotic solvent is tetrahydrofuran. In another embodiment, the base is an aliphatic amine. In yet another embodiment, the base is DIPEA. In some embodiments, the amide coupling partner is independently selected from CDI, TBTU or TCTU. In one or more embodiments, the amide coupling partner is TCTU. In yet another embodiment, the amide coupling partner is CDI.

In other embodiments, suitable deprotection conditions comprise reacting the compound of formula 28 with an acid in the presence of a solvent. In some embodiments, the acid is HCl. In another embodiment, the solvent is 1,4-dioxane.

In yet another embodiment, suitable conditions for forming the amide bond comprise reacting the compound of formula 6a* with the compound of formula 27 in an aprotic solvent under heat. In still other embodiments, the aprotic solvent is independently selected from NMP, pyridine, or DMF. In another embodiment, the aprotic solvent is pyridine. In some embodiments, the reaction is carried out at a temperature of at least 80° C.

Another aspect of the present invention provides a process of preparing a compound of formula 27:

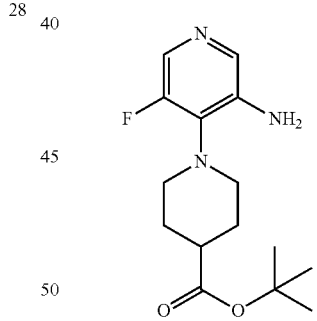

comprising the step of reacting a compound of formula 26:

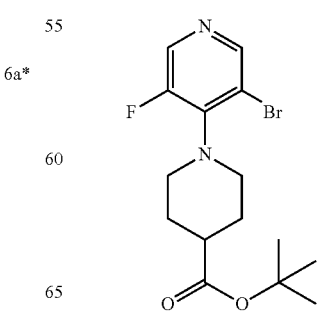

under suitable conditions to form an amine.

In some embodiments, suitable conditions to form an amine comprise reacting the compound of formula 27 under Buchwald-Hartwig amination conditions, known to those skilled in the art.

Yet another embodiment provides a process for preparing a compound of formula 26:

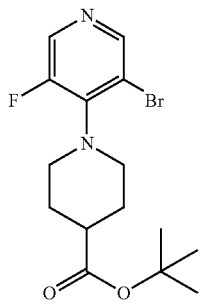

26 by 1) reacting a compound of formula 18:

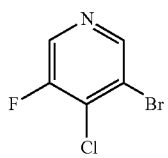

18 under suitable halogen exchange conditions to generate the compound of formula 32

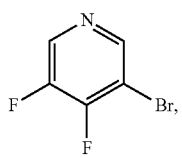

32 and
2) reacting the compound of formula 32:

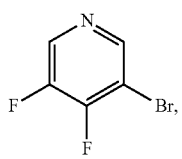

32 with a compound of formula 22:

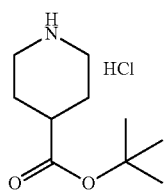

22 under suitable displacement conditions.

In some embodiments, suitable halogen exchange conditions comprise reacting the compound of formula 18 with potassium fluoride in the presence of an aprotic solvent and a phase transfer catalyst. In other embodiments, the aprotic solvent is independently selected from DMSO, DMF, or sulfolane. In still other embodiments, the phase transfer catalyst is Me₄NCl. In still other embodiments, suitable displacement conditions comprise reacting the compound of formula 32 with a compound of formula 22 in the presence of a base. In another embodiment, the base is an aliphatic amine. In some embodiments, the aliphatic amine is DIPEA.

Other embodiments of the present invention provides a process for preparing a compound of formula 18:

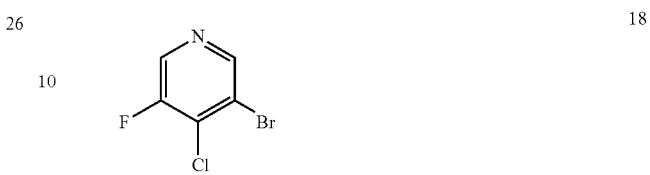

18 by reacting the compound of formula 31:

31 under suitable halogenation conditions.

In some embodiments, suitable halogenation conditions comprise 1) reacting the compound of formula 31 with a base to generate an anion; and 2) reacting the anion with a chlorinating agent. In yet another embodiment, the base is LDA. In another embodiment, the chlorinating agent is 1,1,1,2,2,2-hexachloroethane.

Some embodiments of the present invention provides a process for preparing a compound of formula I-1:

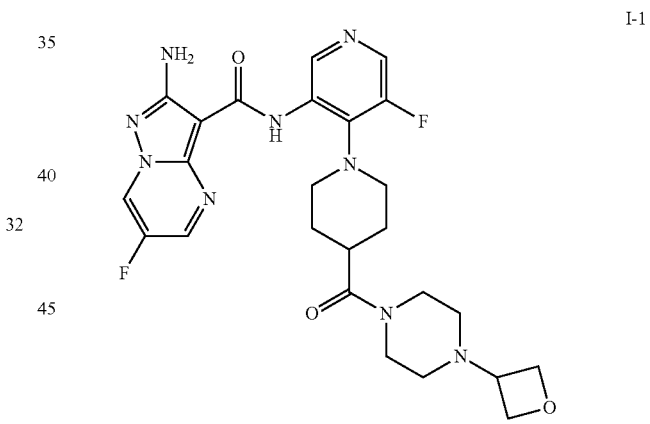

I-1 comprising the step of reacting the compound of formula 33:

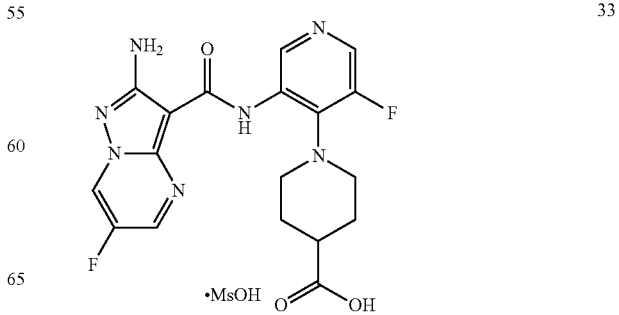

33 with a compound of formula 25:

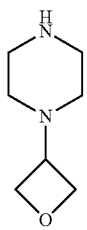

under suitable conditions to form an amide bond.

In some embodiments, suitable conditions for forming the amide bond comprise reacting the compound of formula 33 with the compound of formula 25 in the presence of an amide coupling partner, an aprotic solvent, and a base. In other embodiments, the aprotic solvent is independently selected from NMP, DMF, or tetrahydrofuran. In still other embodiments, the aprotic solvent is tetrahydrofuran. In another embodiment, the base is an aliphatic amine. In yet another embodiment, the base is DIPEA. In some embodiments, the amide coupling partner is independently selected from TBTU or TCTU. In one or more embodiments, the amide coupling partner is TCTU.

Yet another embodiment provides a process for preparing a compound of formula 33:

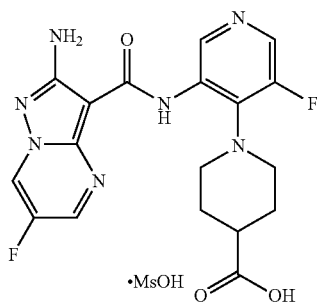

comprising the step of reacting the compound of formula 28:

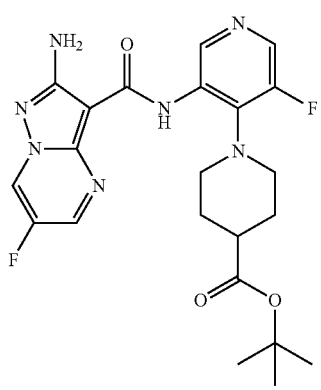

under suitable deprotecting conditions.

In some embodiments, suitable deprotecting conditions for cleaving the tert-butyl ester comprise reacting the compound of formula 28 with an acid in the presence of a solvent. In one embodiment, the acid is selected from, but not limited to, methanesulphonic acid (preferred), PTSA, TFA, or HCl. In still other embodiments, the solvent is selected from, but is not limited to, 1,4-dioxane or acetonitrile. In another embodiment, the solvent is acetonitrile.

Another embodiment provides a process for preparing a compound of formula 4a:

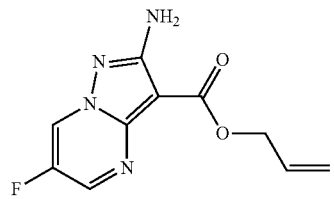

comprising the steps of:
a) reacting a compound of formula 35:

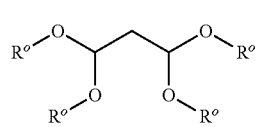

wherein $R^o$ is $C_{1-6}$aliphatic,
under acidic conditions to form a compound of formula 36:

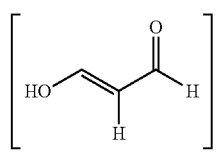

b) reacting a compound of formula 36 with an electrophilic fluorinating agent to form a compound of formula 38:

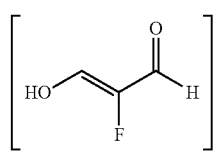

c) reacting a compound of formula 38 with a compound of formula 3:

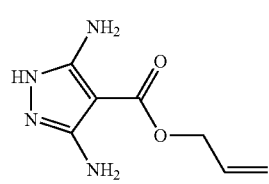

under suitable condensation conditions to form the compound of formula 4a.

In some embodiments, R° is independently selected from methyl, ethyl, propyl, isopropyl, butyl, and pentyl. In still other embodiments, R° is independently selected from methyl or ethyl.

In another embodiment, the electrophilic fluorinating agent is 1-(Chloromethyl)-4-fluoro-1,4-diazoniabicyclo [2.2.2]octane ditetrafluoroborate. In other embodiments, the electrophilic fluorinating agent is fluorine gas.

In yet another embodiment, the suitable condensation conditions comprise reacting the compound of formula 38 with the compound of formula 3 in the presence of a solvent and heat. In some embodiments, the solvent is selected from DMF or DMSO.

Yet another embodiment provides a process for preparing a compound of formula I-1:

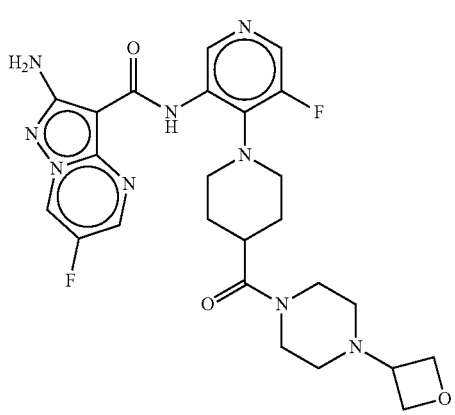

I-1 comprising the steps of:
a) reacting the compound of formula 6a*:

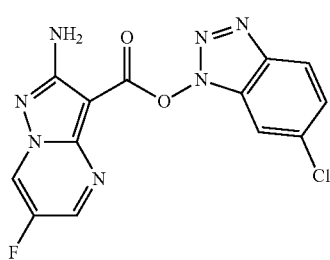

6a* with a compound of formula 27:

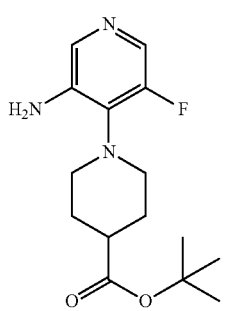

27 under suitable amide bond formation conditions to form a compound of formula 28:

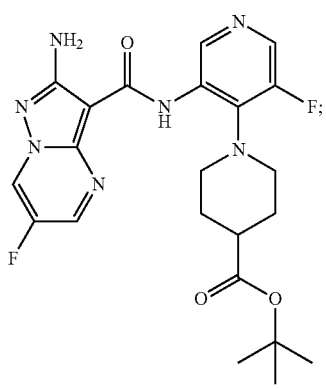

28 b) purifying the compound of formula 28 using a suitable palladium sequestering agent;
c) reacting the compound of formula 28 under suitable deprotection conditions to form a compound of formula 30

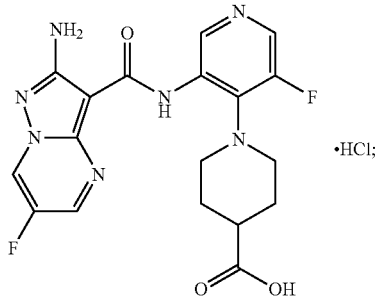

30 and
d) reacting the compound of formula 30 with a compound of formula 25:

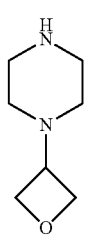

25 under suitable amide bond formation conditions to form the compound of formula I-1.

In some embodiments, the suitable palladium sequestering agent is independently selected from propane-1,2-diamine; ethane-1,2-diamine; ethane-1,2-diamine; propane-1,3-diamine; tetramethylethelenediamine; ethylene glycol; 1,3-bis(diphenylphosphanyl)propane; 1,4-bis(diphenylphosphanyl)butane; and 1,2-bis(diphenylphosphanyl)ethane/Pr-1,2-diamine. In still other embodiments, the suitable palladium sequestering agent is propane-1,2-diamine.

Another embodiment provides a process for preparing a compound of formula 28:

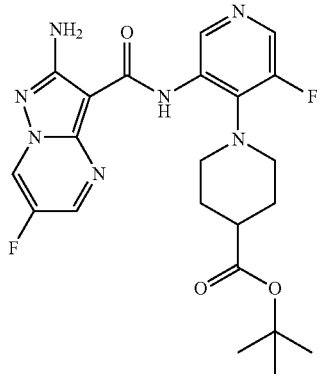

28 comprising the steps of:
a) reacting the compound of formula 5a

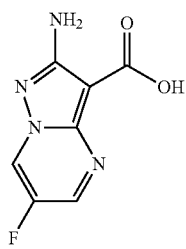

5a under suitable halogenation conditions to form a compound of formula 34:

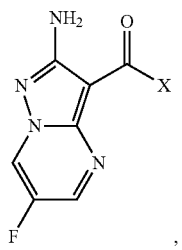

34 wherein X is halogen;
b) reacting the compound of formula 34 with a compound of formula 27:

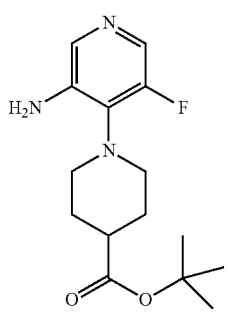

27 under suitable amide bond formation conditions to form a compound of formula 28.

In some embodiments X is independently selected from fluoro or chloro. In another embodiment, X is chloro. In some embodiments, the suitable halogenation conditions comprise reacting the compound of formula 5a with a halogenating agent and a base in the presence of a solvent. In yet another embodiment the halogenating agent is $SOCl_2$. In some embodiments, the base is triethylamine. In still other embodiments, the solvent is DCM.

Yet another aspect of the present invention provides a process for preparing a compound of formula I-1:

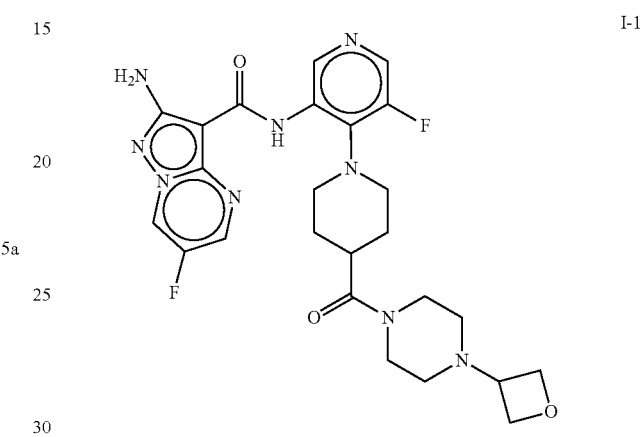

I-1 comprising the steps of:
a) reacting the compound of formula 5a

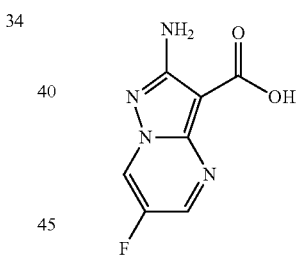

5a under suitable halogenation conditions to form a compound of formula 34:

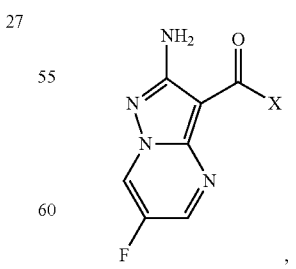

34 wherein X is halogen;
b) reacting the compound of formula 34 with a compound of formula 27:

under suitable amide bond formation conditions to form a compound of formula 28:

c) reacting the compound of formula 28 under suitable deprotection conditions to form a compound of formula 30 d) reacting the compound of formula 30 with a compound of formula 25:

under suitable amide bond formation conditions to form the compound of formula I-1.

Deuterated Compounds

In another embodiment, Isotopes can be introduced into compound I-1 by selecting building blocks that contain the isotopic atoms (either commercially available or that can be prepared according to processes known to those skilled in the art) and engaging them into a sequence similar to the one reported for the unlabelled material.

Another aspect of the present invention provides a compound of Formula I-B:

I-B or a pharmaceutically acceptable salt thereof, wherein:
each $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, and $Y^{19}$, is independently hydrogen or deuterium; provided at least one of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, and $Y^{19}$ is deuterium
each $X^1$, $X^2$, $X^4$, $X^5$, $X^6$, $X^7$, $X^8$, and $X^9$ is independently selected from $^{12}C$ or $^{13}C$; and
$X^3$ is independently selected from —$^{12}C(O)$— or —$^{13}C(O)$—.

The following labeled building blocks, which can be used in the synthetic route for preparing the compound of formula I-B, are all commercially available:
2,2,3,3,5,5,6,6-octadeuteropiperazine;
2,3,5,6-tetra-$^{13}C$-piperazine;
2,2,3,3,4,5,5,6,6-nonadeuteropiperidine-4-carboxylic acid;
1,2-Di$^{13}C$-2-cyanoacetic acid;
1-$^{13}C$-2-cyano($^{13}C$)acetic acid ethyl ester; and
2-$^{13}C$-2-cyano($^{13}C$)acetic acid ethyl ester.

Other labeled building blocks, which may be utilized in the synthetic route for preparing a compound of formula I-B, are known to those skilled in the art. These may include, but are not limited to, the following labeled building blocks:
2-$^{13}C$-oxetan-3-one;
3-$^{13}C$-oxetan-3-one;
2,2,3,3-tetradeuteropiperazine;
2,2,5,5-tetradeuteropiperazine;
4-deuteropiperidine-4-carboxylic acid ethyl ester;
2-cyano($^{13}C$)acetic acid;
1-$^{13}C$-2-cyanoacetic acid;
2-$^{13}C$-2-cyanoacetic acid; and
1-deutero-3-(diethylamino)-2-fluoroacrylaldehyde;

In one or more embodiments, $Y^{12}$, $Y^{13}$, $Y^{14}$, $Y^{15}$, $Y^{16}$, $Y^{17}$, $Y^{18}$, and $Y^{19}$ are deuterium, and $Y^1$, $Y^2$, $Y^3$, $Y^4$, $Y^5$, $Y^6$, $Y^7$, $Y^8$, $Y^9$, $Y^{10}$, and $Y^{11}$ are independently selected from hydrogen or deuterium. In another embodiment $Y^{12}$, $Y^{13}$, $Y^{14}$, $Y^{15}$, $Y^{16}$, $Y^{17}$, $Y^{18}$, and $Y^{19}$ are deuterium, and $Y^1$, $Y^2$, $Y^3$, $Y^4$, $Y^5$, $Y^6$, $Y^7$, $Y^8$, $Y^9$, $Y^{10}$, and $Y^{11}$ are hydrogen.

In yet another embodiment, $X^1$, $X^2$, $X^4$, $X^5$, $X^6$, $X^7$, $X^8$, and $X^9$ are $^{12}C$; and $X^3$ is —$^{12}C(O)$—. In still other embodiments, $X^1$, $X^4$, $X^5$, $X^6$, $X^7$, $X^8$, and $X^9$ are $^{12}C$; $X^3$ is —$^{13}C(O)$—; and $X^2$ is $^{13}C$.

In some embodiments, $Y^{11}$, $Y^{12}$, $Y^{13}$, $Y^{14}$, $Y^{15}$, $Y^{16}$, $Y^{17}$, $Y^{18}$, and $Y^{19}$ are deuterium, and $Y^1$, $Y^2$, $Y^3$, $Y^4$, $Y^5$, $Y^6$, $Y^7$, $Y^8$, $Y^9$, and $Y^{10}$ are independently selected from hydrogen or deuterium. In other embodiments, $Y^{11}$, $Y^{12}$, $Y^{13}$, $Y^{14}$, $Y^{15}$, $Y^{16}$, $Y^{17}$, $Y^{18}$, and $Y^{19}$ are deuterium, and $Y^1$, $Y^2$, $Y^3$, $Y^4$, $Y^5$, $Y^6$, $Y^7$, $Y^8$, $Y^9$, and $Y^{10}$ are hydrogen.

In yet another embodiment, $Y^2$, $Y^{12}$, $Y^{13}$, $Y^{14}$, $Y^{15}$, $Y^{16}$, $Y^{17}$, $Y^{18}$, and $Y^{19}$ are deuterium, and $Y^1$, $Y^3$, $Y^4$, $Y^5$, $Y^6$, $Y^7$, $Y^8$, $Y^9$, $Y^{10}$, and $Y^{11}$ are independently selected from hydrogen or deuterium. In another aspect of the invention, $Y^2$, $Y^{12}$, $Y^{13}$, $Y^{14}$, $Y^{15}$, $Y^{16}$, $Y^{17}$, $Y^{18}$, and $Y^{19}$ are deuterium, and $Y^1$, $Y^3$, $Y^4$, $Y^5$, $Y^6$, $Y^7$, $Y^8$, $Y^9$, $Y^{10}$, and $Y^{11}$ are hydrogen.

In some embodiments, $Y^{12}$, $Y^{13}$, $Y^{18}$, and $Y^{19}$ are deuterium, and $Y^1$, $Y^2$, $Y^3$, $Y^4$, $Y^5$, $Y^6$, $Y^7$, $Y^8$, $Y^9$, $Y^{10}$, $Y^{11}$, $Y^{14}$, $Y^{15}$, $Y^{16}$, and $Y^{17}$ are hydrogen or deuterium. In still other embodiments, $Y^{12}$, $Y^{13}$, $Y^{18}$, and $Y^{19}$ are deuterium, and $Y^1$, $Y^2$, $Y^3$, $Y^4$, $Y^5$, $Y^6$, $Y^7$, $Y^8$, $Y^9$, $Y^{10}$, $Y^{11}$, $Y^{14}$, $Y^{16}$, and $Y^{17}$ are hydrogen.

In one or more embodiments, $Y^3$, $Y^4$, $Y^5$, $Y^6$, $Y^7$, $Y^8$, $Y^9$, $Y^{10}$, and $Y^{11}$ are deuterium, and $Y^1$, $Y^2$, $Y^{12}$, $Y^{13}$, $Y^{14}$, $Y^{15}$, $Y^{16}$, $Y^{17}$, $Y^{18}$, and $Y^{19}$ are independently selected from deuterium or hydrogen. In another embodiment, $Y^3$, $Y^4$, $Y^5$, $Y^6$, $Y^7$, $Y^8$, $Y^9$, $Y^{10}$, and $Y^{11}$ are deuterium $Y^1$, $Y^2$, $Y^{12}$, $Y^{13}$, $Y^{14}$, $Y^{15}$, $Y^{16}$, $Y^{17}$, $Y^{18}$, and $Y^{19}$ are hydrogen.

In yet another embodiment, $Y^2$ and $Y^{11}$ are deuterium, and $Y^1$, $Y^3$, $Y^4$, $Y^5$, $Y^6$, $Y^7$, $Y^8$, $Y^9$, $Y^{10}$, $Y^{12}$, $Y^{13}$, $Y^{14}$, $Y^{15}$, $Y^{16}$, $Y^{17}$, $Y^{18}$, and $Y^{19}$ are deuterium or hydrogen. In other embodiments, $Y^2$ and $Y^{11}$ are deuterium, and $Y^1$, $Y^3$, $Y^4$, $Y^5$, $Y^6$, $Y^7$, $Y^8$, $Y^9$, $Y^{10}$, $Y^{12}$, $Y^{13}$, $Y^{14}$, $Y^{15}$, $Y^{16}$, $Y^{17}$, $Y^{18}$, and $Y^{19}$ are hydrogen.

In some embodiments $Y^2$ is deuterium, and $Y^1$, $Y^3$, $Y^4$, $Y^5$, $Y^6$, $Y^7$, $Y^8$, $Y^9$, $Y^{10}$, $Y^{12}$, $Y^{13}$, $Y^{14}$, $Y^{15}$, $Y^{16}$, $Y^{17}$, $Y^{18}$, and $Y^{19}$ are deuterium or hydrogen. In another embodiment, $Y^2$ is deuterium, and $Y^1$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, and $Y^{19}$ are hydrogen.

In still other embodiments, $X^1$, $X^2$, $X^4$, $X^5$, $X^6$, $X^7$, and $X^8$ are $^{12}C$; $X^3$ is —$^{12}C(O)$—; and $X^9$ is $^{13}C$. In another embodiment, $X^1$, $X^2$, $X^8$, and $X^9$ are $^{12}C$; $X^3$ is —$^{12}C(O)$—; and $X^4$, $X^5$, $X^6$, and $X^7$ are $^{13}C$. In yet another embodiment, $X^2$, $X^4$, $X^5$, $X^6$, $X^7$, $X^8$, and $X^9$ are $^{12}C$; $X^3$ is —$^{12}C(O)$—; and $X^1$ is $^{13}C$. In other embodiments, $X^2$, $X^4$, $X^5$, $X^6$, $X^7$, $X^8$, and $X^9$ are $^{12}C$; $X^3$ is —$^{13}C(O)$—; and $X^1$ and $X^8$ are $^{13}C$.

In some embodiments, $Y^{11}$ is deuterium, and $Y^1$, $Y^2$, $Y^3$, $Y^4$, $Y^5$, $Y^6$, $Y^7$, $Y^8$, $Y^9$, $Y^{10}$, $Y^{12}$, $Y^{13}$, $Y^{14}$, $Y^{15}$, $Y^{16}$, $Y^{17}$, $Y^{18}$, and $Y^{19}$ are independently selected from hydrogen or deuterium. In another embodiment $Y^{11}$ is deuterium and $Y^1$, $Y^2$, $Y^3$, $Y^4$, $Y^5$, $Y^6$, $Y^7$, $Y^8$, $Y^9$, $Y^{10}$, $Y^{12}$, $Y^{13}$, $Y^{14}$, $Y^{15}$, $Y^{16}$, $Y^{17}$, $Y^{18}$, and $Y^{19}$ are hydrogen.

In yet another embodiment, $X^1$, $X^4$, $X^5$, $X^6$, $X^7$, $X^8$, and $X^9$ are $^{12}C$; $X^3$ is —$^{12}C(O)$—; and $X^2$ is $^{13}C$.

In another example, the compounds of formula I-B of this invention are represented in Table 1. It will be appreciated by those skilled in the art that the compounds of the present invention may be represented in varying tautomeric forms.

TABLE 1

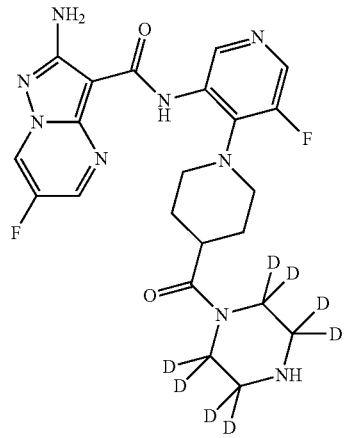 [SMILES: [2H]C1([2H])NC([2H])([2H])C([2H])([2H])N(C(=O)C2CCN(c3c(F)cncc3NC(=O)c3c(N)nn4cc(F)cnc34)CC2)C1([2H])[2H]]

I-2

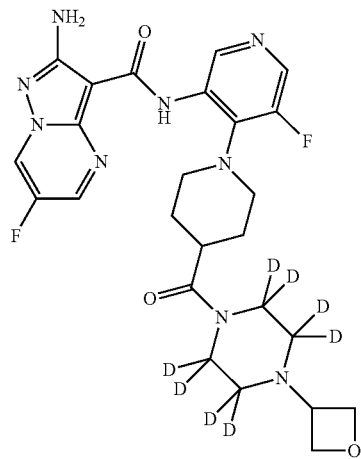 [SMILES: [2H]C1([2H])N(C(=O)C2CCN(c3c(F)cncc3NC(=O)c3c(N)nn4cc(F)cnc34)CC2)C([2H])([2H])C([2H])([2H])N(C2COC2)C1([2H])[2H]]

I-3

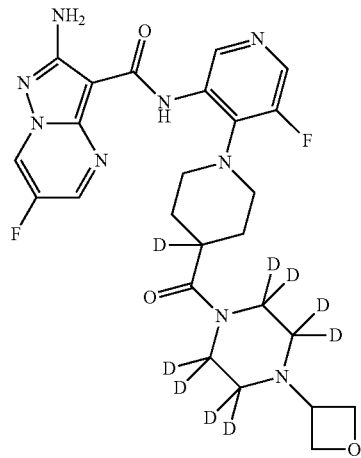 [SMILES: [2H]C1(C(=O)N2C([2H])([2H])C([2H])([2H])N(C3COC3)C([2H])([2H])C2([2H])[2H])CCN(c2c(F)cncc2NC(=O)c2c(N)nn3cc(F)cnc23)CC1]

I-4

TABLE 1-continued
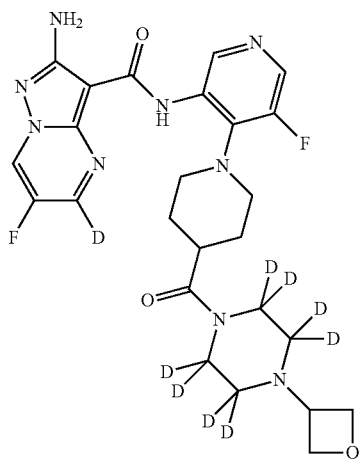
I-5
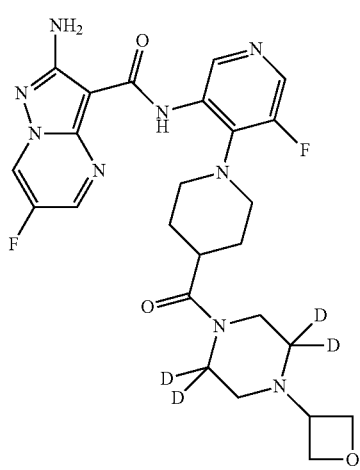 [SMILES: [2H]C1([2H])CN(C2COC2)C([2H])([2H])CN1C(=O)C1CCN(c2c(F)cncc2NC(=O)c2c(N)nn3cc(F)cnc23)CC1]
I-6
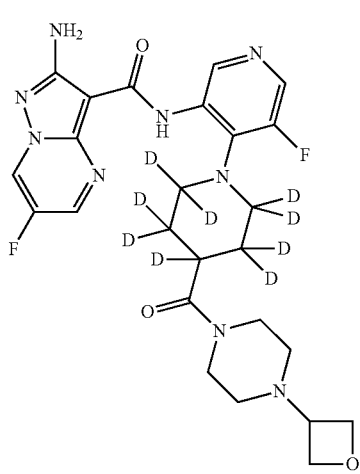
I-7
TABLE 1-continued
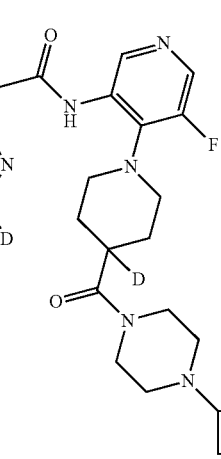
I-8
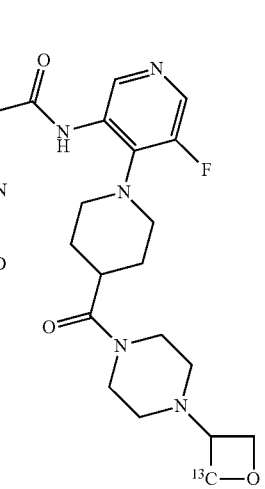
I-9
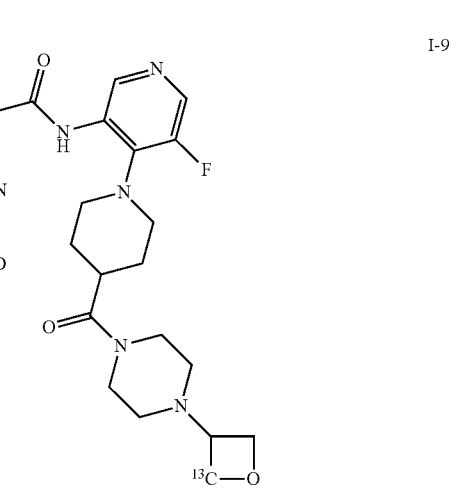
I-10

TABLE 1-continued

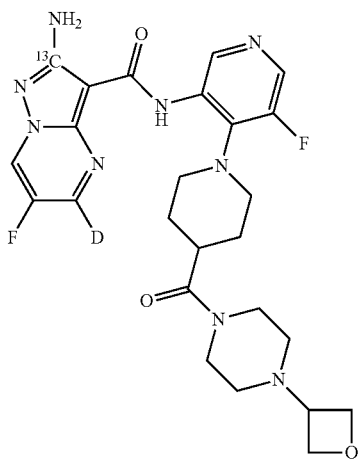

I-11

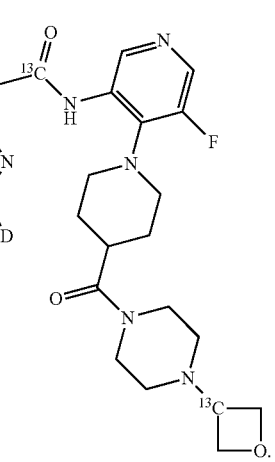

I-14

Solid Forms

Another aspect of the present invention provides a solid form of a compound of formula I-1:

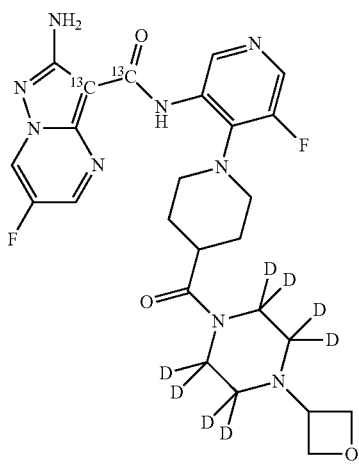

I-12

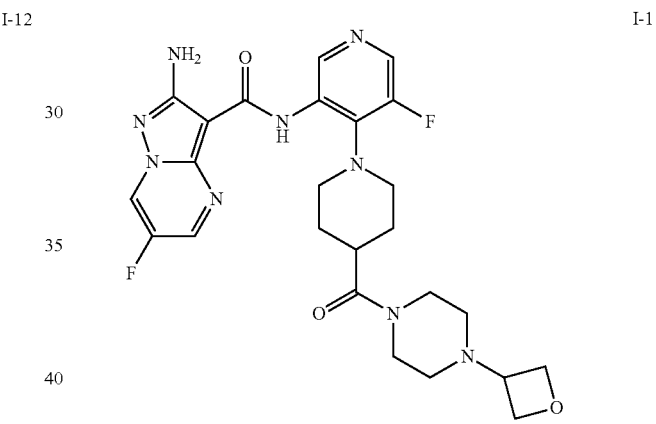

I-1 wherein the form is selected from the group consisting of Compound I-1•ethanol solvate, Compound I-1•hydrate I, Compound I-1•hydrate II, Compound I-1•anhydrous form A, Compound I-1•anhydrous form B, Compound I-1•anhydrous form C, Compound I-1•DMSO solvate, Compound I-1•DMAC solvate, Compound I-1•acetone solvate, and Compound I-1•isopropanol solvate.

Compound I-1•Ethanol Solvate

In some aspects of the present inventions, the solid form is Compound I-1•ethanol solvate. In another aspect of the present invention, the solid form is crystalline Compound I-1•ethanol solvate. In still other embodiments, crystalline Compound I-1•ethanol solvate has a Compound I-1 to ethanol ratio of about 1:0.72. In another aspect of the present invention, the crystalline Compound I-1•ethanol solvate is characterized by a weight loss of from about 5.76% in a temperature range of from about 166° C. to about 219° C. In yet another aspect of the present invention, the crystalline Compound I-1•ethanol solvate is characterized by one or more peaks expressed in 2-theta±0.2 at about 17.2, 19.7, 23.8, 24.4, and 29.0 degrees in an X-Ray powder diffraction pattern obtained using Cu K alpha radiation. In other

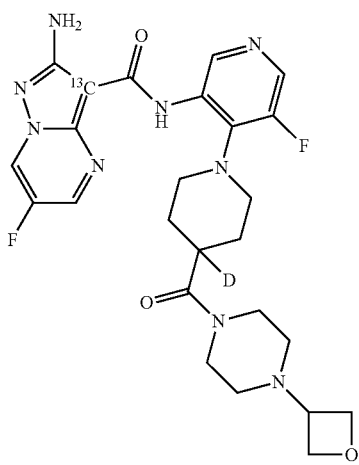 [SMILES: [2H]C1(C(=O)N2CCN(C3COC3)CC2)CCN(c2c(F)cncc2NC(=O)[13c]2c(N)nn3cc(F)cnc23)CC1]

I-13 embodiments, the crystalline Compound I-1•ethanol solvate is characterized as having an X-ray powder diffraction pattern substantially the same as that shown in FIG. 1a. In still other embodiments, the crystalline Compound I-1•ethanol solvate is characterized as having one or more peaks corresponding to 175.4±0.3 ppm, 138.0±0.3 ppm, 123.1±0.3 ppm, 57.8±0.3 ppm, 44.0±0.3 ppm, and 19.5±0.3 ppm in a $C^{13}$ ssNMR spectrum. In yet another embodiment, the crystalline Compound I-1•ethanol solvate is characterized as having one or more peaks corresponding to −136.0±0.3 ppm and −151.6±0.3 ppm in an $F^{19}$ ssNMR spectrum.

Compound I-1•Hydrate I

In some aspects of the present invention, the solid form is Compound I-1•hydrate I. In another aspect of the present invention, the solid form is crystalline Compound I-1•hydrate I. In still other embodiments, the crystalline Compound I-1•hydrate I has a compound I-1 to $H_2O$ ratio of about 1:4.5. In yet another embodiment, crystalline Compound I-1•hydrate I is characterized by a weight loss of from about 14.56% in a temperature range of from about 25° C. to about 100° C. In other embodiments, crystalline Compound I-1•hydrate I is characterized by one or more peaks expressed in 2-theta±0.2 at about 6.5, 12.5, 13.7, 18.8, and 26.0 degrees in an X-Ray powder diffraction pattern obtained using Cu K alpha radiation. In another embodiment, crystalline Compound I-1•hydrate I is characterized as having an X-ray powder diffraction pattern substantially the same as that shown in FIG. 1b.

Compound I-1•Hydrate II

In some aspects of the present invention, the solid form is Compound I-1•hydrate II. In another aspect of the present invention, the solid form is crystalline Compound I-1•hydrate II. In other embodiments, crystalline Compound I-1•hydrate II is characterized by one or more peaks expressed in 2-theta±0.2 at about 10.1, 11.3, 11.9, 20.2, and 25.1 degrees in an X-Ray powder diffraction pattern obtained using Cu K alpha radiation. In still other embodiments, the crystalline Compound I-1•hydrate II is characterized as having one or more peaks corresponding to 177.0±0.3 ppm, 158.2±0.3 ppm, 142.9±0.3 ppm, 85.1±0.3 ppm, 58.9±0.3 ppm, and 31.9±0.3 ppm in a $C^{13}$ ssNMR spectrum. In yet another embodiment, the crystalline Compound I-1•hydrate II is characterized as having one or more peaks corresponding to −138.0±0.3 ppm and −152.7±0.3 ppm in an $F^{19}$ ssNMR spectrum.

Compound I-1•Anhydrous Form A

In one embodiment, the solid form is Compound I-1•anhydrous form A. In another embodiment, the solid form is crystalline Compound I-1•anhydrous form A. In still other embodiments, crystalline Compound I-1•anhydrous form A is characterized by a weight loss of from about 0.96% in a temperature range of from about 25° C. to about 265° C. In other embodiments, crystalline Compound I-1•anhydrous form A is characterized by one or more peaks expressed in 2-theta±0.2 at about 6.1, 12.2, 14.5, 22.3, and 31.8 degrees in an X-Ray powder diffraction pattern obtained using Cu K alpha radiation. In yet another embodiment, the crystalline Compound I-1•anhydrous form A is characterized as having an X-ray powder diffraction pattern substantially the same as that shown in FIG. 1c. In still other embodiments, the crystalline Compound I-1•anhydrous form A is characterized as having one or more peaks corresponding to 175.9±0.3 ppm, 138.9±0.3 ppm, 74.1±0.3 ppm, 42.8±0.3 ppm, and 31.5±0.3 ppm in a $C^{13}$ ssNMR spectrum. In yet another embodiment, the crystalline Compound I-1•anhydrous form A is characterized as having one or more peaks corresponding to −136.8±0.3 ppm and −155.7±0.3 ppm in an $F^{19}$ ssNMR spectrum. One embodiment describes a process for preparing Compound I-1•anhydrous form A comprising stirring a suspension containing Compound I-1•ethanol solvate and a suitable organic solvent. In another embodiment, the suitable organic solvent is tetrahydrofuran. Another aspect of the invention describes a process for preparing Compound I-1•anhydrous form A comprising stirring a suspension containing Compound I-1•amorphous, isopropanol, and water. In some embodiments, the suspension is heated to between about 65° C. and about 80° C. In yet another embodiment, the suspension is heated to between about 70° C. and about 75° C. In other embodiments, Compound I-1•anhydrous form A is characterized as a crystal form of Compound I-1 having a monoclinic crystal system, a $P2_1/c$ centrosymmetric space group, and the following unit cell parameters:
a=15.29(3)Å α=90°
b=12.17(2)Å β=107.22(3)°
c=14.48(3)Å×γ=90°.

Compound I-1•Anhydrous Form B

As used herein, "anhydrous form B" refers to the THF solvate form of Compound I-1. In some embodiments, the solid form is Compound I-1•anhydrous form B. In another embodiment, the solid form is crystalline Compound I-1•anhydrous form B. In yet another embodiment crystalline Compound I-1•anhydrous form B is characterized by a weight loss of from about 2.5% in a temperature range of from about 25° C. to about 175° C. In other embodiments, Compound I-1•anhydrous form B is characterized by one or more peaks expressed in 2-theta±0.2 at about 7.2, 8.3, 12.9, 19.5, and 26.6 degrees in an X-Ray powder diffraction pattern obtained using Cu K alpha radiation. In still other embodiments, crystalline Compound I-1•anhydrous form B is characterized as having an X-ray powder diffraction pattern substantially the same as that shown in FIG. 1d. In still other embodiments, the crystalline Compound I-1•anhydrous form B is characterized as having one or more peaks corresponding to 173.4±0.3 ppm, 164.5±0.3 ppm, 133.5±0.3 ppm, 130.8±0.3 ppm, 67.7±0.3 ppm, 45.3±0.3 ppm, and 25.9±0.3 ppm in a $C^{13}$ ssNMR spectrum. In yet another embodiment, the crystalline Compound I-1•anhydrous form B is characterized as having one or more peaks corresponding to −138.0±0.3 ppm and −153.5±0.3 ppm in an $F^{19}$ ssNMR spectrum.

Compound I-1•Anhydrous Form C

In some embodiments, the solid form is Compound I-1•anhydrous form C.

In another embodiment, the solid form is crystalline Compound I-1•anhydrous form C. In other embodiments, crystalline Compound I-1•anhydrous form C is characterized by one or more peaks expressed in 2-theta±0.2 at about 6.8, 13.4, 15.9, 30.9, and 32.9 degrees in an X-Ray powder diffraction pattern obtained using Cu K alpha radiation. In still other embodiments, crystalline Compound I-1•anhydrous form C is characterized as having an X-ray powder diffraction pattern substantially the same as that shown in FIG. 1 *e*. In still other embodiments, the crystalline Compound I-1•anhydrous form C is characterized as having one or more peaks corresponding to 175.2±0.3 ppm, 142.5±0.3 ppm, 129.6±0.3 ppm, 73.5±0.3 ppm, 54.0±0.3 ppm, and 46.7±0.3 ppm in a $C^{13}$ ssNMR spectrum. In yet another embodiment, the crystalline Compound I-1•anhydrous form C is characterized as having one or more peaks corresponding to −131.2±0.3 ppm and −150.7±0.3 ppm in an $F^{19}$ ssNMR spectrum.

Compound I-1•Amorphous

In some embodiments, the solid form is Compound I-1•amorphous. In another embodiment, the solid form is crystalline Compound I-1•amorphous. In still other embodiments, the crystalline Compound I-1•amorphous is characterized as having one or more peaks corresponding to 173.8±0.3 ppm, 144.2±0.3 ppm, 87.5±0.3 ppm, 45.6±0.3 ppm, and 29.5±0.3 ppm in a $C^{13}$ ssNMR spectrum. In yet another embodiment, the crystalline Compound I-1•amorphous is characterized as having one or more peaks corresponding to −137.7±0.3 ppm and −153.1±0.3 ppm in an $F^{19}$ ssNMR spectrum.

Compound I-1•DMSO Solvate

In one embodiment, the solid form is Compound I-1•DMSO solvate. In another embodiment, the solid form is crystalline Compound I-1•DMSO solvate. In still other embodiments, the crystalline Compound I-1•DMSO solvate has a compound I-1• to DMSO ratio of about 1:1. In yet another embodiment, crystalline Compound I-1•DMSO solvate is characterized by a weight loss of from about 12.44% in a temperature range of from about 146° C. to about 156° C. In some embodiments, crystalline Compound I-1•DMSO solvate characterized by one or more peaks expressed in 2-theta±0.2 at about 8.9, 14.8, 16.5, 18.6, 20.9, 22.2, and 23.4 degrees in an X-Ray powder diffraction pattern obtained using Cu K alpha radiation. In other embodiments, compound I-1•DMSO solvate is characterized as having an X-ray powder diffraction pattern substantially the same as that shown in FIG. 1*g*.

Compound I-1•DMAC Solvate

In some embodiments, the solid form is Compound I-1•DMAC solvate. In another embodiment, the solid form is crystalline Compound I-1•DMAC solvate. In other embodiments, the crystalline Compound I-1•DMAC solvate has a compound I-1 to DMAC ratio of about 1:1.3. In yet another embodiment, crystalline compound I-1•DMAC solvate is characterized by a weight loss of from about 17.76% in a temperature range of from about 85° C. to about 100° C. In still other embodiments, compound I-1•DMAC solvate is characterized by one or more peaks expressed in 2-theta±0.2 at about 6.0, 15.5, 17.7, 18.1, 20.4, and 26.6 degrees in an X-Ray powder diffraction pattern obtained using Cu K alpha radiation. In some embodiments, compound I-1•DMAC solvate is characterized as having an X-ray powder diffraction pattern substantially the same as that shown in FIG. 1*h*.

Compound I-1•Acetone Solvate

In one or more embodiments, the solid form is Compound I-1•acetone solvate. In another embodiment, the solid form is crystalline Compound I-1•acetone solvate. In yet another embodiment, the crystalline Compound I-1•acetone solvate has a compound I-1 to acetone ratio of about 1:0.44. In still other embodiment, Compound I-1•acetone solvate is characterized by a weight loss of from about 4.55% in a temperature range of from about 124° C. to about 151° C. In some embodiments, Compound I-1•acetone solvate is characterized by one or more peaks expressed in 2-theta±0.2 at about 8.9, 15.5, 15.8, 16.7, 22.3, 25.7, and 29.0 degrees in an X-Ray powder diffraction pattern obtained using Cu K alpha radiation. In other embodiments, Compound I-1•acetone solvate is characterized as having an X-ray powder diffraction pattern substantially the same as that shown in FIG. 1*i*.

Compound I-1•Isopropanol Solvate

In one embodiment, the solid form is Compound I-1•isopropanol solvate. In another embodiment, the solid form is crystalline Compound I-1•isopropanol solvate. In still other embodiments, crystalline Compound I-1•isopropanol solvate has a Compound I-1 to isopropanol ratio of about 1:0.35. In yet another embodiment, Compound I-1•isopropanol solvate is characterized by a weight loss of from about 3.76% in a temperature range of from about 136° C. to about 180° C. In some embodiments, Compound I-1•isopropanol solvate is characterized by one or more peaks expressed in 2-theta±0.2 at about 6.9, 17.1, 17.2, 19.1, 19.6, 23.7, 24.4, and 28.9 degrees in an X-Ray powder diffraction pattern obtained using Cu K alpha radiation. In another embodiment, Compound I-1•isopropanol solvate is characterized as having an X-ray powder diffraction pattern substantially the same as that shown in FIG. 1*j*.

Formulation

Some embodiments disclosed herein generally relate to a composition that can include an effective amount of Compound I-1, or a pharmaceutically acceptable salt thereof; and one or more excipients. Compound I-1 is believed to be an ATR inhibitor, and described in WO 2014/089379, which is hereby incorporated by reference in its entirety.

Compound I-1 and Form A can exist in free form or as a salt. Those salts that are pharmaceutically acceptable can be useful in administering Compound I-1 or Form A for medical purposes. Salts that are not pharmaceutically acceptable can be useful for manufacturing, isolating, purifying and/or separating stereoisomeric forms of Compound I-1, Form A and/or one or more intermediates thereof.

As used herein, the term "pharmaceutically acceptable salt" refers to a salt of a compound, which are, within the scope of sound medical judgment, suitable for use in humans and lower animals without undue side effects, such as, toxicity, irritation, allergic response and the like, and are commensurate with a reasonable benefit/risk ratio. Various pharmaceutically acceptable salts can be used. For example, those salts disclosed in S. M. Berge et al., *J. Pharmaceutical Sciences,* 1977, 66, 1-19, which is hereby incorporated by reference. Pharmaceutically acceptable salts of the compounds described herein include those derived from suitable inorganic and organic acids and bases. A salt of a compound described herein (for example, Compound I-1) can be prepared in situ during the final isolation and purification of the compound.

As described above, Compound I-1 can exist in different polymorphic forms (i.e., "solid forms"). Polymorphism is the ability of a compound to exist as more than one distinct crystalline or "polymorphic" species, wherein each species has a different arrangement of its molecules in the crystal lattice. Each distinct crystalline species is a "polymorph."

Each polymorph has the same chemical formula, however, can be display different physical property(ies) as a result of its different arrangement in the crystal lattice. Polymorphs can be characterized by analytical methods such as X-ray powder diffraction (XRPD) pattern, thermogravimetric analysis (TGA), differential scanning calorimetry (DSC), melting point, and/or other techniques known in the art.

Form A, described herein, can be in pure form or in a mixture with other materials. Examples of other materials include, for example, other forms of Compound I-1 (such as amorphous forms, other polymorphic forms, solvates and hydrates); other diastereomers of Compound I-1; and/or other materials besides Compound I-1.

Thus, in some embodiments, a composition can include an effective amount of pure Form A. As used herein, "pure" Form A is over 95% (w/w) (wherein w/w is weight of Form A/weight of Compound I-1 (wherein weight of Compound I-1 is weight of Form A+weight of all other forms of Compound I-1)), for example, over 98% (w/w), over 99% (w/w %), over 99.5% (w/w %), or over 99.9% (w/w %). In some embodiments, a composition can include an effective amount of Form A in an amount at least 95% (w/w %), at least 97% (w/w %) or at least 99% (w/w %) free of any other diastereomers of Compound I-1. In some embodiments, a composition can include an effective amount of Form A in an amount at least 95% (w/w %), at least 97% (w/w %) or at least 99% (w/w %) free of any other polymorphs and amorphous forms of Compound I-1.

In some embodiments, a composition can include Form A with one or more other forms of Compound I-1. Other forms of Compound I-1 include, for example, hydrates, solvates, amorphous forms, other polymorphic forms, or combinations thereof.

In some embodiments, a composition can include an amount of Compound I-1 or Form A (or a pharmaceutically acceptable salt of the aforementioned compounds) in the range of a trace amount (0.1%) up to 100% (w/w %) relative to the total weight of the composition. In some embodiments, a composition can include less than about 50% of Compound I-1 or Form A relative to the total weight of the composition (wherein the total weight includes the weight of Compound I-1 or Form A). For example, a composition can include an amount of Compound I-1 or Form A in a range selected from 0.1%-0.5%, 0.1%-1%, 0.1%-2%, 0.1%-5%, 0.1%-10%, 0.1%-20%, 0.1%-30%, 0.1%-40%, and 0.1%-<50% (w/w %) relative to the total weight of the composition (wherein the total weight includes the weight of Compound I-1 or Form A). In other embodiments, a composition can include equal to or greater than about 50% of Compound I-1 or Form A relative to the total weight of the composition (wherein the total weight includes the weight of Compound I-1 or Form A). For example, a composition can include at least 50%, 60%, 70%, 80%, 90%, 95%, 97%, 98%, 99%, 99.5% or 99.9% (w/w) of Compound I-1 or Form A relative to the total weight of the composition (wherein the total weight includes the weight of Compound I-1 or Form A). In some embodiments, a composition can include an amount of Compound I-1 or Form A in the range of about 1 wt % to about 50 wt %; about 5 wt % to about 40 wt %, about 5 wt % to about 25 wt % or about 5 wt % to about 15 wt % of Compound I-1 or Form A relative to the total weight of the composition (wherein the total weight includes the weight of Compound I-1 or Form A).

As used herein, an "excipient" is used herein in its ordinary sense as understood by those skilled in the art, and includes one or more inert substances that are included in a composition to provide, without limitation, bulk, consistency, stability, binding ability, lubrication, disintegrating ability etc., to the composition. Examples of excipients include fillers, binders, disintegrants, wetting agents, lubricants, glidants, humectants and absorbants.

In some embodiments, a composition can include Compound I-1 or Form A and one or more other components selected from one or more fillers, one or more binders, one or more disintegrants, one or more wetting agents and one or more lubricants. In some embodiments, a composition can include an amount of one or more fillers in the range of about 10 wt % to about 95 wt %; about 25 wt % to about 90 wt %; about 50 wt % to about 90 wt %; or about 70 wt % to about 90 wt % of the filler(s) by total weight of the composition (wherein the total weight includes the weight of one or more fillers). In some embodiments, a composition can include an amount of one or more lubricants in the range of about 0.1 wt % to about 10 wt %, about 0.5 wt % to about 7 wt %, or about 1 wt % to about 5 wt % of the lubricant(s) by total weight of the composition (wherein the total weight includes the weight of one or more lubricants). In some embodiments, a composition can include an amount of one or more disintegrants in the range of about 1 wt % to about 15 wt %, about 1 wt % to about 10 wt %, or about 1 wt % to about 7 wt % of the disintegrant(s) by total weight of the composition (wherein the total weight includes the weight of one or more disintegrants).

The wetting agents, binders, disintegrants, lubricants and fillers suitable for inclusion can be compatible with the ingredients of the compositions, for example, they do not substantially reduce the chemical stability of the active pharmaceutical ingredient(s).

The term "wetting agent" is used herein in its ordinary sense as understood by those skilled in the art, and includes surfactants, such as non-ionic surfactants and anionic surfactants. Wetting agents can enhance the solubility of the composition. Exemplary surfactants include sodium lauryl sulfate (SLS), polyoxyethylene sorbitan fatty acids (e.g., TWEEN™), sorbitan fatty acid esters (e.g., Spans®), sodium dodecylbenzene sulfonate (SDBS), dioctyl sodium sulfosuccinate (Docusate), dioxycholic acid sodium salt (DOSS), sorbitan monostearate, sorbitan tristearate, sodium N-lauroylsarcosine, sodium oleate, sodium myristate, sodium stearate, sodium palmitate, Gelucire 44/14, ethylenediamine tetraacetic acid (EDTA), Vitamin E d-alpha tocopheryl polyethylene glycol 1000 succinate (TPGS), Lecithin, MW 677-692, Glutanic acid monosodium monohydrate, Labrasol, PEG 8 caprylic/capric glycerides, Transcutol, diethylene glycol monoethyl ether, Solutol HS-15, polyethylene glycol/hydroxystearate, Taurocholic Acid, copolymers of polyoxypropylene and polyoxyethylene (e.g., poloxamers also known and commercially available under Pluronics®, such as, Pluronic® L61, Pluronic® F68, Pluronic® F108, and Pluronic® F127), saturated polyglycolized glycerides (Gelucirs®), docusate sodium, polyoxyethylene sorbitan fatty acid esters, polyoxyethylene 20 stearyl ethers, polyoxyethylene alkyl ethers, polyoxyethylene castor oil derivatives, pegylated hydrogenated castor oils, sorbitan esters of fatty acids, Vitamin E or tocol derivatives, vitamin E TPGS, tocopheryl esters, lecithin, phospholipids and their derivatives, stearic acid, oleic acid, oleic alcohol, cetyl alcohol, mono and diglycerides, propylene glycol esters of fatty acids, glycerol esters of fatty acids, ethylene glycol palmitostearate, polyoxylglycerides, propylene glycol monocaprylate, propylene glycol monolaurate, polyglyceryl oleate and any combinations thereof. Sodium lauryl sulfate is an anionic surfactant; and copolymers of polyoxypropylene and polyoxyethylene are non-ionic surfactants. Specific examples of copolymers of polyoxypropylene and polyoxyethylene include poloxamers, such as a poloxamer with a polyoxypropylene molecular mass of 1,800 g/mol and a 80% polyoxyethylene content (e.g., poloxamer 188).

The term "binder" is used herein in its ordinary sense as understood by those skilled in the art, and includes agents used while making granules of the active ingredient (for example, Compound I-1 or Form A), wherein a binder holds the active ingredient together with one or more inactive agents. Exemplary binders include polyvinyl pyrrolidones (PVPs), pregelatinized starch, starch, microcrystalline cellulose, modified cellulose (e.g., hydroxyl propyl methyl cellulose (HPMC), hydroxypropyl cellulose (HPC) and hydroxy ethyl cellulose (HEC)), and any combination thereof. PVP's are commonly characterized by the "K-value," which is a measurement of the polymeric composition's viscosity. PVPs can be commercially purchased (e.g., Tokyo Chemical Industry Co., Ltd.) under the trade name of Povidone® K12, Povidone® K17, Povidone® K25, Povidone® K30, Povidone® K60, and Povidone® K90. Specific examples of PVPs include soluble spray dried PVP. PVPs can have an average molecular weight of 3,000 daltons to 4,000 daltons, such as Povidone® K12 having an average molecular weight of 4,000 daltons. PVP can be used in either a wet or a dry state.

The term "filler" (or "diluent") is used herein in its ordinary sense as understood by those skilled in the art, and includes microcrystalline celluloses (e.g., Avicel® PH 101), lactoses, sorbitols, celluoses, calcium phosphates, starches, sugars (e.g., mannitol, sucrose, or the like), dextrose, maltodextrin, sorbitol, xylitol, powdered cellulose, silicified microcrystalline cellulose, methylcellulose, ethylcellulose, hydroxyethylcellulose, methylhydroxyethylcellulose, pregelatinized starch, dibasic calcium phosphate, calcium sulfate, calcium carbonate and any combination thereof. Specific examples of fillers include microcrystalline celluloses and lactoses. Specific examples of microcrystalline celluloses include commercially available Avicel® series, such as microcrystalline celluloses having a particle size of 200 mesh over 70% and a particle size of 65 mesh less than 10% (e.g., Avicel® PH 101). A specific example of a lactose is lactose monohydrate.

The term "disintegrant" is used herein in its ordinary sense as understood by those skilled in the art, and can enhance the dispersal of a composition. Examples of disintegrants include croscarmellose sodium, starch (e.g., corn starch, potato starch), sodium starch glycolate, crospovidone, microcrystalline cellulose, sodium alginate, calcium alginate, alginic acid, pregelatinized starch, cellulose and its derivatives, carboxymethylcellulose calcium, carboxymethylcellulose sodium, soy polysaccharide, guar gum, ion exchange resins, an effervescent system based on food acids and an alkaline carbonate component, sodium bicarbonate and any combinations thereof. Specific examples of disintegrants include croscarmellose sodium (e.g., Ac-Di-Sol®) and sodium starch glycolate.

The term "lubricant" is used herein in its ordinary sense as understood by those skilled in the art, and can improve the compression and ejection of a composition, e.g., through a die press. Exemplary lubricants include magnesium stearate, stearic acid (stearin), hydrogenated oils, sodium stearyl fumarate, sodium lauryl sulfate, talc, fatty acid, calcium stearate, sodium stearate, glyceryl monostearate, fatty alcohol, fatty acid ester, glyceryl behenate, mineral oil, vegetable oil, leucine, sodium benzoate and any combination thereof. A specific example of a lubricant is sodium stearyl fumarate.

Those skilled in the art understand that a specific compound described as a wetting agent, binder, filler, disintegrant and lubricant can serve one or more purpose. For example, microcrystalline cellulose can be used as a disintegrant and filler.

In some embodiments, a composition can include an amount of Compound I-1 or Form A in the range of about 5 wt % to about 50 wt % by the total weight of the composition; and an amount of one or more fillers in the range of about 10 wt % to about 90 wt % by the total weight of the composition. In other embodiments, a composition can include an amount of Compound I-1 or Form A in the range of about 5 wt % to about 50 wt % by the total weight of the composition; an amount of one or more fillers in the range of about 10 wt % to about 90 wt % by the total weight of the composition; and an amount of one or more disintegrants in the range of about 1 wt % to about 15 wt % by the total weight of the composition. In still other embodiments, a composition can include an amount of Compound I-1 or Form A in the range of about 5 wt % to about 50 wt % by the total weight of the composition; an amount of one or more fillers in the range of about 10 wt % to about 90 wt % by the total weight of the composition; an amount of one or more disintegrants in the range of about 1 wt % to about 15 wt % by the total weight of the composition; and an amount of one or more lubricants in the range of about 0.1 wt % to about 10 wt % by the total weight of the composition.

In some embodiments, a composition can include an amount of Compound I-1 or Form A in the range of about 5 wt % to about 20 wt % by the total weight of the composition; an amount of one or more lubricants in the range of about 1 wt % to about 5 wt % by the total weight of the composition; an amount of one or more disintegrants in the range of about 1 wt % to about 10 wt % by the total weight of the composition; and an amount of one or more fillers in the range of about 70 wt % to about 90 wt % by the total weight of the composition. In other embodiments, a composition can include an amount of Compound I-1 or Form A in the range of about 5 wt % to about 15 wt % by the total weight of the composition; an amount of one or more lubricants in the range of about 1 wt % to about 5 wt % by the total weight of the composition; an amount of one or more disintegrants in the range of about 1 wt % to about 5 wt % by the total weight of the composition; and an amount of one or more fillers in the range of about 70 wt % to about 90 wt % by the total weight of the composition.

In some embodiments, a composition can include an amount of Compound I-1 or Form A of about 10 wt % by the total weight of the composition, an amount of lactose monohydrate of about 28 wt % by the total weight of the composition, an amount of Avicel PH-101 (microcrystalline cellulose) of about 55 wt % by the total weight of the composition, an amount of Ac-Di-Sol (croscarmellose sodium) of about 5 wt % by the total weight of the composition, and an amount of sodium stearyl fumarate of about 3 wt % by the total weight of the composition.

In some embodiments, a composition can further include one or more glidants (or "flow aids"). A glidant enhances the flow properties of a composition by reducing interparticle friction and cohesion. Exemplary glidants include colloidal silicon dioxide, talc, and any combination thereof. A specific example of glidant is amorphous, colloidal silicon dioxide having an average particle size in 0.2-0.3 microns, such as Cab-O-Sil® M5P. The amount of a glidant can vary. For example, the amount of glidant(s) can be in the range of about 0.1 wt % to about 3 wt %, or about 0.1 wt % to about 1 wt % by total weight of the composition (wherein the total weight includes the weight of one or more glidants).

In some embodiments, a composition described herein can further include a coating.

In some embodiments, a composition described herein can be in a solid dosage form, for example, a tablet.

Some embodiments described herein relate to a method of preparing a composition described herein. In some embodiments, a method can include providing a mixture that includes Compound I-1 or Form A and one or more fillers to form a composition. In other embodiments, a method can include providing a mixture that includes Compound I-1 or Form A, a lubricant, a disintegrant, and a filler to form a composition. Examples, including specific examples, of lubricants, disintegrants, and fillers are each and independently described herein.

In some embodiments, a method can include combining Compound I-1 or Form A and one or more first excipients to form a mixture; and combining the mixture (that includes Compound I-1 or Form A and one or more first excipients) with one or more second excipients. In some embodiments, the first excipients can include one or more of the following: one or more fillers, one or more disintegrants, and one or more lubricants. In some embodiments, the second excipients can include one or more of the following: one or more disintegrants and one or more lubricants.

In other embodiments, a method of preparing a composition described herein can include: i) combining Compound I-1 or Form A with one or more first excipients that can include one or more fillers, one or more disintegrants and one or more lubricants, and ii) combining the mixture from i) with one or more second excipients that can include one more disintegrants and one or more lubricants to form a composition. In some embodiments, the one or more first excipients can include an amount of one or more fillers in the range of about 70 wt % to about 90 wt %, an amount of one or more disintegrants in the range of about 1 wt % to about 15 wt %, and an amount of one or more lubricants in the range of about 1 wt % to about 5 wt % each by the total weight of the composition, and the second excipients can include an amount of one or more lubricants in the range of about 0.5 wt % to about 5 wt % and an amount of one or more disintegrants in the range of about 0.5 wt % to about 5 wt % each by the total weight of the composition.

In some embodiments, a method of preparing a composition described herein can include: i) providing granules of Compound I-1 or Form A by combining Compound I-1 or Form A with first excipients that may include one or more fillers, one or more disintegrants, and one or more lubricants; and ii) mixing the granules of Compound I-1 or Form A obtained from i) with second excipients that may include one or more disintegrants and one or more lubricants and optionally one or more fillers to form a composition. In some embodiments, the first excipients can include an amount of one or more fillers in the range of about 70 wt % to about 90 wt %, an amount of one or more disintegrants in the range of about 0.5 wt % to about 5 wt %, and an amount of a first lubricant in the range of about 1% to about 5% each by the total weight of the composition; and the second excipients can include an amount of one or more second lubricants in the range of about 0.5 wt % to about 5 wt % and an amount of one or more disintegrants in the range of about 0.5 wt % to about 5 wt % each by the total weight of the composition. Examples, including specific examples, of suitable lubricants, disintegrants, and fillers are described herein.

In some embodiments, a method of preparing a composition described herein can include passing Compound I-1 or Form A through a sieve; mixing granules of Compound I-1 or Form A with one or more fillers, one or more disintegrants, and one or more lubricants; and blending the resulting granules with one or more disintegrants and one or more lubricants.

In some embodiments, a method of preparing a composition described herein can include compressing granules that include Compound I-1 or Form A through a tablet compression machine to form a tablet that includes Compound I-1 or Form A.

In some embodiments, a tablet that can include Compound I-1 or Form A (for example, the tablets obtained after tablet compression) can be film coated.

The compositions described herein may further include one or more pharmaceutically acceptable carriers other than those described previously. As used herein, "pharmaceutically acceptable" means being inert without unduly inhibiting the biological activity of the compounds. The pharmaceutically acceptable carriers should be biocompatible, e.g., non-toxic, non-inflammatory, non-immunogenic or devoid of other undesired reactions or side-effects upon the administration to a subject. Further, standard pharmaceutical formulation techniques can be employed for integrating the aforementioned one or more pharmaceutically acceptable carriers.

Some examples of materials which can serve as pharmaceutically acceptable carriers include, but are not limited to, ion exchangers; alumina; aluminum stearate; lecithin; serum proteins (such as human serum albumin); buffer substances (such as phosphates or glycine); partial glyceride mixtures of saturated vegetable fatty acids; water; salts or electrolytes (such as protamine sulfate, disodium hydrogen phosphate, potassium hydrogen phosphate, sodium chloride, or zinc salts); colloidal silica; magnesium trisilicate; polyacrylates; waxes; polyethylene-polyoxypropylene-block polymers; methylcellulose; hydroxypropyl methylcellulose; wool fat; sugars such as glucose; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; phosphate buffer solutions; other non-toxic compatible lubricants; coloring agents; releasing agents; sweetening; flavoring agents; perfuming agents; preservatives; sorbents and antioxidants can also be present in the composition, according to the judgment of the formulator.

Some embodiments described herein relate to a method of inhibiting or reducing the activity of ATR in a subject that can include administering to the subject a composition described herein that contains an effective amount of Compound I-1 or Form A, or a pharmaceutically acceptable salt the aforementioned compounds.

Other embodiments described herein relate to a method of treating cancer in a subject that can include administering to the subject a composition described herein that contains an effective amount of Compound I-1 or Form A, or a pharmaceutically acceptable salt the aforementioned compounds.

Yet still other embodiments described herein relate to an use of a composition described herein that contains an effective amount of Compound 1 or Form A, or a pharmaceutically acceptable salt the aforementioned compounds, in the manufacture of a medicament for treating cancer.

In some embodiments, substantially all by weight of Compound I-1 in a composition described herein can be Form A.

In some embodiments, at least 90% by weight of Compound I-1 in a composition described herein can be Form A.

In some embodiments, at least 95% by weight of Compound I-1 in a composition described herein can be Form A.

In some embodiments, at least 98% by weight of Compound I-1 in a composition described herein can be Form A.

In some embodiments, at least 99% by weight of Compound I-1 in a composition described herein can be Form A.

The compositions described herein can be administered to humans and other animals orally, rectally, parenterally, intracisternally, intravaginally, intraperitoneally, topically (as by powders, ointments, or drops), bucally, as an oral or nasal spray, or the like. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. In some embodiments, a composition described herein can be administered orally, intraperitoneally and/or intravenously.

Any orally acceptable dosage form including, but not limited to, capsules, tablets, aqueous suspensions or solutions. In the case of tablets, suitable carriers used include, but are not limited to, lactose and corn starch. Lubricating agents, such as magnesium stearate, and/or wetting agents can be added. When aqueous suspensions are used, the active ingredient can be combined with emulsifying and/or suspending agents. If desired, sweetening, flavoring, coloring agents and/or perfuming agents can be included.

Liquid dosage forms for oral administration include, but are not limited to, pharmaceutically acceptable emulsions, microemulsions, solutions, suspensions, syrups and elixirs. In addition to the active compound, the liquid dosage forms may contain inert excipients, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (such as, cottonseed, groundnut, corn, germ, olive, castor, and sesame oils), glycerol, tetrahydrofurfuryl alcohol, polyethylene glycols and fatty acid esters of sorbitan, and mixtures thereof.

Solid dosage forms for oral administration include capsules (for example, soft and hard-filled gelatin capsules), tablets, pills, powders, and granules. In such solid dosage forms, the active compound can be mixed with at least one inert, pharmaceutically acceptable excipient or carrier such as sodium citrate or dicalcium phosphate and/or a) fillers such as starches, lactose, milk sugar, sucrose, glucose, mannitol, and silicic acid, b) binders such as, for example, carboxymethylcellulose, alginates, gelatin, polyvinyl pyrrolidone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also include a buffering agent.

The solid dosage forms of tablets, dragees, capsules, pills, and granules can be prepared with coatings and shells such as enteric coatings and other coatings known in the pharmaceutical formulating art. They may optionally contain opacifying agents and can also be of a composition that can release the active ingredient(s) only, or preferentially, in a certain part of the intestinal tract, optionally, in a delayed manner. Examples of embedding compositions that can be used include polymeric substances and waxes. The active compound(s) can be in a microencapsulated form with one or more excipients.

Sterile injectable forms may be aqueous or oleaginous suspension. Injectable preparations may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in propylene glycol. Among the acceptable vehicles and solvents that may be employed are water, Ringer's solution, U.S.P. and isotonic sodium chloride solution. In addition, sterile, fixed oils can be employed as a solvent or suspending medium. For this purpose any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Dosage forms for topical or transdermal administration include ointments, pastes, creams, lotions, gels, powders, solutions, sprays, inhalants and patches. The active component can be admixed under sterile conditions with a pharmaceutically acceptable carrier, and any preservatives and/or buffers may be included. Ophthalmic formulation, eardrops, and eye drops can be formulated. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Alternatively, the active compounds and pharmaceutically acceptable compositions thereof may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Surfactants, such as Tweens, Spans and other emulsifying agents or bioavailability enhancers can be included in a solid, liquid and other dosage forms described herein.

The compositions described herein can be formulated in an unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose. The amount of the active compound in a unit dosage form will vary depending upon, for example, the host treated, and the particular mode of administration, for example, from 0.01 mg/kg body weight/dose to 100 mg/kg body weight/dose.

In some embodiments, a compositions described herein can be in the form of a solid dosage form. In some embodiments, a composition described herein can be in the form of a tablet. In still other embodiments, the composition may be in the form of a 100 mg tablet, or a 500 mg tablet.

It will be appreciated that the amount of the active compound (for example, Compound I-1 or Form A) required for use in treatment will vary not only with the particular compound selected but also with the route of administration, the nature of the condition for which treatment is required and the age and condition of the subject and will be ultimately at the discretion of the attendant physician or veterinarian. In general, however, a suitable dose will be in the range of from about 0.1 to about 100 mg/kg of body weight per dose, for example, in the range of 0.5 to 50 mg/kg/dose, or, for example, in the range of 1 to 10 mg/kg/dose.

In some embodiments, a composition described herein can be administered in an amount in the range of about 5 mg to about 100 mg of Compound I-1 or Form A, or a pharmaceutically acceptable salt the aforementioned compounds, per dose.

In some embodiments, a composition described herein can be administered:
  a) in an amount of about 5 mg Compound I-1 or Form A, or a pharmaceutically acceptable salt the aforementioned compounds, per dose;
  b) in an amount of about 10 mg Compound I-1 or Form A, or a pharmaceutically acceptable salt the aforementioned compounds, per dose;
  c) in an amount of about 20 mg Compound I-1 or Form A, or a pharmaceutically acceptable salt the aforementioned compounds, per dose;
  d) in an amount of about 30 mg Compound I-1 or Form A, or a pharmaceutically acceptable salt the aforementioned compounds, per dose;
  e) in an amount of about 50 mg Compound I-1 or Form A, or a pharmaceutically acceptable salt the aforementioned compounds, per dose;
  f) in an amount of about 60 mg Compound I-1 or Form A, or a pharmaceutically acceptable salt the aforementioned compounds, per dose;
  g) in an amount of about 80 mg Compound I-1 or Form A, or a pharmaceutically acceptable salt the aforementioned compounds, per dose; or
  h) in an amount of about 100 mg Compound I-1 or Form A, or a pharmaceutically acceptable salt the aforementioned compounds, per dose.

In some embodiments, a composition described herein can be administered in a fasted state (for example, the subject has not eaten food or liquids, except for water, for at least 8 hours). In other embodiments, a composition described herein can be administered in a fed state (for example, with food or within 1 hour of eating food).

Compound Uses

One aspect of this invention provides compounds or compositions that are inhibitors of ATR kinase, and thus are useful for treating or lessening the severity of a disease, condition, or disorder in a subject or patient where ATR is implicated in the disease, condition, or disorder.

Another aspect of this invention provides compounds or compositions that are useful for the treatment of diseases, disorders, and conditions characterized by excessive or abnormal cell proliferation. Such diseases include a proliferative or hyperproliferative disease. Examples of proliferative and hyperproliferative diseases include, without limitation, cancer and myeloproliferative disorders.

In some embodiments, said compounds are selected from compound I-1 or Form A. In other embodiments, said compositions include compound I-1 or Form A. The term "cancer" includes, but is not limited to the following cancers. Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: non-small cell, bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological/Female: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma, undifferentiated thyroid cancer, medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

In some embodiments, the cancer is selected from a cancer of the lung or the pancreas. In other embodiments, the cancer is selected from lung cancer, head and neck cancer, pancreatic cancer, gastric cancer, or brain cancer. In yet other embodiments, the cancer is selected from non-small cell lung cancer, small cell lung cancer, pancreatic cancer, biliary tract cancer, head and neck cancer, bladder cancer, colorectal cancer, glioblastoma, esophageal cancer, breast cancer, hepatocellular carcinoma, or ovarian cancer.

In some embodiments, the cancer is lung cancer. In other embodiments, the lung cancer is non-small cell lung cancer or small cell lung cancer. In another embodiment, the cancer is non-small cell lung cancer. In yet another embodiment, the non-small cell lung cancer is squamous non-small cell lung cancer.

Thus, the term "cancerous cell" as provided herein, includes a cell afflicted by any one of the above-identified conditions. In some embodiments, the cancer is selected from colorectal, thyroid, or breast cancer. In other embodiments, the cancer is triple negative breast cancer.

The term "myeloproliferative disorders", includes disorders such as polycythemia vera, thrombocythemia, myeloid metaplasia with myelofibrosis, hypereosinophilic syndrome, juvenile myelomonocytic leukemia, systemic mast cell disease, and hematopoietic disorders, in particular, acute-myelogenous leukemia (AML), chronic-myelogenous leukemia (CML), acute-promyelocytic leukemia (APL), and acute lymphocytic leukemia (ALL).

Combination Therapies

Another aspect of this invention is directed towards a method of treating cancer in a subject in need thereof, comprising administration of a compound or composition of this invention or a pharmaceutically acceptable salt thereof, and an additional therapeutic agent. In some embodiments, said method comprises the sequential or co-administration of the compound or composition (or a pharmaceutically acceptable salt thereof), and the additional therapeutic agent.

As used herein, the term "in combination" or "co-administration" can be used interchangeably to refer to the use of more than one therapy (e.g., one or more therapeutic agents). The use of the term does not restrict the order in which therapies (e.g., therapeutic agents) are administered to a subject or the dosing schedule of each therapeutic agent.

In some embodiments, said additional therapeutic agent is an anti-cancer agent. In other embodiments, said additional therapeutic agent is a DNA-damaging agent. In yet other embodiments, said additional therapeutic agent is selected from radiation therapy, chemotherapy, or other agents typically used in combination with radiation therapy or chemotherapy, such as radiosensitizers and chemosensitizers. In yet other embodiments, said additional therapeutic agent is ionizing radiation.

As would be known by one of skill in the art, radiosensitizers are agents that can be used in combination with radiation therapy. Radiosensitizers work in various different ways, including, but not limited to, making cancer cells more sensitive to radiation therapy, working in synergy with radiation therapy to provide an improved synergistic effect, acting additively with radiation therapy, or protecting surrounding healthy cells from damage caused by radiation therapy. Likewise chemosensitizers are agents that can be used in combination with chemotherapy. Similarly, chemosensitizers work in various different ways, including, but not limited to, making cancer cells more sensitive to chemotherapy, working in synergy with chemotherapy to provide an improved synergistic effect, acting additively to chemotherapy, or protecting surrounding healthy cells from damage caused by chemotherapy.

Examples of DNA-damaging agents that may be used in combination with compounds or compositions of this invention include, but are not limited to Platinating agents, such as Cisplatin, Carboplatin, Nedaplatin, Satraplatin and other derivatives; Topo I inhibitors, such as Topotecan, irinotecan/SN38, rubitecan and other derivatives; Antimetabolites, such as Folic family (Methotrexate, Pemetrexed and relatives); Purine antagonists and Pyrimidine antagonists (Thioguanine, Fludarabine, Cladribine, Cytarabine, Gemcitabine, 6-Mercaptopurine, 5-Fluorouracil (5FU) and relatives); Alkylating agents, such as Nitrogen mustards (Cyclophosphamide, Melphalan, Chlorambucil, mechlorethamine, Ifosfamide and relatives); nitrosoureas (eg Carmustine); Triazenes (Dacarbazine, temozolomide); Alkyl sulphonates (eg Busulfan); Procarbazine and Aziridines; Antibiotics, such as Hydroxyurea, Anthracyclines (doxorubicin, daunorubicin, epirubicin and other derivatives); Anthracenediones (Mitoxantrone and relatives); Streptomyces family (Bleomycin, Mitomycin C, actinomycin); and Ultraviolet light.

In some embodiments, the additional therapeutic agent is ionizing radiation. In other embodiments, the additional therapeutic agent is Cisplatin or Carboplatin. In yet other embodiments, the additional therapeutic agent is Etoposide. In yet other embodiments, the additional therapeutic agent is Temozolomide. In still other embodiments, the additional therapeutic agent is irinotecan/SN38.

In certain embodiments, the additional therapeutic agent is selected from one or more of the following: Cisplatin, Carboplatin, irinotecan/SN38, gemcitabine, Etoposide, Temozolomide, or ionizing radiation.

Other therapies or anticancer agents that may be used in combination with the inventive compounds and compositions of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, the DNA damaging agents listed herein, spindle poisons (Vinblastine, Vincristine, Vinorelbine, Paclitaxel), podophyllotoxins (Etoposide, Irinotecan, Topotecan), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide.

A compound or composition of the instant invention may also be useful for treating cancer in combination with any of the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2 CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (Depo-Cyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®)); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®) valrubicin (Valstar®); vinblastine (Velban®); vincristine (Oncovin®); vinorelbine (Navelbine®); zoledronate (Zometa®) and vorinostat (Zolinza®).

For a comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Another embodiment provides administering a compound or composition of this invention with an additional therapeutic agent that inhibits or modulates a base excision repair protein. In some embodiments, the base excision repair protein is selected from UNG, SMUG1, MBD4, TDG, OGG1, MYH, NTH1, MPG, NEIL1, NEIL2, NEIL3 (DNA glycosylases); APE1, APEX2 (AP endonucleases); LIG1, LIG3 (DNA ligases I and III); XRCC1 (LIG3 accessory); PNK, PNKP (polynucleotide kinase and phosphatase); PARP1, PARP2 (Poly(ADP-Ribose) Polymerases); PolB, PolG (polymerases); FEN1 (endonuclease) or Aprataxin. In other embodiments, the base excision repair protein is selected from PARP1, PARP2, or PolB. In yet other embodiments, the base excision repair protein is selected from PARP1 or PARP2. In some embodiments, the agent is selected from Olaparib (also known as AZD2281 or KU-0059436), Iniparib (also known as BSI-201 or SAR240550), Veliparib (also known as ABT-888), Rucaparib (also known as PF-01367338), CEP-9722, INO-1001, MK-4827, E7016, BMN673, or AZD2461.

Methods of Treatment

One aspect of the invention relates to a method of inhibiting ATR kinase activity in a patient, which method comprises administering to the patient a compound described herein, or a composition comprising said compound. In some embodiments, said method is used to treat or prevent a condition selected from proliferative and hyperproliferative diseases, such as cancer.

In some embodiments, the cancer is selected from the cancers described herein. In some embodiments, said cancer is lung cancer, head and neck cancer, pancreatic cancer, gastric cancer, or brain cancer. In other embodiments, the cancer is selected from a cancer of the lung or the pancreas.

In yet other embodiments, the cancer is selected from non-small cell lung cancer, small cell lung cancer, pancreatic cancer, biliary tract cancer, head and neck cancer, bladder cancer, colorectal cancer, glioblastoma, esophageal cancer, breast cancer, hepatocellular carcinoma, or ovarian cancer.

In some embodiments, the lung cancer is small cell lung cancer and the additional therapeutic agents are cisplatin and etoposide. In other examples, the lung cancer is non-small cell lung cancer and the additional therapeutic agents are gemcitabine and cisplatin. In yet other embodiments, the non-small cell lung cancer is squamous non-small cell lung cancer. In another embodiment, the cancer is breast cancer and the additional therapeutic agent is cisplatin. In other embodiments, the cancer is triple negative breast cancer.

In certain embodiments, an "effective amount" of the compound or pharmaceutically acceptable composition is that amount effective in order to treat said disease. The compounds and compositions, according to the method of the present invention, may be administered using any amount and any route of administration effective for treating or lessening the severity of said disease.

One aspect provides a method for inhibiting ATR in a patient comprising administering a compound or composition as described herein. Another embodiment provides a method of treating cancer comprising administering to a patient a compound or composition described herein, wherein the variables are as defined herein.

Another embodiment provides methods for treating pancreatic cancer by administering a compound or composition described herein in combination with another known pancreatic cancer treatment. One aspect of the invention includes administering a compound or composition described herein in combination with gemcitabine. In some embodiments, the pancreatic cancer comprises one of the following cell lines: PSN-1, MiaPaCa-2 or Panc-1. According to another aspect, the cancer comprises one of the following primary tumor lines: Panc-M or MRC5.

Another aspect of the invention includes administering a compound or composition described herein in combination with radiation therapy. Yet another aspect provides a method of abolishing radiation-induced G2/M checkpoint by administering a compound or composition described herein in combination with radiation treatment.

Another aspect provides a method of treating pancreatic cancer by administering to pancreatic cancer cells a compound or composition described herein in combination with one or more cancer therapies. In some embodiments, the compound or composition is combined with chemoradiation, chemotherapy, and/or radiation therapy. As would be understood by one of skill in the art, "chemoradiation" refers to a treatment regime that includes both chemotherapy (such as gemcitabine) and radiation. In some embodiments, the chemotherapy is gemcitabine.

Yet another aspect provides a method of increasing the sensitivity of pancreatic cancer cells to a cancer therapy selected from gemcitabine or radiation therapy by administering a compound or composition described herein in combination with the cancer therapy.

In some embodiments, the cancer therapy is gemcitabine. In other embodiments, the cancer therapy is radiation therapy. In yet another embodiment the cancer therapy is chemoradiation.

Another aspect provides a method of inhibiting phosphorylation of Chk1 (Ser 345) in a pancreatic cancer cell comprising administering a compound or composition described herein after treatment with gemcitabine (100 nM) and/or radiation (6 Gy) to a pancreatic cancer cell.

Another aspect provides a method of disrupting damage-induced cell cycle checkpoints by administering a compound or composition described herein in combination with radiation therapy to a cancer cell.

Another aspect provides a method of inhibiting repair of DNA damage by homologous recombination in a cancer cell by administering a compound or composition described herein in combination with one or more of the following treatments: chemoradiation, chemotherapy, and radiation therapy.

In some embodiments, the chemotherapy is gemcitabine.

Another aspect provides a method of inhibiting repair of DNA damage by homologous recombination in a cancer cell by administering a compound or composition described herein in combination with gemcitabine and radiation therapy.

Another aspect of the invention provides a method of treating non-small cell lung cancer comprising administering to a patient a compound or composition described herein in combination with one or more of the following additional therapeutic agents: Cisplatin or Carboplatin, Etoposide, and ionizing radiation. Some embodiments comprise administering to a patient a compound described herein in combination with Cisplatin or Carboplatin, Etoposide, and ionizing radiation. In some embodiments the combination is Cisplatin, Etoposide, and ionizing radiation. In other embodiments the combination is Carboplatin, Etoposide, and ionizing radiation.

Another embodiment provides a method of promoting cell death in cancer cells comprising administering to a patient a compound described herein, or a composition comprising said compound.

Yet another embodiment provides a method of preventing cell repair of DNA damage in cancer cells comprising administering to a patient a compound described herein, or a composition comprising said compound. Yet another embodiment provides a method of preventing cell repair caused by of DNA damage in cancer cells comprising administering to a patient a compound of the present invention, or composition comprising said compound.

Another embodiment provides a method of sensitizing cells to DNA damaging agents comprising administering to a patient a compound described herein, or a composition comprising said compound.

In some embodiments, the method is used on a cancer cell having defects in the ATM signaling cascade. In some embodiments, said defect is altered expression or activity of one or more of the following: ATM, p53, CHK2, MRE11, RAD50, NBS1, 53BP1, MDC1, H2AX, MCPH1/BRIT1, CTIP, or SMC1. In other embodiments, said defect is altered expression or activity of one or more of the following: ATM, p53, CHK2, MRE11, RAD50, NBS1, 53BP1, MDC1 or H2AX. According to another embodiment, the method is used on a cancer, cancer cell, or cell expressing DNA damaging oncogenes.

In another embodiment, the cell is a cancer cell expressing DNA damaging oncogenes. In some embodiments, said cancer cell has altered expression or activity of one or more of the following: K-Ras, N-Ras, H-Ras, Raf, Myc, Mos, E2F, Cdc25A, CDC4, CDK2, Cyclin E, Cyclin A and Rb.

According to another embodiment, the method is used on a cancer, cancer cell, or cell has a defect in a protein involved in base excision repair ("base excision repair protein"). There are many methods known in the art for determining whether a tumor has a defect in base excision repair. For example, sequencing of either the genomic DNA or mRNA products of each base excision repair gene (e.g., UNG, PARP1, or LIG1) can be performed on a sample of the tumor to establish whether mutations expected to modulate the function or expression of the gene product are present (Wang et al., Cancer Research 52:4824 (1992)). In addition to the mutational inactivation, tumor cells can modulate a DNA repair gene by hypermethylating its promoter region, leading to reduced gene expression. This is most commonly assessed using methylation-specific polymerase chain reaction (PCR) to quantify methylation levels on the promoters of base excision repair genes of interest. Analysis of base excision repair gene promoter methylation is available commercially (http://www.sabiosciences.com/dna_methylation_product/HTML/MEAH-421A.html).

Finally, the expression levels of base excision repair genes can be assessed by directly quantifying levels of the mRNA and protein products of each gene using standard techniques such as quantitative reverse transcriptase-coupled polymerase chain reaction (RT-PCR) and immunohistochemistry (IHC), respectively (Shinmura et al., Carcinogenesis 25: 2311 (2004); Shinmura et al., Journal of Pathology 225:414 (2011)).

In some embodiments, the base excision repair protein is UNG, SMUG1, MBD4, TDG, OGG1, MYH, NTH1, MPG, NEIL1, NEIL2, NEIL3 (DNA glycosylases); APE1, APEX2 (AP endonucleases); LIG1, LIG3 (DNA ligases I and III); XRCC1 (LIG3 accessory); PNK, PNKP (polynucleotide kinase and phosphatase); PARP1, PARP2 (Poly(ADP-Ribose) Polymerases); PolB, PolG (polymerases); FEN1 (endonuclease) or Aprataxin.

In some embodiments, the base excision repair protein is PARP1, PARP2, or PolB. In other embodiments, the base excision repair protein is PARP1 or PARP2.

The methods described above (gene sequence, promoter methylation and mRNA expression) may also be used to characterize the status (e.g., expression or mutation) of other genes or proteins of interesting, such DNA-damaging oncogenes expressed by a tumor or defects in the ATM signaling cascade of a cell.

Yet another embodiment provides use of a compound or composition described herein as a radio-sensitizer or a chemo-sensitizer.

Yet other embodiment provides use of a compound or composition described herein as a single agent (monotherapy) for treating cancer. In some embodiments, the compounds or compositions described herein are used for treating patients having cancer with a DNA-damage response (DDR) defect. In other embodiments, said defect is a mutation or loss of ATM, p53, CHK2, MRE11, RAD50, NBS1, 53BP1, MDC1, or H2AX.

Terminology

The terms "subject," "host," or "patient" includes an animal and a human (e.g., male or female, for example, a child, an adolescent, or an adult). Preferably, the "subject," "host," or "patient" is a human.

Compounds of this invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

Unless otherwise indicated, a substituent connected by a bond drawn from the center of a ring means that the substituent can be bonded to any position in the ring. In example i below, for instance, J$^w$ can be bonded to any position on the pyridyl ring. For bicyclic rings, a bond drawn through both rings indicates that the substituent can be bonded from any position of the bicyclic ring. In example ii below, for instance, J$^w$ can be bonded to the 5-membered ring (on the nitrogen atom, for instance), and to the 6-membered ring.

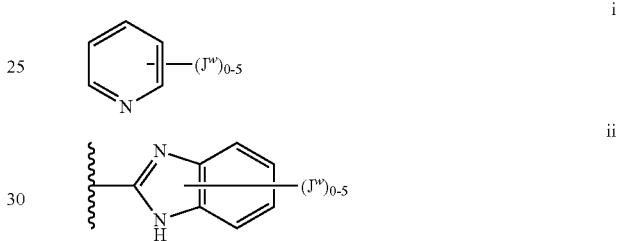

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "dative bond", as used herein, is defined as the coordination bond formed upon interaction between molecular species, one of which serves as a donor and the other as an acceptor of the electron pair to be shared in the complex formed.

The term "aliphatic" or "aliphatic group", as used herein, means a straight-chain (i.e., unbranched), branched, or cyclic, substituted or unsubstituted hydrocarbon chain that is completely saturated or that contains one or more units of unsaturation that has a single point of attachment to the rest of the molecule.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments, aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl. Aliphatic groups may also be cyclic, or have a combination of linear or branched and cyclic groups. Examples of such types of aliphatic groups include, but are not limited to cyclopropyl, cyclobutyl, cyclopentyl, cyclohexyl, cyclohexenyl, —CH₂-cyclopropyl, CH₂CH₂CH(CH₃)-cyclohexyl.

The term "cycloaliphatic" (or "carbocycle" or "carbocyclyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Examples of cycloaliphatic groups include, but are not limited to, cycloalkyl and cycloalkenyl groups. Specific examples include, but are not limited to, cyclohexyl, cyclopropyl, and cyclobutyl.

The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g. cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR' (as in N-substituted pyrrolidinyl)).

The term "unsaturated", as used herein, means that a moiety has one or more units of unsaturation. As would be known by one of skill in the art, unsaturated groups can be partially unsaturated or fully unsaturated. Examples of partially unsaturated groups include, but are not limited to, butene, cyclohexene, and tetrahydropyridine. Fully unsaturated groups can be aromatic, anti-aromatic, or non-aromatic. Examples of fully unsaturated groups include, but are not limited to, phenyl, cyclooctatetraene, pyridyl, thienyl, and 1-methylpyridin-2(1H)-one.

The term "alkoxy", or "thioalkyl", as used herein, refers to an alkyl group, as previously defined, attached through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. This term includes perfluorinated alkyl groups, such as —CF₃ and —CF₂CF₃.

The terms "halogen", "halo", and "hal" mean F, Cl, Br, or I.

The term "aryl" used alone or as part of a larger moiety as in "arylalkyl", "arylalkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroarylalkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Examples of heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

It shall be understood that the term "heteroaryl" includes certain types of heteroaryl rings that exist in equilibrium between two different forms. More specifically, for example, species such hydropyridine and pyridinone (and likewise hydroxypyrimidine and pyrimidinone) are meant to be encompassed within the definition of "heteroaryl."

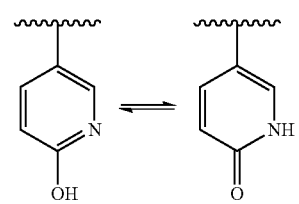 [SMILES: *c1ccc(O)nc1 ; *c1ccc(=O)[nH]c1]

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, a methylene unit of an alkyl or aliphatic chain is optionally replaced with another atom or group. Examples of such atoms or groups include, but are not limited to, nitrogen, oxygen, sulfur, —C(O)—, —C(=N—CN)—, —C(=NR)—, —C(=NOR)—, —SO—, and —SO$_2$—. These atoms or groups can be combined to form larger groups. Examples of such larger groups include, but are not limited to, —OC(O)—, —C(O)CO—, —CO$_2$—, —C(O)NR—, —C(=N—CN), —NRCO—, —NRC(O)O—, —SO$_2$NR—, —NRSO$_2$—, —NRC(O)NR—, —OC(O)NR—, and —NRSO$_2$NR—, wherein R is, for example, H or C$_{1-6}$aliphatic. It should be understood that these groups can be bonded to the methylene units of the aliphatic chain via single, double, or triple bonds. An example of an optional replacement (nitrogen atom in this case) that is bonded to the aliphatic chain via a double bond would be —CH$_2$CH=N—CH$_3$. In some cases, especially on the terminal end, an optional replacement can be bonded to the aliphatic group via a triple bond. One example of this would be CH$_2$CH$_2$CH$_2$C≡N. It should be understood that in this situation, the terminal nitrogen is not bonded to another atom.

It should also be understood that, the term "methylene unit" can also refer to branched or substituted methylene units. For example, in an isopropyl moiety [—CH(CH$_3$)$_2$], a nitrogen atom (e.g. NR) replacing the first recited "methylene unit" would result in dimethylamine [—N(CH$_3$)$_2$]. In instances such as these, one of skill in the art would understand that the nitrogen atom will not have any additional atoms bonded to it, and the "R" from "NR" would be absent in this case.

Unless otherwise indicated, the optional replacements form a chemically stable compound. Optional replacements can occur both within the chain and/or at either end of the chain; i.e. both at the point of attachment and/or also at the terminal end. Two optional replacements can also be adjacent to each other within a chain so long as it results in a chemically stable compound. For example, a C$_3$ aliphatic can be optionally replaced by 2 nitrogen atoms to form —C—N≡N. The optional replacements can also completely replace all of the carbon atoms in a chain. For example, a C$_3$ aliphatic can be optionally replaced by —NR—, —C(O)—, and —NR— to form —NRC(O)NR— (a urea).

Unless otherwise indicated, if the replacement occurs at the terminal end, the replacement atom is bound to a hydrogen atom on the terminal end. For example, if a methylene unit of —CH$_2$CH$_2$CH$_3$ were optionally replaced with —O—, the resulting compound could be —OCH$_2$CH$_3$, —CH$_2$OCH$_3$, or —CH$_2$CH$_2$OH. It should be understood that if the terminal atom does not contain any free valence electrons, then a hydrogen atom is not required at the terminal end (e.g., —CH$_2$CH$_2$CH=O or —CH$_2$CH$_2$C≡N).

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

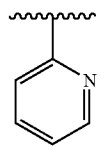

also represents

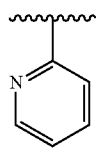

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

"D" and "d" both refer to deuterium.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

As used herein "crystalline" refers to a solid that has a specific arrangement and/or conformation of the molecules in the crystal lattice.

As used herein the term "amorphous" refers to solid forms that consist of disordered arrangements of molecules and do not possess a distinguishable crystal lattice.

As used herein, the term "solvate" refers to a crystalline solid adduct containing either stoichiometric or nonstoichiometric amounts of a solvent incorporated within the crystal structure. If the incorporated solvent is water, such adduct is referred to as a "hydrate".

Abbreviations

The following abbreviations are used:
DMSO dimethyl sulfoxide
DCM dichloromethane
ATP adenosine triphosphate
TFA trifluoroacetic acid
$^1$HNMR proton nuclear magnetic resonance
HPLC high performance liquid chromatography
LCMS liquid chromatography-mass spectrometry
Rt retention time
MTBE Methyl tert-butyl ether
XRPD X-Ray Powder Diffraction
DSC Differential scanning calorimetry TGA Thermogravimetric analysis
RT room temperature
NMP N-methyl-2-pyrrolidone
Bp boiling point
DMF dimethylformamide
PTSA p-Toluenesulfonic acid
DIPEA N,N-diisopropylethylamine
HOBT hydroxybenzotriazole
HATU 1-[Bis(dimethylamino)methylene]-1H-1,2,3-triazolo[4,5-b]pyridinium 3-oxid hexafluorophosphate
TBTU 2-(1H-benzotriazole-1-yl)-1,1,3,3-tetramethyluronium tetrafluoroborate
T3P Propylphosphonic anhydride
COMU 1-[(1-(Cyano-2-ethoxy-2-oxoethylideneaminooxy)-dimethylamino-morpholino)]uroniumhexafluorophosphate
TCTU [(6-chlorobenzotriazol-1-yl)oxy-(dimethylamino)methylene]-dimethyl-ammonium tetrafluoroborate
HBTU O-Benzotriazole-N,N,N',N'-tetramethyl-uronium-hexafluoro-phosphate
ECDI 1-Ethyl-3-(3-dimethylaminopropyl)carbodiimide
LDA Lithium diisopropylamide
CDI 1,1'-Carbonyldiimidazole
Processes Processes and compounds described herein are useful for producing ATR inhibitors that contain an aminopyrazolopyrimidine core. The general synthetic procedures shown in schemes herein are useful for generating a wide array of chemical species which can be used in the manufacture of pharmaceutical compounds.

Compounds of this invention can be synthesised according to methods similar to the one depicted in Scheme A.

Step 1

The anion of commercially available allyl cyanoacetate 1 can react with, e.g., trichloroacetonitrile to provide intermediate 2. In the anion condensation step, the anion of commercially available allyl cyanoacetate 1 can be generated with a base such as potassium acetate in an appropriate solvent such as an alcohol (e.g., isopropylalcohol). The anion then reacts with trichloroacetonitrile at room temperature.

Step 2

Intermediate 2 then reacts with hydrazine to form the diaminopyrazole 3. In the pyrazole formation step, intermediate 2 is reacted with hydrazine (or its hydrate) in an aprotic solvent, such as DMF, to provide the diaminopyrazole 3. The reaction occurs under basic conditions (e.g., in the presence of potassium acetate or AcONa) with heating (e.g., ≥110° C.) to ensure complete cyclisation.

Step 3

Intermediate 3 can further be condensed with a dielectrophilic coupling partner to form the pyrimidine 4a-c. In the pyrimidine formation step, intermediate 3 is reacted with a 1,3-dielectrophilic species (e.g., a 1,3-dialdehyde or a 3-(dialkylamino)-prop-2-enal) in various types of solvents (e.g., DMF or DMSO/water) to furnish the bicyclic cores 4a-c. When one or two of the electrophilic centers is protected/masked (e.g., aldehyde masked as a ketal), introduction of a sulfonic acid (e.g., PTSA) is required to liberate the reactive functional group.

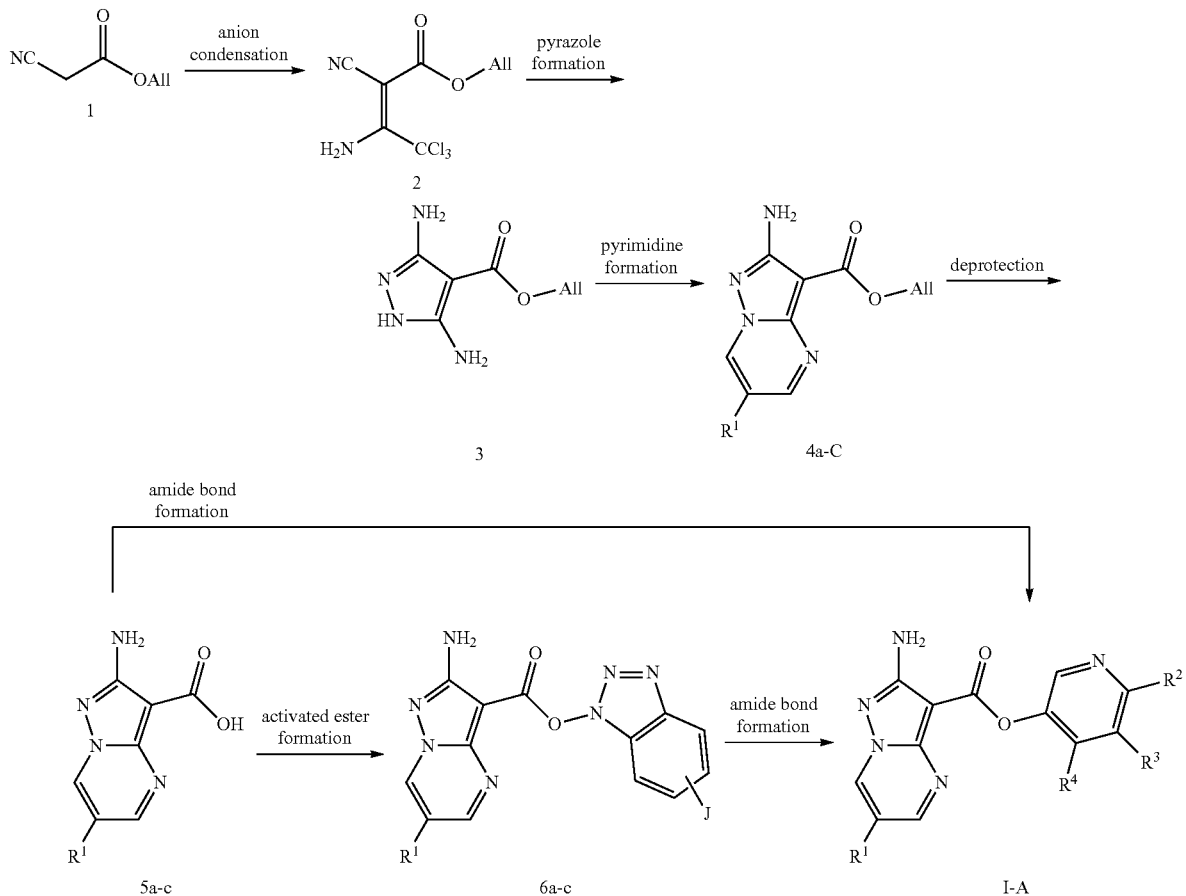

Step 4
Deprotection, e.g, via hydrolysis, of the allyl ester leads to the carboxylic acids 5a-c. In the deprotection step, compound 4a-c is subjected to hydrolytic conditions that are known to those skilled in the art. For example, treatment of 4a-c with phenylsilane or 4-methylbenzenesulfinate in the presence of a catalytic amount of palladium (e.g., Pd(PPh$_3$)$_4$) leads to the formation of the corresponding carboxylic acid 5a-c. Alternatively, compounds 4a-c could be treated with aqueous alkali (e.g., NaOH, LiOH, or KOH) to produce acids 5a-c.

Step 5

In the activated ester formation step, the carboxylic acids 5a-c are reacted with amide coupling agents known to those skilled in the art. Suitable amide coupling partners include, but are not limited to TBTU, TCTU, HATU, T3P, and COMU. When the coupling agent is chosen appropriately, the reactions can proceed rapidly (~1 hr.) at room temperature in the presence of an organic base such as an aliphatic amine (e.g., triethylamine, DIPEA) to provide the activated esters 6a-c. For example, when the amide coupling agents TBTU [J=H] or TCTU[J=Cl] are used, compounds 6a-c are obtained readily by filtration of the reaction mixture.

Formation of the activated esters 6a-c prior to the amide bond formation to prepare I-A is generally preferred, although a direct conversion of 5a-c into the compounds of formula I-A of this invention is also possible. Alternative activated esters can also be utilised (isolated or formed in situ) and will be known to those skilled in the art (e.g., using CDI, TBTU, TCTU, HATU, T3P, COMU coupling agents).

Step 6

In the amide bond formation step, activated esters 6a-c can react with a substituted or unsubstituted 3-aminopyridine to provide compounds of formula I-A of this invention. The reaction conditions for the amide coupling are generally in an aprotic solvent (e.g., NMP, pyridine, DMF, etc. . . . ) with heating (e.g., ≥90° C.). The 3-aminopyridine may be further functionalized following amide bond formation.

Alternatively, the two steps described above can be combined: carboxylic acids 5a-c can be used as starting points for the amide bond formation, the activated esters being generated in situ, using the same amide couplings agents as those described above. Compounds I-A of this invention are isolated in a similar manner to the one described above.

Scheme B

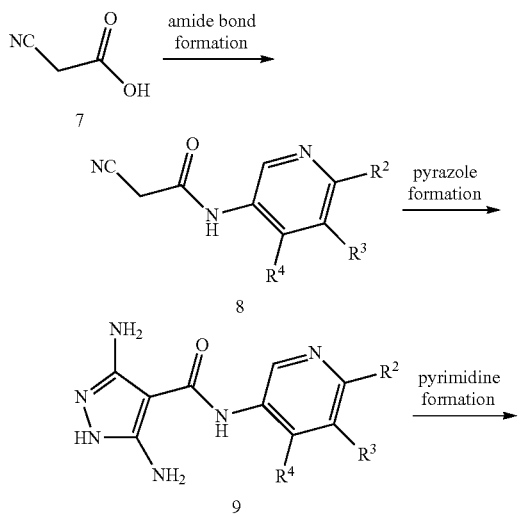

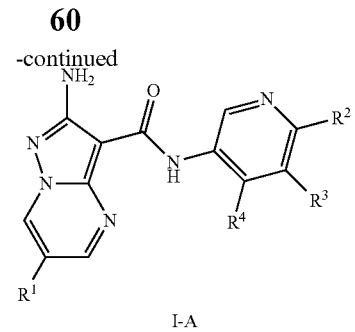

I-A

Alternatively, compounds of the present disclosure can be prepared according to methods similar to the one depicted in Scheme B.

Step 1

The amide 8 can readily be prepared from commercially available cyanoacetic acid 7. In the amide bond formation step, cyanoacetic acid 7 can react with a substituted 3-aminopyridine to provide compounds 8 of this invention. The reaction conditions for the amide coupling are generally in an aprotic solvent (e.g., DCM, NMP, DMF, etc), in the presence of an organic base, such as an aliphatic amine, (e.g., triethylamine or DIPEA) and an amide coupling agent known to those skilled in the art: for example EDCI, TBTU, COMU, T3P, etc. . . .

Step 2

In the pyrazole formation step, the anion of cyanoamide 8 can be generated with a base (such as potassium or sodium acetate) in an appropriate solvent such as an alcohol (e.g., ethanol). The anion then reacts with trichloroacetonitrile at room temperature. The resulting solid, which can be collected by filtration, is then reacted with hydrazine (or its hydrate) in an aprotic solvent, such as DMF or NMP, to provide the diaminopyrazole 9, the latter being further condensed with a dielectrophilic coupling partner to form the pyrimidine portion of the compounds of formula I-A of this invention.

Step 3

In the pyrimidine formation step, intermediate 9 is reacted with a 1,3-dielectrophilic species (e.g., a 1,3-dialdehyde or a 3-(dialkylamino)-prop-2-enal) in various types of solvents (e.g., iPrOH/water, DMF, or DMSO/water) to furnish the desired products I-A. When one or two of the electrophilic centers is protected/masked (e.g., aldehyde masked as a ketal), introduction of a sulfonic acid (e.g., PTSA) is required to liberate the reactive functional group.

PREPARATIONS AND EXAMPLES

All commercially available solvents and reagents were used as received. Microwave reactions were carried out using a CEM Discovery microwave. Flash Chromatography, e.g., was carried out on an ISCO© Combiflash® Companion™ system eluting with a 0 to 100% EtOAc/petroleum ether gradient. Other methods known in the art were also utilized to perform Flash Chromotography. Samples were applied pre-absorbed on silica. Where stated, supercritical fluid chromatography (SFC) was performed on a Berger Minigram SFC machine. All $^1$H NMR spectra were recorded using a Bruker Avance III 500 instrument at 500 MHz. MS samples were analyzed on a Waters SQD mass spectrometer with electrospray ionization operating in positive and negative ion mode. Samples were introduced into the mass spectrometer using chromatography. All final products had a purity ≥95%, unless specified otherwise in the experimental details. HPLC purity was measured on a Waters Acquity UPLC system with a Waters SQD MS instrument equipped with a Waters UPLC BEH C8 1.7 μm, 2.1×50 mm column and a Vanguard BEH C8 1.7 μm, 2.1×5 mm guard column.

As used herein, the term "Rt(min)" refers to the HPLC retention time, in minutes, associated with the compound. Unless otherwise indicated, the HPLC methods utilized to obtain the reported retention times are as described below:
HPLC Method
Instrument: Waters Acquity UPLC-MS;
Column: Waters UPLC BEH C8 1.7 μm, 2.1×50 mm with Vanguard BEH C8 1.7 μm, 2.1×5 mm guard column;
Column temperature: 45° C.;
Mobile Phase A: 10 mM ammonium formate in water: acetonitrile 95:5, pH 9;
Mobile Phase B: acetonitrile;
Detection: 210-400 nm;
Gradient: 0-0.40 min: 2% B, 0.40-4.85 min: 2% B to 98% B, 4.85-4.90 min: 98% B to 2% B, 4.90-5.00 min: hold at 2% B;
Flow rate: 0.6 mL/minute.

Preparation 1: Allyl 3,5-diamino-1H-pyrazole-4-carboxylate

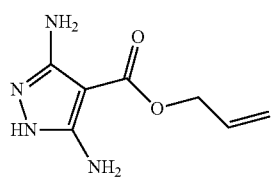

3

Step 1: allyl 3-amino-4,4,4-trichloro-2-cyanobut-2-enoate 2

To a solution of KOAc (589.4 g, 6.006 mol) in isopropanol (3 L) was added allyl cyanoacetate (429.4 g, 403.2 mL, 3.432 mol) and the reaction mixture was cooled to 5° C. Trichloroacetonitrile (495.5 g, 3.432 mol) was added in 50 mL portions, maintaining temperature below 15° C. The reaction mixture was then allowed to warm to 20° C. and stirred for 3 hr. Water (~4 L) was added to dissolve the inorganic materials and precipitate out the desired product. The mixture was stirred for 20 minutes and the solid was isolated by filtration under vacuum. This solid was filtered, washed with water (2×0.5 L) and dried in a vacuum oven overnight at 40° C. to afford allyl 3-amino-4,4,4-trichloro-2-cyanobut-2-enoate 2 as an off-white powder (787 g, 85%).

Step 2: Allyl 3,5-diamino-1H-pyrazole-4-carboxylate 3

To a suspension of allyl 3-amino-4,4,4-trichloro-2-cyanobut-2-enoate 2 (619 g, 2.297 mol) and KOAc (676.3 g, 6.891 mol) in DMF (2.476 L) at 0° C. was slowly added hydrazine hydrate (172.5 g, 167.6 mL, 3.446 mol) over 15 min. The reaction mixture was then stirred at ambient temperature for 2 hr., at which stage $^1$H NMR shows complete consumption of the starting material. Reaction mixture was then heated overnight at 110° C. before being allowed to cool to ambient and stirred for another 48 hr. The mixture was filtered through a sintered glass funnel to remove the precipitated solid and the filtrate was evaporated under reduced pressure to give a thick liquid. DCM (approx. 2 L) was added, and the mixture filtered again to remove additional solids that have precipitated. The filtrate was purified through a 1 kg silica gel plug (gradient of DCM/MeOH as an eluent), and the solvent was removed to afford an orange solid which was suspended in acetonitrile and heated at about 70° C. until all the solid went into solution, at which point the solution was allowed to cool to ambient temperature, then to 2° C. The precipitate that formed was isolated by filtration under vacuum, washed with chilled MeCN (~50 mL) and dried to constant mass in a vacuum oven to furnish the title compound as an off-white powder (171.2 g, 41%).

Preparation 2a: 1H-benzo[d][1,2,3]triazol-1-yl 2-amino-6-fluoropyrazolo[1,5-a]pyrimidine-3-carboxylate

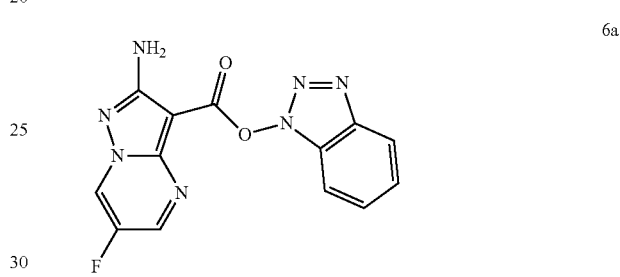

6a

Step 1: allyl 2-amino-6-fluoro-pyrazolo[1,5-a]pyrimidine-3-carboxylate 4a

To a suspension of allyl 3,5-diamino-1H-pyrazole-4-carboxylate 3 (42.72 g, 234.5 mmol) in DMSO (270.8 mL)/Water (270.8 mL), was added p-TsOH hydrate (46.72 g, 245.6 mmol) and 3-(diisopropylamino)-2-fluoro-prop-2-enal (described in *Tetrahedron Letters*, 33(3), 357-60; 1992) (38.69 g, 223.3 mmol). The reaction mixture was heated to 100° C. for 3 hr. during which time a solid slowly precipitated out of solution. The orange suspension was allowed to cool down to RT overnight. The solid was filtered, washed with water and dried under vacuum to give allyl 2-amino-6-fluoro-pyrazolo[1,5-a]pyrimidine-3-carboxylate 4a as a sand solid (45.05 g, 85% yield).

In an alternative method, allyl 2-amino-6-fluoro-pyrazolo[1,5-a]pyrimidine-3-carboxylate 4a may be synthesized via generic Scheme C-1, below.

Scheme C-1

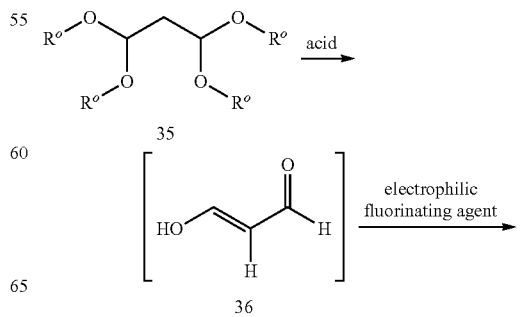

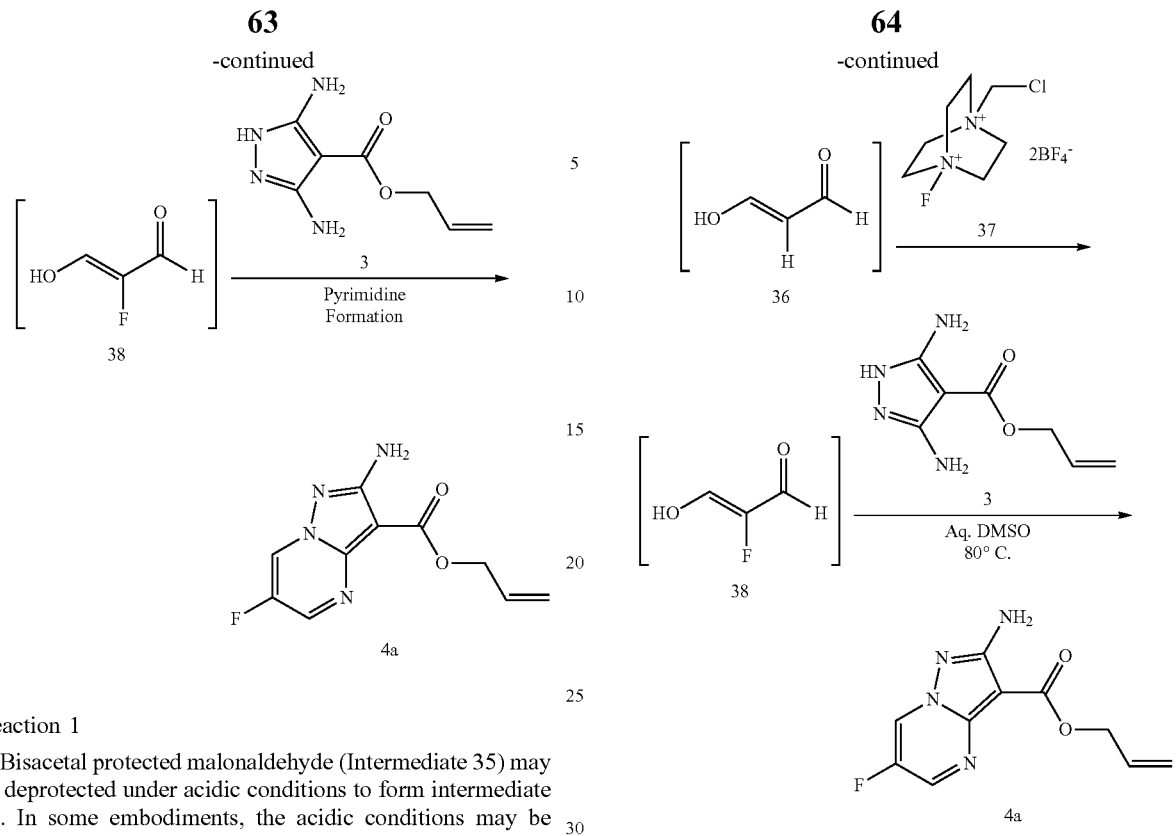

Reaction 1

Bisacetal protected malonaldehyde (Intermediate 35) may be deprotected under acidic conditions to form intermediate 36. In some embodiments, the acidic conditions may be generated by utilizing an acid independently selected from HCl, $H_2SO_4$, $MeSO_2H$, TFA, $HBF_4$, or pTSA in a suitable solvent, e.g., water. Preferably, the acid used in the reaction is selected from pTSA or $MeSO_2H$. $R^o$ is preferably a $C_{1-6}$aliphatic group. In some embodiments, $R^o$ is selected from methyl, ethyl, propyl, isopropyl, butyl or pentyl. In still other embodiments, $R^o$ is selected from methyl or ethyl.

Reaction 2

Intermediate 36 may be reacted with an electrophilic fluorinating agent to form intermediate 38. In some embodiments, the electrophilic fluorinating agent is independently selected from 1-(Chloromethyl)-4-fluoro-1,4-diazoniabicyclo[2.2.2]octane ditetrafluoroborate (Selectfluor®), Accufluor®, N-fluorobenzenesulfonamide, substituted 1-fluoropyridinium salts, or fluorine gas.

Reaction 3

Intermediate 38 may be reacted with intermediate 3 under suitable condensation conditions to form intermediate 4a. In some embodiments, the suitable condensation conditions may include reacting intermediate 38 with intermediate 3 in the presence of a solvent and heat to furnish the bicyclic core of 4a. The reaction may take place in various types of solvents, e.g., water, DMSO/water, or DMF.

In one example, intermediate 4a is formed using the methodology described in Scheme C-2.

Scheme C-2

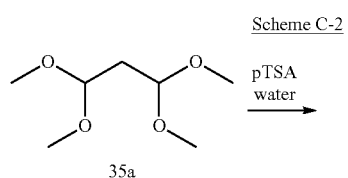

1,1,3,3-tetramethoxypropane 35a (20 g, 121.8 mmol) was dissolved in water (200 ml). p-Toluenesulphonic acid monohydrate (23.17 g, 121.8 mmol) was added and the mixture stirred at 19-20° C. for 90 minutes. 1-(Chloromethyl)-4-fluoro-1,4-diazoniabicyclo[2.2.2]octane ditetrafluoroborate 37 (Selectfluor, 1.4 eqv, 60.4 g, 170.5 mmol) was added portionwise. The addition was endothermic (20.1° C. to 19.4° C.) however the temperature began to rise slowly once the addition was complete (temp increased to 25.4° C. over 45 minutes). The selectfluor dissolved over 1 hr. The mixture was allowed to stir at ambient temperature for 18 hrs. The mixture was homogeneous after this time. DMSO (150 ml) was added slowly over 5 minutes. The addition was exothermic—the temperature increased from 20.4° C. to 34.2° C. during the addition. The mixture then began to cool. The resulting mixture was stirred for 45 minutes. Compound 3 (21.4 g, 115.7 mmol) was then added portionwise. The addition was not exothermic. The mixture was heated to 85° C. for 4 hrs (Lc/Ms profile was identical at 2 hr and 4 hr time points). The stirred mixture was then allowed to cool to ambient temperature overnight. The resulting reaction mixture was a slurry. Water (150 ml) was added slowly to the resulting slurry. The temperature increased from 20.4° C. to 21.5° C. The slurry was stirred for 2 hrs, and then the product was isolated by filtration. The cake was washed with water and dried on the sinter to a beige solid (15.5 g). The product was further dried in a vac oven at 40° C. for 20 hrs. This gave compound 4a as a beige solid (13.5 g, 50% yield). HPLC purity 97.7% area; $^1$H NMR (500 MHz, DMSO-d6) δ 4.83 (2H, d), 5.29 (1H, d), 5.49 (1H, d), 6.04-6.14 (1H, m), 6.57 (2H, brs), 8.80 (1H, m), 9.40 (1H, m); 19F NMR (500 MHz, DMSO-d6) δ −153.1.

Step 2: 2-amino-6-fluoro-pyrazolo[1,5-a]pyrimidine-3-carboxylic acid 5a

To a suspension of allyl 2-amino-6-fluoro-pyrazolo[1,5-a]pyrimidine-3-carboxylate 4a (45 g, 190.5 mmol) in DCM (1.35 L) was added phenylsilane (41.23 g, 46.96 mL, 381.0 mmol), followed by Pd(PPh$_3$)$_4$ (8.805 g, 7.620 mmol). The reaction was stirred at room temperature for 2 hr. 30 min. The reaction mixture was filtered and the solid was washed with DCM to give a light yellow solid (43.2 g). This solid was triturated further in DCM (225 mL) at RT for 45 min, then filtered and dried overnight under vacuum to provide 2-amino-6-fluoro-pyrazolo[1,5-a]pyrimidine-3-carboxylic acid 5a as a light yellow solid (37.77 g, 100% yield).

In an alternative method, sodium-4-methylbenzenesulfinate (anhydrous, 1.2 eqv, 22.6 g, 127 mmol) was suspended in dry DMSO (20 vol, 500 ml). The stirred mixture was warmed to 30° C. under a nitrogen atmosphere. Upon complete dissolution Pd(PPh$_3$)$_4$ (2 mol %, 2.4 g, 2.1 mmol) was added. The mixture was stirred for 10 min at 25-30° C. after which time a turbid yellow solution was present. Allyl 2-amino-6-fluoro-pyrazolo[1,5-a]pyrimidine-3-carboxylate 4a (25 g, 105.8 mmol) was added portionwise, maintaining the temperature at 25-30° C. Once addition was complete the cloudy solution was stirred until the reaction was complete by HPLC (2-3 hrs). A heavy precipitate formed after 15 minutes post addition of the substrate. The mixture became thicker as the reaction proceeded. The reaction mixture was diluted with water (125 ml) and 2M HCl (66 ml) was added slowly, maintaining the temperature at 25-30° C. The slurry was stirred for 30 minutes, then filtered. The filtration was slow (2 hrs). The resulting solid was washed with water, then dried on the sinter. The solid was slurried in DCM (8 vol) for 1 hr. The solid was filtered (rapid filtration) and washed with DCM. The solid was re-slurried in chloroform (8 vol) for 1 hr. The acid was filtered and dried on the sinter. It was further dried in a vacuum oven at 50° C. for 24 hrs. The product 5a was obtained as an off-white solid (18.6 g, 85%); $^1$H NMR (500 MHz, DMSO-d6) δ 12.14 (1H, brs), 9.31 (1H, dd), 8.69 (1H, m), 6.47 (2H, brS); 19F NMR (500 MHz, DMSO-d6) δ −153.65; MS (ES+) 197.1.

Step 3: 1H-benzo[d][1,2,3]triazol-1-yl 2-amino-6-fluoropyrazolo[1,5-a]pyrimidine-3-carboxylate 6a To a suspension of 2-amino-6-fluoro-pyrazolo[1,5-a]pyrimidine-3-carboxylic acid 5a (20 g, 102.0 mmol) in chloroform (300 mL) was added Et$_3$N (11.35 g, 15.63 mL, 112.2 mmol). The suspension was stirred for ~5 mins and then (benzotriazol-1-yloxy-dimethylamino-methylene)-dimethyl-ammonium Boron Tetrafluoride was added (32.75 g, 102.0 mmol). The suspension was heated to 60° C. for 1 hr. before the thick suspension was allowed to cool down to RT. The resulting suspension was filtered, washed with chloroform (200 mL) and dried under vacuum overnight to afford the title compound 6a as a light yellow powder (32.5 g, 88%).

Preparation 2b: (6-chlorobenzotriazol-1-yl)-2-amino-6-fluoro-pyrazolo[1,5-a]pyrimidine-3-carboxylate

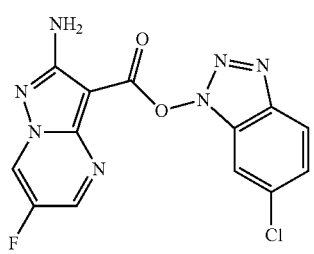

6a*

In a 2.5 L three-necked flask equipped with stirrer bar, condenser, nitrogen line and Hanna temperature probe was charged 2-amino-6-fluoro-pyrazolo[1,5-a]pyrimidine-3-carboxylic acid 5a (60 g, 305.9 mmol), chloroform (900.0 mL) and triethylamine (32.44 g, 44.68 mL, 320.6 mmol). [(6-chlorobenzotriazol-1-yl)oxy-(dimethylamino)methylene]-dimethyl-ammonium (Boron Tetrafluoride Ion (1)) (87.00 g, 244.7 mmol) was added portionwise over 5 mins (internal dropped from 22.7 to 21.5° C. on complete addition). Mixture heated at 60° C. (internal temp) for 2 hr., still a cream suspension. Mixture cooled to room temperature then solid collected by filtration, washed well with chloroform (until filtrate runs essentially colourless) and dried by suction to leave product 6a* as a cream solid (82.2 g, 77% yield). $^1$H NMR (500 MHz, DMSO-d$_6$) δ 9.55 (dd, 1H), 8.91 (d, 1H), 8.22 (dd, 1H), 8.09 (dd, 1H), 7.57 (dd, 1H) and 6.87 (s, 2H). MS (ES+) 348.1.

In an alternative method, 2-Amino-6-fluoropyrazolo[1,5-a]pyrimidine-3-carboxylic acid 5a (30 g, 153 mmol) was slurried in acetonitrile (540 ml). Triethylamine (22.5 ml, 153 mmol) was added, followed by [(6-chlorobenzotriazol-1yl) oxy-(dimethylamino)methylene]-dimethylammonium tetrafluoroborate (TCTU, 54.4 g, 153 mmol). The mixture was stirred at room temperature for 2 hrs. The product was isolated by filtration—the filter cake was washed with acetonitrile (2×60 ml). The product was obtained as a brown solid (49.3 g, 93%); $^1$H NMR (500 MHz, DMSO-d$_6$) δ 9.55 (dd, 1H), 8.91 (d, 1H), 8.22 (dd, 1H), 8.09 (dd, 1H), 7.57 (dd, 1H) and 6.87 (s, 2H); 19F NMR (500 MHz, DMSO-d6) δ −150.1; MS (ES+) 348.1.

Preparation 3: 1H-benzo[d][1,2,3]triazol-1-yl 2-amino-6-chloropyrazolo[1,5-a]pyrimidine-3-carboxylate

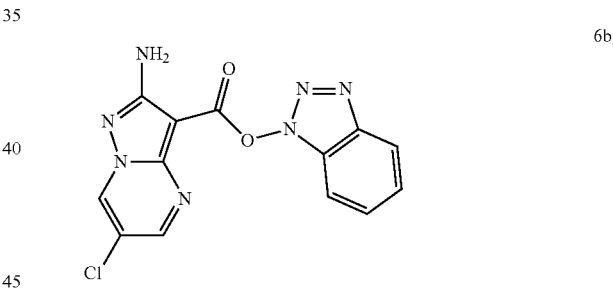

6b

Step 1: 2-amino-6-chloro-pyrazolo[1,5-a]pyrimidine-3-carboxylate 4b

To a suspension of allyl 3,5-diamino-1H-pyrazole-4-carboxylate 3 (1 g, 5.489 mmol) in DMF (5 mL) was added (Z)-2-chloro-3-dimethylamino-prop-2-enylidene]-dimethylammonium hexafluorophosphate (1.683 g, 5.489 mmol), followed by triethylamine (722.1 mg, 994.6 µL, 7.136 mmol). The reaction mixture was heated to 60° C. for 4 hr. during which time a solid slowly precipitated out of solution. The brown suspension was allowed to cool down to RT. The solid was filtered, washed with water and dried under vacuum to give allyl 2-amino-6-chloro-pyrazolo[1,5-a]pyrimidine-3-carboxylate 4b as a brown solid (1.092 g, 72% yield).

Step 2: 2-amino-6-chloro-pyrazolo[1,5-a]pyrimidine-3-carboxylic acid 5b

To a suspension of allyl 2-amino-6-chloro-pyrazolo[1,5-a]pyrimidine-3-carboxylate 4b (1 g, 3.96 mmol) in DCM (15 mL) was added phenylsilane (856.6 mg, 0.9756 mL, 7.916 mmol), followed by Pd(PPh₃)₄ (182.9 mg, 0.1583 mmol). The reaction was stirred at room temperature for 7 hr. The reaction mixture was filtered and the solid was washed with DCM to give a light yellow solid (43.2 g). This solid was triturated further in DCM (225 mL) at RT for 45 min, then filtered and dried overnight under vacuum to provide 2-amino-6-chloro-pyrazolo[1,5-a]pyrimidine-3-carboxylic acid 5b as a yellow solid (791 m, 94% yield).

Step 3: 1H-benzo[d][1,2,3]triazol-1-yl 2-amino-6-chloropyrazolo[1,5-a]pyrimidine-3-carboxylate 6b To a solution of 2-amino-6-chloro-pyrazolo[1,5-a]pyrimidine-3-carboxylic acid 5b (1.51 g, 7.103 mmol) in chloroform (15.1 mL) was added TBTU boron tetrafluoride (2.737 g, 8.524 mmol) and TEA (862.5 mg, 1.188 mL, 8.524 mmol). The reaction mixture was stirred at 50° C. for one hour. The resulting suspension was filtered, and the solid triturated in ethyl acetate to afford the title compound 6b as a yellow solid (2.05 g, 88%).

Preparation 4: 1H-benzo[d][1,2,3]triazol-1-yl 2-amino-6-(cyanomethyl)pyrazolo[1,5-a]pyrimidine-3-carboxylate

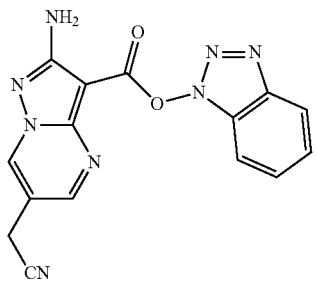

Step 1: allyl 2-amino-6-(cyanomethyl)-pyrazolo[1,5-a]pyrimidine-3-carboxylate 4c To a suspension of allyl 3,5-diamino-1H-pyrazole-4-carboxylate 3 (63.49 g, 348.5 mmol) in a mixture of DMSO (340 mL) and water (340 mL), was added 3-(dimethoxymethyl)-4,4-dimethoxy-butanenitrile (prepared according to Preparation 5, below) (85 g, 418.2 mmol), followed by para-toluene Sulfonic acid hydrate (1) (11.27 g, 59.24 mmol). The reaction mixture was heated to 85° C. and stirred overnight. The reaction mixture was cooled with an ice bath. The mixture was diluted with EtOAc (680 mL) and a saturated aqueous solution of NaHCO₃ (1.36 L). The precipitate was filtered and rinsed with water, then with a mixture of water and EtOAc. The brown solid was dried under vacuum to give allyl 2-amino-6-(cyanomethyl)-pyrazolo[1,5-a]pyrimidine-3-carboxylate 4c as a brown solid (55.94 g, 62% yield).

Step 2: 2-amino-6-(cyanomethyl)-pyrazolo[1,5-a]pyrimidine-3-carboxylic acid 5c

To a suspension of allyl 2-amino-6-(cyanomethyl)-pyrazolo[1,5-a]pyrimidine-3-carboxylate 4c (10.2 g, 39.65 mmol) in DCM (350 mL) was added phenylsilane (8.581 g, 9.773 mL, 79.3 mmol), followed by Pd(PPh₃)₄ (1.5 g, 1.298 mmol). The reaction was stirred at room temperature for 2 hr. The reaction mixture was filtered and the solid was washed with DCM and dried under vacuum to provide 2-amino-6-(cyanomethyl)-pyrazolo[1,5-a]pyrimidine-3-carboxylic acid 5c as a yellow solid (8.61 g, 100% yield).

Step 3: 1H-benzo[d][1,2,3]triazol-1-yl 2-amino-6-(cyanomethyl)pyrazolo[1,5-a]pyrimidine-3-carboxylate 6c To a solution of 2-amino-6-(cyanomethyl)-pyrazolo[1,5-a]pyrimidine-3-carboxylic acid 5c (5.11 g, 23.53 mmol) in DCM (51 mL) was added TBTU boron tetrafluoride (9.067 g, 28.24 mmol) and TEA (2.858 g, 3.937 mL, 28.24 mmol). The reaction mixture was stirred at room temperature for one hour. The resulting suspension was filtered, and the solid triturated in hot chloroform to afford the title compound 6c as a beige solid (6.59 g, 84%).

Example 1: Synthesis of 2-amino-6-fluoro-N-[5-fluoro-4-[4-[4-(oxetan-3-yl)piperazine-1-carbonyl]-1-piperidyl]-3-pyridyl]pyrazolo[1,5-a]pyrimidine-3-carboxamide (Compound I-1)

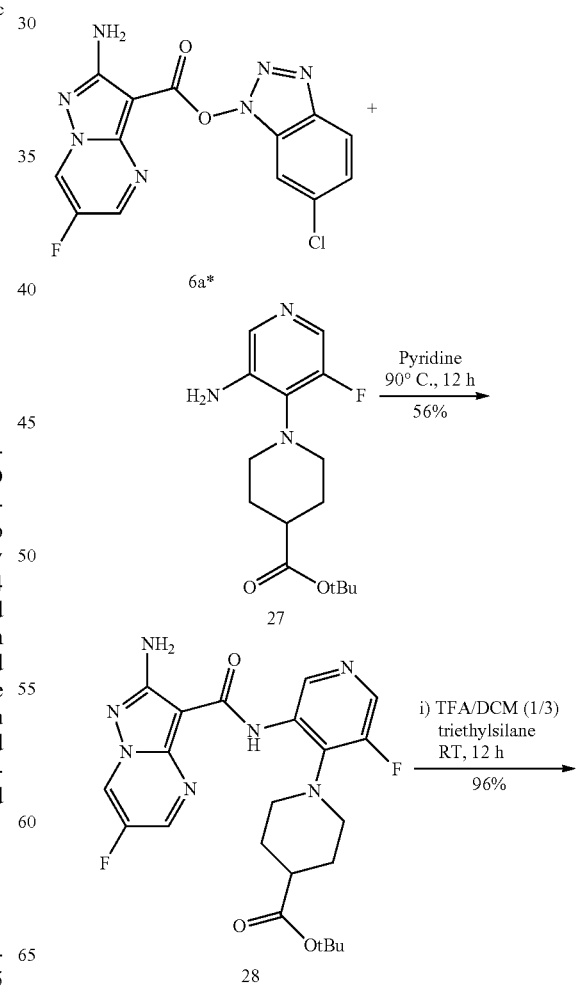

-continued

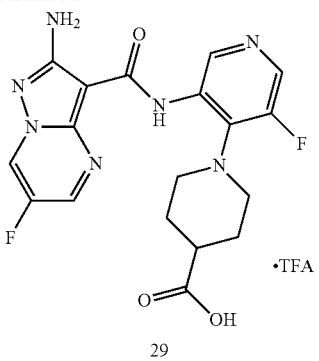

29

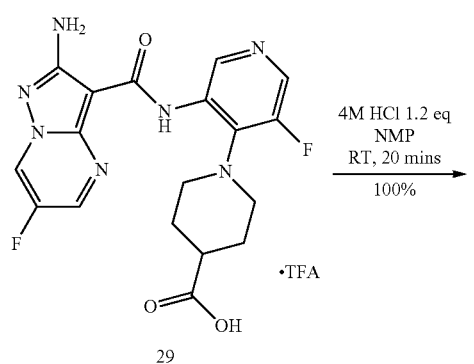

Step 1: tert-butyl 1-[3-[(2-amino-6-fluoro-pyrazolo[1,5-a]pyrimidine-3-carbonyl)amino]-5-fluoro-4-pyridyl]piperidine-4-carboxylate 28

A mixture of (6-chlorobenzotriazol-1-yl) 2-amino-6-fluoro-pyrazolo[1,5-a]pyrimidine-3-carboxylate 6a* (44.02 g, 126.6 mmol) and tert-butyl 1-(3-amino-5-fluoro-4-pyridyl)piperidine-4-carboxylate 27 (prepared according to Preparation 7b) (34 g, 115.1 mmol) in pyridine (510.0 mL) was heated at 95° C. internally overnight (18 hr.). Mixture was cooled to room temperature (product precipitated) then added ethanol (340.0 mL) and stirred at room temperature for 10 mins. Collected yellow solid by filtration, washed well with ethanol, dried by suction, then on high vac line for 1 hr. to leave product 28 as a yellow solid, (32.5 g 56% yield). $^1$H NMR (500 MHz, DMSO-d6) δ 10.45 (s, 1H), 9.58 (s, 1H), 9.51 (dd, 1H), 8.72 (dd, 1H), 8.25 (d, 1H), 6.81 (s, 2H), 3.15-2.93 (m, 4H), 2.55-2.47 (masked signal, 1H), 2.02-1.91 (m, 4H), 1.47 (s, 9H). MS (ES+) 474.2.

Step 2: 1-[3-[(2-amino-6-fluoro-pyrazolo[1,5-a]pyrimidine-3-carbonyl)amino]-5-fluoro-4-pyridyl]piperidine-4-carboxylic acid trifluorocetate 29

To a suspension of tert-butyl 1-[3-[(2-amino-6-fluoro-pyrazolo[1,5-a]pyrimidine-3-carbonyl)amino]-5-fluoro-4-pyridyl]piperidine-4-carboxylate 28 (69.7 g, 147.2 mmol) in DCM (348.5 mL) and triethylsilane (18.83 g, 25.87 mL, 161.9 mmol) was added TFA (151.1 g, 102.1 mL, 1.325 mol) (mixture sets solid on initial addition of TFA then goes into solution after complete addition). Resulting orange solution was stirred at room temperature overnight. Additional TFA (16.78 g, 11.34 mL, 147.2 mmol) was added and the mixture stirred at room temperature for 2 hr. Mixture then heated at 40° C. for 20 mins to force reaction to completion. Mixture was concentrated in vacuo, chloroform (300 mL) was added and mixture again concentrated in vacuo to leave an orange solid suspension. Mixture triturated in DCM (approx. 200 mL), stirred for 20 mins then solid collected by filtration, washed with minimal DCM and dried by suction to leave a yellow solid. Filtrate was concentrated in vacuo, residue re-slurried in DCM (approx. 50 mL), stirred for 20 mins then solid collected by filtration, washed with minimal DCM and dried by suction to leave a yellow solid which was combined with first crop of solid. Solid dried under vacuum overnight to leave desired product 29 as a yellow solid (82.8 g, 96%). $^1$H NMR (500 MHz, DMSO-d6) δ 10.44 (s, 1H), 9.59 (s, 1H), 9.50 (dd, 1H), 8.84 (dd, 1H), 8.33 (d, 1H), 3.13-3.10 (m, 4H), 2.57-2.47 (masked signal, 1H) and 2.08-1.93 (m, 4H). MS (ES+) 418.1.

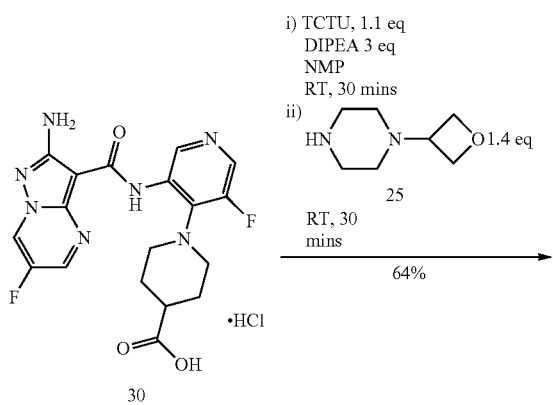

Step 3: 1-[3-[(2-amino-6-fluoro-pyrazolo[1,5-a]pyrimidine-3-carbonyl)amino]-5-fluoro-4-pyridyl]piperidine-4-carboxylic acid hydrochloride 30

To a solution of 1-[3-[(2-amino-6-fluoro-pyrazolo[1,5-a]pyrimidine-3-carbonyl)amino]-5-fluoro-4-pyridyl]piperidine-4-carboxylic acid (Trifluoroacetic Acid) 29 (73 g, 124.7 mmol) in NMP (662.7 mL) was added hydrogen chloride (4M in 1,4-dioxane) (37.40 mL of 4 M, 149.6 mmol). After a few seconds a yellow precipitate formed. Mixture stirred at room temperature for 20 mins, then solid collected by filtration, washed with minimal NMP then MTBE, and dried by suction to leave pure product 30 as a light yellow solid, (59.7 g, quantitative yield). MS (ES+) 418.1.

Step 4: 2-amino-6-fluoro-N-[5-fluoro-4-[4-[4-(oxetan-3-yl)piperazine-1-carbonyl]-1-piperidyl]-3-pyridyl]pyrazolo[1,5-a]pyrimidine-3-carboxamide (Compound I-1)

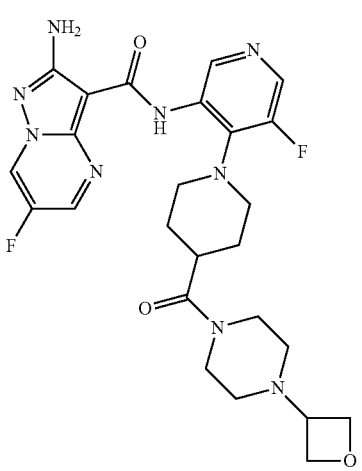

I-1

To a yellow suspension of 1-[3-[(2-amino-6-fluoro-pyrazolo[1,5-a]pyrimidine-3-carbonyl)amino]-5-fluoro-4- pyridyl]piperidine-4-carboxylic acid (Hydrochloric Acid) 30 (59.7 g, 131.5 mmol) in NMP (477.6 mL) was added DIPEA (50.99 g, 68.72 mL, 394.5 mmol) then [(6-chlorobenzotriazol-1-yl)oxy-(dimethylamino)methylene]-dimethyl-ammonium (Boron Tetrafluoride Ion (1)) (51.44 g, 144.7 mmol). A yellow suspension forms after a few minutes. The mixture was stirred for 30 mins at room temperature then 1-(oxetan-3-yl)piperazine 25 (prepared according to Preparation 8, below) (26.18 g, 184.1 mmol) was added. The cream/tan suspension turns to an orange solution (exotherms from 23.9 to 29.4° C.). The flask was placed on ice/water bath until internal temperature was at 24° C., then ice bath was removed and internal temperature steady at 24° C. thereafter.

The solution was stirred for 30 mins at room temperature then cooled on an ice/salt/water bath to 10° C. before the slow addition of water (1.015 L) in 100 mL portions. Prior to adding the next 100 mL of water, waited for exotherm to between 17° C. and 20° C. (internal) then allow to cool to between 10 and 15° C. Repeated until all water added. Once exotherm had ceased, ice/salt/water bath removed and mixture stirred at ambient temperature for 20 mins (thick yellow/cream suspension forms). Solid collected by filtration through a sinter funnel, washed well with water then dried by suction for 10 mins. Vacuum removed and solid slurried in water on sinter funnel, then vacuum reapplied and solid dried by suction overnight then dried in vacuum oven for 24 h at 40° C.<10 mBar.

Solid (54.5 g) suspended in ethanol (545 mL, 10 vol eq.) and heated under reflux for 2 hr. then cooled to room temperature over 2 h. Solid collected by filtration, washed with minimum ethanol and dried by suction for 1 h to leave product as a pale yellow solid. Solid placed in vacuum oven at 23.5° C. and <10 mBar overnight to leave the ethanol solvate solid form of I-1 as a pale yellow solid, (51 g, 64% yield). $^1$H NMR (500 MHz, DMSO-d6) δ 10.64 (s, 1H), 9.67 (s, 1H), 9.48 (dd, 1H), 9.26 (dd, 1H), 8.26 (d, 1H), 6.79 (s, 2H), 4.55 (t, 2H), 4.47 (t, 2H), 4.34 (t, 0.7H), 3.61 (dt, 4H), 3.48-3.41 (m, 2.5H), 3.22-3.17 (m, 2H), 3.05-3.03 (m, 2H), 3.99-2.93 (m, 1H), 2.28 (dt, 4H), 2.17-2.10 (m, 2H), 1.74 (d, 2H), 1.07 (t, 2H). MS (ES+) 542.3.

Example 2: Alternative approach to synthesis of 2-amino-6-fluoro-N-[5-fluoro-4-[4-[4-(oxetan-3-yl)piperazine-1-carbonyl]-1-piperidyl]-3-pyridyl]pyrazolo[1,5-a]pyrimidine-3-carboxamide (Compound I-1)

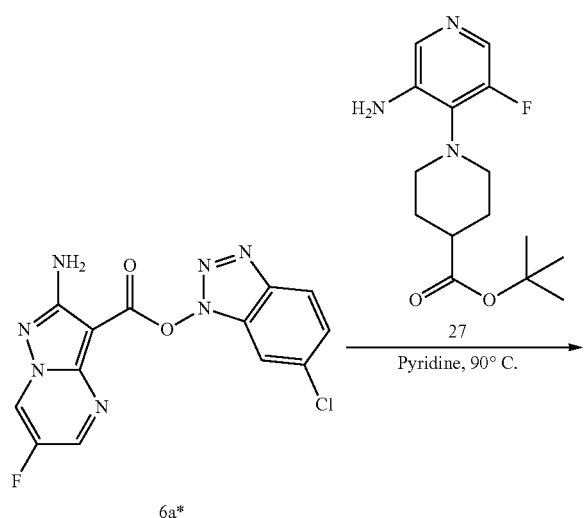

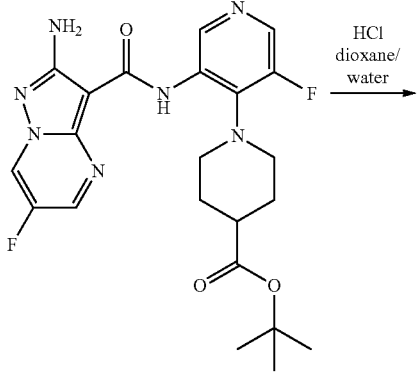

Step 1: tert-butyl 1-(3-(2-amino-6-fluoropyrazolo[1,5-a]pyrimidine-3-carboxamido)-5-fluoropyridin-4-yl)piperidine-4-carboxylate 28

6-chloro-1H-benzo[d][1,2,3]triazol-1-yl 2-amino-6-fluoropyrazolo[1,5-a]pyrimidine-3-carboxylate 6a* (45 g, 129.4 mmol) and tert-butyl 1-(3-amino-5-fluoropyridin-4-yl)piperidine-4-carboxylate 27 (prepared according to Preparation 7b, described below) (40.1 g, 135.9 mmol) were slurried in pyridine (675 ml). The mixture was heated at 95° C. under nitrogen until the reaction was complete (determined by HPLC analysis). The mixture was cooled and ethanol (450 ml) was added dropwise. The mixture was filtered and the filter cake washed with ethanol (2×70 ml). The damp cake was dried to give the product 28 as a yellow crystalline solid (47.7 g, 78%); $^1$H NMR (500 MHz, DMSO-d$_6$) δ 10.45 (s, 1H), 9.58 (s, 1H), 9.51 (dd, 1H), 8.72 (dd, 1H), 8.25 (d, 1H), 6.81 (s, 2H), 3.15-2.93 (m, 4H), 2.55-2.47 (masked signal, 1H), 2.02-1.91 (m, 4H), 1.47 (s, 9H); 19F NMR (500 MHz, DMSO-d6) δ −153.5, −136.3; MS (ES+) 474.2.

In an alternative embodiment, intermediate 28 may be purified prior to performing step 2 by using a procedure similar to the following:

Step 1a: Purification of tert-butyl 1-[3-[(2-amino-6-fluoro-pyrazolo[1,5-a]pyrimidine-3-carbonyl)amino]-5-fluoro-4-pyridyl]piperidine-4-carboxylate 28 tert-Butyl 1-[3-[(2-amino-6-fluoro-pyrazolo[1,5-a]pyrimidine-3-carbonyl)amino]-5-fluoro-4-pyridyl]piperidine-4-carboxylate 28 (530 g; 1.12 moles) was added to a mixture of NMP (5.3 L) and 1,2-diaminopropane (249 g; 3.36 moles) and the resulting thin suspension was stirred at 20-25° C. for 15 hours. Ethanol (10.4 L) was added to the suspension and the suspension was stirred for 4 hours at 20-25° C. The crystalline golden solid was collected by filtration, washed with ethanol (2×2.6 L), dried by suction then dried in a vacuum oven for 24 hours at 35-40° C. to give 28 as a crystalline golden solid (479 g; 90%). $^1$H NMR (500 MHz, DMSO-$d_6$) δ 10.45 (s, 1H), 9.57 (s, 1H), 9.49 (dd, 1H), 8.71 (d, 1H), 8.24 (d, 1H), 6.79 (s, 2H), 3.44-3.33 (m, 1H), 3.34-3.20 (m, 4H), 3.07 (dt, 4H), 2.01-1.89 (m, 4H), 1.46 (s, 9H). $^{19}$F NMR (500 MHz, DMSO-$d_6$) δ −136.3, −153.4.

Step 2: 1-(3-(2-amino-6-fluoropyrazolo[1,5-a]pyrimidine-3-carboxamido)-5-fluoropyridin-4-yl)piperidine-4-carboxylic acid hydrochloride 30

Tert-butyl 1-(3-(2-amino-6-fluoropyrazolo[1,5-a]pyrimidine-3-carboxamido)-5-fluoropyridin-4-yl)piperidine-4-carboxylate 28 (36 g, 76 mmol) was suspended in a solution of HCl in 1,4-dioxane (4M, 670 ml). Water (36 ml) was added dropwise to the rapidly stirred slurry. The mixture was stirred under nitrogen until the reaction was complete (determined by HPLC analysis). The mixture was diluted with 1,4-dioxane (180 ml) and filtered. The filter cake was washed with TBME (2×72 ml). The damp cake was dried to give a pale brown solid (hydrochloride salt, 32.7 g, 95%); $^1$H NMR (500 MHz, DMSO-$d_6$) δ 10.34 (s, 1H), 9.53-9.49 (m, 2H), 8.82 (m, 1H), 8.50 (m, 1H), 3.13-3.22 (m, 4H), 2.57-2.47 (masked signal, 1H) and 2.08-1.93 (m, 4H); 19F NMR (500 MHz, DMSO-d6) δ −152.9, −133.8; MS (ES+) 418.1.

Step 3: 2-amino-6-fluoro-N-[5-fluoro-4-[4-[4-(oxetan-3-yl)piperazine-1-carbonyl]-1-piperidyl]-3-pyridyl]pyrazolo[1,5-a]pyrimidine-3-carboxamide (Compound I-1•Amorphous)

To a solution of 1-(oxetan-3-yl)piperazine 25 (525 mg, 3.69 mmol) in THF (12 ml) was added DIPEA (1.72 ml, 9.91 mmol), followed by 1-(3-(2-amino-6-fluoropyrazolo[1,5-a]pyrimidine-3-carboxamido)-5-fluoropyridin-4-yl)piperidine-4-carboxylic acid (hydrochloride salt, 1.5 g, 3.3 mmol). [(6-chlorobenzotriazol-1-yl)oxy-(dimethylamino)methylene]-dimethyl-ammonium tetrafluoroborate (TCTU, 1.29 g, 3.64 mmol) was added and the mixture stirred under nitrogen until reaction completion (determined by HPLC analysis). The mixture was cooled and water (24 ml) was added dropwise. The mixture was allowed to warm to ambient and stirred for 3 hrs, then filtered. The filter cake was washed with (3×3 ml). The damp cake was dried under vacuum (with a nitrogen bleed) at 40° C. An amorphous form of compound I-1 was obtained. (1.54 g, 86%); $^1$H NMR (500 MHz, DMSO-d6) δ 10.64 (s, 1H), 9.67 (s, 1H), 9.48 (dd, 1H), 9.26 (dd, 1H), 8.26 (d, 1H), 6.79 (s, 2H), 4.55 (t, 2H), 4.47 (t, 2H), 4.34 (t, 0.7H), 3.61 (dt, 4H), 3.48-3.41 (m, 2.5H), 3.22-3.17 (m, 2H), 3.05-3.03 (m, 2H), 3.99-2.93 (m, 1H), 2.28 (dt, 4H), 2.17-2.10 (m, 2H), 1.74 (d, 2H), 1.07 (t, 2H); 19F NMR (500 MHz, DMSO-d6) δ −152.8, −136.1; MS (ES+) 542.3.

Compound I-1•amorphous may be prepared using an alternative method from Example 2, Step 3, above.

In another example, Compound I-1•amorphous was prepared by adding N,N-Diisopropylethylamine (461 uL; 342 mg; 2.64 mmol) to a suspension of 1-[3-[(2-amino-6-fluoro-pyrazolo[1,5-a]pyrimidine-3-carbonyl)amino]-5-fluoropyridin-4-yl]piperidine-4-carboxylic acid hydrochloride 30 (1.00 g; 2.20 mmol; LR) in THF (20 mL). 1,1'-Carbonyldiimidazole (CDI) (430 mg; 2.65 mmol) was added and the mixture was heated at 40-50° C. Additional charges of 1,1'-Carbonyldiimidazole (CDI) (213 mg total; 1.31 mmol) were made and the mixture heated until reaction completion (determined by HPLC analysis). 1-(oxetan-3-yl)piperazine 25 (375 mg; 2.64 mmol) was added and the mixture was heated at 55-60° C. until reaction completion (determined by HPLC analysis). The reaction was cooled to 20-25° C. Water (40 mL) and 2M NaOH(aq) (551 uL) were added and the suspension was stirred for 5-10 minutes. The solids were collected by filtration, washed with water (2×5 mL), dried by suction then dried in a vacuum oven at 45-50° C. for 16 hours to give I-1 as a yellow solid (869 mg; 73%).

Preparation 5: Alternative approach to synthesis of tert-butyl 1-(3-(2-amino-6-fluoropyrazolo[1,5-a]pyrimidine-3-carboxamido)-5-fluoropyridin-4-yl)piperidine-4-carboxylate (Compound 28)

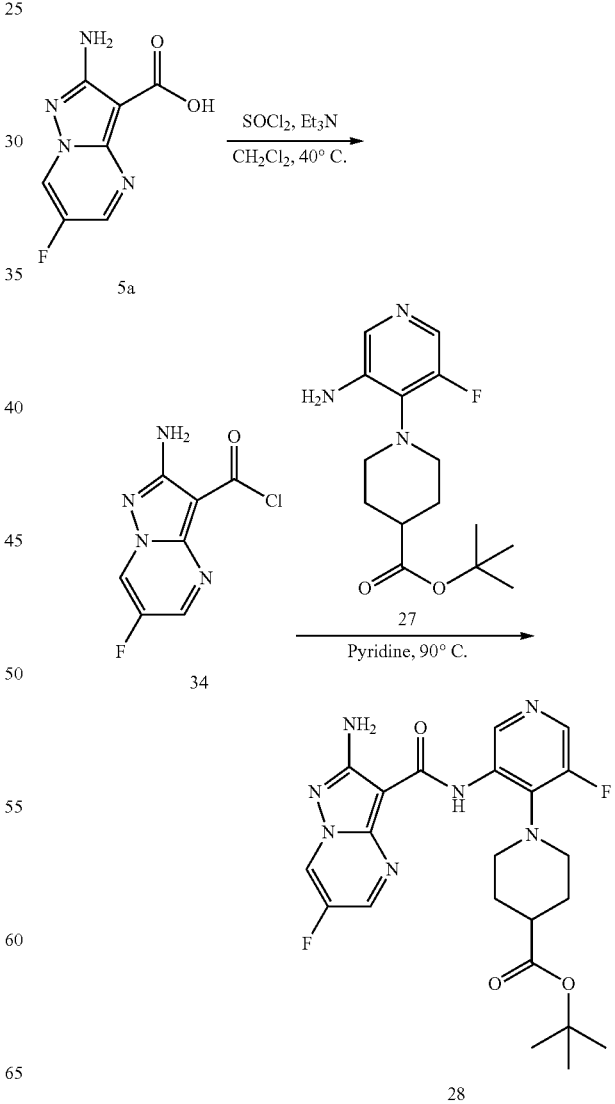

Step 1: 2-amino-6-fluoro-pyrazolo[1,5-a]pyrimidine-3-carbonyl chloride 34

To a suspension of 2-amino-6-fluoro-pyrazolo[1,5-a]pyrimidine-3-carboxylic acid 5a (500 mg, 2.55 mmol) in dichloromethane (7.5 mL) was added triethylamine (409 uL, 297 mg, 2.93 mmol). Thionyl chloride (205 uL, 334 mg, 2.80 mmol) was added and the mixture heated at 35-40° C. for 2 hours. The mixture was cooled to ambient temperature and stirred at ambient temperature until reaction completion (monitored by HPLC). The solid was collected by filtration, washed with dichloromethane (2×1 mL) and dried by suction to give the product 34 as a beige solid (465 mg, 85%); $^1$H NMR (500 MHz, DMSO-d$_6$) δ 9.30 (dd, J=4.9, 2.7 Hz, 1H), 8.68 (d, J=2.7 Hz, 1H); 19F NMR (500 MHz, DMSO-d6) δ −154.1.

Step 2: tert-butyl 1-(3-(2-amino-6-fluoropyrazolo[1,5-a]pyrimidine-3-carboxamido)-5-fluoropyridin-4-yl)piperidine-4-carboxylate 28

2-amino-6-fluoro-pyrazolo[1,5-a]pyrimidine-3-carbonyl chloride 34 (100 mg, 0.466 mmol) and tert-butyl 1-(3-amino-5-fluoropyridin-4-yl)piperidine-4-carboxylate 27 (138 mg, 0.466 mmol) were slurried in pyridine (1.5 mL). The mixture was heated to 90-100° C. for 16 hours. The mixture was cooled and ethanol (3 mL) was added. The mixture was stirred for 1-2 hours, filtered and the filter cake washed with ethanol (0.5 mL). The solids were dried by suction to give the product 28 (162 mg, 73%). 1H NMR (400 MHz, DMSO-d6) δ 10.45 (s, 1H), 9.57 (s, 1H), 9.50 (dd, J=4.8, 2.5 Hz, 1H), 8.71 (d, J=2.5 Hz, 1H), 8.24 (d, J=2.5 Hz, 1H), 6.80 (s, 2H), 3.07 (dd, J=6.5, 3.3 Hz, 4H), 2.11-1.80 (m, 4H), 1.46 (s, 9H); 19F NMR (500 MHz, DMSO-d6) δ −136.8, −153.9; MS (ES+) 474.2.

Example 3: Alternative Approach to Synthesis of 2-amino-6-fluoro-N-[5-fluoro-4-[4-[4-(oxetan-3-yl)piperazine-1-carbonyl]-1-piperidyl]-3-pyridyl]pyrazolo[1,5-a]pyrimidine-3-carboxamide (Compound I-1)

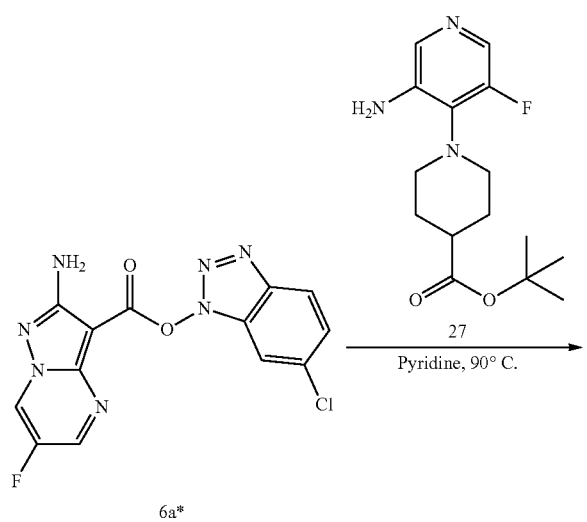

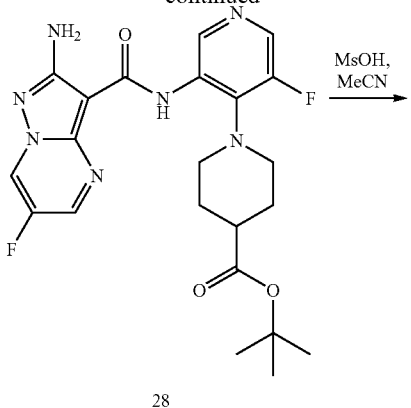

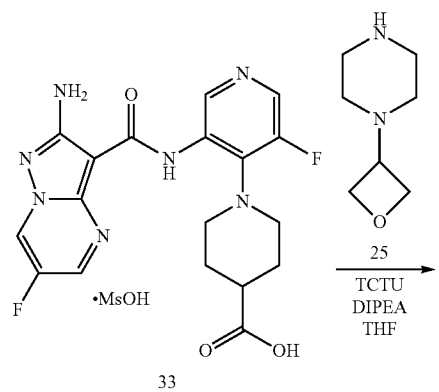

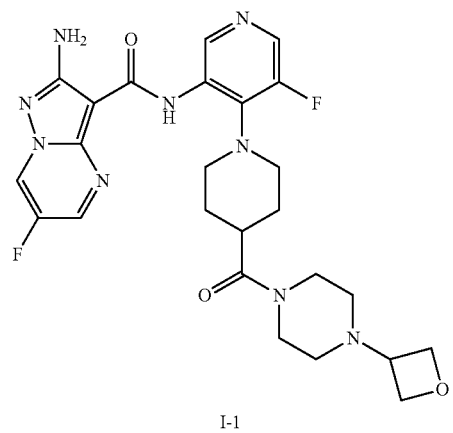

Step 1: tert-butyl 1-(3-(2-amino-6-fluoropyrazolo[1,5-a]pyrimidine-3-carboxamido)-5-fluoropyridin-4-yl)piperidine-4-carboxylate 28

6-chloro-1H-benzo[d][1,2,3]triazol-1-yl 2-amino-6-fluoropyrazolo[1,5-a]pyrimidine-3-carboxylate 6a* (45 g, 129.4 mmol) and tert-butyl 1-(3-amino-5-fluoropyridin-4-yl)piperidine-4-carboxylate 27 (prepared according to Preparation 7b, described below) (40.1 g, 135.9 mmol) were slurried in pyridine (675 ml). The mixture was heated at 95° C. under nitrogen until the reaction was complete (determined by HPLC analysis). The mixture was cooled and ethanol (450 ml) was added dropwise. The mixture was filtered and the filter cake washed with ethanol (2×70 ml). The damp cake was dried to give the product 28 as a yellow crystalline solid (47.7 g, 78%); $^1$H NMR (500 MHz, DMSO-d$_6$) δ 10.45 (s, 1H), 9.58 (s, 1H), 9.51 (dd, 1H), 8.72 (dd, 1H), 8.25 (d, 1H), 6.81 (s, 2H), 3.15-2.93 (m, 4H), 2.55-2.47 (masked signal, 1H), 2.02-1.91 (m, 4H), 1.47 (s, 9H); 19F NMR (500 MHz, DMSO-d6) δ −153.5, −136.3; MS (ES+) 474.2.

Step 2: 1-[3-[(2-amino-6-fluoro-pyrazolo[1,5-a]pyrimidine-3-carbonyl)amino]-5-fluoro-4-pyridyl]piperidine-4-carboxylic acid mesylate 33

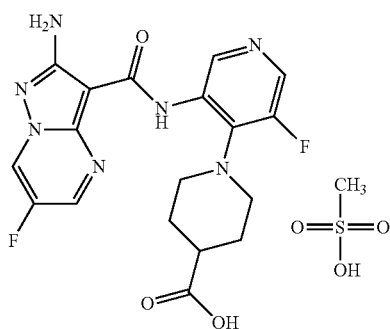

Methanesulphonic acid (274 uL; 406 mg; 4.22 mmol) was added to a suspension of tert-butyl 1-[3-[(2-amino-6-fluoro-pyrazolo[1,5-a]pyrimidine-3-carbonyl)amino]-5-fluoro-4-pyridyl]piperidine-4-carboxylate 28 (1.00 g; 2.11 mmol) in acetonitrile (15 mL) and the mixture was heated to 75-80° C. for 16 hours. The solids were collected by filtration, washed with acetonitrile (2×2 mL) and dried under vacuum to give 1-[3-[(2-amino-6-fluoro-pyrazolo[1,5-a]pyrimidine-3-carbonyl)amino]-5-fluoro-4-pyridyl]piperidine-4-carboxylic acid mesylate 33 (0.94 g; 87%). $^1$H NMR (500 MHz, DMSO-d6) δ 10.43 (s, 1H), 9.58 (s, 1H), 9.49 (dd, 1H), 8.83 (d, 1H), 8.32 (d, 1H), 6.85 (bs, 2H), 3.11 (dt, 4H), 2.31 (s, 3H), 1.99 (m, 4H); $^{19}$F NMR (500 MHz, DMSO-d6) δ −135.5, −153.1; MS (ES+) 418.1.

Step 3: 2-amino-6-fluoro-N-[5-fluoro-4-[4-[4-(oxetan-3-yl)piperazine-1-carbonyl]-1-piperidyl]-3-pyridyl]pyrazolo[1,5-a]pyrimidine-3-carboxamide (Compound I-1 Amorphous)

N,N-Diisopropylethylamine (51 uL; 38 mg; 0.29 mmol) was added to a suspension of 1-[3-[(2-amino-6-fluoro-pyrazolo[1,5-a]pyrimidine-3-carbonyl)amino]-5-fluoro-4-pyridyl]piperidine-4-carboxylic acid mesylate (50 mg; 0.097 mmol) and 1-(oxetan-3-yl)piperazine (15 mg; 0.11 mmol) in THF (1.00 mL). [(6-chlorobenzotriazol-1-yl)oxy-(dimethylamino)methylene]-dimethyl-ammonium tetrafluoroborate (TCTU, 36.3 mg; 0.10 mmol) was added and the mixture stirred under nitrogen until reaction completion (determined by HPLC analysis). Water (2 mL) was added to the suspension and stirred for 5 hours. The solids were collected by filtration, washed with water (2×200 uL), dried by suction then dried in a vacuum oven for 24 hours at 45-50° C. to give I-1 as a pale yellow solid (31 mg; 59%).

Preparation 6: Preparation of Butanenitrile Intermediates

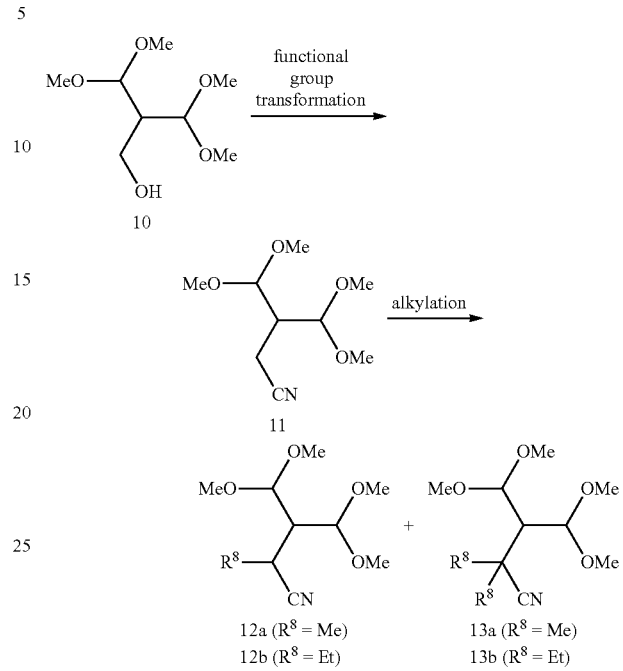

Step 1: 3-(dimethoxymethyl)-4,4-dimethoxybutanenitrile 11

2-(dimethoxymethyl)-3,3-dimethoxy-propan-1-ol 10 (*Journal of the American Chemical Society* (1973), 95(26), 8741) (92 g, 473.7 mmol) was dissolved in dry THF (920 mL) and the mixture was cooled down with an ice bath. Triethylamine (143.8 g, 198.1 mL, 1.421 mol) was added at once, followed by dropwise addition of methane sulfonyl chloride (59.69 g, 40.33 mL, 521.1 mmol), over 1 hr. and keeping the internal temperature below 5° C. The reaction mixture was stirred for 1 hr. and then allowed to warm to room temperature. The mixture was diluted with ethyl acetate (920 mL) and water (920 mL). The layers were separated and the organic layer was isolated, washed with a saturated solution of NaHCO$_3$, then brine. The organics were dried over MgSO$_4$, filtered and evaporated to give [2-(dimethoxymethyl)-3,3-dimethoxypropyl]methanesulfonate as an orange oil (125.31 g, 97%) which was used directly without further purification.

Tetraethylammonium cyanide (142.3 g, 910.8 mmol) was added portionwise over 10 minutes to a solution of [2-(dimethoxymethyl)-3,3-dimethoxypropyl]methanesulfonate (124 g, 455.4 mmol) in MeCN (1.24 L). The reaction mixture was stirred at room temperature for 72 hr., then portioned between ethyl acetate (1.24 L) and water (1.24 L). The layers were separated and the organic layer was isolated, washed with brine. The organics were dried over MgSO$_4$, filtered and evaporated to give 3-(dimethoxymethyl)-4,4-dimethoxybutanenitrile 11 as a dark brown oil (86.1 g).

Step 2: 3-(dimethoxymethyl)-4,4-dimethoxy-2-methylbutanenitrile 12a and 3-(dimethoxymethyl)-4,4-dimethoxy-2,2-dimethylbutanenitrile 13a To a solution of 3-(dimethoxymethyl)-4,4-dimethoxybutanenitrile 11 (250 mg, 1.205 mmol) in THF (3 mL) at −75° C. was added a solution of iodomethane (513.1 mg, 225.0 μL, 3.615 mmol) in THF (1 ml). A THF solution of (bis(trimethylsilyl)amino)sodium (1.808 mL of 2M, 3.615 mmol) was then added, keeping the temperature below −60° C. After addition, the reaction mixture was stirred at −75° C. for 2 hrs and then slowly quenched with aqueous saturated $NH_4Cl$ solution (5 ml). The mixture diluted with water and ether and layers separated. The organic layer was washed with brine, dried ($Na_2SO_4$) and concentrated in vacuo to afford a yellow oil which was purified by chromatography on silica gel, eluting with a petroleum ether:EtOAc gradient of 100:0 to 80:20. Solvents were concentrated in vacuo to afford a clear oil (194 mg). NMR proved this oil to be a mixture of 80% mono methyl compound 12a with and 20% bis methyl compound 13a. This mixture was used directly in subsequent steps.

Step 3: 3-(dimethoxymethyl)-2-ethyl-4,4-dimethoxybutanenitrile 12b and 3-(dimethoxymethyl)-2-diethyl-4,4-dimethoxybutanenitrile 13b When ethyl iodide was used instead of methyl iodide in a similar procedure to Preparation 6, step 2, above, a mixture of monosubstituted compound 12b and disubstituted compound 13b was isolated and used directly in subsequent steps.

Preparation 7a: Synthesis of tert-butyl 1-(3-amino-5-fluoro-4-pyridyl)piperidine-4-carboxylate

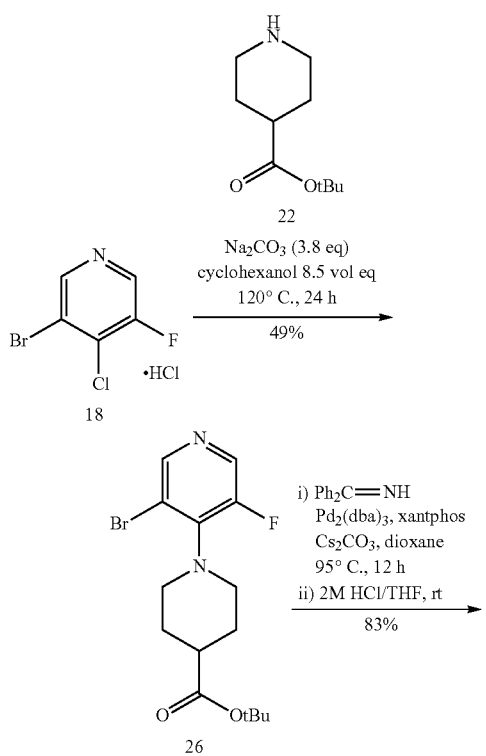

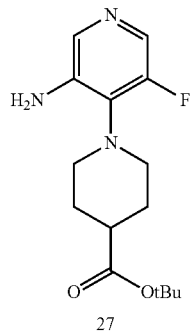

Step 1: tert-butyl 1-(3-bromo-5-fluoro-4-pyridyl)piperidine-4-carboxylate 26

A 3 L flange flask equipped with a thermometer, condenser, nitrogen line and overhead stirrer was heated at 40° C. (external) then charged with cyclohexanol (750 mL), disodium carbonate (129.8 g, 1.225 mol), 3-bromo-4-chloro-5-fluoro-pyridine (Hydrochloric Acid 18) (137.5 g, 556.8 mmol) and tert-butyl piperidine-4-carboxylate (123.8 g, 668.2 mmol) rinsed in with cyclohexanol (350 mL). Mixture was heated to 120° C. internal temperature overnight (18 hr.). Reaction mixture was removed from hotplate and allowed to cool to room temperature. Water (687.5 mL) and EtOAc (687.5 mL) were added, stirred for 10 mins then transferred to separating funnel. Additional EtOAc (1.238 L) was added, mixed and aqueous phase was removed. Organic phase was further washed with water (687 mL), aqueous phase removed, organic layer collected. Aqueous phases were combined and back extracted with EtOAc (687.5 mL), aqueous layer removed and organic phase combined with other organics. Organics concentrated in vacuo (water bath temp=60° C., vacuum down to 2 mBar) leaving a viscous brown oil.

Oil was dissolved in 25% EtOAc/petrol then passed through a short silica pad, eluting with 25% EtOAc/petrol until no more product came off. Filtrate was concentrated in vacuo to leave a brown oil, 127.1 g. Product re-purified by ISCO companion (1.5 Kg Silica, loaded in DCM, eluting 0 to 20% EtOAc/petrol), product fractions combined and concentrated in vacuo to leave desired product 26 as a pale yellow to cream solid, (98 g, 49% yield). $^1$H NMR (500 MHz, DMSO-d6) δ 8.47 (s, 1H), 8.41 (d, 1H), 3.39-3.36 (m, 2H), 3.12 (tt, 2H), 2.49-2.43 (m, 1H), 1.91-1.87 (m, 2H), 1.71-1.64 (m, 2H) and 1.43 (s, 9H). MS (ES+) 361.0.

Step 2: tert-butyl 1-(3-amino-5-fluoro-4-pyridyl)piperidine-4-carboxylate 27

To a solution of tert-butyl 1-(3-bromo-5-fluoro-4-pyridyl)piperidine-4-carboxylate 26 (98 g, 272.8 mmol), diphenylmethanimine (59.34 g, 54.94 mL, 327.4 mmol) and $Cs_2CO_3$ (177.8 g, 545.6 mmol) in 1,4-dioxane (1.274 L) was added Xantphos (15.78 g, 27.28 mmol) and $Pd_2(dba)_3$ (12.49 g, 13.64 mmol). The mixture was stirred under nitrogen at 95° C. overnight. The mixture was cooled to room temperature then partitioned between EtOAc (1000 mL, 10 vol eq.) and water (490 mL, 5 vol eq.), mixed and organic layer separated. Organics washed further with water (1×250 mL), brine (250 mL), dried ($MgSO_4$), filtered and concentrated in vacuo to leave crude product as a dark red viscous oil, 185.3 g.

The obtained product oil (185.3 g) was dissolved in THF (882.0 mL) and HCl (545.5 mL of 2 M, 1.091 mol) was added. The resulting mixture was stirred at room temperature for 20 mins. THF was removed in vacuo then additional (HCl (2M) (588.0 mL) was added. The aqueous was washed twice with EtOAc (294.0 mL). A large amount of a yellow precipitate formed during extraction in both organic and aqueous phase, the solid from both the organic and aqueous phase was collected by filtration and dried by suction. The mixed organic and aqueous filtrate was added to separating funnel, extracted with 2M HCl (2×200 mL). All aqueous phases plus solid collected on sinter (product) were combined to give a suspension. The pH was adjusted to 6 using 2M NaOH and extracted with DCM (3×600 mL). The organics were combined, dried (MgSO$_4$), filtered and concentrated in vacuo to leave a pale orange waxy solid, 112.2 g. This solid was slurried in MeCN (200 mL), stirred for 10 mins then solid collected by filtration, washed with minimal MeCN and dried by suction to leave product 27 as a white solid (66.8 g, 83% yield). $^1$H NMR (500 MHz, DMSO-d6) δ 7.82 (d, 1H), 7.63 (d, 1H), 5.22 (s, 2H), 3.11-3.00 (m, 2H), 2.91 (tt, 2H), 2.36 (tt, 1H), 1.88-1.83 (m, 2H), 1.79-1.71 (m, 2H), 1.43 (s, 9H). MS (ES+) 297.1.

Scheme 7b: Alternative Approach to Synthesize tert-butyl 1-(3-amino-5-fluoro-4-pyridyl)piperidine-4-carboxylate

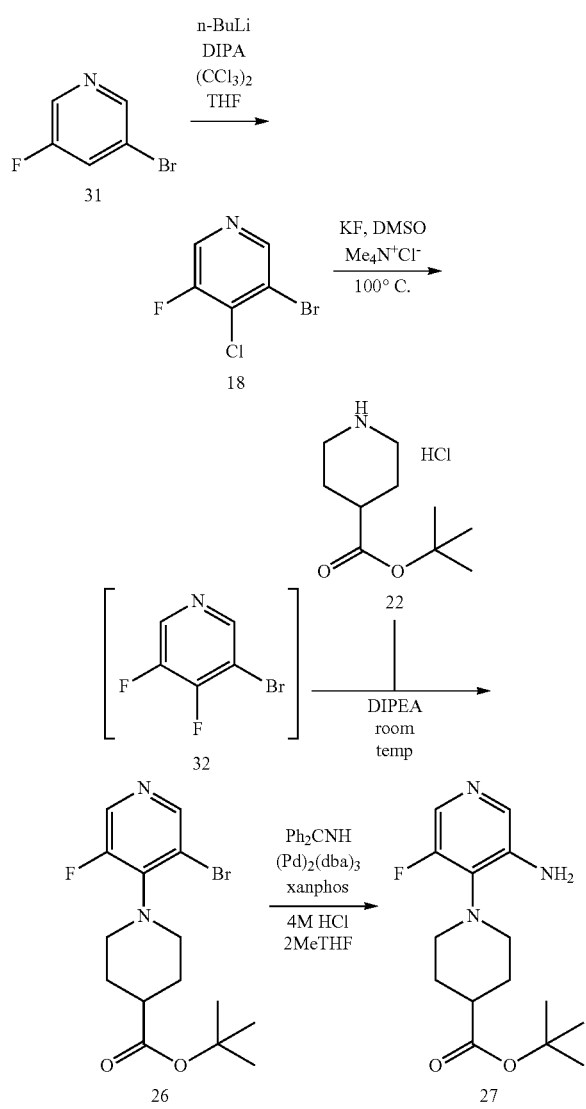

Step 1: 3-bromo-4-chloro-5-fluoropyridine hydrochloride 18

A solution of diisopropylamine (101.2 g, 140.2 mL, 1.000 mol) in tetrahydrofuran (1.148 L) was cooled to between −25° C. and −20° C. Butyllithium (2.5M in hexanes) (400 mL of 2.5 M, 1.000 mol) was added at such a rate as to maintain the reaction temperature below −20° C. (addition 20 minutes). The mixture was then allowed to warm to 4° C. over 1 hour, then re-cooled to −78° C. 3-bromo-5-fluoropyridine (153.0 g, 869.6 mmol) in tetrahydrofuran (382.5 mL) was added over 40 minutes. The mixture was stirred for 90 minutes, then a solution of 1,1,1,2,2,2-hexachloroethane (205.9 g, 869.6 mmol) in tetrahydrofuran (350.0 mL) was added dropwise over 40 minutes. Once the addition was complete the mixture was allowed to warm to ambient overnight. The mixture was cooled to 0° C. then transferred into cold water (2 L), stirred for 20 mins then MTBE (2.5 L) added and stirred vigorously for 30 mins then transferred to separating funnel and organic layer separated. Aqueous was transferred back to reaction vessel and further extracted with MTBE (2.5 L), stirred for 10 mins vigorously then transferred to separating funnel and organic layer separated. Organics were combined, dried (MgSO$_4$), filtered and concentrated to a brown oil. The oil was dissolved in pentane (500 ml) and ether (300 ml). HCl (2M in ether) (434.8 mL of 2 M, 869.6 mmol) was added slowly with stirring. On complete addition the mixture was stirred for 20 mins then solid collected by filtration, washed with ether and dried under vacuum for 1 hr. to leave product 18 as a beige solid (148.9 g, 69%); $^1$H NMR (500 MHz, DMSO-d6) δ 8.77 (2H, s); 19F NMR (500 MHz, DMSO-d6) δ −124.8; MS 210.8.

Step 2: tert-butyl 1-(3-bromo-5-fluoropyridin-4-yl) piperidine-4-carboxylate 26

3-bromo-4-chloro-5-fluoro-pyridine hydrochloride 18 (62 g, 251.1 mmol) was suspended in DCM (600 mL) and stirred. The mixture was cooled in an ice bath and sodium hydroxide (276.2 mL of 1 M, 276.2 mmol) was added slowly. The resulting mixture was stirred for 1 hour. The mixture was phase-separated. More DCM/water was added to aid phase separation. Some tarry particulates remained in the aqueous phase. The organic phase was washed with brine, dried (MgSO$_4$), filtered and concentrated. The residue was triturated with heptane. The heptane solution was filtered through a florsil pad, eluting with heptane. The filtrate was concentrated to an oil which solidified. This gave 41 g of free base.

A thoroughly stirred mixture of 3-bromo-4-chloro-5-fluoropyridine free base (55 g, 0.26 mol), potassium fluoride (31 g, 0.53 mol) and Me$_4$NCl (5.8 g, 53 mmol) in DMSO (400 mL) was heated to 130° C. for 2 hours. The reaction mixture was cooled to room temperature and tert-butyl piperidine-4-carboxylate hydrochloride 22 (66 g, 0.30 mol) and DIPEA (65 g, 0.50 mol) were added. The reaction mixture was stirred at room temperature overnight. The solvent was evaporated in vacuo. The residue was portioned between DCM/water. The organic layer was washed with water (3×), dried over Na$_2$SO$_4$, and filtered over silica gel using DCM as eluent. The filtrated was evaporated to give tert-butyl 1-(3-bromo-5-fluoropyridin-4-yl)piperidine-4-carboxylate 26 (61 g, 65%) as a light yellow solid; $^1$H NMR (500 MHz, DMSO-d$_6$) δ 8.47 (s, 1H), 8.41 (d, 1H), 3.39-3.36 (m, 2H), 3.12 (tt, 2H), 2.49-2.43 (m, 1H), 1.91-1.87 (m, 2H), 1.71-1.64 (m, 2H) and 1.43 (s, 9H); 19F NMR (500 MHz, DMSO-d6) δ −135.2; MS (ES+) 361.0.

Step 3: tert-butyl 1-(3-amino-5-fluoropyridin-4-yl)piperidine-4-carboxylate 27

Tert-butyl 1-(3-bromo-5-fluoropyridin-4-yl)piperidine-4-carboxylate 26 (800 g, 2.23 mol) was dissolved in 1,4-dioxane (7.5 L). Diphenylmethanimine (484 g, 2.67 mol) was added in one portion followed by cesium carbonate (1.45 kg, 4.45 mol), Xantphos (129 g, 223 mmol) and Pd$_2$(dba)$_3$ (102 g, 111 mmol). Additional 1,4-dioxane (2.9 L) was added and the mixture heated to 95° C. under nitrogen until the reaction was complete (determined by HPLC analysis). The mixture was cooled to 20° C. and ethyl acetate (8 L) and water (4 L) were added. The organic phase was isolated and washed with water (4 L) and brine (3.5 L) and dried over magnesium sulphate and filtered. The filtrate was concentrated to a brown oil (1.3 Kg). The oil was dissolved in 2-methyltetrahydrofuran (7.2 L) and 2M HCl was added at 20° C. and the mixture stirred for 30 minutes. The aqueous layer was isolated and the organic layer extracted with 2M HCl (1.2 L). The combined aqueous was neutralised with 2M NaOH (5.4 L, pH 8-9). The product was extracted into 2-methyltetrahydrofuran (14 L then 2×5 L). The combined extracts were washed with water (1.6 L) and the organic solution concentrated. The residue was slurried in acetonitrile (2 L), filtered and dried. This gave the product 27 as a white solid (568.7 g, 86.5%); 1H NMR (500 MHz, DMSO-d$_6$) δ 7.82 (d, 1H), 7.63 (d, 1H), 5.22 (s, 2H), 3.11-3.00 (m, 2H), 2.91 (tt, 2H), 2.36 (tt, 1H), 1.88-1.83 (m, 2H), 1.79-1.71 (m, 2H), 1.43 (s, 9H); 19F NMR (500 MHz, DMSO-d6) δ −140.0; MS (ES+) 297.1.

Preparation 8: Synthesis of tert-butyl piperidine-4-carboxylate

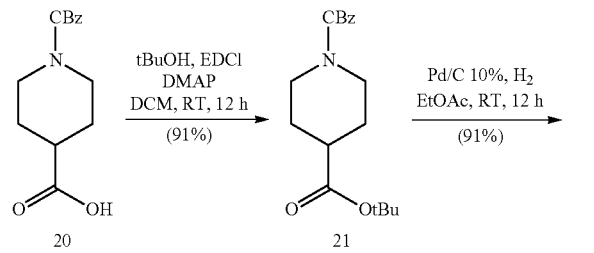

Step 1: 1-benzyl-4-tert-butyl piperidine-1,4-dicarboxylate 21

In a 5 L flange flask was charged 1-benzyloxycarbonylpiperidine-4-carboxylic acid 20 (200 g, 759.6 mmol) in DCM (500.0 mL) followed by additional DCM (2.000 L), t-butanol (140.8 g, 181.7 mL, 1.899 mol) and DMAP (46.40 g, 379.8 mmol). The mixture was cooled on ice/salt/water bath (internal −3.4° C.). 3-(ethyliminomethyleneamino)-N,N-dimethyl-propan-1-amine (Hydrochloric Acid (1)) (145.6 g, 759.6 mmol) was added portionwise over 15 mins, with addition funnel rinsed with DCM (500.0 mL). Mixture was stirred on ice bath for 2 hr. Ice bath was then removed (internal 3° C.) and allowed to warm to room temperature overnight. Mixture was washed with 5% citric acid (2×500 mL), then sat. NaHCO$_3$ (500 mL), water (500 mL), and organics dried over MgSO$_4$, which was then filtered and concentrated in vacuo to leave product 21 as a viscous light yellow oil which turned to a white solid on standing. (246.1 g, 101%). $^1$H NMR (500 MHz, DMSO-d6) δ 7.40-7.31 (m, 5H), 5.08 (s, 2H), 3.90 (dt, 2H), 2.93 (br s, 2H), 2.43 (tt, 1H), 1.80-1.76 (m, 2H) and 1.45-1.37 (m, 11H).

Step 2: tert-butyl piperidine-4-carboxylate 22

To a 3 L flask under nitrogen was charged Pd on C, wet, Degussa (10% Pd, 50% water) (8.120 g, 76.30 mmol) then EtOAc (1.706 L). The mixture was degassed via N$_2$/vacuum cycles (3×), then a solution of 1-benzyl-4-tert-butyl piperidine-1,4-dicarboxylate 21 (243.7 g, 763.0 mmol) in EtOAc (243.7 mL) was added. Mixture was stirred under a hydrogen atmosphere overnight. Hydrogen was replenished and mixture was stirred for a further 3.5 hr. Methanol (60 mL) was added to aid dissolution of precipitate then filtered through celite, washing through with methanol. Filtrate concentrated in vacuo to leave a brown oil with a slight suspension of a white solid, 138.6 g. Solid removed by filtration, and washed with minimal EtOAc. Filtrate was concentrated in vacuo to leave desired product as a light brown oil (129 g, 91%). $^1$H NMR (500 MHz, DMSO-d6) δ 2.88 (dt, 2H), 2.44 (td, 2H), 2.23 (tt, 1H), 1.69-1.64 (m, 2H) and 1.41-1.33 (m, 11H).

Preparation 9: Synthesis of 1-(oxetan-3-yl)piperazine

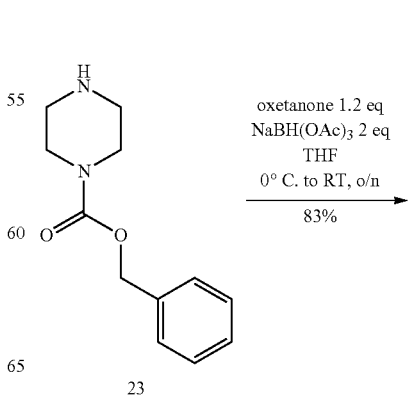

85

-continued

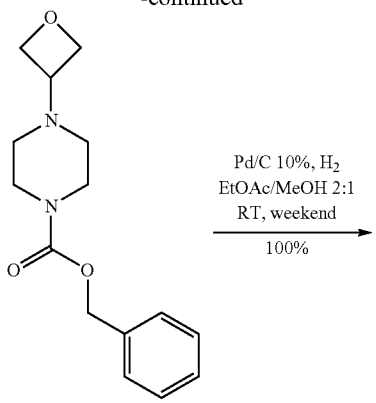

Step 1: benzyl 4-(oxetan-3-yl)piperazine-1-carboxylate 24

Benzyl piperazine-1-carboxylate 23 (27.3 mL, 142.2 mmol) was dissolved in dry THF (313.1 mL) and oxetan-3-one (12.29 g, 10.93 mL, 170.6 mmol) was added. The resulting solution was cooled in an ice-bath. NaBH(Oac)$_3$ (59.99 g, 284.4 mmol) was added portionwise over 30 mins, about a quarter was added. Mixture removed from ice bath, allowed to warm to room temperature then continued adding the NaBH(Oac)$_3$ portionwise over 30 mins. On complete addition, an exotherm from 22° C. slowly to 32° C. was observed, whereby the mixture was subsequently cooled on an ice bath until an internal of 22° C. was reached. The ice bath was removed and the reaction mixture's internal temp was steady at 22° C. The mixture was stirred at room temperature overnight.

The resulting white suspension was quenched by addition of 2M sodium carbonate solution (approx 150 mL) (pH=8) and concentrated under reduced pressure to remove THF. Product was then extracted with EtOAc (3×250 mL). Organics were combined, dried over MgSO$_4$, filtered and concentrated under reduced pressure to leave product 24 as a white solid (32.7 g 83% yield). $^1$H NMR (500 MHz, DMSO-d6) δ 7.39-7.30 (m, 5H), 5.07 (s, 2H), 4.52 (t, 2H), 4.42 (t, 2H), 3.43-3.39 (m, 5H) and 2.22 (t, 4H). MS (ES+) 276.8.

Step 2: 1-(oxetan-3-yl)piperazine 25

In a 1 L flask was added Pd(OH)$_2$ (1.661 g, 2.366 mmol) under nitrogen. MeOH (130.8 mL) and EtOAc (261.6 mL) were added and the mixture degassed via vacuum/nitrogen cycles (3×). Benzyl 4-(oxetan-3-yl)piperazine-1-carboxylate 24 (32.7 g, 118.3 mmol) was then added and the mixture stirred under a hydrogen atmosphere over the weekend. Mixture was filtered through a pad of Celite, washing through with EtOAc then methanol. Filtrate was concentrated in vacuo to leave product 25 as an orange oil 1 (8.1 g, quantitative yield). $^1$H NMR (500 MHz, DMSO-d6) δ 4.51 (t, 2H), 4.41 (t, 2H), 3.36-3.30 (masked signal, 1H), 2.69 (t, 4H) and 2.14 (br s, 4H).

86

Example 4: Synthesis of 2-amino-6-fluoro-N-(5-fluoro-4-(4-(2,2,3,3,5,5,6,6-octadeutero-piperazine-1-carbonyl)piperidin-1-yl)-3-pyridyl)pyrazolo[1,5-a]pyrimidine-3-carboxamide (Compound I-2) and 2-amino-6-fluoro-N-(5-fluoro-4-(4-(2,2,3,3,5,5,6,6-octadeutero-4-(oxetan-3-yl)piperazine-1-carbonyl)piperidin-1-yl)-3-pyridyl)pyrazolo[1,5-a]pyrimidine-3-carboxamide (Compound I-3)

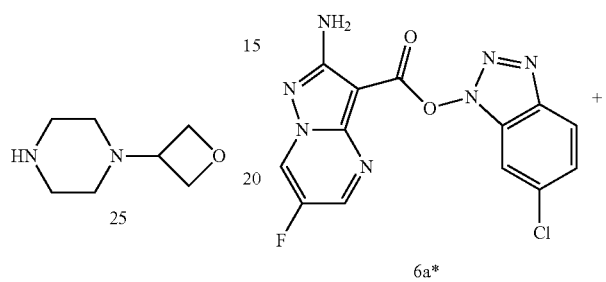

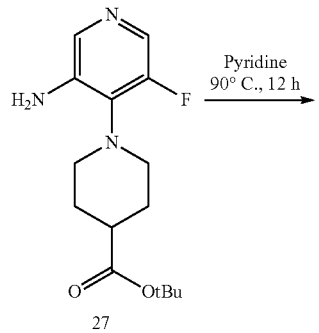

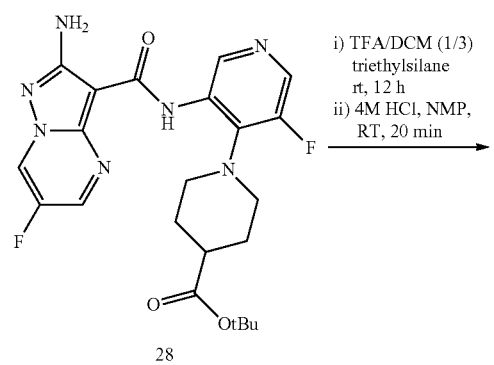

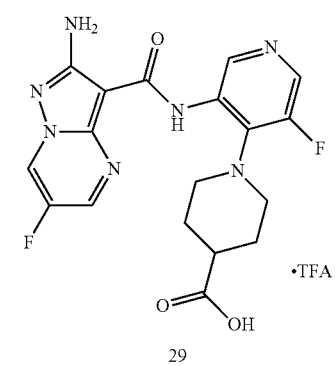

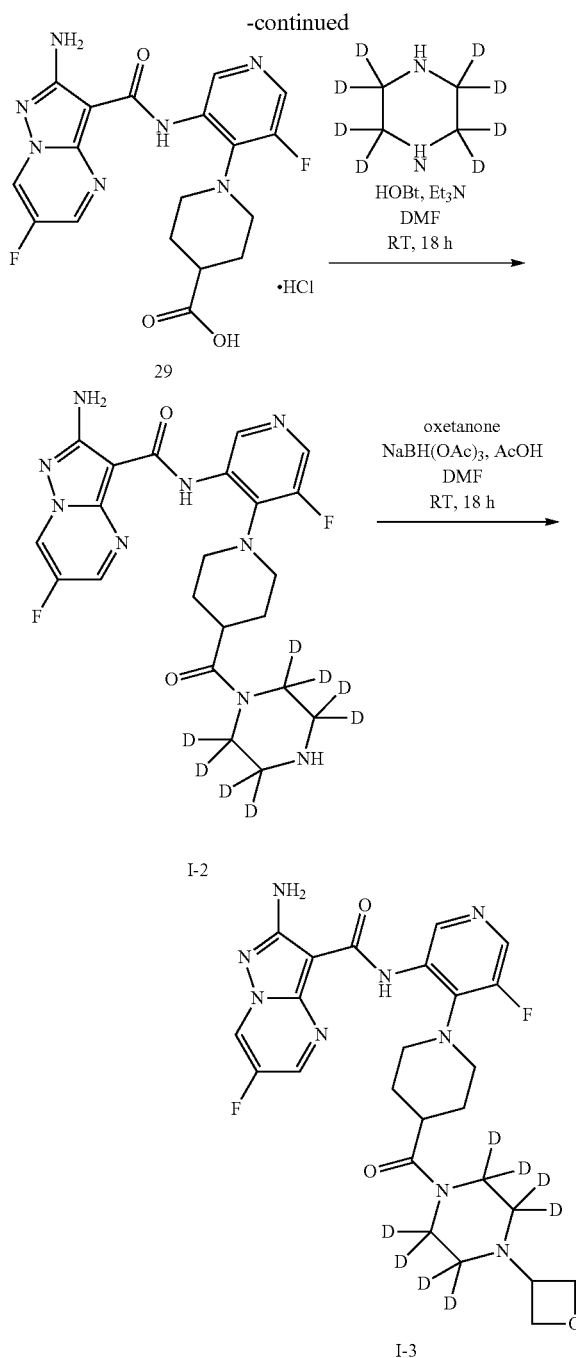

Step 1: tert-butyl 1-(3-(2-amino-6-fluoropyrazolo[1,5-a]pyrimidine-3-carboxamido)-5-fluoropyridin-4-yl)piperidine-4-carboxylate 28

A mixture of (6-chlorobenzotriazol-1-yl) 2-amino-6-fluoro-pyrazolo[1,5-a]pyrimidine-3-carboxylate 6a* (41.69 g, 119.9 mmol) and tert-butyl 1-(3-amino-5-fluoro-4-pyridyl)piperidine-4-carboxylate 27 (32.2 g, 109.0 mmol) in pyridine (483 mL) was heated at 90° C. for 12 h. The reaction was cooled to RT, EtOH was added (322 mL), and the mixture stirred at RT for 10 mins. The solid was collected by filtration, washed well with ethanol and dried by suction to leave 28 as a yellow solid (33 g, 64%).

Step 2: 1-(3-(2-amino-6-fluoropyrazolo[1,5-a]pyrimidine-3-carboxamido)-5-fluoropyridin-4-yl)piperidine-4-carboxylic acid 29

To a suspension of tert-butyl 1-[3-[(2-amino-6-fluoro-pyrazolo[1,5-a]pyrimidine-3-carbonyl)amino]-5-fluoro-4-pyridyl]piperidine-4-carboxylate 28 (69.7 g, 147.2 mmol) in DCM (348.5 mL) were added triethylsilane (18.83 g, 25.87 mL, 161.9 mmol) followed by TFA (151.1 g, 102.1 mL, 1.325 mol). The resulting solution was stirred at RT for 12 h. The mixture was concentrated in vacuo to leave an orange solid which was triturated in DCM (200 mL) for 20 mins. The solid was collected by filtration, washed with minimal DCM and dried by suction to afford the desired the trifluoroactate product as a yellow solid (75.2 g, 96%).

To a solution of 1-[3-[(2-amino-6-fluoro-pyrazolo[1,5-a]pyrimidine-3-carbonyl)amino]-5-fluoro-4-pyridyl]piperidine-4-carboxylic acid trifluoroacetate (73 g, 124.7 mmol) in NMP (662.7 mL) was added hydrogen chloride (4M in dioxane) (37.4 mL of 4 M, 149.6 mmol). The reaction was stirred at RT for 20 mins then the solid was collected by filtration, washed with minimal NMP then MTBE, dried by suction to afford pure product hydrochloride 29 as a light yellow solid.

Step 3: 2-amino-6-fluoro-N-(5-fluoro-4-(4-(2,2,3,3,5,5,6,6-octadeutero-piperazine-1-carbonyl)piperidin-1-yl)-3-pyridyl)pyrazolo[1,5-a]pyrimidine-3-carboxamide (Compound I-2)

(Benzotriazol-1-yloxy-dimethylamino-methylene)-dimethyl-ammonium trifluoroborate (127.3 mg, 0.3966 mmol) was added to a mixture of 1-[3-[(2-amino-6-fluoro-pyrazolo[1,5-a]pyrimidine-3-carbonyl)amino]-5-fluoro-4-pyridyl]piperidine-4-carboxylic acid hydrochloride 29 (150 mg, 0.3305 mmol), 2,2,3,3,5,5,6,6-octadeuteriopiperazine (155.6 mg, 1.652 mmol) and Et$_3$N (83.6 mg, 115.2 µL, 0.8262 mmol) in DMF (5 mL). The reaction mixture was stirred at RT for 18 h. The crude mixture was purified by preparative HPLC to afford I-2 as a white solid (114 mg, 48%).

Step 4: 2-amino-6-fluoro-N-(5-fluoro-4-(4-(2,2,3,3,5,5,6,6-octadeutero-4-(oxetan-3-yl)piperazine-1-carbonyl)piperidin-1-yl)pyridine-3-yl)pyrazolo[1,5-a]pyrimidine-3-carboxamide (Compound I-3)

Sodium triacetoxyborohydride (24.67 mg, 0.1164 mmol) was added to a solution of oxetan-3-one (7.271 mg, 0.1009 mmol), 2-amino-6-fluoro-N-(5-fluoro-4-(4-(2,2,3,3,5,5,6,6-octadeutero-piperazine-1-carbonyl)piperidin-1-yl)pyridine-3-yl)pyrazolo[1,5-a]pyrimidine-3-carboxamide 13 (56 mg, 0.07761 mmol) and acetic acid (13.98 mg, 13.24 µL, 0.2328 mmol) in DMF (2 mL). The reaction mixture was stirred at RT for 18 h. The solution was quenched with methanol and water and the crude mixture was purified by preparative HPLC to afford the desired product I-3 (20 mg, 46%). $^1$H NMR (500 MHz, DMSO-d6) δ 10.64 (s, 1H), 9.67 (s, 1H), 9.48 (dd, 1H), 9.26 (dd, 1H), 8.26 (d, 1H), 6.79 (s, 2H), 4.55 (t, 2H), 4.47 (t, 2H), 3.63 (m, 1H), 3.20 (m, 2H), 3.15 (m, 2H), 2.95 (m, 1H), 2.10 (m, 2H), 1.74 (d, 2H); ES+550.4.

Compound Analytical Data

| Cmpd No. | LCMS ES+ | LCMS (Rt min) | HNMR |
|---|---|---|---|
| I-1 | 542.3 | 2.14 | $^1$H NMR (500 MHz, methanol-d4) δ 1.87 (2 H, m), 2.27-2.33 (2 H, m), 2.55 (4 H, m), 2.97-3.03 (1 H, m), 3.18 (2 H, m), 3.70-3.85 (4 H, m), 4.67-4.70 (2 H, m), 4.75-4.78 (2 H, m), 8.16 (1 H, d), 9.00 (1 H, dd), 9.17 (1 H, dd), 9.68 (1 H, s), 10.65 (1 H, s). |
| I-2 | 494.3 | — | $^1$H NMR (500 MHz, DMSO-d6) δ 10.64 (s, 1 H), 9.67 (s, 1 H), 9.48 (dd, 1 H), 9.26 (dd, 1 H), 8.26 (d, 1 H), 6.79 (s, 2 H), 3.20-3.25 (m, 2 H), 3.05-3.07 (m, 2 H), 2.95-2.98 (m, 1 H), 2.07-2.12 (m, 2 H), 1.74 (d, 2 H). |
| I-3 | 550.4 | 2.13 | $^1$H NMR (500 MHz, DMSO-d6) δ 10.64 (s, 1 H), 9.67 (s, 1 H), 9.48 (dd, 1 H), 9.26 (dd, 1 H), 8.26 (d, 1 H), 6.79 (s, 2 H), 4.55 (t, 2 H), 4.47 (t, 2 H), 3.63 (m, 1 H), 3.20 (m, 2 H), 3.15 (m, 2 H), 2.95 (m, 1 H), 2.10 (m, 2 H), 1.74 (d, 2 H). |

Solid Forms of Compound I-1

Compound I-1 has been prepared in various solid forms, including salts, solvates, hydrates, and anhydrous forms. The solid forms of the present invention are useful in the manufacture of medicaments for the treatment of cancer. One embodiment provides use of a solid form described herein for treating cancer. In some embodiments, the cancer is triple negative breast cancer, pancreatic cancer, small cell lung cancer, colorectal cancer, ovarian cancer, or non-small cell lung cancer. Another embodiment provides a pharmaceutical composition comprising a solid form described herein and a pharmaceutically acceptable carrier.

Applicants describe herein a plurality of novel solid forms of Compound I-1. The names and stoichiometry for each of these solid forms are provided in Table 2 below:

TABLE 2

| Example | Forms | Stoichiometry |
|---|---|---|
| Example 5 | Compound I-1•ethanol solvate | 1:0.72 |
| Example 6a | Compound I-1•hydrate I | 1:4.5 |
| Example 6b | Compound I-1•hydrate II | — |
| Example 7 | Compound I-1•anhydrous form A | N/A |
| Example 8 | Compound I-1•anhydrous form B | — |
| Example 9 | Compound I-1•anhydrous form C | N/A |
| Example 10 | Compound I-1•amorphous | N/A |
| Example 11 | Compound I-1•DMSO solvate | 1:1 |
| Example 12 | Compound I-1•DMAC solvate | 1:1.3 |
| Example 13 | Compound I-1•acetone solvate | 1:0.44 |
| Example 14 | Compound I-1•isopropanol solvate | 1:0.35 | ssNMR Experimental Method

Solid state NMR spectra were acquired on the Bruker-Biospin 400 MHz Advance III wide-bore spectrometer equipped with Bruker-Biospin 4 mm HFX probe. Samples were packed into 4 mm $ZrO_2$ rotors (approximately 70 mg or less, depending on sample availability). Magic angle spinning (MAS) speed of typically 12.5 kHz was applied. The temperature of the probe head was set to 275K to minimize the effect of frictional heating during spinning. The proton relaxation time was measured using $^1$H MAS $T_1$ saturation recovery relaxation experiment in order to set up proper recycle delay of the $^{13}$C cross-polarization (CP) MAS experiment. The recycle delay of $^{13}$C CPMAS experiment was adjusted to be at least 1.2 times longer than the measured $^1$H $T_1$ relaxation time in order to maximize the carbon spectrum signal-to-noise ratio. The CP contact time of $^{13}$C CPMAS experiment was set to 2 ms. A CP proton pulse with linear ramp (from 50% to 100%) was employed. The Hartmann-Hahn match was optimized on external reference sample (glycine). Fluorine spectra were acquired using proton decoupled MAS setup with recycled delay set to approximately 5 times of the measured $^{19}$F $T_1$ relaxation time The fluorine relaxation time was measured using proton decoupled $^{19}$F MAS $T_1$ saturation recovery relaxation experiment. Both carbon and fluorine spectra were acquired with SPINAL 64 decoupling was used with the field strength of approximately 100 kHz. The chemical shift was referenced against external standard of adamantane with its upfield resonance set to 29.5 ppm.

Example 5: Compound I-1 (Ethanol Solvate)

Compound I-1 ethanol solvate can be prepared according to the methods described in Example 1, Step 4.

XRPD of Compound I-1 (Ethanol Solvate)

The XRPD pattern of Compound I-1•ethanol solvate was recorded at room temperature in reflection mode using a PANalytical diffractometer equipped with an Empyrean tube source and a PIXcel 1D detector (PANalytical, The Netherlands). The X-ray generator was operating at a voltage of 45 kV and a current of 40 mA. The powder sample was placed in a silicon holder. The data were over the range of 3°-39° 2 theta with a step size of 0.013° and a dwell time of 121 s per step. FIG. 1a shows the X-ray powder diffractogram of the sample which is characteristic of crystalline drug substance.

Table 3a depicts representative XRPD peaks from Compound I-1•ethanol solvate:

TABLE 3a

| Representative XRPD Peaks | | |
|---|---|---|
| XRPD Peaks | Angle (2-Theta ± 0.2) | Intensity % |
| 1* | 10.9 | 20.6 |
| 2 | 12.7 | 6.4 |
| 3 | 13.6 | 12.2 |
| 4 | 14.3 | 7.5 |
| 5 | 14.9 | 9.5 |
| 6 | 15.5 | 5.7 |
| 7 | 16.2 | 15.7 |
| 8* | 17.2 | 50.6 |
| 9 | 18.0 | 1.4 |
| 10* | 19.7 | 35.3 |
| 11 | 20.4 | 26.2 |
| 12 | 20.6 | 23.1 |
| 13 | 21.7 | 3.5 |
| 14 | 22.2 | 3.7 |
| 15 | 22.8 | 11.2 |
| 16 | 23.2 | 18.2 |
| 17* | 23.8 | 100 |
| 18 | 23.8 | 91.4 |
| 19 | 24.3 | 71.3 |
| 20* | 24.4 | 72.8 |
| 21 | 24.9 | 15.1 |
| 22 | 25.7 | 15.9 |
| 23 | 26.3 | 6.0 |
| 24 | 27.5 | 5.8 |
| 25* | 29.0 | 44.9 |
| 26 | 30.0 | 9.7 |
| 27 | 30.9 | 4.6 |
| 28 | 31.5 | 4.5 |
| 29 | 32.4 | 2 |
| 30 | 32.9 | 3.4 |
| 31 | 34.5 | 3.4 |
| 32 | 34.9 | 2.7 |
| 33 | 35.7 | 2.8 |
| 34 | 37.5 | 1.2 |

Thermo Analysis of Compound I-1 (Ethanol Solvate)

A thermal gravimetric analysis of Compound I-1•ethanol solvate was performed to determine the percent weight loss as a function of temperature using the Discovery TGA (TA Instruments Trios). A sample (8.338 mg) was added to a pre-tared aluminum pan and heated from ambient temperature to 310° C. at 20° C./min. The TGA results seen in FIG. 2a show a large weight loss of 5.76% between 166° C. (onset) and 219° C. (end point). This weight loss corresponds to approximately 0.72 molar equivalents of ethanol. The subsequent weight loss seen at 290° C. is a result of melting/degradation.

Differential Scanning Calorimetry of Compound I-1 (Ethanol Solvate)

Differential scanning calorimetry of Compound I-1•ethanol solvate was measured using the TA Instrument DSC Q2000. A sample (1.84 mg) was weighed in a pre-punched pinhole aluminum hermetic pan and heated from ambient temperature to 300° C. at 20° C./min. The DSC results seen in FIG. 3a show a desolvation endotherm at 169° C. (onset) followed by a single melting endotherm at 258° C. (onset).

ssNMR of Compound I-1 (Ethanol Solvate)

A solid state $^{13}$C NMR spectrum of Compound I-1•ethanol solvate is shown in FIG. 4a. Table 3b provides chemical shifts of the relevant peaks.

TABLE 3b

Solid State $^{13}$C NMRspectrum of Compound I-1 (ethanol solvate)

| Peak # | Compound I-1 (ethanol solvate) $^{13}$C Chem. Shifts | |
|---|---|---|
|  | F1 [ppm] | Intensity |
| 1* | 175.4 | 53.9 |
| 2 | 162.4 | 58.4 |
| 3 | 160.0 | 14.1 |
| 4 | 157.4 | 17.6 |
| 5 | 150.7 | 19.1 |
| 6 | 148.2 | 25.1 |
| 7 | 145.8 | 39.9 |
| 8 | 140.1 | 42.1 |
| 9* | 138.0 | 48.7 |
| 10 | 136.1 | 48.2 |
| 11 | 134.3 | 85.7 |
| 12* | 123.1 | 45.6 |
| 13 | 89.0 | 41.6 |
| 14 | 76.8 | 67.5 |
| 15 | 76.1 | 75.8 |
| 16* | 57.8 | 79.7 |
| 17 | 51.6 | 100.0 |
| 18 | 48.9 | 90.9 |
| 19* | 44.0 | 60.5 |
| 20 | 42.2 | 61.4 |
| 21 | 38.8 | 74.7 |
| 22 | 30.9 | 64.3 |
| 23 | 28.7 | 70.2 |
| 24* | 19.5 | 33.2 |

A solid state $^{19}$F NMR spectrum of Compound I-1•ethanol solvate is shown in FIG. 5a. Table 3c provides chemical shifts of the relevant peaks.

TABLE 3c

Solid State $^{19}$F NMR Spectrum of Compound I-1 (ethanol solvate)

| Peak # | Compound (I-1 (ethanol solvate) $^{19}$F Chem. Shifts | |
|---|---|---|
|  | F1 [ppm] | Intensity |
| 1* | −136.0 | 8.5 |
| 2* | −151.6 | 12.5 |

Example 6a: Compound I-1 (Hydrate I)

Compound I-1•ethanol solvate (1000 mg), prepared according to the methods described in Example 1, Step 4, was slurried in water (20 mL) for 4 days at room temperature. The suspension was centrifuged and the residual solids were isolated then dried overnight in a 35° C. vacuum oven to afford Compound I-1•hydrate I as a yellow powder.

XRPD of Compound I-1 (Hydrate I)

The XRPD pattern of Compound I-1•hydrate I was recorded at room temperature in reflection mode using a Bruker D8 Discover diffractometer equipped with a sealed tube source and a Hi-Star area detector (Bruker AXS, Madison, Wis., Asset V012842). The X-ray generator was operating at a voltage of 40 kV and a current of 35 mA. The powder sample was placed in a nickel holder. Two frames were registered with an exposure time of 120 seconds each. The data were subsequently integrated over the range of 3.5°-39° 2-theta with a step size of 0.02° and merged into one continuous pattern. FIG. 1b shows the X-ray powder diffractogram of the sample which is characteristic of crystalline drug substance.

Table 4a depicts representative XRPD peaks from Compound I-1•hydrate I:

TABLE 4a

Representative XRPD Peaks

| XRPD Peaks | Angle (2-Theta ± 0.2) | Intensity % |
|---|---|---|
| 1 | 4.0 | 1.4 |
| 2 | 4.8 | 3.0 |
| 3 | 5.7 | 7.8 |
| 4 | 6.3 | 100.0 |
| 5* | 6.5 | 51.0 |
| 6 | 9.1 | 3.0 |
| 7 | 10.1 | 10.5 |
| 8 | 10.4 | 10.8 |
| 9 | 11.2 | 5.9 |
| 10 | 11.5 | 8.7 |
| 11 | 11.8 | 11.5 |
| 12* | 12.5 | 16.0 |
| 13* | 13.7 | 10.9 |
| 14 | 14.3 | 7.2 |
| 15 | 15.0 | 9.2 |
| 16 | 15.5 | 10.5 |
| 17 | 16.9 | 14.8 |
| 18* | 18.8 | 10.8 |
| 19 | 20.1 | 14.1 |
| 20 | 20.6 | 11.6 |
| 21 | 22.6 | 10.2 |
| 22 | 23.9 | 4.5 |
| 23 | 24.7 | 7.8 |
| 24* | 26.0 | 13.6 |
| 25 | 27.3 | 10.9 |
| 26 | 28.6 | 4.9 |
| 27 | 32.3 | 2.2 |

Thermo Analysis of Compound I-1 (Hydrate I)

A thermal gravimetric analysis of Compound I-1•hydrate I was performed to determine the percent weight loss as a function of time using the TA Instrument TGA Q5000 (Asset V014258). A sample (7.380 mg) was added to a pre-tared aluminum pan and heated from ambient temperature to 350° C. at 10° C./min. The TGA results seen in FIG. 2b show a large initial weight loss up to 100° C. followed by a small amount of additional weight loss prior to melting/degradation. The initial weight loss of 14.56% corresponds to approximately 4.5 molar equivalents of water. The onset temperature of melting/degradation is 292° C.

Differential Scanning Calorimetry of Compound I-1 (Hydrate I)

Differential scanning calorimetry of Compound I-1•hydrate I was measured using the TA Instrument DSC Q200 (Asset V005642). A sample (5.598 mg) was weighed in a pre-punched pinhole aluminum hermetic pan and heated from ambient temperature to 350° C. at 10° C./min. The DSC results seen in FIG. 3b show an initial broad endothermic event that corresponds to de-hydration and subsequent melting to an amorphous form. Following the melt there is a Tg at 125° C., re-crystallization at 180° C., a melt at 257° C., then a final melt/degradation event at 278° C.

Example 6b: Compound I-1 (Hydrate II)

Compound I-1•ethanol solvate (1000 mg), prepared according to the methods described in Example 1, Step 4, was slurried in water (20 mL) for 4 days at room temperature. The suspension was centrifuged and the residual solids were isolated to afford Compound I-1•hydrate II as a yellow paste.

XRPD of Compound I-1 (Hydrate II)

The XRPD pattern of Compound I-1•hydrate II was recorded at room temperature in reflection mode using a Bruker D8 Discover diffractometer equipped with a sealed tube source and a Hi-Star area detector (Bruker AXS, Madison, Wis., Asset V012842). The X-ray generator was operating at a voltage of 40 kV and a current of 35 mA. The powder sample was placed in a nickel holder. Two frames were registered with an exposure time of 120 seconds each. The data were subsequently integrated over the range of 3.5°-39° 2-theta with a step size of 0.02° and merged into one continuous pattern. FIG. 4b shows the X-ray powder diffractogram of the sample which is characteristic of crystalline drug substance.

Table 4b depicts representative XRPD peaks from Compound I-1•hydrate II:

TABLE 4b

Representative XRPD Peaks

| XRPD Peaks | Angle (2-Theta ± 0.2) | Intensity % |
|---|---|---|
| 1 | 4.2 | 4.2 |
| 2 | 5.7 | 12.7 |
| 3 | 6.4 | 100.0 |
| 4 | 8.0 | 12.2 |
| 5* | 10.1 | 15.4 |
| 6* | 11.3 | 22.6 |
| 7 | 11.6 | 21.2 |
| 8* | 11.9 | 29.9 |
| 9 | 12.5 | 45.6 |
| 10 | 14.3 | 25.2 |
| 11 | 15.1 | 22.2 |
| 12 | 17.0 | 19.7 |
| 13 | 17.7 | 17.2 |
| 14 | 18.8 | 39.7 |
| 15 | 19.8 | 21.1 |
| 16* | 20.2 | 24.7 |
| 17 | 21.9 | 10.3 |
| 18 | 22.6 | 28.6 |
| 19 | 24.0 | 12.0 |
| 20 | 24.7 | 8.8 |
| 21* | 25.1 | 13.0 |
| 22 | 25.9 | 12.6 |
| 23 | 27.2 | 5.3 |
| 24 | 28.3 | 12.2 |
| 25 | 28.7 | 9.5 |
| 26 | 29.4 | 9.2 |
| 27 | 31.9 | 14.9 | ssNMR of Compound I-1 (Hydrate II)

A solid state $^{13}C$ NMR spectrum of Compound I-1•hydrate II is shown in FIG. 5b. Table 4c provides chemical shifts of the relevant peaks.

TABLE 4c

Solid State $^{13}C$ NMR spectrum of Compound I-1 (hydrate II)

Compound I-1 (hydrate II) $^{13}C$ Chem. Shifts

| Peak # | F1 [ppm] | Intensity |
|---|---|---|
| 1* | 177.0 | 49.2 |
| 2 | 161.8 | 24.9 |
| 3 | 161.3 | 39.9 |
| 4 | 160.9 | 31.4 |
| 5 | 159.7 | 20.1 |
| 6* | 158.2 | 35.5 |
| 7 | 151.9 | 15.0 |
| 8 | 149.1 | 20.5 |
| 9* | 142.9 | 68.3 |
| 10 | 136.3 | 37.6 |
| 11 | 133.7 | 78.7 |
| 12 | 132.9 | 40.1 |
| 13 | 130.5 | 34.2 |
| 14 | 122.8 | 23.3 |
| 15* | 85.1 | 40.3 |
| 16 | 76.9 | 73.5 |
| 17 | 76.4 | 95.7 |
| 18* | 58.9 | 72.4 |
| 19 | 50.2 | 100.0 |
| 20 | 49.5 | 66.0 |
| 21 | 48.5 | 47.3 |
| 22 | 45.0 | 48.6 |
| 23 | 41.8 | 45.0 |
| 24 | 37.2 | 84.6 |
| 25* | 31.9 | 67.5 |
| 26 | 28.9 | 65.8 |

A solid state $^{19}F$ NMR spectrum of Compound I-1•hydrate II is shown in FIG. 6b. Table 4d provides chemical shifts of the relevant peaks.

TABLE 4d

Solid State $^{19}$F NMR Spectrum of Compound I-1•hydrate II

| Peak # | Compound I-1 (hydrate II) $^{19}$F Chem. Shifts | |
|---|---|---|
| | F1 [ppm] | Intensity |
| 1* | −138.0 | 8.2 |
| 2* | −152.7 | 12.5 |

Example 7: Compound I-1 (Anhydrous Form A)

Compound I-1•ethanol solvate (1000 mg), prepared according to the methods described in Example 1, Step 4, was slurried in THF (20 mL) for 72 hr at room temperature. The suspension was centrifuged and the residual solids were isolated then dried overnight in a 35° C. vacuum oven to afford compound I-1•anhydrous form A ("form A") as a yellow powder.

In an alternative process, compound I-1•amorphous form (15.1 g; 0.028 mol), prepared according to the method in Example 2, step 3, was suspended in a mixture of 2-propanol (300 mL) and water (100 mL). The mixture was stirred and heated to 70-75° C. and filtered whilst hot. The resulting clear filtrate was heated and distilled and solvent replaced with 2-propanol until the contents temperature reached 82.5° C. The resulting suspension was cooled to 15° C. over 10 hours and stirred for a further 5 hours. The solids were collected by filtration, dried by suction for 1 hour then dried in a vacuum oven for 20 hours at 60° C. to give compound I-1•anhydrous form A (13.9 g; 92%).

A number of other solvents may be utilized to prepare compound I-1•anhydrous form A. Table 5a below summarizes the methods.

TABLE 5a

Solvents Used to Prepare Form A

| Vehicle | Re-crystallization method | Results of residue solid |
|---|---|---|
| Anisole | Slurry | Form A |
| 2-Butanone | Slurry | Form A |
| Ethyl acetate | Slurry | N/A |
| Heptane | Slurry | Form A |
| Isopropanol | Hot Slurry | Form A |
| Isopropyl acetate | Slurry | Form A |
| TBME | Slurry | Form A |
| THF | Slurry | Form A |

XRPD of Compound I-1 (Anhydrous Form A)

The XRPD pattern of Compound I-1•anhydrous form A was recorded at room temperature in reflection mode using a Bruker D8 Discover diffractometer equipped with a sealed tube source and a Hi-Star area detector (Bruker AXS, Madison, Wis., Asset V012842). The X-ray generator was operating at a voltage of 40 kV and a current of 35 mA. The powder sample was placed in a nickel holder. Two frames were registered with an exposure time of 120 seconds each. The data were subsequently integrated over the range of 3.5°-39° 2-theta with a step size of 0.02° and merged into one continuous pattern. FIG. 1c shows the X-ray powder diffractogram of the sample which is characteristic of crystalline drug substance.

Table 5b depicts representative XRPD peaks form Compound I-1•anhydrous form A:

TABLE 5b

Representative XRPD Peaks

| XRPD Peaks | Angle (2-theta ± 0.2) | Intensity % |
|---|---|---|
| 1 | 3.6 | 12.5 |
| 2 | 3.9 | 17.4 |
| 3* | 6.1 | 51.0 |
| 4 | 9.7 | 20.5 |
| 5* | 12.2 | 22.8 |
| 6 | 14.0 | 23.5 |
| 7* | 14.5 | 22.2 |
| 8 | 16.4 | 33.5 |
| 9 | 17.1 | 25.0 |
| 10 | 17.8 | 36.0 |
| 11 | 19.1 | 21.5 |
| 12 | 20.2 | 26.5 |
| 13 | 21.3 | 16.1 |
| 14* | 22.3 | 31.6 |
| 15 | 24.4 | 23.7 |
| 16 | 25.3 | 100.0 |
| 17 | 28.4 | 11.9 |
| 18* | 31.8 | 16.0 |

Thermo Analysis of Compound I-1 (Anhydrous Form A)

A thermal gravimetric analysis of Compound I-1•anhydrous form A was performed to determine the percent weight loss as a function of time using the TA Instrument TGA Q5000 (Asset V014258). A sample (7.377 mg) was added to a pre-tared aluminum pan and heated from ambient temperature to 350° C. at 10° C./min. The TGA results seen in FIG. 2c show very little observed weight loss prior to melting or thermal degradation. From ambient temperature to 265° C., the weight loss is 0.96%. The onset temperature of degradation is 292° C.

Differential Scanning Calorimetry of Compound I-1 (Anhydrous Form A)

Differential scanning calorimetry of Compound I-1•anhydrous form A was measured using the TA Instrument DSC Q2000 (Asset V014259). A sample (3.412 mg) was weighed in a pre-punched pinhole aluminum hermetic pan and heated from ambient temperature to 350° C. at 10° C./min. The DSC results seen in FIG. 3c show a single endothermic melting event at 262° C. There are two distinct peaks contained within the melting event which are separated by about 1° C.

Composition and Preparation of Active Tablets Containing Anhydrous Form A

Composition of Form A 10 mg Tablet

The formulation compositions for both the dry granulation and tablet blends of the active Form A 10 mg tablets are described in Tables 5c and 5d. The overall composition specification of the tablets is described in Table 5e.

TABLE 5c

Form A (10 mg) Intragranular Blending

| Component | Amount (mg) per tablet | % W/W |
|---|---|---|
| Form A | 10.00 | 10.26 |
| Lactose Monohydrate, #316, NF, PhEur, JP | 27.50 | 28.20 |
| Avicel PH-101 (microcrystalline cellulose), NF, PhEur, JP | 55.00 | 56.41 |
| Ac-Di-Sol (croscarmellose sodium), NF, PhEur, JP | 3.00 | 3.08 |
| Sodium Stearyl Fumarate, NF, PhEur, JP | 2.00 | 2.05 |
| Total | 97.50 | 100.00 |

TABLE 5d

Form A (10 mg) Tablet Composition

| Component | Amount (mg) per tablet | % W/W |
|---|---|---|
| Form A Intragranular Blend (Milled) | 97.50 | 97.50 |
| Ac-Di-Sol (croscarmellose sodium), NF, PhEur, JP | 1.50 | 1.50 |
| Sodium Stearyl Fumarate, NF, PhEur, JP | 1.00 | 1.00 |
| Total | 100.00 | 100.00 |

TABLE 5e

Form A (10 mg) Tablet Overall Composition

| | | % in dry granule | % in core tablet |
|---|---|---|---|
| intra granular | Form A | 10.26 | 10.00 |
| | Lactose Monohydrate, #316, NF, PhEur, JP | 28.20 | 27.50 |
| | Avicel PH-101, NF, PhEur, JP | 56.41 | 55.00 |
| | Ac-Di-Sol, NF, PhEur, JP | 3.08 | 3.00 |
| | Sodium Stearyl Fumarate, NF, PhEur, JP | 2.05 | 2.00 |
| | total granules: | 100.00 | 97.50 |
| extra granular | Ac-Di-Sol, NF, PhEur, JP | | 1.50 |
| | Sodium Stearyl Fumarate, NF, PhEur, JP | | 1.00 |
| | total core tablet: | | 100.00 |

Composition of Form A 50 mg Tablet

The formulation compositions for both the dry granulation and tablet blends of the active Form A 50 mg tablets are described in Tables 5f and 5g. The overall composition specification of the tablets is described in Table 5h.

TABLE 5f

Form A (50 mg) Intragranular Blending

| Component | Amount (mg) per tablet | % W/W |
|---|---|---|
| Form A | 50.00 | 10.26 |
| Lactose Monohydrate, #316, NF, PhEur, JP | 137.50 | 28.20 |
| Avicel PH-101 (microcrystalline cellulose), NF, PhEur, JP | 275.00 | 56.41 |
| Ac-Di-Sol (croscarmellose sodium), NF, PhEur, JP | 15.00 | 3.08 |
| Sodium Stearyl Fumarate, NF, PhEur, JP | 10.00 | 2.05 |
| Total | 487.50 | 100.00 |

TABLE 5g

Form A (50 mg) Tablet Composition

| Component | Amount (mg) per tablet | % W/W |
|---|---|---|
| Form A Intragranular Blend (Milled) | 487.50 | 97.50 |
| Ac-Di-Sol (croscarmellose sodium), NF, PhEur, JP | 7.50 | 1.50 |
| Sodium Stearyl Fumarate, NF, PhEur, JP | 5.00 | 1.00 |
| Total | 100.00 | 100.00 |

TABLE 5h

Form A (50 mg) Tablet Overall Composition

| | | % in dry granule | % in core tablet |
|---|---|---|---|
| intra granular | Form A | 10.26 | 10.00 |
| | Lactose Monohydrate, #316, NF, PhEur, JP | 28.20 | 27.50 |
| | Avicel PH-101, NF, PhEur, JP | 56.41 | 55.00 |
| | Ac-Di-Sol, NF, PhEur, JP | 3.08 | 3.00 |
| | Sodium Stearyl Fumarate, NF, PhEur, JP | 2.05 | 2.00 |
| | total granules: | 100.00 | 97.50 |
| extra granular | Ac-Di-Sol, NF, PhEur, JP | | 1.50 |
| | Sodium Stearyl Fumarate, NF, PhEur, JP | | 1.00 |
| | total core tablet: | | 100.00 |

Process for Preparing Form A 10 mg and 50 mg Tablets

Step I. Pre-Granulation Mixing:

Form A was passed through a cone mill assembled with a 24R round holed screen and a rounded edge type impeller at an impeller rate of 1500 rpms. Lactose monohydrate, microcrystalline cellulose, and intra-granular croscarmellose sodium were screened through a #30 mesh sieve. The cone milled Form A and all the screened components were then blended for 10 minutes at 26 rpm. Sodium stearyl fumarate was hand sieved through a 60 mesh screen and then charged into the blender and blended with the materials for 3 minutes at 26 rpm. Samples were pulled for blend uniformity analysis.

Step II. Dry Granulation:

The blend was dry granulated on a Gerteis Minipactor. The blend was passed through the roller compactor, assembled with a combination of smooth faced and knurled faced compaction rolls, at a 2 rpm roll speed with 5 KN/cm roll force and a 2 mm roll gap. Compacted powder was then granulated with a pocketed type milling roll through a 1 mm screen with 80 rpm mill speed.

Step III. Final Blending:

Extra-granular croscarmellose sodium and sodium stearyl fumarate were hand sieved through 30 and 60 mesh screens, respectively. Extra-granular croscarmellose sodium was blended with the dry granulate for 5 minutes at 32 rpm. Extra-granular sodium stearyl fumarate was then added to the bulk mixture and mixed for 3 minutes at 32 rpm. Samples were pulled for blend uniformity analysis. The blend was sealed in double Low Density Polyethylene bags within a hard secondary container to protect from puncture.

Step IV. Tablet Compression:

A tablet compression machine (Piccola D-8 Rotatory Press) was partially tooled (2 stations out of 8 stations) with a 0.25" standard round concave tooling for 10 mg strength and 0.568"×0.2885" caplet tooling for 50 mg strength. Turret speed was 25-35 rpm. The in-process control testing for tablets included average weight, individual weight, and hardness, as shown in Table 5i.

TABLE 5i

Form A (10 mg and 50 mg) Tablet Compression In-process Control Specifications

| Parameter | 10 mg strength | | | 50 mg strength | | |
|---|---|---|---|---|---|---|
| | Minimum | Target | Maximum | Minimum | Target | Maximum |
| Average & Individual weight (mg) | 92 | 100 | 108 | 460 | 500 | 540 |
| Hardness (kP) | 3.6 | 5.3 | 7.0 | 11.9 | 15.9 | 19.9 |

Crystal Preparation of Form A

Form A was crystallized from a DCM/heptane mixture by slow evaporation of the solvents. A colorless needle shaped crystal with dimensions 0.10×0.02×0.02 mm was chosen for the diffraction experiment on a Bruker APEX II CCD diffractometer with Cu Kα radiation at room temperature. The structure was solved by direct methods and refined by the SHELXTL package.

Form A Crystal Experimental:

The crystal shows monoclinic cell with $P2_1/c$ centrosymmetric space group. The lattice parameters are a=15.29(3)Å, b=12.17(2)Å, c=14.48(3)Å, α=90°, β=107.22(3°), γ=90°, volume=2573(9)Å$_3$. The refinement gave the R factor of 6.9%. Conformational plots of Compound I-1•anhydrous form A based on single crystal X-ray analyses are shown in FIGS. 4c and 5c. Compound I-1•anhydrous form A appears ordered in the asymmetric unit (FIG. 4c). As shown in FIG. 5c, Compound I-1•anhydrous form A molecules form a one-dimensional chain along the b-axis that is stabilized by the inter-molecular hydrogen bonds between the amine and pyridine groups. Multiple chains stack in three dimensions with approximately 4.3 Å inter-layer spacing.

TABLE 5j

Crystal data for Form A

| | |
|---|---|
| $C_{25}H_{29}F_2N_9O_3$ | Z = 4 |
| $M_r$ = 541.57 | F(000) = 1136 |
| Monoclinic, $P2_1/c$ | $D_x$ = 1.398 Mg m$^{-3}$ |
| a = 15.29 (3) Å | Cu Kα radiation, λ = 1.54178 Å |
| b = 12.17 (2) Å | μ = 0.89 mm$^{-1}$ |
| c = 14.48 (3) Å | T = 296K |
| β = 107.22 (3)° | Needle, colorless |
| V = 2573 (9) Å$^3$ | 0.100 × 0.02 × 0.02 mm |

Geometry:

All esds (except the esd in the dihedral angle between two l.s. planes) are estimated using the full covariance matrix. The cell esds are taken into account individually in the estimation of esds in distances, angles and torsion angles; correlations between esds in cell parameters are only used when they are defined by crystal symmetry. An approximate (isotropic) treatment of cell esds is used for estimating esds involving ls. planes.

TABLE 5k

Data collection parameters for Form A crystal

| | |
|---|---|
| Bruker APEX II CCD diffractometer | $R_{int}$ = 0.084 |
| Radiation source: sealed tube | $θ_{max}$ = 53.6°, $θ_{min}$ = 3.0° |
| oscillation photos around ω and φ scans | h = −15→15 |
| 9104 measured reflections | k = −12→11 |
| 2939 independent reflections | l = −11→14 |
| 1165 reflections with I > 2σ(I) | |

Data collection: Apex II; cell refinement: Apex II; data reduction: Apex II; program(s) used to solve structure: SHELXS97 (Sheldrick, 1990); program(s) used to refine structure: SHELXL97 (Sheldrick, 1997); molecular graphics: Mercury; software used to prepare material for publication: publCIF.

TABLE 5m

Refinement parameters for Form A crystal

| | |
|---|---|
| Refinement on $F^2$ | 0 restraints |
| Least-squares matrix: full | Hydrogen site location: inferred from neighbouring sites |
| $R[F^2 > 2σ(F^2)]$ = 0.069 | H-atom parameters constrained |
| $wR(F^2)$ = 0.179 | $w = 1/[σ^2(F_o^2) + (0.0743P)^2]$ where $P = (F_o^2 + 2F_c^2)/3$ |
| S = 0.94 | $(Δ/σ)_{max}$ < 0.001 |
| 2939 reflections | $Δ_{max}$ = 0.23 e Å$^{-3}$ |
| 352 parameters | $Δ_{min}$ = −0.26 e Å$^{-3}$ |

Refinement: Refinement of $F^2$ against ALL reflections. The weighted R-factor wR and goodness of fit S are based on $F^2$, conventional R-factors R are based on F, with F set to zero for negative $F^2$. The threshold expression of $F^2 > 2\text{sigma}(F^2)$ is used only for calculating R-factors (gt) etc. and is not relevant to the choice of reflections for refinement. R-factors based on $F^2$ are statistically about twice as large as those based on F, and R-factors based on ALL data will be even larger.

ssNMR of Compound I-1 (Anhydrous Form A)

A solid state $^{13}$C NMR spectrum of Compound I-1•anhydrous form A is shown in FIG. 6c. Table 5n provides chemical shifts of the relevant peaks.

TABLE 5n

Solid State $^{13}$C NMRspectrum of Form A

| | Compound I-1 (anhydrous form A) $^{13}$C Chem. Shifts | |
|---|---|---|
| Peak # | F1 [ppm] | Intensity |
| 1* | 175.9 | 67.9 |
| 2 | 163.1 | 46.9 |
| 3 | 162.0 | 59.1 |
| 4 | 160.1 | 18.1 |
| 5 | 157.3 | 24.5 |
| 6 | 151.2 | 21.8 |
| 7 | 148.7 | 30.9 |
| 8 | 145.9 | 49.9 |
| 9 | 139.8 | 65.6 |
| 10* | 138.9 | 66.8 |
| 11 | 135.8 | 57.2 |
| 12 | 134.3 | 82.8 |
| 13 | 122.6 | 60.6 |
| 14 | 89.3 | 54.0 |
| 15 | 76.2 | 86.5 |
| 16* | 74.1 | 92.0 |

TABLE 5n-continued

Solid State $^{13}$C NMR spectrum of Form A

| | Compound I-1 (anhydrous form A) $^{13}$C Chem. Shifts | |
|---|---|---|
| Peak # | F1 [ppm] | Intensity |
| 17 | 59.8 | 84.5 |
| 18 | 51.7 | 77.2 |
| 19 | 50.3 | 98.8 |
| 20 | 49.4 | 91.4 |
| 21* | 42.8 | 100.0 |
| 22 | 38.4 | 97.7 |
| 23* | 31.5 | 84.2 |
| 24 | 28.3 | 85.4 |

A solid state $^{19}$F NMR spectrum of Compound I-1•anhydrous form A is shown in FIG. 7c. Table 5p provides chemical shifts of the relevant peaks.

TABLE 5p

Solid State $^{19}$F NMR Spectrum of Form A

| | Compound I-1 (anhydrous form A) $^{19}$F Chem. Shifts | |
|---|---|---|
| Peak # | F1 [ppm] | Intensity |
| 1.0* | −136.8 | 6.8 |
| 2.0* | −155.7 | 12.5 |

Example 8: Compound I-1 (Anhydrous Form B)

Charged Compound I-1•amorphous (3.50 g), prepared according to the methods described in Example 2, Step 3, was placed in a 250 mL 3-neck flask, THF (70 mL) was added, and agitated using an overhead stirrer at ambient temperature overnight (e.g., at least 12 hr.). The suspension was filtered under vacuum (4.25 cm diameter Whatman filter paper), washed with THF (7 mL), and pulled under vacuum for about 35 minutes to give a fairly hard yellow solid (2.25 g). Dried the solids under vacuum with a good bleed at 35° C. overnight affording 1.921 g of Compound I-1•anhydrous form B as a yellow solid.

XRPD of Compound I-1 (Anhydrous Form B)

The XRPD pattern of Compound I-1•anhydrous form B was recorded at room temperature in reflection mode using a Bruker D8 Discover diffractometer equipped with a sealed tube source and a Hi-Star area detector (Bruker AXS, Madison, Wis., Asset V012842). The X-ray generator was operating at a voltage of 40 kV and a current of 35 mA. The powder sample was placed in a nickel holder. Two frames were registered with an exposure time of 300 seconds each. The data were subsequently integrated over the range of 3.5°-39° 2-theta with a step size of 0.02° and merged into one continuous pattern. FIG. 1d shows the X-ray powder diffractogram of the sample which is characteristic of crystalline drug substance.

Table 6a depicts representative XRPD peaks form Compound I-1•anhydrous form B:

TABLE 6a

Representative XRPD Peaks

| XRPD Peaks | Angle (2-theta ± 0.2) | Intensity % |
|---|---|---|
| 1 | 5.2 | 19.0 |
| 2 | 5.9 | 33.8 |
| 3* | 7.2 | 52.9 |
| 4* | 8.3 | 79.0 |
| 5 | 9.8 | 88.8 |
| 6 | 11.1 | 60.8 |
| 7 | 11.7 | 65.4 |
| 8* | 12.9 | 62.9 |
| 9 | 14.8 | 62.0 |
| 10 | 15.6 | 100.0 |
| 11 | 16.3 | 62.7 |
| 12 | 16.8 | 57.1 |
| 13 | 18.0 | 52.6 |
| 14* | 19.5 | 33.9 |
| 15 | 20.4 | 11.5 |
| 16 | 21.3 | 8.3 |
| 17 | 23.2 | 22.1 |
| 18 | 25.2 | 39.9 |
| 19 | 25.9 | 27.3 |
| 20* | 26.6 | 22.9 |
| 21 | 27.4 | 30.0 |
| 22 | 28.0 | 44.8 |
| 23 | 28.9 | 26.9 |
| 24 | 30.6 | 18.0 |
| 25 | 32.2 | 11.6 |
| 26 | 36.0 | 3.1 |

Thermo Analysis of Compound I-1 (Anhydrous Form B)

A thermal gravimetric analysis of Compound I-1•anhydrous form B was performed to determine the percent weight loss as a function of time using the TA Instrument TGA Q500 (Asset V014840). A sample (2.728 mg) was added to a pre-tared platinum pan and heated from ambient temperature to 350° C. at 10° C./min. The TGA results seen in FIG. 2d show two distinct weight loss events totaling 2.5% up to 175° C. The onset temperature of melting/degradation is 284° C.

Differential Scanning Calorimetry of Compound I-1 (Anhydrous Form B)

Differential scanning calorimetry of Compound I-1•anhydrous form B was measured using the TA Instrument DSC Q2000 (Asset V012390). A sample (2.125 mg) was weighed in a pre-punched pinhole aluminum hermetic pan and heated from 30° C. to 350° C. at 3° C./min, modulating ±1° C. every 60 seconds. The DSC results seen in FIG. 3d show an exothermic event at 177° C. (likely a slight re-arrangement of the crystal structure), an endothermic melt at 257° C., re-crystallization at 258° C., then a final melt/degradation event at 280° C.

ssNMR Compound I-1 (Anhydrous Form B)
A solid state $^{13}$C NMR spectrum of Compound I-1•anhydrous form B is shown in FIG. 4d. Table 6b provides chemical shifts of the relevant peaks.

TABLE 6b

Solid State $^{13}$C NMR spectrum of Form B

| | Compound I-1 (anhydrous form B) $^{13}$C Chem. Shifts | |
|---|---|---|
| Peak # | F1 [ppm] | Intensity |
| 1* | 173.4 | 43.0 |
| 2* | 164.5 | 30.6 |
| 3 | 162.3 | 98.7 |

TABLE 6b-continued

Solid State $^{13}$C NMR spectrum of Form B

| Peak # | Compound I-1 (anhydrous form B) $^{13}$C Chem. Shifts F1 [ppm] | Intensity |
|---|---|---|
| 4 | 159.9 | 16.0 |
| 5 | 157.4 | 22.4 |
| 6 | 151.8 | 15.7 |
| 7 | 149.5 | 23.9 |
| 8 | 144.9 | 42.7 |
| 9 | 141.6 | 32.6 |
| 10 | 136.3 | 63.8 |
| 11* | 133.5 | 58.5 |
| 12* | 130.8 | 35.3 |
| 13 | 124.4 | 26.2 |
| 14 | 86.9 | 52.3 |
| 15 | 74.9 | 58.9 |
| 16 | 72.0 | 29.5 |
| 17* | 67.7 | 26.8 |
| 18 | 59.5 | 69.8 |
| 19 | 50.8 | 100.0 |
| 20* | 45.3 | 86.3 |
| 21 | 40.4 | 28.8 |
| 22 | 37.9 | 60.0 |
| 23 | 30.3 | 85.3 |
| 24* | 25.9 | 31.3 |

A solid state $^{19}$F NMR spectrum of Compound I-1•anhydrous form B is shown in FIG. 5d. Table 6c provides chemical shifts of the relevant peaks.

TABLE 6c

Solid State $^{19}$F NMR Spectrum of Form B

| Peak # | Compound I-1 (anhydrous form B) $^{19}$F Chem. Shifts F1 [ppm] | Intensity |
|---|---|---|
| 1* | −138.0 | 7.0 |
| 2* | −153.5 | 12.5 |

Example 9: Compound I-1 (Anhydrous Form C)

Compound I-1•anhydrous form B (~15 mg), prepared according to the method described in Example 8, was added to pre-punched pinhole aluminum hermetic pans and heated via DSC to 265° C. at a rate of 5° C./min (3 pans, ~5 mg each) to afford compound I-1•anhydrous form C as a dark yellow powder.

XRPD of Compound I-1 (Anhydrous Form C)

The XRPD pattern of Compound I-1•anhydrous form C was recorded at room temperature in reflection mode using a Bruker D8 Discover diffractometer equipped with a sealed tube source and a Hi-Star area detector (Bruker AXS, Madison, Wis., Asset V012842). The X-ray generator was operating at a voltage of 40 kV and a current of 35 mA. The powder sample was placed in a nickel holder. Two frames were registered with an exposure time of 120 seconds each. The data were subsequently integrated over the range of 3.5°-39° 2-theta with a step size of 0.02° and merged into one continuous pattern. FIG. 1e shows the X-ray powder diffractogram of the sample which is characteristic of crystalline drug substance.

Table 7a depicts representative XRPD peaks form Compound I-1•anhydrous form C:

TABLE 7a

Representative XRPD Peaksn

| XRPD | Angle (2-theta ± 0.2) | Intensity % |
|---|---|---|
| 1 | 3.6 | 1.1 |
| 2 | 4.0 | 1.1 |
| 3* | 6.8 | 44.8 |
| 4 | 7.6 | 11.1 |
| 5 | 8.1 | 12.7 |
| 6 | 10.3 | 13.3 |
| 7 | 11.4 | 100.0 |
| 8* | 13.4 | 29.1 |
| 9 | 14.2 | 51.8 |
| 10 | 14.9 | 23.8 |
| 11* | 15.9 | 31.1 |
| 12 | 16.3 | 14.2 |
| 13 | 16.7 | 17.6 |
| 14 | 17.0 | 26.9 |
| 15 | 18.2 | 37.9 |
| 16 | 19.1 | 50.4 |
| 17 | 20.7 | 31.7 |
| 18 | 22.6 | 3.8 |
| 19 | 23.3 | 16.0 |
| 20 | 23.9 | 15.0 |
| 21 | 24.5 | 10.1 |
| 22 | 25.5 | 24.0 |
| 23 | 25.8 | 33.3 |
| 24 | 27.1 | 17.3 |
| 25 | 27.9 | 23.8 |
| 26 | 29.1 | 19.2 |
| 27* | 30.9 | 22.3 |
| 28 | 32.0 | 12.9 |
| 29* | 32.9 | 12.8 |
| 30 | 33.7 | 7.5 |
| 31 | 35.1 | 4.5 |

Thermo Analysis of Compound I-1 (Anhydrous Form C)

A thermal gravimetric analysis of Compound I-1•anhydrous form C was performed to determine the percent weight loss as a function of time using the TA Instrument TGA Q500 (Asset V014840). A sample (3.363 mg) was added to a pre-tared platinum pan and heated from ambient temperature to 350° C. at 10° C./min. The TGA results seen in FIG. 2e show no distinct weight loss events prior to melting/degradation. The onset temperature of melting/degradation is 292° C.

Differential Scanning Calorimetry of Compound I-1 (Anhydrous Form C)

Differential scanning calorimetry of Compound I-1•anhydrous form C was measured using the TA Instrument DSC Q2000 (Asset V012390). A sample (4.100 mg) was weighed in a pre-punched pinhole aluminum hermetic pan and heated from 30° C. to 350° C. at 3° C./min, modulating ±1° C. every 60 seconds. The DSC results seen in FIG. 3e show a single endothermic melting/degradation event at 281° C.

ssNMR

A solid state $^{13}$C NMR spectrum of Compound I-1•anhydrous form C form is shown in FIG. 4e. Table 7b provides chemical shifts of the relevant peaks.

TABLE 7b

Solid State $^{13}$C NMR spectrum of Form C

| Peak # | Compound I-1 (anhydrous form B) $^{13}$C Chem. Shifts F1 [ppm] | Intensity |
|---|---|---|
| 1* | 175.2 | 86.8 |
| 2 | 163.3 | 42.2 |

TABLE 7b-continued

Solid State $^{13}$C NMR spectrum of Form C

| Peak # | Compound I-1 (anhydrous form B) $^{13}$C Chem. Shifts F1 [ppm] | Intensity |
|---|---|---|
| 3 | 162.1 | 43.3 |
| 4 | 158.2 | 10.2 |
| 5 | 152.4 | 12.6 |
| 6 | 149.9 | 17.5 |
| 7 | 144.9 | 42.2 |
| 8* | 142.5 | 55.9 |
| 9 | 137.9 | 100.0 |
| 10 | 135.7 | 43.6 |
| 11* | 129.6 | 64.4 |
| 12 | 123.6 | 44.4 |
| 13 | 86.5 | 47.6 |
| 14 | 76.6 | 87.7 |
| 15* | 73.5 | 72.6 |
| 16 | 59.6 | 93.7 |
| 17* | 54.0 | 53.5 |
| 18 | 51.2 | 67.4 |
| 19 | 49.7 | 58.8 |
| 20* | 46.7 | 86.3 |
| 21 | 42.3 | 55.8 |
| 22 | 37.2 | 97.6 |
| 23 | 31.4 | 79.4 |
| 24 | 28.9 | 79.5 |

A solid state $^{19}$F NMR spectrum of Compound I-1•anhydrous form C is shown in FIG. 5e. Table 7c provides chemical shifts of the relevant peaks.

TABLE 7c

Solid State $^{19}$F NMR Spectrum of Form C

| Peak # | Compound I-1 (anhydrous form C) $^{19}$F Chem. Shifts F1 [ppm] | Intensity |
|---|---|---|
| 1* | −131.2 | 4.8 |
| 2* | −150.7 | 12.5 |

Example 10: Compound I-1 (Amorphous Form)

Compound I-1•amorphous form was prepared according to the methods described in Example 2, Step 3, or in Example 3, Step 3, above.

XRPD of Compound I-1 (Amorphous Form)

The XRPD pattern of Compound I-1•amorphous form was recorded at room temperature in reflection mode using a PANalytical diffractometer equipped with an Empyrean Cu tube source and a PIXcel 1D detector (PANalytical, The Netherlands). The X-ray generator was operating at a voltage of 45 kV and a current of 40 mA. The powder sample was placed in a silicon holder. The data were over the range of 3°-39° 2 theta with a step size of 0.013° and a dwell time of 0.5 s per step. Figure if shows the X-ray powder diffractogram of the sample which is characteristic of amorphous drug substance.

Differential Scanning Calorimetry of Compound I-1 (Amorphous Form)

Differential scanning calorimetry of Compound I-1•amorphous form was measured using the TA Instrument DSC Q2000. A sample (2.61 mg) was weighed in an aluminum non-hermetic pan and heated using the modulated mode from ambient temperature to 350° C. at a heating rate of 2° C./min, with a modulation amplitude of +/−0.5° C. and a period of 60 s. The DSC results seen in FIG. 2f show a glass transition (Tg) at 128° C. (onset) with heat capacity change of 0.3 J/(g. ° C.). Glass transition was followed by a crystallization exotherm at 174° C. (onset), which was in turn followed by a melt/degradation event at 250° C.

ssNMR of Compound I-1 (Amorphous)

A solid state $^{13}$C NMR spectrum of Compound I-1•amorphous form is shown in FIG. 3f. Table 8a provides chemical shifts of the relevant peaks.

TABLE 8a

Solid State $^{13}$C NMR spectrum of amorphous form

| Peak # | Compound I-1 (anhydrous form) $^{13}$C Chem. Shifts F1 [ppm] | Intensity |
|---|---|---|
| 1* | 173.8 | 27.7 |
| 2 | 162.3 | 49.2 |
| 3 | 157.6 | 18.0 |
| 4 | 149.3 | 21.9 |
| 5* | 144.2 | 30.0 |
| 6 | 134.7 | 59.6 |
| 7 | 123.1 | 20.3 |
| 8* | 87.5 | 24.0 |
| 9 | 75.6 | 39.7 |
| 10 | 59.4 | 32.7 |
| 11 | 50.8 | 100.0 |
| 12* | 45.6 | 36.0 |
| 13 | 41.8 | 28.6 |
| 14 | 38.3 | 39.3 |
| 15* | 29.5 | 57.2 |

A solid state $^{19}$F NMR spectrum of Compound I-1•amorphous is shown in FIG. 4f. Table 8b provides chemical shifts of the relevant peaks.

TABLE 8b

Solid State $^{19}$F NMR Spectrum of amorphous form

| Peak # | Compound I-1 (amorphous) $^{19}$F Chem. Shifts F1 [ppm] | Intensity |
|---|---|---|
| 1.0* | −137.7 | 9.8 |
| 2.0* | −153.1 | 12.5 |

Example 11: Compound I-1 (DMSO Solvate)

Compound I-1•anhydrous form A (10.0 g; 18.47 mmol), prepared according to the methods described in Example 7, was suspended in DMSO (200 mL) and heated to 55° C. The mixture was filtered whilst hot. The hot filtrate was stirred in a clean flask and cooled to 20-25° C. then stirred for an additional 2 hours. The solids were collected by filtration, washed with DMSO (10 mL), dried by suction then dried in a vacuum oven for 14 hours at 40-45° C. to give compound I-1•DMSO solvate (7.23 g; 63%). $^1$H NMR (500 MHz, DMSO-d6) δ 10.63 (s, 1H), 9.66 (s, 1H), 9.47 (dd, 1H), 9.24 (dd, 1H), 8.24 (d, 1H), 6.78 (s, 2H), 4.54 (t, 2H), 4.46 (t, 2H), 3.60 (dt, 4H), 3.43 (m, 1H), 3.18 (m, 2H), 2.97 (m, 3H), 2.54 (s, 6H), 2.26 (dt, 4H), 2.12 (qd, 2H), 1.73 (d, 2H); 19F NMR (500 MHz, DMSO-d6) δ −136.1, −152.8.

XRPD of Compound I-1 (DMSO Solvate)

The XRPD pattern of compound I-1•DMSO solvate was recorded at room temperature in reflection mode using a PANalytical diffractometer equipped with an Empyrean tube source and a PIXcel 1D detector (PANalytical, The Netherlands). The X-ray generator was operating at a voltage of 45 kV and a current of 40 mA. The powder sample was placed in a silicon holder. The data was recorded over the range of 3°-39° 2 theta with a step size of 0.013° and a dwell time of 121 s per step. FIG. 1g shows the X-ray powder diffractogram of the sample which is characteristic of crystalline drug substance.

Table 9 depicts representative XRPD peaks form Compound I-1•DMSO solvate:

TABLE 9

Representative XRPD Peaks

| XRPD | Angle (2-theta ± 0.2) | Intensity % |
|---|---|---|
| 1 | 7.0034 | 8.33 |
| 2* | 8.9204 | 11.28 |
| 3 | 10.4007 | 10.11 |
| 4 | 12.4735 | 6.81 |
| 5 | 12.7962 | 12.32 |
| 6 | 13.3976 | 12.25 |
| 7* | 14.8102 | 29.16 |
| 8 | 15.439 | 15.1 |
| 9 | 15.7477 | 14.37 |
| 10* | 16.5454 | 82.57 |
| 11 | 17.051 | 15.34 |
| 12 | 18.1033 | 20.25 |
| 13* | 18.6354 | 29.71 |
| 14 | 19.593 | 3.68 |
| 15 | 20.1178 | 6.42 |
| 16* | 20.9143 | 35.76 |
| 17 | 21.3593 | 11.65 |
| 18* | 22.1801 | 100 |
| 19 | 22.8306 | 25.4 |
| 20* | 23.3866 | 51.08 |
| 21 | 23.8312 | 16.31 |
| 22 | 24.5088 | 15.65 |
| 23 | 25.6545 | 25.59 |
| 24 | 27.0136 | 3.06 |
| 25 | 27.4405 | 2.43 |
| 26 | 27.6871 | 3.27 |
| 27 | 28.5715 | 8.73 |
| 28 | 28.9693 | 11.53 |
| 29 | 29.555 | 8.95 |
| 30 | 30.1186 | 5.69 |
| 31 | 30.5402 | 8.63 |
| 32 | 31.2969 | 6.42 |
| 33 | 32.0663 | 8.71 |
| 34 | 33.2165 | 3.04 |
| 35 | 34.1902 | 7.02 |
| 36 | 34.6067 | 3.57 |
| 37 | 35.45 | 1.47 |
| 38 | 36.5669 | 3.23 |
| 39 | 38.6972 | 2.19 |

Thermo Analysis of Compound I-1 (DMSO Solvate)

A thermal gravimetric analysis of compound I-1•DMSO solvate was performed to determine the percent weight loss as a function of temperature using the Discovery TGA (TA Instruments Trios). A sample (3.26 mg) was added to a pre-tared aluminum pan and heated from ambient temperature to 350° C. at 10° C./min. The TGA results seen in FIG. 2g show a large weight loss of 12.44% between 146° C. (onset) and 156° C. (end point). This weight loss corresponds to approximately 1 molar equivalents of DMSO. A second weight loss of 0.52% was then seen between 254° C. (onset) and 262° C. (end point). The subsequent weight loss seen at 304° C. is a result of melting/degradation.

Differential Scanning Calorimetry of Compound I-1 (DMSO Solvate)

Differential scanning calorimetry of compound I-1•DMSO solvate was measured using the TA Instrument DSC Q2000. A sample (1.77 mg) was weighed in a pinholed aluminum hermetic pan and heated from ambient temperature to 350° C. at 10° C./min. The DSC results seen in FIG. 3g show a desolvation endotherm at 143° C. (onset) followed by a single melting endotherm at 258° C. (onset).

Example 12: Compound I-1 (DMAC Solvate)

Compound I-1•anhydrous form A (100 mg; 0.18 mmol), prepared according to the methods described in Example 7, was suspended in DMAC (2000 uL) and stirred for 20 hours at 20-25° C. The solids were collected by filtration, washed with DMAC (500 uL), dried by suction then dried in a vacuum oven at 40-50° C. to give compound I-1•DMAC solvate (84 mg). $^1$H NMR (500 MHz, DMSO-$d_6$) δ 10.62 (s, 1H), 9.66 (s, 1H), 9.46 (dd, 1H), 9.26-9.22 (m, 1H), 8.24 (d, 1H), 6.77 (s, 2H), 4.54 (t, 2H), 4.46 (t, 2H), 3.66-3.54 (m, 4H), 3.43 (p, 1H), 3.18 (tt, 2H), 2.94 (s, 8H), 2.78 (s, 4H), 2.26 (dt, 4H), 2.12 (qd, 2H), 1.96 (s, 4H), 1.76-1.69 (m, 2H).

XRPD of Compound I-1 (DMAC Solvate)

The XRPD pattern of compound I-1•DMAC solvate was recorded at room temperature in reflection mode using a PANalytical diffractometer equipped with an Empyrean tube source and a PIXcel 1D detector (PANalytical, The Netherlands). The X-ray generator was operating at a voltage of 45 kV and a current of 40 mA. The powder sample was placed in a silicon holder. The data were recorded over the range of 3°-39° 2 theta with a step size of 0.013° and a dwell time of 121 s per step. FIG. 1h shows the X-ray powder diffractogram of the sample which is characteristic of crystalline drug substance.

Table 10 depicts representative XRPD peaks form Compound I-1•DMAC solvate:

TABLE 10

Representative XRPD Peaks

| XRPD | Angle (2-theta ± 0.2) | Intensity % |
|---|---|---|
| 1* | 6.0169 | 75.51 |
| 2 | 7.5182 | 7.99 |
| 3 | 8.5957 | 32.29 |
| 4 | 9.7593 | 33.98 |
| 5 | 10.9655 | 15.95 |
| 6 | 11.3688 | 7.25 |
| 7 | 12.0406 | 12.17 |
| 8 | 13.6703 | 19.18 |
| 9 | 14.1108 | 36.56 |
| 10 | 14.2831 | 23.2 |
| 11 | 14.5895 | 9.33 |
| 12 | 15.1755 | 25.52 |
| 13* | 15.4632 | 20.85 |
| 14 | 16.0919 | 71.07 |
| 15 | 16.9423 | 0.92 |
| 16* | 17.7117 | 82.12 |
| 17* | 18.1371 | 77.28 |
| 18 | 18.5857 | 4.73 |
| 19 | 19.0786 | 16.95 |
| 20 | 19.745 | 7.05 |
| 21* | 20.3531 | 40.38 |
| 22 | 20.7384 | 29.95 |
| 23 | 21.2654 | 10.22 |
| 24 | 21.7978 | 9.56 |
| 25 | 22.4818 | 2.27 |
| 26 | 22.8051 | 5.51 |
| 27 | 23.3945 | 6.33 |

TABLE 10-continued

Representative XRPD Peaks

| XRPD | Angle (2-theta ± 0.2) | Intensity % |
|---|---|---|
| 28 | 23.829 | 19.65 |
| 29 | 24.6486 | 3.69 |
| 30 | 25.343 | 5.43 |
| 31 | 25.6712 | 7.83 |
| 32* | 26.6041 | 100 |
| 33 | 27.6488 | 39.15 |
| 34 | 28.1311 | 10.68 |
| 35 | 28.47791 | 5.9 |
| 36 | 28.763 | 13.68 |
| 37 | 29.2517 | 17.62 |
| 38 | 29.5534 | 13.91 |
| 39 | 29.9062 | 12.28 |
| 40 | 30.5467 | 7.27 |
| 41 | 31.4852 | 9.17 |
| 42 | 32.228 | 2.69 |
| 43 | 32.6692 | 3.7 |
| 44 | 34.7188 | 1.29 |
| 45 | 36.4642 | 1.43 |
| 46 | 37.1111 | 1.9 |
| 47 | 38.0592 | 1.92 |

Thermo Analysis of Compound I-1 (DMAC Solvate)

A thermogravimetric analysis of compound I-1•DMAC solvate was performed to determine the percent weight loss as a function of temperature using the Discovery TGA (TA Instruments Trios). A sample (5.12 mg) was added to a pre-tared aluminum pan and heated from ambient temperature to 350° C. at 10° C./min. The TGA results seen in FIG. 2h show a large weight loss of 17.76% between 85° C. (onset) and 100° C. (end point). This weight loss corresponds to approximately 1.3 molar equivalents of DMAC. The subsequent weight loss seen at 306° C. is a result of melting/degradation.

Differential Scanning Calorimetry of Compound I-1 (DMAC Solvate)

Differential scanning calorimetry of compound I-1•DMAC solvate was measured using the TA Instrument DSC Q2000. A sample (1.93 mg) was weighed in a pinholed aluminum hermetic pan and heated from ambient temperature to 350° C. at 10° C./min. The DSC results seen in FIG. 3h show a desolvation endotherm at 81° C. (onset) followed by a single melting endotherm at 261° C. (onset).

Example 13: Compound I-1 (Acetone Solvate)

Compound I-1•amorphous (100 mg; 0.18 mmol), prepared according to the methods described in Example 2, Step 3, above, was suspended in acetone (2000 uL) and stirred for 22 hours. Compound I-1•acetone solvate was collected by filtration. $^1$H NMR (500 MHz, DMSO-$d_6$) δ 10.63 (s, 1H), 9.66 (s, 1H), 9.46 (dd, 1H), 9.24 (dd, 1H), 8.24 (d, 1H), 6.78 (s, 2H), 4.54 (t, 2H), 4.46 (t, 2H), 3.65-3.54 (m, 4H), 3.43 (p, 1H), 3.19 (tt, 2H), 3.06-2.90 (m, 3H), 2.26 (dt, 4H), 2.18-2.05 (m, 3H), 1.72 (d, 2H).

XRPD of Compound I-1 (Acetone Solvate)

The XRPD pattern of compound I-1•acetone solvate was recorded at room temperature in reflection mode using a PANalytical diffractometer equipped with an Empyrean tube source and a PIXcel 1D detector (PANalytical, The Netherlands). The X-ray generator was operating at a voltage of 45 kV and a current of 40 mA. The powder sample was placed in a silicon holder. The data were recorded over the range of 3°-39° 2 theta with a step size of 0.013° and a dwell time of 121 s per step. FIG. 1i shows the X-ray powder diffractogram of the sample which is characteristic of crystalline drug substance.

Table 11 depicts representative XRPD peaks form Compound I-1•acetone solvate:

TABLE 10

Representative XRPD Peaks

| XRPD | Angle (2-theta ± 0.2) | Intensity % |
|---|---|---|
| 1 | 6.9871 | 31.75 |
| 2* | 8.9148 | 62.84 |
| 3 | 10.4145 | 7.38 |
| 4 | 12.4529 | 6.65 |
| 5 | 12.7486 | 9.09 |
| 6 | 13.4567 | 7.37 |
| 7 | 14.8093 | 10.97 |
| 8* | 15.528 | 35.3 |
| 9* | 15.826 | 19.22 |
| 10* | 16.6652 | 22.77 |
| 11 | 17.1217 | 6.15 |
| 12 | 17.9563 | 10.57 |
| 13 | 18.1349 | 9.4 |
| 14 | 18.589 | 7.22 |
| 15 | 19.5447 | 3.06 |
| 16 | 20.0055 | 2.55 |
| 17 | 20.8656 | 6.29 |
| 18 | 21.3488 | 6.36 |
| 19* | 22.2722 | 100 |
| 20 | 22.6595 | 13.43 |
| 21 | 22.9581 | 19.8 |
| 22 | 23.465 | 21.26 |
| 23 | 23.7918 | 8.65 |
| 24 | 24.5843 | 8.65 |
| 25* | 25.7222 | 13.01 |
| 26 | 26.0003 | 3.74 |
| 27 | 27.696 | 2.49 |
| 28 | 28.7335 | 4.74 |
| 29* | 29.0658 | 13.52 |
| 30 | 29.6743 | 8.03 |
| 31 | 30.2154 | 6.04 |
| 32 | 30.6427 | 4.67 |
| 33 | 31.36 | 4.28 |
| 34 | 32.2601 | 3.86 |
| 35 | 33.3871 | 0.66 |
| 36 | 33.8459 | 1.15 |
| 37 | 34.2253 | 1.42 |
| 38 | 35.6517 | 2.34 |
| 39 | 35.9083 | 2 |
| 40 | 36.4752 | 2.17 |

Thermo Analysis of Compound I-1 (Acetone Solvate)

A thermogravimetric analysis of compound I-1•acetone solvate was performed to determine the percent weight loss as a function of temperature using the Discovery TGA (TA Instruments Trios). A sample (2.45 mg) was added to a pre-tared aluminum pan and heated from ambient temperature to 350° C. at 10° C./min. The TGA results seen in FIG. 2i show an initial weight loss of 1.46%. A larger weight loss of 4.55% was then seen between 124° C. (onset) and 151° C. (end point), which corresponds to approximately 0.44 molar equivalents of Acetone. The subsequent weight loss seen at 302° C. is a result of melting/degradation.

Differential Scanning Calorimetry of Compound I-1 (Acetone Solvate)

Differential scanning calorimetry of compound I-1•acetone solvate was measured using the TA Instrument DSC Q2000. A sample (1.42 mg) was weighed in a pinholed aluminum hermetic pan and heated from ambient temperature to 350° C. at 10° C./min. The DSC results seen in FIG. 3i show a desolvation endotherm at 136° C. (onset) followed by a melting endotherm at 166° C. (onset). This was in turn followed by immediate recrystallization exotherm at 175° C. Another melting endotherm was then recorded at 259° C. This was also followed by a recrystallization exotherm at 261° C. A final melting endotherm was observed at 279° C.

Example 14: Compound I-1 (Isopropanol Solvate)

Compound I-1•amorphous (100 mg; 0.18 mmol), prepared according to the methods described in Example 2, Step 3, above, was suspended in 2-propanol (2000 uL) and stirred for 22 hours at 20-25° C. Compound I-1•isopropanol solvate was collected by filtration.

XRPD of Compound I-1 (Isopropanol Solvate)

The XRPD pattern of compound I-1•isopropanol solvate was recorded at room temperature in reflection mode using a PANalytical diffractometer equipped with an Empyrean tube source and a PIXcel 1D detector (PANalytical, The Netherlands). The X-ray generator was operating at a voltage of 45 kV and a current of 40 mA. The powder sample was placed in a silicon holder. The data were recorded over the range of 3°-39° 2 theta with a step size of 0.013° and a dwell time of 121 s per step. FIG. 1j shows the X-ray powder diffractogram of the sample which is characteristic of crystalline drug substance.

Table 12 depicts representative XRPD peaks form Compound I-1•isopropanol solvate:

TABLE 12

Representative XRPD Peaks

| XRPD | Angle (2-theta ± 0.2) | Intensity % |
|---|---|---|
| 1* | 6.937 | 100 |
| 2 | 11.0107 | 7.85 |
| 3 | 12.8255 | 8.34 |
| 4 | 13.6694 | 3.53 |
| 5 | 14.1876 | 2.27 |
| 6 | 14.8878 | 7.9 |
| 7 | 16.1846 | 4.17 |
| 8* | 17.1027 | 18.84 |
| 9* | 17.2424 | 19.04 |
| 10 | 18.0956 | 0.47 |
| 11* | 19.1139 | 5.27 |
| 12* | 19.6437 | 15.33 |
| 13 | 20.3628 | 10.96 |
| 14 | 21.4978 | 1.13 |
| 15 | 22.769 | 5.81 |
| 16* | 23.6531 | 41.5 |
| 17* | 24.3573 | 39.72 |
| 18 | 24.8556 | 17.48 |
| 19 | 25.8121 | 8.63 |
| 20 | 27.2638 | 2.35 |
| 21* | 28.8751 | 21.82 |
| 22 | 30.0648 | 2.34 |
| 23 | 31.4229 | 1.58 |
| 24 | 32.9263 | 1.14 |
| 25 | 34.4773 | 2.29 |
| 26 | 35.6844 | 1.53 |
| 27 | 37.3825 | 0.46 |

Thermo Analysis of Compound I-1 (Isopropanol Solvate)

A thermogravimetric analysis of Compound I-1•isopropanol solvate was performed to determine the percent weight loss as a function of temperature using the Discovery TGA (TA Instruments Trios). A sample (3.39 mg) was added to a pre-tared aluminum pan and heated from ambient temperature to 300° C. at 10° C./min. The TGA results seen in FIG. 2j show a large weight loss of 3.76% between 136° C. (onset) and 180° C. (end point). This weight loss corresponds to approximately 0.35 molar equivalents of IPA. The subsequent weight loss seen at 278° C. is a result of melting/degradation.

Differential Scanning Calorimetry of Compound I-1 (Isopropanol Solvate)

Differential scanning calorimetry of compound I-1•isopropanol solvate was measured using the TA Instrument DSC Q2000. A sample (1.03 mg) was weighed in a T-zero aluminum pan and heated from ambient temperature to 320° C. at 10° C./min. The DSC results seen in FIG. 3j show a broad desolvation endotherm at 135° C. (onset) followed by a single melting endotherm at 258° C. (onset).

Example 15: Cellular ATR Inhibition Assay

Compounds can be screened for their ability to inhibit intracellular ATR using an immunofluorescence microscopy assay to detect phosphorylation of the ATR substrate histone H2AX in hydroxyurea treated cells. HT29 cells are plated at 14,000 cells per well in 96-well black imaging plates (BD 353219) in McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds are then added to the cell media from a final concentration of 25 µM in 3-fold serial dilutions and the cells are incubated at 37° C. in 5% $CO_2$. After 15 min, hydroxyurea (Sigma H8627) is added to a final concentration of 2 mM.

After 45 min of treatment with hydroxyurea, the cells are washed in PBS, fixed for 10 min in 4% formaldehyde diluted in PBS (Polysciences Inc 18814), washed in 0.2% Tween-20 in PBS (wash buffer), and permeabilized for 10 min in 0.5% Triton X-100 in PBS, all at room temperature. The cells are then washed once in wash buffer and blocked for 30 min at room temperature in 10% goat serum (Sigma G9023) diluted in wash buffer (block buffer). To detect H2AX phosphorylation levels, the cells are then incubated for 1 hr. at room temperature in primary antibody (mouse monoclonal anti-phosphorylated histone H2AX Ser139 antibody; Upstate 05-636) diluted 1:250 in block buffer. The cells are then washed five times in wash buffer before incubation for 1 hr. at room temperature in the dark in a mixture of secondary antibody (goat anti-mouse Alexa Fluor 488 conjugated antibody; Invitrogen A11029) and Hoechst stain (Invitrogen H3570); diluted 1:500 and 1:5000, respectively, in wash buffer. The cells are then washed five times in wash buffer and finally 100 ul PBS is added to each well before imaging.

Cells are imaged for Alexa Fluor 488 and Hoechst intensity using the BD Pathway 855 Bioimager and Attovision software (BD Biosciences, Version 1.6/855) to quantify phosphorylated H2AX Ser139 and DNA staining, respectively. The percentage of phosphorylated H2AX-positive nuclei in a montage of 9 images at 20× magnification is then calculated for each well using BD Image Data Explorer software (BD Biosciences Version 2.2.15). Phosphorylated H2AX-positive nuclei are defined as Hoechst-positive regions of interest containing Alexa Fluor 488 intensity at 1.75-fold the average Alexa Fluor 488 intensity in cells not treated with hydroxyurea. The percentage of H2AX positive nuclei is finally plotted against concentration for each compound and IC50s for intracellular ATR inhibition are determined using Prism software (GraphPad Prism version 3.0cx for Macintosh, GraphPad Software, San Diego Calif., USA).

The compounds described herein can also be tested according to other methods known in the art (see Sarkaria et al, "Inhibition of ATM and ATR Kinase Activities by the Radiosensitizing Agent, Caffeine: *Cancer Research* 59: 4375-5382 (1999); Hickson et al, "Identification and Characterization of a Novel and Specific Inhibitor of the Ataxia-Telangiectasia Mutated Kinase ATM" *Cancer Research* 64: 9152-9159 (2004); Kim et al, "Substrate Specificities and Identification of Putative Substrates of ATM Kinase Family Members" *The Journal of Biological Chemistry,* 274(53): 37538-37543 (1999); and Chiang et al, "Determination of the catalytic activities of mTOR and other members of the phosphoinositide-3-kinase-related kinase family" *Methods Mol. Biol.* 281:125-41 (2004)).

Example 16: ATR Inhibition Assay

Compounds can be screened for their ability to inhibit ATR kinase using a radioactive-phosphate incorporation assay. Assays are carried out in a mixture of 50 mM Tris/HCl (pH 7.5), 10 mM $MgCl_2$ and 1 mM DTT. Final substrate concentrations are 10 μM [γ-33P]ATP (3 mCi 33P ATP/mmol ATP, Perkin Elmer) and 800 μM target peptide (ASELPASQPQPFSAKKK).

Assays are carried out at 25° C. in the presence of 5 nM full-length ATR. An assay stock buffer solution is prepared containing all of the reagents listed above, with the exception of ATP and the test compound of interest. 13.5 μL of the stock solution is placed in a 96 well plate followed by addition of 2 μL of DMSO stock containing serial dilutions of the test compound (typically starting from a final concentration of 15 μM with 3-fold serial dilutions) in duplicate (final DMSO concentration 7%). The plate is pre-incubated for 10 minutes at 25° C. and the reaction initiated by addition of 15 μL [γ-33P]ATP (final concentration 10 μM).

The reaction is stopped after 24 hours by the addition of 30 μL 0.1M phosphoric acid containing 2 mM ATP. A multiscreen phosphocellulose filter 96-well plate (Millipore, Cat no. MAPHN0B50) is pretreated with 100 μL 0.2M phosphoric acid prior to the addition of 45 μL of the stopped assay mixture. The plate is washed with 5×2004 0.2M phosphoric acid. After drying, 100 μL Optiphase 'SuperMix' liquid scintillation cocktail (Perkin Elmer) is added to the well prior to scintillation counting (1450 Microbeta Liquid Scintillation Counter, Wallac).

After removing mean background values for all of the data points, Ki(app) data are calculated from non-linear regression analysis of the initial rate data using the Prism software package (GraphPad Prism version 3.0cx for Macintosh, GraphPad Software, San Diego Calif., USA).

In general, the compounds of the present invention are effective for inhibiting ATR. Compounds I-1 and I-3 inhibit ATR at Ki values below 1 μM.

Example 17: Cisplatin Sensitization Assay

Compounds can be screened for their ability to sensitize HCT116 colorectal cancer cells to Cisplatin using a 96 h cell viability (MTS) assay. HCT116 cells, which possess a defect in ATM signaling to Cisplatin (see, Kim et al.; *Oncogene* 21:3864 (2002); see also, Takemura et al.; *JBC* 281:30814 (2006)) are plated at 470 cells per well in 96-well polystyrene plates (Costar 3596) in 150 μl of McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds and Cisplatin are then both added simultaneously to the cell media in 2-fold serial dilutions from a top final concentration of 10 μM as a full matrix of concentrations in a final cell volume of 200 μl, and the cells are then incubated at 37° C. in 5% $CO_2$. After 96 h, 40 μl of MTS reagent (Promega G358a) is added to each well and the cells are incubated for 1 hr. at 37° C. in 5% $CO_2$. Finally, absorbance is measured at 490 nm using a SpectraMax Plus 384 reader (Molecular Devices) and the concentration of compound required to reduce the IC50 of Cisplatin alone by at least 3-fold (to 1 decimal place) can be reported.

In general, the compounds of the present invention are effective for sensitizing cancer cells to Cisplatin. Compounds I-1 and I-3 have Cisplatin sensitization values of <0.2 μM.

Example 18: Single Agent HCT116 Activity

Compounds can be screened for single agent activity against HCT116 colorectal cancer cells using a 96 h cell viability (MTS) assay. HCT116 are plated at 470 cells per well in 96-well polystyrene plates (Costar 3596) in 150 μl of McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds are then added to the cell media in 2-fold serial dilutions from a top final concentration of 10 μM as a full matrix of concentrations in a final cell volume of 200 μl, and the cells are then incubated at 37° C. in 5% $CO_2$. After 96 h, 40 μl of MTS reagent (Promega G358a) is added to each well and the cells are incubated for 1 hr. at 37° C. in 5% $CO_2$. Finally, absorbance is measured at 490 nm using a SpectraMax Plus 384 reader (Molecular Devices) and IC50 values can be calculated.

Example 19: ATR-Complex Inhibition Assay

Compounds were screened for their ability to inhibit ATR kinase, in the presence of partner proteins ATRIP, CLK2 and TopBP1, using a radioactive-phosphate incorporation assay. Assays were carried out in a mixture of 50 mM Tris/HCl (pH 7.5), 10 mM $MgCl_2$ and 1 mM DTT. Final substrate concentrations were 10 μM [g-33P]ATP (3.5 μCi 33P ATP/nmol ATP, Perkin Elmer, Massachusetts, USA) and 800 μM target peptide (ASELPASQPQPFSAKKK, Isca Biochemicals, Cambridgeshire, UK).

Assays were carried out at 25° C. in the presence of 4 nM full-length ATR, 40 nM full-length ATRIP, 40 nM full-length CLK2 and 600 nM TopBP1 (A891-S1105). An enzyme stock buffer solution was prepared containing all of the reagents listed above, with the exception of target peptide, ATP and the test compound of interest. This enzyme stock was pre-incubated for 30 minutes at 25° C. 8.5 μL of the enzyme stock solution was placed in a 96-well plate followed by addition of 5 μl of target peptide and 2 μL of DMSO stock containing serial dilutions of the test compound (typically starting from a final concentration of 1.5 μM with 2.5-fold serial dilutions) in duplicate (final DMSO concentration 7%). The plate was pre-incubated for 10 minutes at 25° C. and the reaction initiated by addition of 15 μL [g-33P]ATP (final concentration 10 μM).

The reaction was stopped after 20 hours by the addition of 30 μL 0.3 M phosphoric acid containing 2 mM ATP. A phosphocellulose filter 96-well plate (Multiscreen HTS MAPHNOB50, Merck-Millipore, Massachusetts, USA) was pretreated with 100 μL 0.1 M phosphoric acid prior to the addition of 45 μL of the stopped assay mixture. The plate was washed with 5×200 μL 0.1 M phosphoric acid. After drying, 50 μL Optiphase 'SuperMix' liquid scintillation cocktail (Perkin Elmer, Massachusetts, USA) was added to the well prior to scintillation counting (Wallac 1450 Microbeta Liquid Scintillation Counter, Perkin Elmer, Massachusetts, USA).

After removing mean background values for all of the data points, Ki(app) data were calculated from non-linear regression analysis of the initial rate data using the Prism software package (GraphPad Prism version 6.0c for Macintosh, GraphPad Software Inc., San Diego, USA).

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

We claim:

1. A solid form of a compound of formula I-1:

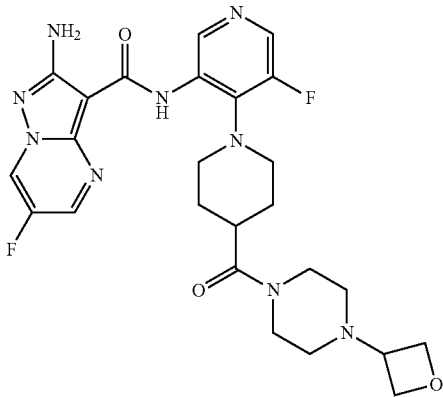

wherein the form is crystalline Compound I-1 anhydrous form A.

2. A crystal form of a compound I-1:

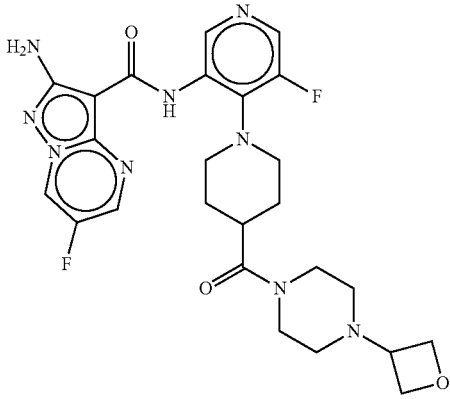

having a monoclinic crystal system, a P21/c centrosymmetric space group, and the following unit cell parameters:

a=15.29(3)Å α=90°
b=12.17(2)Å β=107.22(3)°
c=14.48(3)Å γ=90°.

3. A process for preparing Compound I-1•anhydrous form A:

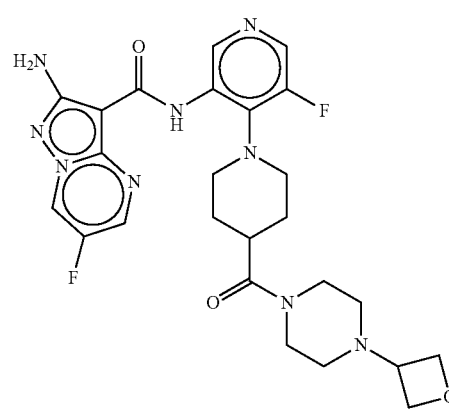

comprising stirring a suspension containing Compound I-1•ethanol solvate and tetrahydrofuran, and removing at least a portion of the ethanol and the tetrahydrofuran.

4. A process for preparing Compound I-1•anhydrous form A:

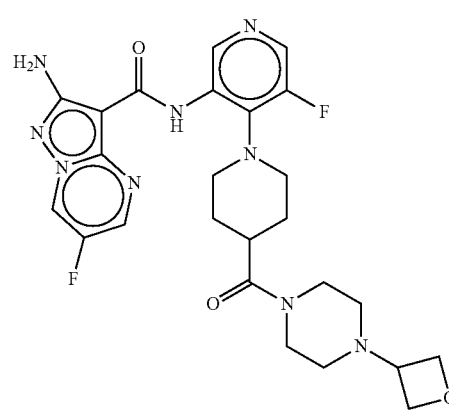

comprising stirring a suspension containing Compound I-1•amorphous, isopropanol, and water; and removing at least a portion of the water and the isopropanol.

5. The solid form of claim 1, characterized by three or more peaks expressed in 2-theta±0.2 at about 6.1, 12.2, 14.5, 22.3, and 31.8 degrees in an X-ray powder diffraction pattern obtained using Cu K alpha radiation.

6. The solid form of claim 1, characterized as having an X-ray powder diffraction pattern substantially the same as that shown in FIG. 1c.

7. The solid form of claim 1, characterized as having three or more peaks corresponding to 175.9±0.3 ppm, 138.9±0.3 ppm, 74.1±0.3 ppm, 42.8±0.3 ppm, and 31.5±0.3 ppm in a $^{13}$C ssNMR spectrum.

8. The solid form of claim 1, characterized as having peaks corresponding to −136.8±0.3 ppm and −155.7±0.3 ppm in an $^{19}$F ssNMR spectrum.

9. A solid form of a compound of formula I-1:

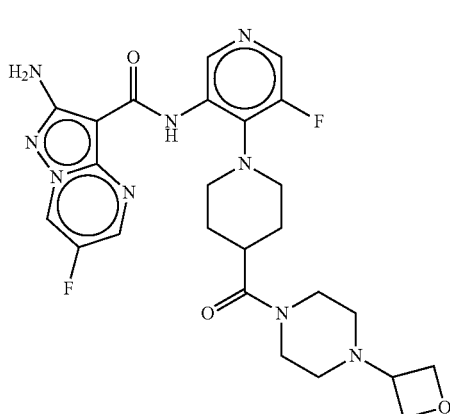

wherein the form is crystalline Compound I-1 hydrate I.

10. The solid form of claim 9, characterized by three or more peaks expressed in 2-theta±0.2 at about 6.5, 12.5, 13.7, 18.8, and 26.0 degrees in an X-ray powder diffraction pattern obtained using Cu K alpha radiation.

11. The solid form of claim 10, wherein the crystalline compound I-1•hydrate I has a Compound I-1 to H$_2$O ratio of about 1:4.5.

12. The solid form of claim 9, characterized as having an X-ray powder diffraction pattern substantially the same as that shown in FIG. 1b.

13. A solid form of a compound of formula I-1:

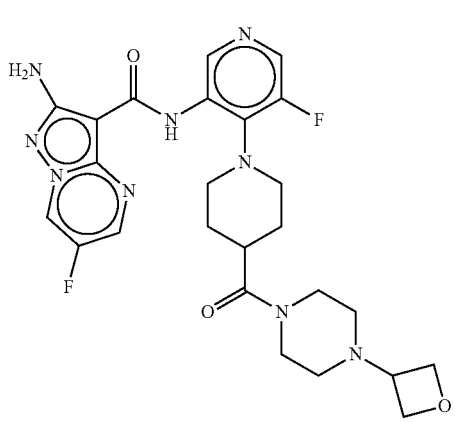

wherein the form is crystalline Compound I-1 anhydrous form B.

14. The solid form of claim 13, characterized by three or more peaks expressed in 2-theta±0.2 at about 7.2, 8.3, 12.9, 19.5, and 26.6 degrees in an X-ray powder diffraction pattern obtained using Cu K alpha radiation.

15. The solid form of claim 13, characterized as having an X-ray powder diffraction pattern substantially the same as that shown in FIG. 1d.

16. The solid form of claim 13, characterized as having three or more peaks corresponding to 173.4±0.3 ppm, 164.5±0.3 ppm, 133.5±0.3 ppm, 130.8±0.3 ppm, 67.7±0.3 ppm, 45.3±0.3 ppm, and 25.9±0.3 ppm in a $^{13}$C ssNMR spectrum.

17. The solid form of claim 13, characterized as having peaks corresponding to −138.0±0.3 ppm and −153.5±0.3 ppm in an $^{19}$F ssNMR spectrum.

18. A solid form of a compound of formula I-1

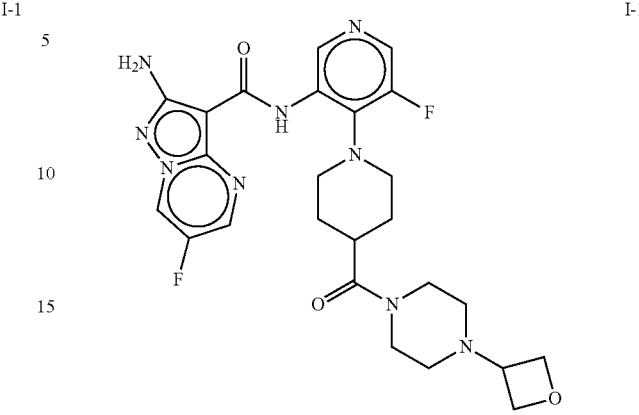

wherein the form is crystalline Compound I-1 anhydrous form C.

19. The solid form of claim 18, characterized by three or more peaks expressed in 2-theta±0.2 at about 6.8, 13.4, 15.9, 30.9, and 32.9 degrees in an X-ray powder diffraction pattern obtained using Cu K alpha radiation.

20. The solid form of claim 18, characterized as having an X-ray powder diffraction pattern substantially the same as that shown in FIG. 1e.

21. The solid form of claim 18, characterized as having three or more peaks corresponding to 175.2±0.3 ppm, 142.5±0.3 ppm, 129.6±0.3 ppm, 73.5±0.3 ppm, 54.0±0.3 ppm, and 46.7±0.3 ppm in a $^{13}$C ssNMR spectrum.

22. The solid form of claim 18, characterized as having peaks corresponding to −131.2±0.3 ppm and −150.7±0.3 ppm in an $^{19}$F ssNMR spectrum.

23. A solid form of a compound of formula I-1:

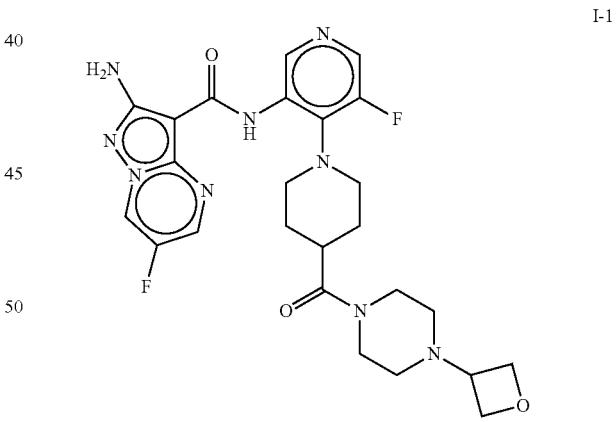

wherein the form is crystalline Compound I-1 DMSO solvate.

24. The solid form of claim 23, characterized by three or more peaks expressed in 2-theta±0.2 at about 8.9, 14.8, 16.5, 18.6, 20.9, 22.2, and 23.4 degrees in an X-ray powder diffraction pattern obtained using Cu K alpha radiation.

25. The solid form of claim 24, wherein the crystalline compound I-1•DMSO solvate has a compound I-1 to DMSO ratio of about 1:1.

26. The solid form of claim 23, characterized as having an X-ray powder diffraction pattern substantially the same as that shown in FIG. 1g.

27. A solid form of a compound of formula I-1:

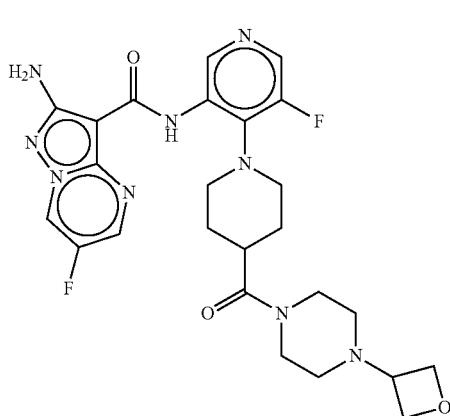

I-1 wherein the form is crystalline Compound I-1 dimethylacetamide solvate.

28. The solid form of claim 27, characterized by three or more peaks expressed in 2-theta±0.2 at about 6.0, 15.5, 17.7, 18.1, 20.4, and 26.6 degrees in an X-Ray powder diffraction pattern obtained using Cu K alpha radiation.

29. The solid form of claim 28, wherein the crystalline Compound I-1•dimethylacetamide solvate has a compound I-1 to dimethylacetamide ratio of about 1:1.3.

30. The solid form of claim 27, characterized as having an X-ray powder diffraction pattern substantially the same as that shown in FIG. 1h.

31. A solid form of a compound of formula I-1:

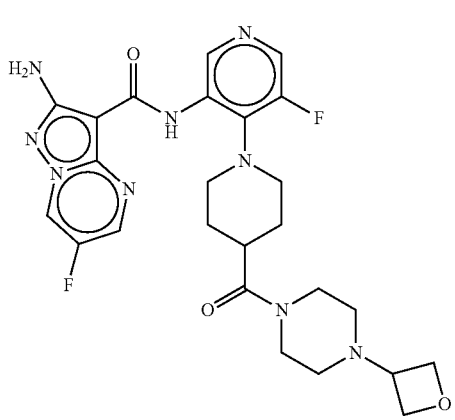

I-1 wherein the form is crystalline Compound I-1 acetone solvate.

32. The solid form of claim 31, characterized by three or more peaks expressed in 2-theta±0.2 at about 8.9, 15.5, 15.8, 16.7, 22.3, 25.7, and 29.0 degrees in an X-Ray powder diffraction pattern obtained using Cu K alpha radiation.

33. The solid form of claim 32, wherein the crystalline compound I-1•acetone solvate has a compound I-1 to acetone ratio of about 1:0.44.

34. The solid form of claim 31, characterized as having an X-ray powder diffraction pattern substantially the same as that shown in FIG. 1i.

35. A solid form of a compound of formula I-1:

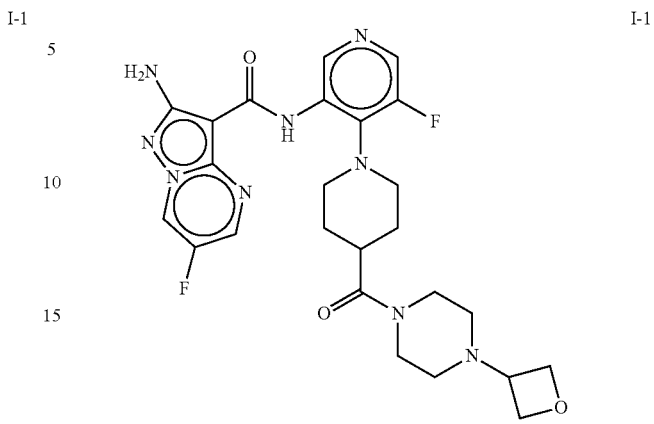

I-1 wherein the form is crystalline Compound I-1 isopropanol solvate.

36. The solid form of claim 35, characterized by three or more peaks expressed in 2-theta±0.2 at about 6.9, 17.1, 17.2, 19.1, 19.6, 23.7, 24.4, and 28.9 degrees in an X-Ray powder diffraction pattern obtained using Cu K alpha radiation.

37. The solid form of claim 36, wherein the crystalline compound I-1•isopropanol solvate has a compound I-1 to isopropanol ratio of about 1:0.35.

38. The solid form of claim 35, characterized as having an X-ray powder diffraction pattern substantially the same as that shown in FIG. 1j.

39. A composition comprising,
a) an amount of the solid form of claim 1 in the range of about 5 wt % to about 50 wt % by the total weight of the composition;
b) an amount of one or more lubricants in the range of about 0.1 wt % to about 10 wt % by the total weight of the composition;
c) an amount of one or more disintegrants in the range of about 1 wt % to about 15 wt % by the total weight of the composition; and
d) an amount of one or more fillers in the range of about 10 wt % to about 90 wt % by the total weight of the composition.

40. A composition, comprising:
a) an amount of the solid form of claim 1 of about 10 wt % by the total weight of the composition;
b) an amount of lactose monohydrate of about 28 wt % by the total weight of the composition;
c) an amount of microcrystalline cellulose of about 55 wt % by the total weight of the composition;
d) an amount of croscarmellose sodium of about 5 wt % by the total weight of the composition; and
e) an amount of sodium stearyl fumarate of about 3 wt % by the total weight of the composition.

41. A composition comprising the solid form of claim 1, wherein at least 90% by weight of Compound I-1 is crystalline Compound I-1 anhydrous form A.

42. The composition of claim 41, wherein at least 95% by weight of Compound I-1 is crystalline Compound I-1 anhydrous form A.

43. The composition of claim 41, wherein at least 98% by weight of Compound I-1 is crystalline Compound I-1 anhydrous form A.

44. A pharmaceutical composition comprising the solid form of claim 1 and one or more excipients.

45. A pharmaceutical composition comprising the solid form of claim 9, and one or more excipients.

46. A pharmaceutical composition comprising the solid form of claim 13, and one or more excipients.

47. A pharmaceutical composition comprising the solid form of claim 18, and one or more excipients.

48. A pharmaceutical composition comprising the solid form of claim 23, and one or more excipients.

49. A pharmaceutical composition comprising the solid form of claim 27, and one or more excipients.

50. A pharmaceutical composition comprising the solid form of claim 31, and one or more excipients.

51. A pharmaceutical composition comprising the solid form of claim 35, and one or more excipients.

52. The solid form of claim 1, characterized by a weight loss of about 0.96% in a temperature range of about 25° C. to about 265° C.

53. The solid form of claim 9, characterized by a weight loss of about 14.56% in a temperature range of about 25° C. to about 100° C.

54. The solid form of claim 13, characterized by a weight loss of about 2.5% in a temperature range of about 25° C. to about 175° C.

55. The solid form of claim 23, characterized by a weight loss of about 12.44% in a temperature range of about 146° C. to about 156° C.

56. The solid form of claim 27, characterized by a weight loss of about 17.76% in a temperature range of about 85° C. to about 100° C.

57. The solid form of claim 31, characterized by a weight loss of about 4.55% in a temperature range of about 124° C. to about 151° C.

58. The solid form of claim 35, characterized by a weight loss of about 3.76% in a temperature range of about 136° C. to about 180° C.

59. The solid form of claim 1, wherein the solid form is over 95% (w/w) crystalline Compound I-1 anhydrous form A.

60. The solid form of claim 1, wherein the solid form is over 98% (w/w) crystalline Compound I-1 anhydrous form A.

61. The solid form of claim 1, wherein the solid form is over 99% (w/w) crystalline Compound I-1 anhydrous form A.

62. The solid form of claim 59, wherein the crystalline Compound I-1 anhydrous form A is characterized by three or more peaks expressed in 2-theta±0.2 at about 6.1, 12.2, 14.5, 22.3, and 31.8 degrees in an X-ray powder diffraction pattern obtained using Cu K alpha radiation.

63. The solid form of claim 1, having a monoclinic crystal system, a P21/c centrosymmetric space group.

* * * * *